(12) United States Patent
Baeschlin et al.

(10) Patent No.: US 8,097,617 B2
(45) Date of Patent: Jan. 17, 2012

(54) ORGANIC COMPOUNDS

(75) Inventors: Daniel Kaspar Baeschlin, Arlesheim (CH); Nils Ostermann, Binzen (DE); Francois Gessier, Illfurth (FR); Finton Sirockin, St. Louis (FR); Kenji Namoto, Basel (CH)

(73) Assignee: Novartis AG, Basel (CH)

( * ) Notice: Subject to any disclaimer, the term of this patent is extended or adjusted under 35 U.S.C. 154(b) by 439 days.

(21) Appl. No.: 12/295,549

(22) PCT Filed: Mar. 29, 2007

(86) PCT No.: PCT/EP2007/053064
§ 371 (c)(1),
(2), (4) Date: Sep. 30, 2008

(87) PCT Pub. No.: WO2007/113226
PCT Pub. Date: Oct. 11, 2007

(65) Prior Publication Data
US 2009/0253689 A1 Oct. 8, 2009

Related U.S. Application Data

(60) Provisional application No. 60/788,294, filed on Mar. 31, 2006.

(51) Int. Cl.
*A61K 31/437* (2006.01)
*A61K 31/5377* (2006.01)
*A61K 31/541* (2006.01)
*C07D 471/04* (2006.01)
*C07D 413/14* (2006.01)
*C07D 279/12* (2006.01)
*A61P 9/00* (2006.01)
*A61P 3/00* (2006.01)
*A61P 25/00* (2006.01)

(52) U.S. Cl. .......... 514/228.2; 514/233.2; 514/300; 546/121; 544/127; 544/58.2

(58) Field of Classification Search .............. 546/121; 544/127, 58.2; 514/228.2, 233.2, 300
See application file for complete search history.

(56) References Cited

U.S. PATENT DOCUMENTS

| | | | |
|---|---|---|---|
| 5,559,158 A | 9/1996 | Al-Razzak et al. | |
| 2005/0272765 A1 | 12/2005 | Feng et al. | |
| 2006/0014764 A1 | 1/2006 | Feng et al. | |

FOREIGN PATENT DOCUMENTS

| | | | |
|---|---|---|---|
| WO | 96/21662 | * | 7/1996 |
| WO | 96/21662 A | | 7/1996 |
| WO | 02/066477 A | | 8/2002 |
| WO | 03014123 | * | 2/2003 |
| WO | WO-03/068748 A1 | | 8/2003 |
| WO | WO-03/068757 A1 | | 8/2003 |

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
Bundgaard, H. ed. (1985). *Design of Prodrugs*. Elsevier.
Greene, T. W. and Wuts, P. G. M. (1991). *Protective Groups in Organic Synthesis*, 2nd edition, Wiley-Interscience.
Higuchi, T. and Stella, V. (Sep. 10, 1974). "Pro-drugs as Novel Delivery Systems," *A.C.S. Symposium Series*, vol. 14. Edward B. Roche, ed.
Judkins, B. et al. (1996). "A Versatile Synthesis of Amides from Nitriles via Amidoximes," *Synthetic Communications* 26(23), 4351-4367.
Katritzky et al. (2003). "Regiospecific Synthesis of 3-Substituted Imidazo[1,2-a]pyridines, Imidazo[1,2-a]pyrimidines, and Imidazo[1,2-c]pyrimidine," *J. Org. Chem.* 68:4935-4937.
Katritzky et al. (May 11, 1990). "A Novel method for the Synthesis of Symmetrical Vicinal Tertiary and Secondary Diamines," *J. Org. Chem.* 55(10):3209-3213.
Korom, S. et al. (May 27, 1997). "Inhibition of CD26/dipeptidyl peptidase IV activity in vivo prolongs cardiac allograft survival in rat recipients," *Transplantation* 63(10):1495-1500.
Mcomie, J W F, Ed. (1973) *Protective Groups in Organic Chemistry*. Plenum Press.
Prescott, Ed., (1976). *Methods in Cell Biology*, vol. XIV, Academic Press, New York, N.Y., p. 33.
Ravin, L. J. (1985). "Preformulation," Chapter 76 in *Remington's Pharmaceutical Sciences*, 17th ed., Mack Publishing Company, Easton, Pa., US, pp. 1409-1423.
Roche, E. B., Ed. (1987). *Bioreversible Carriers in Drug Design*, American Pharmaceutical Association and Pergamon Press.
Silverman, R B., Ed. (2004). *The Organic Chemistry of Drug Design and Drug Action*, 2nd edition, Elsevier.
Stahl et al, Eds, (2002). *Handbook of Pharmaceutical Salts: Properties, Selection, and Use*. Verlag Helvetica Chimica Acta and Wiley-VCH.

* cited by examiner

*Primary Examiner* — Janet Andres
*Assistant Examiner* — Niloofar Rahmani
(74) *Attorney, Agent, or Firm* — John B. Alexander

(57) ABSTRACT

New compounds of the Formula (I):

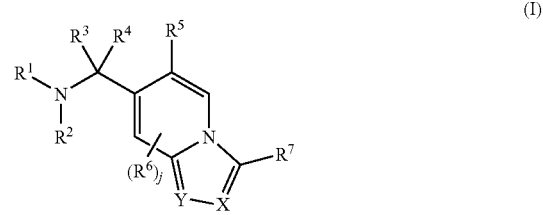

for the treatment of non-insulin-dependent diabetes mellitus.

17 Claims, No Drawings

ORGANIC COMPOUNDS

This application is the National Stage of Application No. PCT/EP2007/053064, filed on Mar. 29, 2007, which claims benefit under 35 U.S.C. §119(e) of U.S. Provisional Application No. 60/788,294, filed Mar. 31, 2006, the contents of which are incorporated herein by reference in their entirety.

FIELD OF THE INVENTION

The present invention relates to compounds and their use in therapy.

BACKGROUND TO THE INVENTION

Dipeptidylpeptidase-IV (DPP-IV) is a serine protease which cleaves N-terminal dipeptides from a peptide chain containing, in general, a proline residue in the penultimate position. DPP-IV is widely expressed in mammalian tissue as a type II integral membrane protein. The protease is expressed on the surface of differentiated epithelial cells of the intestine, liver, kidney proximal tubules, prostate, corpus luteum, and on leukocyte subsets such as lymphocytes and macrophages. A soluble form of the enzyme is found in serum that has structure and function identical to the membrane-bound form of the enzyme but lacks the hydrophobic transmembrane domain.

DPP-IV has many physiologically relevant substrates including chemokines (e.g. eotaxin and macrophage-derived chemokine), neuropeptides (e.g. neuropeptide Y and substance P), vasoactive peptides, and incretins (e.g. GLP-1 and GIP). GLP-1 (glucagon-like peptide-1) is a hormone produced in the L cells of the distal small intestine in response to ingested nutrients. GLP-1 receptor binding on various tissues stimulates insulin gene expression, biosynthesis and glucose-dependent insulin secretion, inhibits glucagon secretion, promotes satiety, slows gastric emptying and promotes growth of pancreatic beta cells.

Although the biological role of DPP-IV in mammalian systems has not been completely established, it is believed to play an important role in neuropeptide metabolism, T-cell activation, attachment of cancer cells to the endothelium and the entry of HIV into lymphoid cells. It has also been discovered that DPP-IV is responsible for inactivating glucagon-like peptide-1 (GLP-1). Since GLP-1 is a major stimulator of pancreatic insulin secretion and has direct beneficial effects on glucose disposal, DPP-IV inhibition appears to represent an attractive approach for treating, for example, non-insulin-dependent diabetes mellitus (NIDDM).

DPP-IV has also been shown to play a part in the immune response. Expressed by T-CD4+ lymphocytes, where it is synonymous with the antigen CD26, DPP-IV plays an important part in the mechanism of transplant rejection (Transplantation 1997, 63 (10), 1495-500). By allowing more selective suppression of the immune response, inhibition of DPP-IV accordingly represents an extremely promising approach in the prevention of transplant rejection in transplant patients.

Inhibitors of DPP-IV are described inter alia in WO-A-2003/068748, WO-A-20031068757, US-A-2006/0014764 and U.S. Pat. No. 2,005,10272765.

SUMMARY OF THE INVENTION

A first aspect of the invention is a compound of the Formula (I):

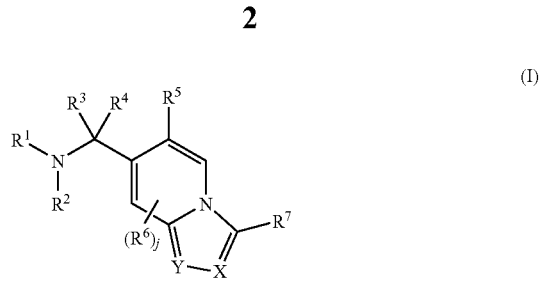

wherein
X is =N— or =C($R^8$)—;
Y is =N— or =C($R^9$)—;
$R^1$ and $R^2$ are each independently selected from $R^{10}$, —O$R^{10}$, —C(O)$R^{10}$, —C(O)O$R^{10}$ and —S(O)$_i R^{10}$;
$R^3$ and $R^4$ are each independently hydrogen or $R^{13}$; or $R^3$ and $R^4$ taken together with the carbon atom to which they are attached form carbocyclyl or heterocyclyl, either of which is optionally substituted with 1, 2, 3, 4 or 5 $R^{13}$;
$R^5$ is aryl or heteroaryl, either of which is optionally substituted with 1, 2, 3, 4 or 5 $R^{13}$;
$R^6$ is selected from halogen, trifluoromethyl, cyano, nitro, oxo, $R^{10}$, —O$R^{10}$, —C(O)$R^{10}$, —C(O)O$R^{10}$, —OC(O)$R^{10}$, —S(O)$_i R^{11}$, —N($R^{11}$)($R^{12}$) and —C(O)N($R^{11}$)($R^{12}$);
$R^7$, $R^8$ and $R^9$ are each independently selected from hydrogen, halogen and moieties comprising from 1 to 30 plural valent atoms selected from C, N, O and S; for example $R^7$, $R^8$ and $R^9$ are each independently selected from halogen, trifluoromethyl, cyano, nitro, $R^{10}$, —O$R^{10}$, —C(O)$R^{10}$, —C(O)O$R^{10}$, —OC(O)$R^{10}$, —S(O)$_i R^{11}$, —N($R^{11}$)($R^{12}$) and —C(O)N($R^{11}$)($R^{12}$);
$R^{10}$ is hydrogen, hydrocarbyl optionally substituted with 1, 2, 3, 4 or 5 $R^{13}$; or —(CH$_2$)$_k$-heterocyclyl optionally substituted with 1, 2, 3, 4 or 5 $R^{13}$;
$R^{11}$ and $R^{12}$ are each independently selected from $R^{10}$, —O$R^{10}$, —C(O)$R^{10}$, —C(O)O$R^{10}$ and —S(O)$_i R^{10}$; or $R^{11}$ and $R^{12}$ taken together with a nitrogen atom to which they are attached form heterocyclyl optionally substituted with 1, 2, 3, 4 or 5 $R^{13}$; or
$R^{11}$ and $R^{12}$ are each independently selected from $R^{10}$, —O$R^{10}$, —C(O)$R^{10}$, —C(O)O$R^{10}$, —(CH$_2$)$_k$—$R^{10}$, —C(O)—(CH$_2$)$_k$—$R^{10}$ and —S(O)$_i R^{10}$; or $R^{11}$ and $R^{12}$ taken together with a nitrogen atom to which they are attached form heterocyclyl optionally substituted with 1, 2, 3, 4 or 5 $R^{13}$;
each $R^{13}$ is independently selected from halogen, trifluoromethyl, cyano, nitro, oxo, =N$R^{14}$, —O$R^{14}$, —C(O)$R^{14}$, —C(O)O$R^{14}$, —OC(O)$R^{14}$, —S(O)$_i R^4$, —N($R^{14}$)$R^{15}$—C(O)N($R^{14}$)$R^{15}$ and $R^{16}$;
$R^{14}$ and $R^{15}$ are each independently hydrogen or $R^{16}$;
$R^{16}$ is selected from hydrocarbyl and —(CH$_2$)$_k$-heterocyclyl, either of which is optionally substituted with 1, 2, 3, 4 or 5 substituents independently selected from halogen, cyano, amino, hydroxy, $C_{1-6}$ alkyl and $C_{1-6}$ alkoxy; or
$R^{16}$ is selected from a spiro group, hydrocarbyl, —(CH$_2$)$_k$-hydrocarbyl, —(CH$_2$)$_k$-heterocyclyl and —(CH$_2$)$_k$—C(O)-heterocyclyl, either of which is optionally substituted with 1, 2, 3, 4 or 5 substituents independently selected from halogen, cyano, oxo, amino, hydroxy, —C(O)—$C_{1-6}$ alkyl, $C_{1-6}$ alkyl and $C_{1-6}$ alkoxy.
j is 0, 1 or 2;
k is 0, 1, 2, 3, 4, 5 or 6; and
l is 0, 1, or 2;
or a pharmaceutically acceptable salt or prodrug thereof.

A second aspect of the invention is a compound of the invention for therapeutic use.

Another aspect of the invention is a pharmaceutical formulation comprising a compound of the invention and, optionally, a pharmaceutically acceptable diluent or carrier.

A further aspect of the invention is a product comprising a compound of the invention and a therapeutic agent; as a combined preparation for simultaneous, separate or sequential use in therapy.

Another aspect of the invention is the use of a compound of the invention for the manufacture of a medicament for the treatment or prevention of a disease or condition selected from non-insulin-dependent diabetes mellitus, arthritis, obesity, allograft transplantation, calcitonin-osteoporosis, heart failure, impaired glucose metabolism or impaired glucose tolerance, neurodegenerative diseases, cardiovascular or renal diseases, and neurodegenerative or cognitive disorders.

Another aspect of the invention is the use of a compound of the invention for the manufacture of a medicament for producing a sedative or anxiolytic effect, attenuating post-surgical catabolic changes or hormonal responses to stress, reducing mortality and morbidity after myocardial infarction, modulating hyperlipidemia or associated conditions, or lowering VLDL, LDL or Lp(a) levels.

Another aspect of the invention is a method of treating or preventing a disease or condition in a patient, which comprises administering a therapeutically effective amount of a compound of the invention.

The compounds of the invention can exist in different forms, such as free acids, free bases, esters and other prodrugs, salts and tautomers, for example, and the disclosure includes all variant forms of the compounds.

The extent of protection includes counterfeit or fraudulent products which contain or purport to contain a compound of the invention irrespective of whether they do in fact contain such a compound and irrespective of whether any such compound is contained in a therapeutically effective amount.

Included in the scope of protection are packages which include a description or instructions which indicate that the package contains a species or pharmaceutical formulation of the invention and a product which is or comprises, or purports to be or comprise, such a formulation or species. Such packages may be, but are not necessarily, counterfeit or fraudulent.

Features, integers, characteristics, compounds, chemical moieties or groups described in conjunction with a particular aspect, embodiment or example of the invention are to be understood to be applicable to any other aspect, embodiment or example described herein unless incompatible therewith.

DESCRIPTION OF VARIOUS EMBODIMENTS

Hydrocarbyl

The term "hydrocarbyl" as used herein includes reference to a moiety consisting exclusively of hydrogen and carbon atoms; such a moiety may comprise an aliphatic and/or an aromatic moiety. The moiety may comprise 1, 2, 3, 4, 5, 6, 7, 8, 9, 10, 11, 12, 13, 14, 15, 16, 17, 18, 19 or 20 carbon atoms. Examples of hydrocarbyl groups include alkyl such as $C_{1-6}$ alkyl (e.g. $C_1$, $C_2$, $C_3$ or $C_4$ alkyl, for example methyl, ethyl, propyl, isopropyl, n-butyl, sec-butyl or tert-butyl); $C_{1-6}$ alkyl substituted by aryl (e.g. benzyl) or by cycloalkyl (e.g cyclopropylmethyl); cycloalkyl (e.g. cyclopropyl, cyclobutyl, cyclopentyl or cyclohexyl); aryl (e.g. phenyl, naphthyl or fluorenyl) and the like.

Alkyl

The terms "alkyl" and "$C_{1-6}$ alkyl" as used herein include reference to a straight or branched chain alkyl moiety having 1, 2, 3, 4, 5 or 6 carbon atoms. This term includes reference to groups such as methyl, ethyl, propyl (n-propyl or isopropyl), butyl (n-butyl, sec-butyl or tert-butyl), pentyl, hexyl and the like. In particular, alkyl may have 1, 2, 3 or 4 carbon atoms.

Alkenyl

The terms "alkenyl" and "$C_{2-6}$ alkenyl" as used herein include reference to a straight or branched chain alkyl moiety having 2, 3, 4, 5 or 6 carbon atoms and having, in addition, at least one double bond, of either E or Z stereochemistry where applicable. This term includes reference to groups such as ethenyl, 2-propenyl, 1-butenyl, 2-butenyl, 3-butenyl, 1-pentenyl, 2-pentenyl, 3-pentenyl, 1-hexenyl, 2-hexenyl and 3-hexenyl and the like.

Alkynyl

The terms "alkynyl" and "$C_{2-6}$ alkynyl" as used herein include reference to a straight or branched chain alkyl moiety having 2, 3, 4, 5 or 6 carbon atoms and having, in addition, at least one triple bond. This term includes reference to groups such as ethynyl, 1-propynyl, 2-propynyl, 1-butynyl, 2-butynyl, 3-butynyl, 1-pentynyl, 2-pentynyl, 3-pentynyl, 1-hexynyl, 2-hexynyl and 3-hexynyl and the like.

Alkoxy

The terms "alkoxy" and "$C_{1-6}$ alkoxy" as used herein include reference to —O-alkyl, wherein alkyl is straight or branched chain and comprises 1, 2, 3, 4, 5 or 6 carbon atoms. In one class of embodiments, alkoxy has 1, 2, 3 or 4 carbon atoms. This term includes reference to groups such as methoxy, ethoxy, propoxy, isopropoxy, butoxy, tert-butoxy, pentoxy, hexoxy and the like.

Cycloalkyl

The term "cycloalkyl" as used herein includes reference to an alicyclic moiety having 3, 4, 5, 6, 7 or 8 carbon atoms. The group may be a bridged or polycyclic ring system. More often cycloalkyl groups are monocyclic. This term includes reference to groups such as adamantly, cyclopropyl, cyclobutyl, cyclopentyl, cyclohexyl, norbornyl, bicyclo[2.2.2]octyl, bicyclo[2.2.1]heptyl and the like.

Aryl

The term "aryl" as used herein includes reference to an aromatic ring system comprising 6, 7, 8, 9, 10, 11, 12, 13, 14, 15 or 16 ring carbon atoms. Aryl is often phenyl but may be a polycyclic ring system, having two or more rings, at least one of which is aromatic. This term includes reference to groups such as phenyl, naphthyl, fluorenyl, azulenyl, indenyl, anthryl and the like.

Carbocyclyl

The term "carbocyclyl" as used herein includes reference to a saturated (e.g. cycloalkyl) or unsaturated (e.g. aryl) ring moiety having 3, 4, 5, 6, 7, 8, 9, 10, 11, 12, 13, 14, 15 or 16 carbon ring atoms. In particular, carbocyclyl includes a 3- to 10-membered ring or ring system and, in particular, a 5- or 6-membered ring, which may be saturated or unsaturated. A carbocyclic moiety is, for example, selected from cyclopropyl, cyclobutyl, cyclopentyl, cyclohexyl, norbornyl, bicyclo [2.2.2]octyl, phenyl, naphthyl, fluorenyl, azulenyl, indenyl anthryl and the like.

Heterocyclyl

The term "heterocyclyl" as used herein includes reference to a saturated (e.g. heterocycloalkyl) or unsaturated (e.g. heteroaryl) heterocyclic ring moiety having from 3, 4, 5, 6, 7, 8, 9, 10, 11, 12, 13, 14, 15 or 16 ring atoms, at least one of which is selected from nitrogen, oxygen, phosphorus, silicon and sulphur. In particular, heterocyclyl includes a 3- to 10-membered ring or ring system and more particularly a 5- or 6-membered ring, which may be saturated or unsaturated.

A heterocyclic moiety is, for example, selected from oxiranyl, azirinyl, 1,2-oxathiolanyl, imidazolyl, thienyl, furyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, imidazolyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyrazinyt, pyrimidinyl, piperidyl, piperazinyl, pyridazinyl, morpholinyl, thiomorpholinyl, especially thiomorpholino, indolizinyl, isoindolyl, 3H-indolyi, indolyl, benzimidazolyl, cumaryl, indazolyl, triazolyl, tetrazolyl, purinyl, 4H-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazolyl, β-carbolinyl, phenanthridinyl, acridinyl, perimidinyl, phenanthrolinyl, furazanyl, phenazinyl, phenothiazinyl, phenoxazinyl, chromenyl, isochromanyl, chromanyl, tetrahydro-2H-pyridopyridazinyl e.g. 3,5,7,8-tetrahydro-2H-pyrido[4,3-c]pyridazine, 1-methyl-1H-pyridinyl-2-one and the like.

Heterocycloalkyl

The term "heterocycloalkyl" as used herein includes reference to a saturated heterocyclic moiety having 3, 4, 5, 6 or 7 ring carbon atoms and 1, 2, 3, 4 or 5 ring heteroatoms selected from nitrogen, oxygen, phosphorus and sulphur. The group may be a polycyclic ring system but more often is monocyclic. This term includes reference to groups such as azetidinyl, pyrrolidinyl, tetrahydrofuranyl, piperidinyl, oxiranyl, pyrazolidinyl, imidazolyl, indolizidinyl, piperazinyl, thiazolidinyl, morpholinyl, thiomorpholinyl, quinolizidinyl and the like.

Heteroaryl

The term "heteroaryl" as used herein includes reference to an aromatic heterocyclic ring system having 5, 6, 7, 8, 9, 10, 11, 12, 13, 14, 15 or 16 ring atoms, at least one of which is selected from nitrogen, oxygen and sulphur. The group may be a polycyclic ring system, having two or more rings, at least one of which is aromatic, but is more often monocyclic. This term includes reference to groups such as pyrimidinyl, furanyl, benzo[b]thiophenyl, thiophenyl, pyrrolyl, imidazolyl, pyrrolidinyl, pyridinyl, benzo[b]furanyl, pyrazinyl, purinyl, indolyl, benzimidazolyl, quinolinyl, phenothiazinyl, triazinyl, phthalazinyl, 2H-chromenyl, oxazolyl, isoxazolyl, thiazolyl, isoindolyl, indazolyl, purinyl, isoquinolinyl, quinazolinyl, pteridinyl and the like.

Halogen

The term "halogen" as used herein includes reference to F, Cl, Br or I. In a particular, halogen may be F or Cl, of which F is more common.

Spiro

The term "spiro" as used herein includes 5- to 6-cycloalkyl or 5- to 6-heterocycloalkyl groups which can optionally be substituted by 1, 2, 3 or 4, $R^{13}$. Non limitative examples of sipro groups are;

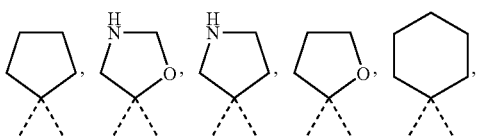

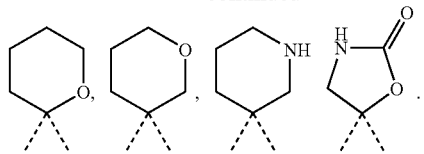

Substituted

The term "alkoxycarbonyl" refers to alkyl-O—C(O)—.

In the present application, the terms "—N($C_{1-6}$ alkyl)$_2$" and "—N($C_{1-6}$ alkyl)($C_{1-6}$ alkyl)" have the same meaning. For both terms the two alkyl groups may be the same or different and cover e.g. N($CH_3$)($CH_2CH_3$) or N($CH_3$)($CH_3$).

The term "substituted" as used herein in reference to a moiety means that one or more, especially up to 5, more especially 1, 2 or 3, of the hydrogen atoms in said moiety are replaced independently of each other by the corresponding number of the described substituents. The term "optionally substituted" as used herein means substituted or unsubstituted.

It will, of course, be understood that substituents are only at positions where they are chemically possible, the person skilled in the art being able to decide (either experimentally or theoretically) without inappropriate effort whether a particular substitution is possible. For example, amino or hydroxy groups with free hydrogen may be unstable if bound to carbon atoms with unsaturated (e.g. olefinic) bonds. Additionally, it will of course be understood that the substituents described herein may themselves be substituted by any substituent, subject to the aforementioned restriction to appropriate substitutions as recognised by the skilled man.

Pharmaceutically Acceptable

The term "pharmaceutically acceptable" as used herein includes reference to those compounds, materials, compositions, and/or dosage forms which are, within the scope of sound medical judgment, suitable for use in contact with the tissues of human beings or animals without excessive toxicity, irritation, allergic response, or other problem or complication, commensurate with a reasonable benefit/risk ratio. This term includes acceptability for both human and veterinary purposes.

Independently

Where two or more moieties are described as being "each independently" selected from a list of atoms or groups, this means that the moieties may be the same or different. The identity of each moiety is therefore independent of the identities of the one or more other moieties.

Compounds

The present invention provides compounds of the Formula (I):

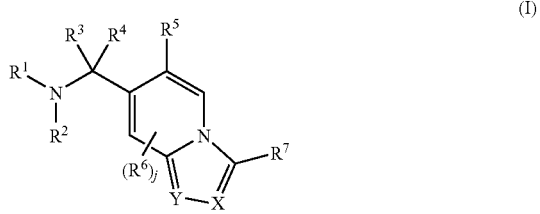

wherein X, Y, $R^1$, $R^2$, $R^3$, $R^4$, $R^5$, $R^6$, $R^7$ and j are as defined herein;

or a pharmaceutically acceptable salt or prodrug thereof.

Embodiments of the invention are described below. It will be appreciated that the features specified in each embodiment may be combined with other specified features, to provide further embodiments.

X & Y

In Formula (I), X is =N— or =C($R^8$)—; and Y is =N— or =C($R^9$)—. The invention therefore includes compounds of the following Formulae:

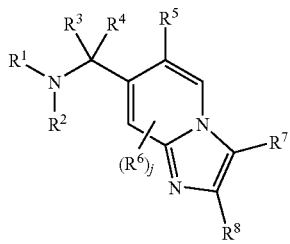
(II)

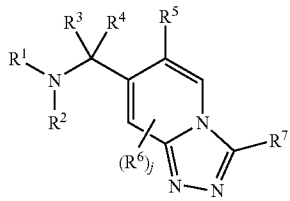
(III)

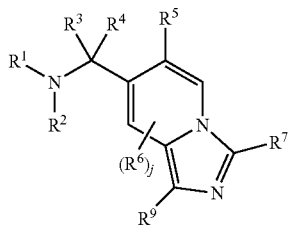
(IV)

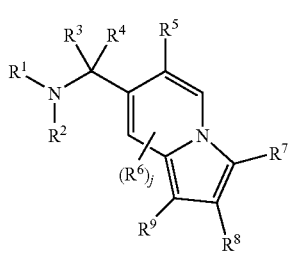
(V)

or, in each case, a pharmaceutically acceptable salt or prodrug thereof.

Of particular mention are compounds of the Formula (II) and compounds of the Formula (III), and pharmaceutically acceptable salts or prodrugs thereof.

In the above Formulae, $R^8$ and $R^9$ are each independently selected from hydrogen, halogen and moieties comprising from 1 to 30 plural valent atoms selected from C, N, O and S. For example, $R^8$ and $R^9$ may be each independently selected from halogen, trifluoromethyl, cyano, nitro, $R^{10}$, —$OR^{10}$, —$C(O)R^{10}$, —$C(O)OR^{10}$, —$OC(O)R^{10}$, —$S(O)_iR^{11}$, —$N(R^{11})(R^{12})$ and —$C(O)N(R^{11})(R^{12})$; wherein $R^{10}$ is hydrogen, hydrocarbyl optionally substituted with 1, 2, 3, 4 or 5 $R^{13}$; or —$(CH_2)_k$-heterocyclyl optionally substituted with 1, 2, 3, 4 or 5 $R^{13}$; and $R^{11}$ and $R^{12}$ are each independently selected from $R^{10}$, —$OR^{10}$, —$C(O)R^{10}$, —$C(O)OR^{10}$ and —$S(O)_iR^{10}$; or $R^{11}$ and $R^{12}$ taken together with the nitrogen atom to which they are attached form heterocyclyl optionally substituted with 1, 2, 3, 4 or 5 $R^{13}$. Typically, $R^8$ and/or $R^9$ are each independently hydrogen or $C_{1-6}$ alkyl optionally substituted with 1, 2, 3, 4 or 5 $R^{13}$.

$R^1$ & $R^2$ $R^1$ and $R^2$ are each independently selected from $R^{10}$, —$OR^{10}$, —$C(O)R^{10}$, —$C(O)OR^{10}$ and —$S(O)_iR^{10}$, wherein $R^{10}$ is hydrogen, hydrocarbyl optionally substituted with 1, 2, 3, 4 or 5 $R^{13}$; or —$(CH_2)_k$-heterocyclyl optionally substituted with 1, 2, 3, 4 or 5 $R^{13}$. Where $R^{10}$ is hydrocarbyl, it may be, for example, $C_{1-6}$ alkyl (e.g. $C_1$, $C_2$, $C_3$ or $C_4$ alkyl) or —$(CH_2)_k$-carbocyclyl (e.g. —$(CH_2)_k$-cycloalkyl or —$(CH_2)_k$-aryl), either of which is optionally substituted with 1, 2, 3, 4 or 5 $R^{13}$. In particular, hydrocarbyl may be $C_{1-6}$ alkyl (e.g. $C_1$, $C_2$, $C_3$ or $C_4$ alkyl) or —$(CH_2)_k$-aryl (e.g. phenyl or benzyl), either of which is optionally substituted with 1, 2, 3, 4 or 5 $R^{13}$. Where $R^{10}$ is —$(CH_2)_k$-heterocyclyl, it may be, for example, —$(CH_2)_k$-heterocycloalkyl or —$(CH_2)_k$-heteroaryl, either of which is optionally substituted with 1, 2, 3, 4 or 5 $R^{13}$.

In one embodiment, $R^1$ and $R^2$ are each independently selected from hydrogen; $C_{1-6}$ alkyl optionally substituted with 1, 2, 3, 4 or 5 $R^{13}$; and —$(CH_2)_k$-carbocyclyl (e.g. —$(CH_2)_k$-cycloalkyl or —$(CH_2)_k$-aryl) optionally substituted with 1, 2, 3, 4 or 5 $R^{13}$.

In another embodiment, $R^1$ is hydrogen; and $R^2$ is hydrogen or $C_{1-6}$ alkyl (e.g. $C_1$, $C_2$, $C_3$ or $C_4$ alkyl) optionally substituted with 1, 2, 3, 4 or 5 $R^{13}$.

In another embodiment, $R^1$ and $R^2$ are each hydrogen. The invention therefore includes compounds of the following Formula:

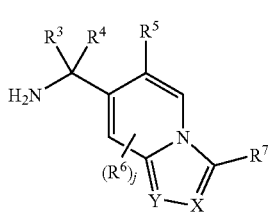
(VI)

or a pharmaceutically acceptable salt or prodrug thereof.

$R^3$ & $R^4$ $R^3$ and $R^4$ are each independently hydrogen or $R^{13}$; or $R^3$ and $R^4$ taken together with the carbon atom to which they are attached form carbocyclyl or heterocyclyl, either of which is optionally substituted with 1, 2, 3, 4 or 5 $R^{13}$.

Where $R^3$ and/or $R^4$ is $R^3$, the or each $R^{13}$ is often independently selected from halogen (e.g. fluorine, chlorine or bromine), hydroxy, cyano, amino, —C(O)OH, $C_{1-6}$ alkyl, $C_{1-6}$ alkoxy (e.g. $C_1$, $C_2$, $C_3$ or $C_4$ alkoxy), —C(O)—$C_{1-6}$ alkyl, —C(O)O—$C_{1-6}$ alkyl, —$SO_i$—$C_{1-6}$ alkyl, —NH($C_{1-6}$ alkyl) and —N($C_{1-6}$ alkyl)$_2$, wherein any $C_{1-6}$ alkyl group present is optionally substituted with 1, 2, 3, 4 or 5 substituents independently selected from halogen, cyano, amino, hydroxy and $C_{1-6}$ alkoxy, and wherein the alkyl groups of the di($C_{1-6}$ alkyl)amino group may be the same or different.

In one embodiment, $R^3$ and $R^4$ are each independently selected from hydrogen, $C_{1-6}$ alkyl optionally substituted with 1, 2, 3, 4 or 5 $R^{13}$, and —$(CH_2)_k$-carbocyclyl optionally substituted with 1, 2, 3, 4 or 5 $R^{13}$.

In a further embodiment, $R^3$ and $R^4$ taken together with the carbon atom to which they are attached form carbocyclyl optionally substituted with 1, 2, 3, 4 or 5 $R^{13}$. In this case, carbocyclyl is often cycloalkyl, usually $C_{3-6}$ cycloalkyl (e.g. cyclopropyl or cyclohexyl), optionally substituted with 1, 2, 3, 4 or 5 $R^{13}$.

In another embodiment, $R^3$ and $R^4$ are each hydrogen. The invention therefore includes compounds of the following Formula:

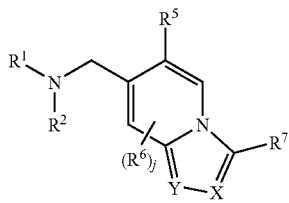

(VII)

or a pharmaceutically acceptable salt or prodrug thereof.

$R^5$ $R^5$ is aryl or heteroaryl, either of which is optionally substituted with 1, 2, 3, 4 or 5 $R^{13}$. Typically, the aryl or heteroaryl ring is a 5- or 6-membered ring.

In one embodiment, $R^5$ is heteroaryl, for example pyrimidinyl, furanyl, benzo[b]thiophenyl, thiophenyl, pyrrolyl, imidazolyl, pyrrolidinyl, pyridinyl, benzo[b]furanyl, pyrazinyl, purinyl, indolyl, benzimidazolyl, quinolinyl, phenothiazinyl, triazinyl, phthalazinyl, 2H-chromenyl, oxazolyl, isoxazolyl, thiazolyl, isoindolyl, indazolyl, purinyl, isoquinolinyl, quinazolinyl or pteridinyl, and is optionally substituted with 1, 2, 3, 4 or 5 $R^{13}$.

In another embodiment, $R^5$ is aryl, for example phenyl or naphthyl, optionally substituted with 1, 2, 3, 4 or 5 $R^{13}$. The or each $R^{13}$ may be independently selected from halogen, cyano, amino, hydroxy, $C_{1-6}$ alkyl and $C_{1-6}$ alkoxy.

In a further embodiment, $R^5$ is phenyl substituted with 0, 1, 2, 3, 4 or 5 (e.g. 0, 1, 2 or 3) $R^{13}$. The invention therefore includes compounds of the following Formula:

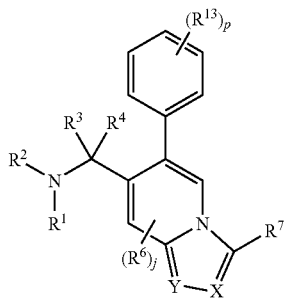

(VIII)

wherein p is 0, 1, 2, 3, 4 or 5;

or a pharmaceutically acceptable salt or prodrug thereof.

In a further embodiment, $R^5$ is phenyl substituted with 0, 1, 2, 3, 4 or 5 (e.g. 0, 1, 2 or 3) substituents independently selected from halogen, cyano, amino, hydroxy, $C_{1-6}$ alkyl and $C_{1-6}$ alkoxy.

In a further embodiment, $R^5$ is phenyl comprising substituents at the 2- and 4-positions, wherein the substituents are independently selected from halogen (e.g. fluorine or chlorine), methyl and methoxy.

In a further embodiment, $R^5$ is one of the following groups:

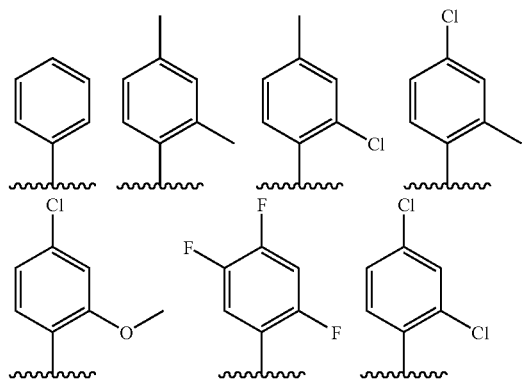

In a further embodiment, $R^5$ is 2,4-dichlorophenyl. In other embodiments, one of a Cl or F atom shown in the above groups is exchanged for the other. Methyl and methoxy may be similarly exchanged.

$R^6$ $R^6$ is present when j is 1 or 2, and is selected from halogen, trifluoromethyl, cyano, nitro, oxo, $R^{10}$, —$OR^{10}$, —$C(O)R^{10}$, —$C(O)OR^{10}$, —$OC(O)R^{10}$, —$S(O)_jR^{11}$, —$N(R^{11})(R^{12})$ and —$C(O)N(R^{11})(R^{12})$; wherein $R^{10}$ is hydrogen, hydrocarbyl optionally substituted with 1, 2, 3, 4 or 5 $R^{13}$; or —$(CH_2)_k$-heterocyclyl optionally substituted with 1, 2, 3, 4 or 5 $R^{13}$; and $R^{11}$ and $R^{12}$ are each independently selected from $R^{10}$, —$OR^{10}$, —$C(O)R^{10}$, —$C(O)OR^{10}$ and —$S(O)_jR^{10}$; or $R^{11}$ and $R^{12}$ taken together with the nitrogen atom to which they are attached form heterocyclyl optionally substituted with 1, 2, 3, 4 or 5 $R^{13}$.

Where present, the or each $R^6$ is often independently selected from halogen (e.g. fluorine, chlorine or bromine), hydroxy, cyano, amino, —C(O)OH, $C_{1-6}$ alkyl, $C_{1-6}$ alkoxy (e.g. $C_1$, $C_2$, $C_3$ or $C_4$ alkoxy), —C(O)—$C_{1-6}$ alkyl, —C(O)O—$C_{1-6}$ alkyl, —$S(O)_j$—$C_{1-6}$ alkyl, —NH($C_{1-6}$ alkyl) and —N($C_{1-6}$ alkyl)$_2$, wherein any $C_{1-6}$ alkyl group present is optionally substituted with 1, 2, 3, 4 or 5 substituents independently selected from halogen, cyano, amino, hydroxy and $C_{1-6}$ alkoxy. Exemplary are halogen, methyl, methoxy, hydroxy and cyano.

In one embodiment, j is 0 or 1.

More usually, j is 0. The invention therefore includes compounds of the following Formula:

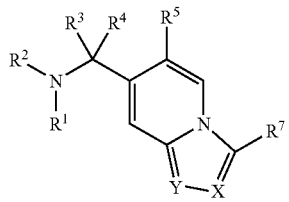

(IX)

or a pharmaceutically acceptable salt or prodrug thereof.

$R^7$ $R^7$ is selected from hydrogen, halogen and moieties comprising from 1 to 30 (e.g. 1 to 20) plural valent atoms selected from C, N, O and S.

Typically, $R^7$ is selected from halogen, trifluoromethyl, cyano, nitro, $R^{10}$, —$OR^{10}$, —$C(O)R^{10}$, —$C(O)OR^{10}$, —$OC(O)R^{10}$, —$S(O)_jR^{11}$, —$N(R^{11})(R^{12})$ and —$C(O)N(R^{11})(R^{12})$, wherein $R^{10}$ is hydrogen, hydrocarbyl optionally substituted with 1, 2, 3, 4 or 5 $R^{13}$; or —$(CH_2)_k$-heterocyclyl optionally substituted with 1, 2, 3, 4 or 5 $R^{13}$; and $R^{11}$ and $R^{12}$ are each independently selected from $R^{10}$, —$OR^{10}$, —$C(O)R^{10}$, —$C(O)OR^{10}$ and —$S(O)_jR^{10}$; or $R^{11}$ and $R^{12}$ taken together with the nitrogen atom to which they are attached form heterocyclyl optionally substituted with 1, 2, 3, 4 or 5 $R^{13}$. Where $R^{10}$ is hydrocarbyl, it may be, for example, a saturated or unsaturated aliphatic group having 1, 2, 3, 4, 5 or 6 carbon atoms and is unsubstituted or substituted with 1, 2, 3, 4 or 5 $R^{13}$. Thus, $R^{10}$ may be $C_{1-6}$ alkyl (e.g. $C_1$, $C_2$, $C_3$ or $C_4$ alkyl) or —$(CH_2)_k$-carbocyclyl (e.g. —$(CH_2)_k$-cycloalkyl or —$(CH_2)_k$-aryl), either of which is optionally substituted with 1, 2, 3, 4 or 5 $R^{13}$. In particular, hydrocarbyl may be $C_{1-6}$ alkyl (e.g. $C_1$, $C_2$, $C_3$ or $C_4$ alkyl) or —$(CH_2)_k$-aryl (e.g. phenyl or benzyl), either of which is optionally substituted with 1, 2, 3, 4 or 5 $R^{13}$. Where $R^{10}$ is —$(CH_2)_k$-heterocyclyl, it may be, for example, —$(CH_2)_k$-heterocycloalkyl or —$(CH_2)_k$-heteroaryl, either of which is optionally substituted with 1, 2, 3, 4 or 5 $R^{13}$.

In one embodiment, $R^7$ is hydrogen.

In another embodiment, $R^7$ is —$(CH_2)_k$-carbocyclyl (e.g. —$(CH_2)_k$-cycloalkyl or —$(CH_2)_k$-aryl) optionally substituted with 1, 2, 3, 4 or 5 $R^{13}$. In this case, k is usually 0 or 1, often 0. In particular, carbocyclyl may be aryl (e.g. phenyl or naphthyl), cycloalkenyl or cycloalkyl (e.g. $C_{3-6}$ cycloalkyl), any of which is optionally substituted with 1, 2, 3, 4 or 5 $R^{13}$. The carbocyclyl group may be mono- or bicyclic, e.g. $C_{3-7}$ monocyclic or $C_{8-12}$ bicyclic. More particularly, $R^7$ may be phenyl or cyclohexyl, either of which is optionally substituted with 1, 2, 3, 4 or 5 (e.g. 1, 2 or 3) $R^{13}$.

In a further embodiment, $R^7$ is heterocyclyl optionally substituted with 1, 2, 3, 4 or 5 $R^{13}$. Of particular mention are 5- or 6-membered heterocyclyl groups, especially 6-membered heterocyclyl group, which are optionally substituted with 1, 2, 3, 4 or 5 (e.g. 1, 2 or 3) $R^{13}$. In particular, $R^7$ may be imidazolyl, pyridinyl, pyrimidinyl, pyrazinyl, piperidinyl, piperazinyl, morpholinyl, thiomorpholinyl or tetrahydropyranyl, any of which is optionally substituted with 1, 2 or 3 $R^{13}$.

In a further embodiment, $R^7$ is —$N(R^{11})(R^{12})$ or —$C(O)N(R^{11})(R^{12})$. In particular, $R^7$ may be —$N(R^{11})(R^{12})$. In particular, $R^7$ may be $C(O)N(R^{11})(R^{12})$. The invention therefore includes compounds of the following Formulas (X) and (Xb):

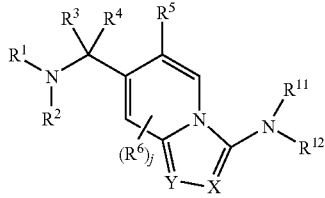

(X)

(Xb)

or a pharmaceutically acceptable salt or prodrug thereof.

Where $R^7$ is —$N(R^{11})(R^{12})$ or —$C(O)N(R^{11})(R^{12})$, $R^{11}$ and $R^{12}$ may be each independently hydrogen or $C_{1-6}$ alkyl or —$(CH_2)_k$-carbocyclyl (e.g. —$(CH_2)_k$-cycloalkyl or —$(CH_2)_k$-aryl), or —$(CH_2)_k$-heterocyclyl, or —$C(O)$—$(CH_2)_k$-heterocyclyl, —$C(O)$—$(CH_2)_k$-cycloalkyl or —$C(O)$—$C_{1-6}$ alkyl, either of which is optionally substituted with 1, 2, 3, 4 or 5 $R^{13}$. In particular, $R^{11}$ and $R^{12}$ may be each independently hydrogen or $C_{1-6}$ alkyl optionally substituted with 1, 2, 3, 4 or 5 substituents independently selected from —$OR^{14}$, —$C(O)R^{14}$ and —$C(O)OR^{14}$; wherein $R^{14}$ is usually hydrogen or selected from $C_{1-6}$ alkyl optionally substituted with 1, 2, 3, 4 or 5 $R^{13}$.

or

Where $R^7$ is —$N(R^{11})(R^{12})$ or —$C(O)N(R^{11})(R^{12})$, $R^{11}$ and $R^{12}$ may be each independently hydrogen or $C_{1-6}$ alkyl or —$(CH_2)_k$-carbocyclyl (e.g. —$(CH_2)_k$-cycloalkyl or —$(CH_2)_k$-aryl), either of which is optionally substituted with 1, 2, 3, 4 or 5 $R^{13}$. In particular, $R^{11}$ and $R^{12}$ may be each independently hydrogen or $C_{1-6}$ alkyl optionally substituted with 1, 2, 3, 4 or 5 substituents independently selected from —$OR^{14}$, —$C(O)R^{14}$ and —$C(O)OR^{14}$; wherein $R^{14}$ is usually hydrogen or selected from $C_{1-6}$ alkyl optionally substituted with 1, 2, 3, 4 or 5 $R^{13}$.

In another embodiment, $R^{11}$ is a $R^{10}$ moiety; and $R^{12}$ is —$C(O)R^{10}$. In this case, $R^{11}$ may be hydrogen or $C_{1-6}$ alkyl optionally substituted with 1, 2, 3, 4 or 5 $R^{13}$; and $R^{12}$ may be —$C(O)$—$C_{1-6}$ alkyl, —$C(O)$—$(CH_2)_k$-carbocyclyl —$C(O)$—$(CH_2)_k$-heterocyclyl, any of which is optionally substituted with 1, 2, 3, 4 or 5 $R^{13}$.

The invention includes compounds in which $R^7$ is —$N(R^{11})(R^{12})$ or —$C(O)N(R^{11})(R^{12})$ and $R^7$ includes two cyclic groups, for example a heterocycle, which may be unsaturated but is more commonly saturated, and a carbocycle which, independently of the identity of the heterocycle, may be saturated or, more usually, unsaturated as in the case of aromatic carbocycles. In some such compounds, the cyclic groups are monocyclic, e.g. having 5 or 6 ring members.

To be mentioned are four sub-classes of the compounds in which $R^7$ is —$C(O)N(R^{11})(R^{12})$ or, more particularly, —$N(R^{11})(R^{12})$ and $R^7$ includes two cyclic groups, namely:

(i) compounds in which $R^{11}$ and $R^{12}$ taken together with the nitrogen atom to which they are attached form heterocyclyl (e.g. heterocycloalkyl or heteroaryl) substituted with 1, 2, 3, 4 or 5 $R^{13}$ moieties of which at least one and often exactly one is a moiety $R^{17}$ and any additional $R^{13}$ moieties are typically selected from halogen, hydroxy, amino, $C_{1-6}$ alkyl (e.g. $C_{1-6}$ alkyl) and $C_{1-6}$ alkoxy (e.g. $C_{1-6}$ alkoxy), wherein:

$R^{17}$ is selected from =$NR^{16}$, —$OR^{16}$, —$C(O)R^{16}$, —$C(O)OR^{16}$, —$OC(O)R^{16}$, —$S(O)_jR^{16}$, —$N(R^{16})R^{15}$, —$C(O)N(R^{16})R^{15}$ and $R^{16}$, wherein $R^{15}$ is as previously described, e.g. is H, and $R^{16}$ is selected from —$(CH_2)_k$-carbocyclyl and —$(CH_2)_k$-heterocyclyl, wherein carbocyclyl and heterocyclyl are optionally substituted with 1, 2, 3, 4 or 5 $R^{13}$ moieties (e.g. selected from halogen, hydroxy, amino, alkyl and alkoxy wherein alkyl and alkoxy have from 1 to 6 and often from 1 to 4 carbon atoms) and for example are saturated or more particularly unsaturated monocyclic rings having up to 7 ring members, e.g. having 6 ring members, and as in the case of aromatic rings (e.g. phenyl);

(ii) compounds in which $R^{11}$ is as previously described, e.g. is H, and $R^{12}$ is selected from —$C(O)$—$(CH_2)_t$-carbocyclyl and —$C(O)$—$(CH_2)_t$-heterocyclyl substituted with 1, 2, 3, 4 or 5 $R^{13}$ moieties of which at least one and often exactly one is a moiety $R^{17}$ as described above and any additional $R^{13}$ moieties are typically selected from halogen, hydroxy, amino, $C_{1-6}$ alkyl and $C_{1-6}$ alkoxy, t being 0, 1, 2, 3, 4, 5 or 6;

(iii) compounds in which $R^{11}$ and $R^{12}$ taken together with the nitrogen atom to which they are attached form heterocyclyl (e.g. heterocycloalkyl or heteroaryl) substituted with 1, 2, 3, 4 or 5 $R^{13}$ moieties of which at least one and often exactly one is a moiety $R^{17}$ and any additional $R^{13}$ moieties are typically selected from halogen, hydroxy, amino, $C_{1-6}$ alkyl (e.g. $C_{1-6}$ alkyl) and $C_{1-6}$ alkoxy (e.g. $C_{1-6}$ alkoxy), wherein:

$R^{17}$ is selected from oxo, spiro, =$NR^{16}$, —$OR^{16}$, —$C(O)R^{16}$, —$C(O)OR^{16}$, —$OC(O)R^{16}$, —$S(O)_tR^{16}$, —$N(R^{16})R^{15}$, —$C(O)N(R^{16})R^{15}$ and $R^{16}$, wherein $R^{15}$ is as previously described, e.g. is H, and $R^{16}$ is selected from hydrocaryl, —$(CH_2)_k$-carbocyclyl, —$(CH_2)_k$-heterocyclyl and —$(CH_2)_k$—$C(O)$-heterocyclyl, wherein carbocyclyl and heterocyclyl are optionally substituted with 1, 2, 3, 4 or 5 $R^{13}$ moieties (e.g. selected from halogen, hydroxy, oxo, amino, alkyl and alkoxy wherein alkyl and alkoxy have from 1 to 6 and often from 1 to 4 carbon atoms) and for example are saturated or more particularly unsaturated monocyclic rings having up to 7 ring members, e.g. having 6 ring members, and as in the case of aromatic rings (e.g. phenyl);

(iv) compounds in which $R^{11}$ is as previously described, e.g. is H, and $R^{12}$ is selected from —$C(O)$—$(CH_2)_t$-carbocyclyl and —$C(O)$—$(CH_2)_t$-heterocyclyl unsubstituted or substituted with 1, 2, 3, 4 or 5 $R^{13}$ moieties of which at least one and often exactly one is a moiety $R^{17}$ as described above and any additional $R^{13}$ moieties are typically selected from halogen, hydroxy, amino, oxo, —$C(O)$—$O$—$(C_{1-6}$ alkyl), $C_{1-6}$ alkyl and $C_{1-6}$ alkoxy, t being 0, 1, 2, 3, 4, 5 or 6;

In some compounds of sub-paragraph (i) above, $R^{17}$ is —$C(O)OR^{16}$ and/or k is 1 or 2. In some compounds of sub-paragraph (ii) above, $R^{17}$ is $R^{16}$ and/or k and t are each independently 1 or 2.

In one class of compounds in which $R^7$ is —$N(R^{11})(R^{12})$, $R^{11}$ is H and $R^{12}$ is not H; in these compounds, $R^{12}$ may be as described in the preceding paragraphs. This applies also to a class of compounds in which $R^7$ is —$C(O)N(R^{11})(R^{12})$.

Alternatively, $R^{11}$ and $R^{12}$ taken together with the nitrogen atom to which they are attached may form heterocyclyl (e.g. heterocycloalkyl or heteroaryl) optionally substituted with 1, 2, 3, 4 or 5 $R^{13}$. Of particular mention are 5- or 6-membered heterocyclyl groups, especially 6-membered heterocyclyl groups, which are optionally substituted with 1, 2, 3, 4 or 5 (e.g. 1, 2 or 3) $R^{13}$. In particular, $R^{11}$ and $R^{12}$ taken together with the attached nitrogen atom may form heterocycloalkyl (e.g. piperidinyl, piperazinyl, morpholinyl or thiomorpholinyl) optionally substituted with 1, 2, 3, 4 or 5 (e.g. 1, 2, or 3) $R^{13}$. In this case, the heterocycloalkyl ring is often a 5- or 6-membered ring, especially a 6-membered ring.

Alternatively, $R^{11}$ and $R^{12}$ taken together with the nitrogen atom to which they are attached may form heterocyclyl (e.g. heterocycloalkyl or heteroaryl) optionally substituted with 1, 2, 3, 4 or 5 $R^{13}$. Of particular mention are 5- or 6-membered monocyclic heterocyclyl groups, especially 6-membered heterocyclyl groups, 9- or 10-membered bicyclic heterocyclyl groups, which are optionally substituted with 1, 2, 3, 4 or 5 (e.g. 1, 2 or 3) $R^{13}$. In particular, $R^{11}$ and $R^{12}$ taken together with the attached nitrogen atom may form heterocycloalkyl (e.g. triazolopyrazinyl, piperidinyl, piperazinyl, morpholinyl or thiomorpholinyl) optionally substituted with 1, 2, 3, 4 or 5 (e.g. 1, 2, or 3) $R^{13}$. In this case, the heterocycloalkyl ring is often a 5- or 6-membered ring, especially a 6-membered ring or 9- or 10-membered bicyclic heterocyclyl groups.

In a further embodiment when $R^7$ is —$N(R^{11})(R^{12})$ or —$C(O)N(R^{11})(R^{12})$ and when $R^{11}$ and $R^{12}$ taken together with the nitrogen atom to which they are attached form heterocyclyl the formed heterocyclyl can be selected from

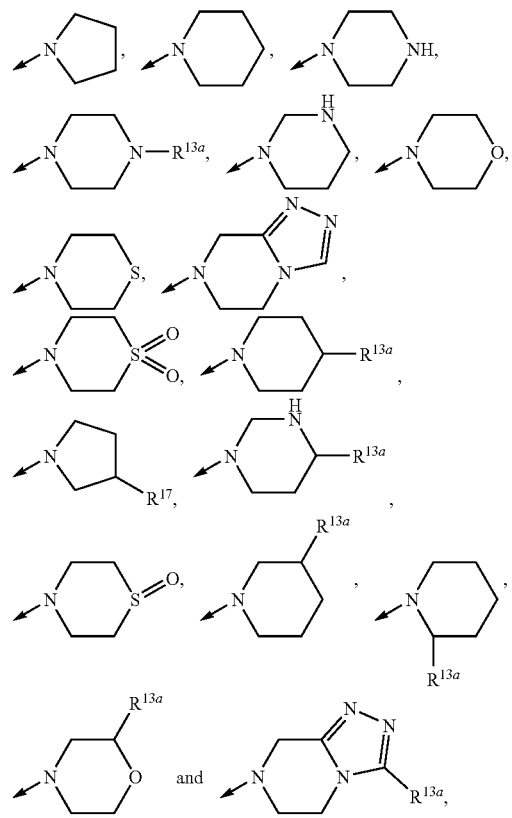

and can optionally be substituted with 1, 2 or 3 $R^{13}$ moieties preferably selected from oxo, trifluoromethyl, halogen, $C_{1-6}$ alkyl and $C_{1-6}$ alkoxy. In the above heterocyclyl formulas, the arrows represent the bound to the rest of the compound i.e. directly to the compound of formula (I) when $R^7$ is —$N(R^{11})(R^{12})$ or indirectly throught the carbonyl group when $R^7$ is —$C(O)N(R^{11})(R^{12})$.

$R^{13a}$ is hydrogen or is $R^{13}$. $R^{13a}$ is preferably selected from hydrogen, halogen, trifluoromethyl, cyano, nitro, a spiro group, amino, oxo, alkyl (preferably $C_{1-6}$ alkyl), —$(CH_2)_k$-heterocyclyl, —$(CH_2)_k$-aryl, $C_{1-6}$ alkoxy, —$C(O)$—$C_{1-6}$ alkyl, —$C(O)$—$(CH_2)_k$-cycloalkyl, —$C(O)$—$(CH_2)_k$-heterocyclyl, —$C(O)O$—$(CH_2)_k$-aryl, —$C(O)O$—$(C_{1-6}$ alkyl), —$(CH_2)_k$—$C(O)$-heterocyclyl, —$S(O)_2$—$(C_{1-6}$ alkyl), —$NH$—$(C_{1-6}$ alkyl), —$N(C_{1-6}$ alkyl)$(C_{1-6}$ alkyl), —$C(O)NH$—$(C_{1-6}$ alkyl), —$C(O)N(C_{1-6}$ alkyl)$(C_{1-6}$ alkyl). When $R^{13a}$ contains a spiro group, a heterocyclyl group, a cycloalkyl group, an aryl group, or an alkyl group, such group is optionally substituted with 1, 2, 3, 4 or 5 substituents independently selected from halogen, cyano, oxo, amino, hydroxy, —$C(O)$—$C_{1-6}$ alkyl, $C_{1-6}$ alkyl and $C_{1-6}$ alkoxy. When $R^{13a}$ contains a heterocyclyl group it is a 5- or 6-membered monocyclic heterocycloalkyl group (in particular piperidinyl, morpholinyl, tetrahydropyranyl, tetrahydrofuranyl, imidazolidinyl) or a 9- or 10-membered bicyclic heterocycloalkyl group, or 5- or 6-membered monocyclic heteroaryl group (in particular pyridinyl, furanyl, pyrimidinyl, pyrazinyl, imidazolyl, 1-methyl-1H-pyridinyl-2-one) or a 9- or 10-membered bicyclic heteroaryl group. When $R^{13}$ contains a cycloalkyl group it is in particular a $C_{3-6}$ cycloalkyl group e.g. cyclopropane, cyclobutane, cyclopentane, cyclohexane. When $R^{13a}$ contains an aryl group it is in particular a phenyl group. When $R^{13a}$ contains a spiro group it is in particular a 5-membered heterocyclic group (in particular oxazolan or azolan-2-one). When $R^{13a}$ is —$S(O)_2$—($C_{1-6}$ alkyl) it is in particular —$S(O)_2$—$CH_3$ or —$S(O)_2$—$CH_2CH_3$.

In one family of compounds the only substituent is $R^{13a}$.

In a second family of compounds, $R^{13a}$ is different from hydrogen and the heterocyclyl is substituted by one or two substituents, selected independently from each other, from methyl, methoxy and oxo.

In a third family of compounds, $R^{13a}$ is hydrogen and the heterocyclyl is substituted by one or two substituents, selected independently from each other, from methyl, trifluoromethyl, methoxy and oxo.

In a further class of compounds $R^{11}$ may be hydrogen or $C_{1-6}$ alkyl optionally substituted with 1, 2, 3, 4 or 5 $R^{13}$ (preferably $R^{13}$ is then selected from halogen, cyano, amino, hydroxy and $C_{1-6}$ alkoxy), and $R^{12}$ may be hydrogen or $C_{1-6}$ alkyl or —$(CH_2)_k$-cycloalkyl or —$(CH_2)_k$-aryl, or —$(CH_2)_k$-heterocyclyl, or —$C(O)$—$(CH_2)_k$-heterocyclyl, —$C(O)$—$(CH_2)_k$-cycloalkyl or —$C(O)$—$C_{1-6}$ alkyl, either of which is optionally substituted with 1, 2, 3, 4 or 5 $R^{13}$. Typically, each $R^{13}$ is independently selected from oxo, halogen (e.g. fluorine, chlorine or bromine), hydroxy, cyano, amino, —$C(O)OH$, $C_{1-6}$ alkyl, $C_{1-6}$ alkoxy (e.g. $C_1$, $C_2$, $C_3$ or $C_4$ alkoxy), —$C(O)$—$C_{1-6}$ alkyl, —$C(O)O$—$C_{1-6}$ alkyl, —$S(O)_f$—$C_{1-6}$ alkyl, —$NH(C_{1-6}$ alkyl) and —$N(C_{1-6}$ alkyl)$_2$, benzyl, phenyl, wherein any $C_{1-6}$ alkyl group or aryl group, present is optionally substituted with 1, 2, 3, 4 or 5 substituents independently selected from halogen, cyano, amino, hydroxy and $C_{1-6}$ alkoxy. When $R^{12}$ contains a heterocyclyl group it is in particular a 5- or 6-membered monocyclic heterocycloalkyl group (in particular piperidinyl, morpholinyl, tetrahydropyranyl, tetrahydrofuranyl, imidazolidinyl) or a 9- or 10-membered bicyclic heterocycloalkyl group, or 5- or 6-membered monocyclic heteroaryl group (in particular pyridinyl, furanyl, pyrimidinyl, pyrazinyl, imidazolyl, 1-methyl-1H-pyridinyl-2-one) or a 9- or 10-membered bicyclic heteroaryl group. When $R^{12}$ contains a cycloalkyl group it is in particular a $C_{3-6}$-cycloalkyl group (e.g. cyclopropyl, cyclobutyl, cyclopentyl, cyclohexyl) or a $C_{7-10}$ bicyclic cycloalkyl (e.g. adamantly, bicycloheptyl). When $R^{12}$ contains an aryl group it is in particular a phenyl group.

$R^{13}$

Each $R^{13}$ is independently selected from halogen, trifluoromethyl, cyano, nitro, oxo, =$NR^{14}$, —$OR^{14}$, —$C(O)R^{14}$, —$C(O)OR^{14}$, —$OC(O)R^{14}$, —$S(O)_fR^{14}$, —$N(R^{14})R^{15}$, —$C(O)N(R^{14})R^{15}$, and $R^{16}$; wherein $R^{14}$ and $R^{15}$ are each independently hydrogen or $R^{16}$; and $R^{16}$ is selected from a spiro group, hydrocarbyl, —$(CH_2)_k$-hydrocarbyl (in particular; —$(CH_2)_k$-aryl or —$(CH_2)_k$-cycloalkyl), —$(CH_2)_k$-heterocyclyl and —$(CH_2)_k$—$C(O)$-heterocyclyl, either of which is optionally substituted with 1, 2, 3, 4 or 5 substituents independently selected from halogen, cyano, oxo, amino, hydroxy, —$C(O)$—$C_{1-6}$ alkyl, $C_{1-6}$ alkyl and $C_{1-6}$ alkoxy.

Each $R^{13}$ is independently selected from halogen, trifluoromethyl, cyano, nitro, oxo, =$NR^{14}$, —$OR^{14}$, —$C(O)R^{14}$, —$C(O)OR^{14}$, —$OC(O)R^{14}$, —$S(O)_fR^{14}$, —$N(R^{14})R^{15}$, —$C(O)N(R^{14})R^{15}$ and $R^{16}$; wherein $R^{14}$ and $R^{15}$ are each independently hydrogen or $R^{16}$; and $R^{16}$ is selected from hydrocarbyl and —$(CH_2)_k$-heterocyclyl, either of which is optionally substituted with 1, 2, 3, 4 or 5 substituents independently selected from halogen, cyano, amino, hydroxy, $C_{1-6}$ alkyl and $C_{1-6}$ alkoxy.

Typically, each $R^{13}$ is independently selected from oxo, halogen (e.g. fluorine, chlorine or bromine), hydroxy, cyano, amino, —$C(O)OH$, $C_{1-6}$ alkyl, $C_{1-6}$ alkoxy (e.g. $C_1$, $C_2$, $C_3$ or $C_4$ alkoxy), —$C(O)$—$C_{1-6}$ alkyl, —$C(O)O$—$C_{1-6}$ alkyl, —$S(O)_f$—$C_{1-6}$ alkyl, —$NH(C_{1-6}$ alkyl) and —$N(C_{1-6}$ alkyl)$_2$, wherein any $C_{1-6}$ alkyl group present is optionally substituted with 1, 2, 3, 4 or 5 substituents independently selected from halogen, cyano, amino, hydroxy and $C_{1-6}$ alkoxy.

When $R^{13}$ is —$S(O)_2$—($C_{1-6}$ alkyl) it is in particular —$S(O)_2$—$CH_3$ or —$S(O)_2$—$CH_2CH_3$.

For the avoidance of doubt, where a group is substituted with more than one $R^{13}$, each $R^{13}$ is independently selected from the range of substituents specified. The same applies to compounds of the invention comprising more than one $R^{13}$ substituent; each $R^{13}$ is selected independently of any other $R^{13}$ substituent present in the compound. As previously indicated, where $R^{13}$ is halo, particularly fluoro, any number of hydrogens may in principle be replaced.

A particular embodiment of the invention is a compound of the Formula (XI):

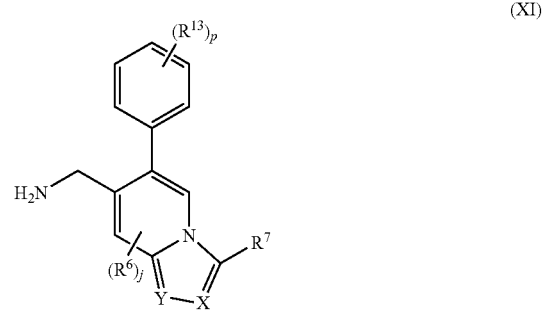

(XI)

wherein p is 0, 1, 2, 3, 4 or 5;

or a pharmaceutically acceptable salt or prodrug thereof.

Particular embodiments of Formula (XI) include the following compounds:

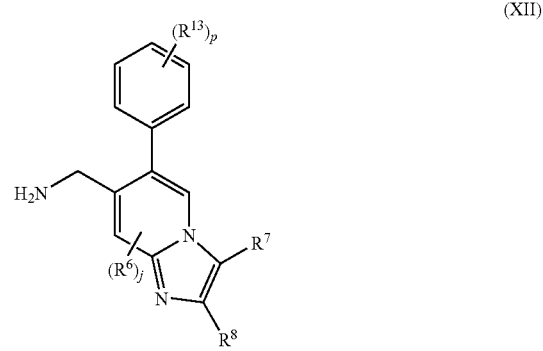

(XII)

-continued

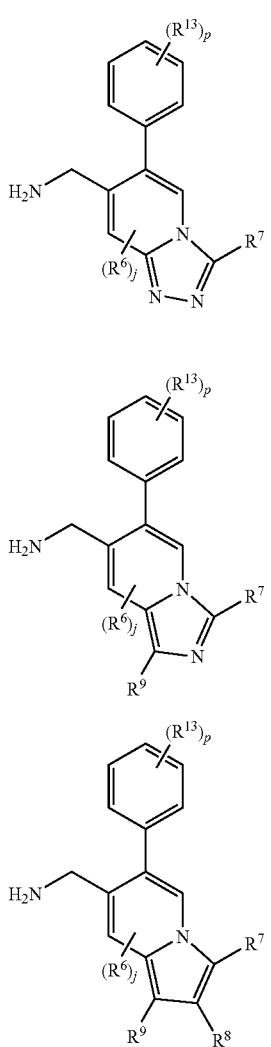

(XIII)

(XIV)

(XV)

or, in each case, a pharmaceutically acceptable salt or prodrug thereof.

With regard to Formulae (XI) to (XV), j is usually 0.

With regard to Formulae (XI) to (XV), j is usually 0 or 1.

Also with regard to the above Formulae, $R^7$ may be —$N(R^{11})(R^{12})$ or —$C(O)N(R^{11})(R^{12})$.

In particular, $R^7$ may be —$N(R^{11})(R^{12})$. The invention therefore includes compounds of the following Formula:

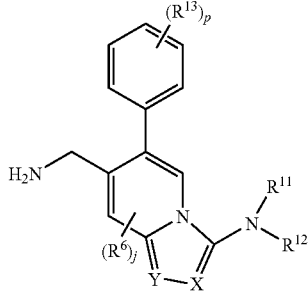

(XVI)

or a pharmaceutically acceptable salt or prodrug thereof.

Particular embodiments of Formula (XVI) include the following compounds:

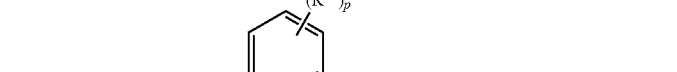

(XVII)

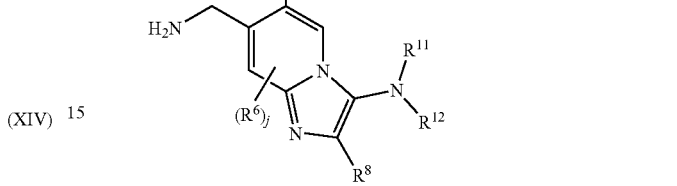

(XVIII)

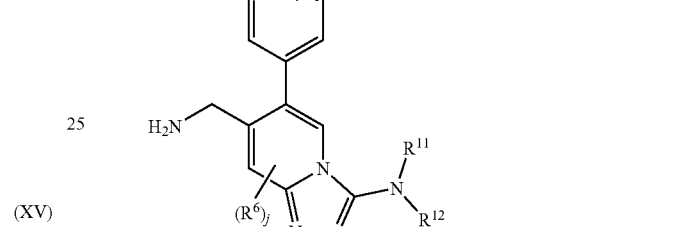

(XIX)

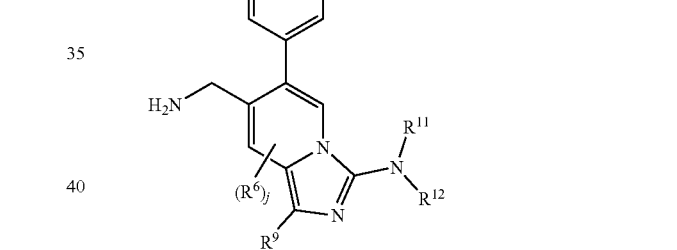

(XX)

or, in each case, a pharmaceutically acceptable salt or prodrug thereof.

With regard to Formulae (XVI) to (XX), $R^8$ and/or $R^9$ is often hydrogen or $C_{1-6}$ alkyl optionally substituted with 1, 2, 3, 4 or 5 $R^{13}$. In this case, the or each $R^{11}$ is often independently selected from hydroxy, halogen (e.g. fluorine or chlorine) or $C_{1-6}$ (e.g. $C_1$, $C_2$, $C_3$ or $C_4$) alkoxy. More usually, $R^8$ and/or $R^9$ is hydrogen.

With regard to Formulae (XVI) to (XX), $R^{11}$ and $R^{12}$ may be each independently hydrogen or $C_{1-6}$ alkyl or —$(CH_2)_k$- carbocyclyl (e.g. —(CH$_2$)$_k$-cycloalkyl or —(CH$_2$)$_k$-aryl), either of which is optionally substituted with 1, 2, 3, 4 or 5 R$^{13}$. In particular, R$^{11}$ and R$^{12}$ may be each independently hydrogen or C$_{1-6}$ alkyl optionally substituted with 1, 2, 3, 4 or 5 substituents independently selected from —OR$^{14}$, —C(O)R$^{14}$ and —C(O)OR$^{14}$; wherein R$^{14}$ is usually hydrogen or selected from C$_{1-6}$ alkyl optionally substituted with 1, 2, 3, 4 or 5 R$^{13}$.

Alternatively, R$^{11}$ and R$^{12}$ taken together with the nitrogen atom to which they are attached may form heterocyclyl (e.g. heterocycloalkyl or heteroaryl) optionally substituted with 1, 2, 3, 4 or 5 R$^{13}$. Of particular mention are 5- or 6-membered heterocyclyl groups, especially 6-membered heterocyclyl groups, or a 9- or 10-membered ring, especially a 9-membered heterocyclyl groups, which are optionally substituted with 1, 2, 3, 4 or 5 (e.g. 1, 2 or 3) R$^{13}$. In particular, R$^{11}$ and R$^{12}$ taken together with the attached nitrogen atom may form heterocycloalkyl (e.g. pyrrolidinyl, piperidinyl, piperazinyl, morpholinyl, thiomorpholinyl, or triazolopyrazinyl (e.g. [1,2,4]triazolo[4,3-a]pyrazin-7-yl)) optionally substituted with 1, 2, 3, 4 or 5 (e.g. 1, 2, or 3) R$^{13}$. In this case, the heterocycloalkyl ring is often a 5- or 6-membered ring, especially a 6-membered ring or a 9- or 10-membered ring, especially a 9-membered ring.

In another embodiment, R$^{11}$ is R$^{10}$; and R$^{12}$ is —C(O)R$^{10}$. In this case, R$^{11}$ may be hydrogen or C$_{1-6}$ alkyl optionally substituted with 1, 2, 3, 4 or 5 R$^{13}$; and R$^{12}$ may be —C(O)—C$_{1-6}$ alkyl, —C(O)—(CH$_2$)$_k$-carbocyclyl —C(O)—(CH$_2$)$_k$-heterocyclyl, any of which is optionally substituted with 1, 2, 3, 4 or 5R$^{13}$.

In particular, R$^7$ may be —C(O)N(R$^{11}$)(R$^{12}$). The invention therefore includes compounds of the following Formula:

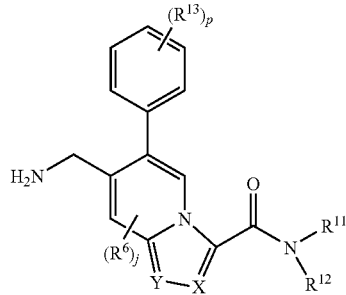

(XVIb)

or a pharmaceutically acceptable salt or prodrug thereof.
Particular embodiments of Formula (XVIb) include the following compounds:

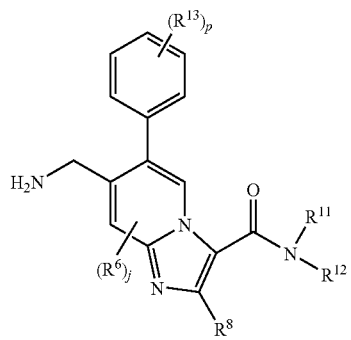

(XVIIb)

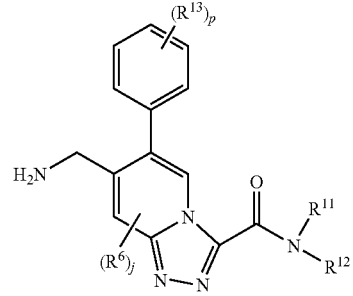

(XVIIIb)

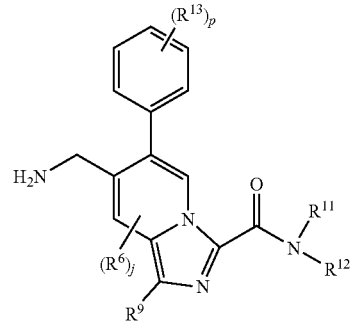

(XIXb)

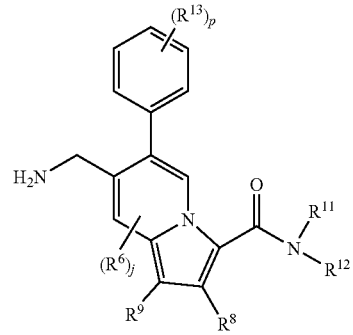

(XXb)

or, in each case, a pharmaceutically acceptable salt or prodrug thereof.

With regard to Formulae (XVIb) to (XXb), R$^8$ and/or R$^9$ is often hydrogen or C$_{1-6}$ alkyl optionally substituted with 1, 2, 3, 4 or 5 R$^{13}$. In this case, the or each R$^{11}$ is often independently selected from hydroxy, halogen (e.g. fluorine or chlorine) or C$_{1-6}$ (e.g. C$_1$, C$_2$, C$_3$ or C$_4$) alkoxy. More usually, R$^8$ and/or R$^9$ is hydrogen.

With regard to Formulae (XVIb) to (XXb), R$^{11}$ and R$^{12}$ may be each independently hydrogen or C$_{1-6}$ alkyl or —(CH$_2$)$_k$-carbocyclyl (e.g. —(CH$_2$)$_k$-cycloalkyl or —(CH$_2$)$_k$-aryl), either of which is optionally substituted with 1, 2, 3, 4 or 5 R$^{13}$. In particular, R$^{11}$ and R$^{12}$ may be each independently hydrogen or C$_{1-6}$ alkyl optionally substituted with 1, 2, 3, 4 or 5 substituents independently selected from —OR$^{14}$, —C(O)R$^{14}$ and —C(O)OR$^{14}$; wherein R$^{14}$ is usually hydrogen or selected from C$_{1-6}$ alkyl optionally substituted with 1, 2, 3, 4 or 5 R$^{13}$.

Alternatively, R$^{11}$ and R$^{12}$ taken together with the nitrogen atom to which they are attached may form heterocyclyl (e.g. heterocycloalkyl or heteroaryl) optionally substituted with 1, 2, 3, 4 or 5 R$^{13}$. Of particular mention are 5- or 6-membered heterocyclyl groups, especially 6-membered heterocyclyl groups, or a 9- or 10-membered ring, especially a 9-membered heterocyclyl groups, which are optionally substituted with 1, 2, 3, 4 or 5 (e.g. 1, 2 or 3) R$^{13}$. In particular, R$^{11}$ and R$^{12}$ taken together with the attached nitrogen atom may form heterocycloalkyl (e.g. pyrrolidinyl, piperidinyl, piperazinyl, morpholinyl, thiomorpholinyl, or triazolopyrazinyl (e.g. [1,2,4]triazolo[4,3-a]pyrazin-7-yl)) optionally substituted with 1, 2, 3, 4 or 5 (e.g. 1, 2, or 3) $R^{13}$. In this case, the heterocycloalkyl ring is often a 5- or 6-membered ring, especially a 6-membered ring or a 9- or 10-membered ring, especially a 9-membered ring.

In another embodiment, $R^{11}$ is $R^{10}$; and $R^{12}$ is —C(O)$R^{10}$. In this case, $R^{11}$ may be hydrogen or $C_{1-6}$ alkyl optionally substituted with 1, 2, 3, 4 or 5 $R^{13}$; and $R^{12}$ may be —C(O)—$C_{1-6}$ alkyl, —C(O)—(CH$_2$)$_k$-carbocyclyl —C(O)—(CH$_2$)$_k$-heterocyclyl, any of which is optionally substituted with 1, 2, 3, 4 or 5 $R^{13}$.

Particular embodiments of Formula (XI) include the following compounds:

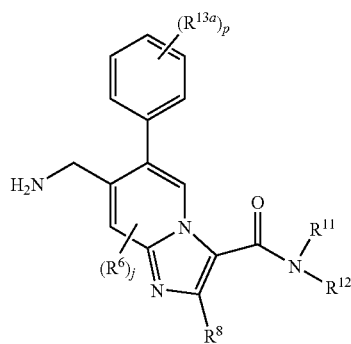

(XXI)

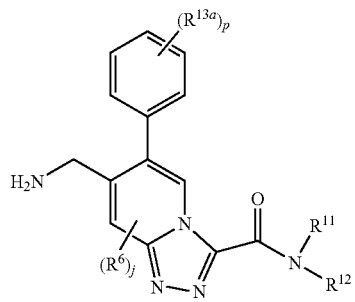

(XXII)

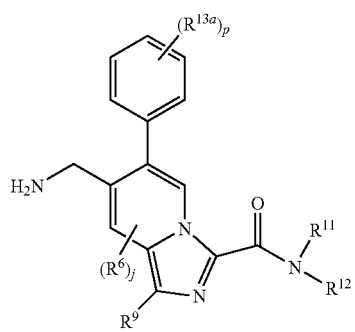

(XXIII)

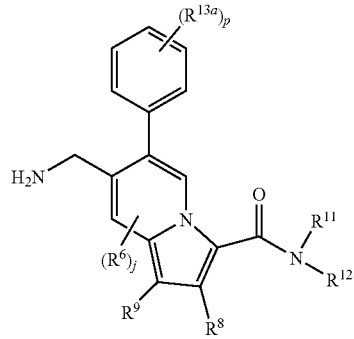

(XXIV)

or, in each case, a pharmaceutically acceptable salt or prodrug thereof.

With regard to Formulae (XXI) to (XXIV), $R^{13a}$ is $R^{13}$. In a preferred embodiment the $R^{13a}$ substituents are independently from each other selected from halogen (preferably —Cl or —F) or $C_{1-6}$ alkyl (preferably methyl or ethyl) or $C_{1-6}$ alkoxy (preferably methoxy or ethoxy).

In compounds of the above Formulae, p is 0, 1, 2 or 3.

In compounds of the above Formulae, the phenyl group substituted with the $R^{13a}$ substituents is one of the following groups:

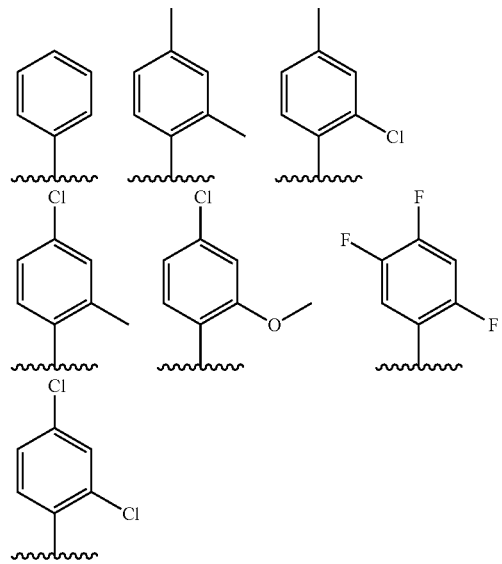

In other embodiments, one of a Cl or F atom shown in the above groups is exchanged for the other. Methyl and methoxy may be similarly exchanged.

In compounds of the above Formulae, $R^8$ and/or $R^9$ is often hydrogen or $C_{1-6}$ alkyl optionally substituted with 1, 2, 3, 4 or 5 $R^{13}$.

In a preferred embodiment $R^8$ and/or $R^9$ is hydrogen.

With regard to Formulae (XCI) to (XXIV), $R^{11}$ and $R^{12}$ may be each independently hydrogen or $C_{1-6}$ alkyl or —(CH$_2$)$_k$-carbocyclyl (e.g. —(CH$_2$)$_k$-cycloalkyl or —(CH$_2$)$_k$-aryl), or —(CH$_2$)$_k$-heterocyclyl, or —C(O)—(CH$_2$)$_k$-heterocyclyl, —C(O)—(CH$_2$)$_k$-cycloalkyl or —C(O)—$C_{1-6}$ alkyl, either of which is optionally substituted with 1, 2, 3, 4 or 5 $R^{13}$.

In particular, $R^{11}$ and $R^{12}$ may be each independently hydrogen or $C_{1-6}$ alkyl optionally substituted with 1, 2, 3, 4 or 5 substituents independently selected from —OR$^{14}$, —C(O)R$^{14}$ and —C(O)OR$^{14}$; wherein R$^{14}$ is usually hydrogen or selected from C$_{1-6}$ alkyl optionally substituted with 1, 2, 3, 4 or 5 R$^{13}$.

In a further embodiment R$^{11}$ may be hydrogen or C$_{1-6}$ alkyl optionally substituted with 1, 2, 3, 4 or 5 R$^{13}$ (preferably R$^{13}$ is then selected from halogen, cyano, amino, hydroxy and C$_{1-6}$ alkoxy), and R$^{12}$ may be hydrogen or C$_{1-6}$ alkyl or —(CH$_2$)$_k$-carbocyclyl (e.g. —(CH$_2$)$_k$-cycloalkyl or —(CH$_2$)$_k$-aryl), or —(CH$_2$)$_k$-heterocyclyl, or —C(O)—(CH$_2$)$_k$-heterocyclyl, —C(O)—(CH$_2$)$_k$-cycloalkyl or —C(O)—C$_{1-6}$ alkyl, either of which is optionally substituted with 1, 2, 3, 4 or 5 R$^{13}$. Typically, each R$^{13}$ is independently selected from oxo, halogen (e.g. fluorine, chlorine or bromine), hydroxy, cyano, amino, —C(O)OH, C$_{1-6}$ alkyl, C$_{1-6}$ alkoxy (e.g. C$_1$, C$_2$, C$_3$ or C$_4$ alkoxy), —C(O)—C$_{1-6}$ alkyl, —C(O)O—C$_{1-6}$ alkyl, —S(O)$_t$—C$_{1-6}$ alkyl, —NH(C$_{1-6}$ alkyl) and —N(C$_{1-6}$ alkyl)$_2$, benzyl, phenyl, wherein any C$_{1-6}$ alkyl group or aryl group, present is optionally substituted with 1, 2, 3, 4 or 5 substituents independently selected from halogen, cyano, amino, hydroxy and C$_{1-6}$ alkoxy.

In particular, R$^{11}$ may be hydrogen and R$^{12}$ may be each independently hydrogen or C$_{1-6}$ alkyl optionally substituted with 1, 2, 3, 4 or 5 substituents independently selected from —OR$^{14}$, —C(O)R$^{14}$ and —C(O)OR$^{14}$; wherein R$^{14}$ is usually hydrogen or selected from C$_{1-6}$ alkyl optionally substituted with 1, 2, 3, 4 or 5 R$^{13}$.

In a further embodiment R$^{11}$ may be hydrogen or C$_{1-6}$ alkyl optionally substituted with 1, 2, 3, 4 or 5 R$^{13}$ (preferably R$^{13}$ is then selected from halogen, cyano, amino, hydroxy and C$_{1-6}$ alkoxy), and R$^{12}$ may be hydrogen or C$_{1-6}$ alkyl or —(CH$_2$)$_k$-cycloalkyl or —(CH$_2$)$_k$-aryl, or —(CH$_2$)$_k$-heterocyclyl, or —C(O)—(CH$_2$)$_k$-heterocyclyl, —C(O)—(CH$_2$)$_k$-cycloalkyl or —C(O)—C$_{1-6}$ alkyl, either of which is optionally substituted with 1, 2, 3, 4 or 5 R$^{13}$. Typically, each R$^{13}$ is independently selected from oxo, halogen (e.g. fluorine, chlorine or bromine), hydroxy, cyano, amino, —C(O)OH, C$_{1-6}$ alkyl, C$_{1-6}$ alkoxy (e.g. C$_1$, C$_2$, C$_3$ or C$_4$ alkoxy), —C(O)—C$_{1-6}$ alkyl, —C(O)O—C$_{1-6}$ alkyl, —S(O)$_t$—C$_{1-6}$ alkyl, —NH(C$_{1-6}$ alkyl) and —N(C$_{1-6}$ alkyl)$_2$, benzyl, phenyl, wherein any C$_{1-6}$ alkyl group or aryl group, present is optionally substituted with 1, 2, 3, 4 or 5 substituents independently selected from halogen, cyano, amino, hydroxy and C$_{1-6}$ alkoxy. When R$^{12}$ contains a heterocyclyl group it is in particular a 5- or 6-membered monocyclic heterocycloalkyl group (in particular piperidinyl, morpholinyl, tetrahydropyranyl, tetrahydrofuranyl, imidazolidinyl) or a 9- or 10-membered bicyclic heterocycloalkyl group, or 5- or 6-membered monocyclic heteroaryl group (in particular pyridinyl, furanyl, pyrimidinyl, pyrazinyl, imidazolyl, 1-methyl-1H-pyridinyl-2-one) or a 9- or 10-membered bicyclic heteroaryl group. When R$^{12}$ contains a cycloalkyl group it is in particular a C$_{3-6}$ cycloalkyl group (e.g. cyclopropyl, cyclobutyl, cyclopentyl, cyclohexyl) or a C$_{7-10}$ bicyclic cycloalkyl (e.g. adamantly, bicycloheptyl). When R$^{12}$ contains an aryl group it is in particular a phenyl group.

Alternatively, R$^{11}$ and R$^{12}$ taken together with the nitrogen atom to which they are attached may form heterocyclyl (e.g. heterocycloalkyl or heteroaryl) optionally substituted with 1, 2, 3, 4 or 5 R$^{13}$. Of particular mention are 5- or 6-membered heterocyclyl groups, especially 6-membered heterocyclyl groups, or a 9- or 10-membered ring, especially a 9-membered ring, which are optionally substituted with 1, 2, 3, 4 or 5 (e.g. 1, 2 or 3) R$^{13}$. In particular, R$^{11}$ and R$^{12}$ taken together with the attached nitrogen atom may form heterocycloalkyl (e.g. pyrrolidinyl, piperidinyl, piperazinyl, morpholinyl, thiomorpholinyl, or triazolopyrazinyl (e.g. [1,2,4]triazolo[4,3-a]pyrazin-7-yl)) optionally substituted with 1, 2, 3, 4 or 5 (e.g. 1, 2, or 3) R$^{13}$. In this case, the heterocycloalkyl ring is often a 5- or 6-membered ring, especially a 6-membered ring or a 9- or 10-membered ring, especially a 9-membered ring. In particular each R$^{13}$ is independently selected from halogen, trifluoromethyl, cyano, nitro, a spiro group, amino, oxo, alkyl (preferably C$_{1-6}$ alkyl), —(CH$_2$)$_k$-heterocyclyl, —(CH$_2$)$_k$-aryl, C$_{1-6}$ alkoxy, —C(O)—C$_{1-6}$ alkyl, —C(O)—(CH$_2$)$_k$-cycloalkyl, —C(O)—(CH$_2$)$_k$-heterocyclyl, —C(O)O—(CH$_2$)$_k$-aryl, —C(O)O—(C$_{1-6}$ alkyl), —(CH$_2$)$_k$—C(O)-heterocyclyl, —S(O)$_2$—(C$_{1-6}$ alkyl), —NH—(C$_{1-6}$ alkyl), —N(C$_{1-6}$ alkyl)(C$_{1-6}$ alkyl), —C(O)NH—(C$_{1-6}$ alkyl), —C(O)N(C$_{1-6}$ alkyl)-(C$_{1-6}$ alkyl). When R$^{13}$ contains a spiro group, a heterocyclyl group, a cycloalkyl group, an aryl group, or an alkyl group, such group is optionally substituted with 1, 2, 3, 4 or 5 substituents independently selected from halogen, cyano, oxo, amino, hydroxy, —C(O)—C$_{1-6}$ alkyl, C$_{1-6}$ alkyl and C$_{1-6}$ alkoxy. When R$^{13}$ contains a heterocyclyl group it is a 5- or 6-membered monocyclic heterocycloalkyl group (in particular piperidinyl, morpholinyl, tetrahydropyranyl, tetrahydrofuranyl, imidazolidinyl) or a 9- or 10-membered bicyclic heterocycloalkyl group, or 5- or 6-membered monocyclic heteroaryl group (in particular pyridinyl, furanyl, pyrimidinyl, pyrazinyl, imidazolyl, 1-methyl-1H-pyridinyl-2-one) or a 9- or 10-membered bicyclic heteroaryl group. When R$^{13}$ contains a cycloalkyl group it is in particular a C$_{3-6}$ cycloalkyl group e.g. cyclopropane, cyclobutane, cyclopentane, cyclohexane. When R$^{13}$ contains an aryl group it is in particular a phenyl group. When R$^{13}$ contains a spiro group it is in particular a 5-membered heterocyclic group (in particular oxazolan).

In a further embodiment when R$^{11}$ and R$^{12}$ taken together with the nitrogen atom to which they are attached form heterocyclyl the formed heterocyclyl can be selected from

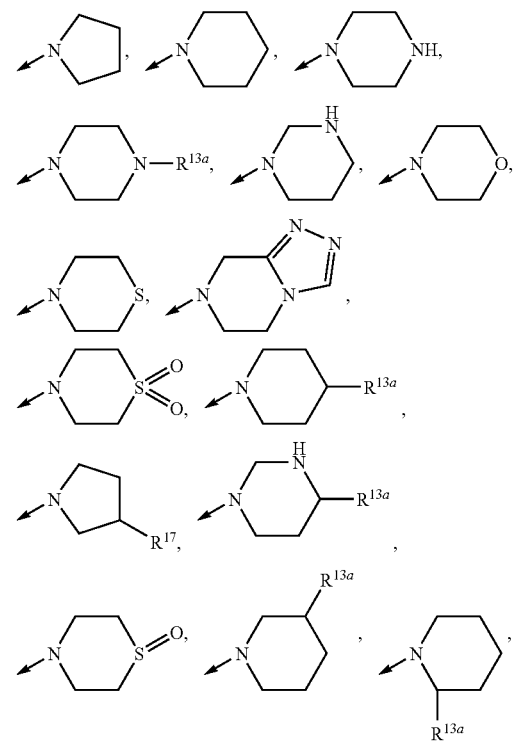

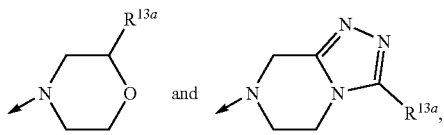

and can optionally be substituted with 1, 2 or 3 $R^{13}$ moieties preferably selected from oxo, trifluoromethyl, halogen, $C_{1-6}$ alkyl and $C_{1-6}$ alkoxy.

$R^{13a}$ is hydrogen or is $R^{13}$. $R^{13a}$ is preferably selected from hydrogen, halogen, trifluoromethyl, cyano, nitro, a Spiro group, amino, oxo, alkyl (preferably $C_{1-6}$ alkyl), —$(CH_2)_k$-heterocyclyl, —$(CH_2)_k$-aryl, $C_{1-6}$ alkoxy, —C(O)—$C_{1-6}$ alkyl, —C(O)—$(CH_2)_k$-cycloalkyl, —C(O)—$(CH_2)_k$-heterocyclyl, —C(O)O—$(CH_2)_k$-aryl, —C(O)O—$(C_{1-6}$, alkyl), —$(CH_2)_k$—C(O)-heterocyclyl, —S(O)$_2$—$(C_{1-6}$ alkyl), —NH—$(C_{1-6}$ alkyl), —N$(C_{1-6}$ alkyl)$(C_{1-6}$ alkyl), —C(O)NH—$(C_{1-6}$ alkyl), —C(O)N$(C_{1-6}$ alkyl)$(C_{1-6}$ alkyl). When $R^{13a}$ contains a spiro group, a heterocyclyl group, a cycloalkyl group, an aryl group, or an alkyl group, such group is optionally substituted with 1, 2, 3, 4 or 5 substituents independently selected from halogen, cyano, oxo, amino, hydroxy, —C(O)—$C_{1-6}$ alkyl, $C_{1-6}$ alkyl and $C_{1-6}$ alkoxy. When $R^{13a}$ contains a heterocyclyl group it is a 5- or 6-membered monocyclic heterocycloalkyl group (in particular piperidinyl, morpholinyl, tetrahydropyranyl, tetrahydrofuranyl, imidazolidinyl) or a 9- or 10-membered bicyclic heterocycloalkyl group, or 5- or 6-membered monocyclic heteroaryl group (in particular pyridinyl, furanyl, pyrimidinyl, pyrazinyl, imidazolyl, 1-methyl-1H-pyridinyl-2-one) or a 9- or 10-membered bicyclic heteroaryl group. When $R^{13}$ contains a cycloalkyl group it is in particular a $C_{3-6}$ cycloalkyl group e.g. cyclopropane, cyclobutane, cyclopentane, cyclohexane. When $R^{13a}$ contains an aryl group it is in particular a phenyl group. When $R^{13a}$ contains a spiro group it is in particular a 5-membered heterocyclic group (in particular oxazolan or azolan-2-one). When $R^{13a}$ is —S(O)$_2$—$(C_{1-6}$ alkyl) it is in particular —S(O)$_2$—$CH_3$ or —S(O)$_2$—$CH_2CH_3$.

In one family of compounds the only substituent is $R^{13a}$.

In a second family of compounds, $R^{13a}$ is different from hydrogen and the heterocyclyl is substituted by one or two substituents, selected independently from each other, from methyl, methoxy and oxo.

In a third family of compounds, $R^{13a}$ is hydrogen and the heterocyclyl is substituted by one or two substituents, selected independently from each other, from methyl, trifluoromethyl, methoxy and oxo.

In another embodiment, $R^{11}$ is $R^{10}$; and $R^{12}$ is —C(O)$R^{10}$. In this case, $R^{11}$ may be hydrogen or $C_{1-6}$ alkyl optionally substituted with 1, 2, 3, 4 or 5 $R^{13}$; and $R^{12}$ may be —C(O)—$C_{1-6}$ alkyl, —C(O)—$(CH_2)_k$-carbocyclyl or —C(O)—$(CH_2)_k$-heterocyclyl, any of which is optionally substituted with 1, 2, 3, 4 or 5 $R^{13}$.

Particular embodiments of Formula (XVI) include the following compounds:

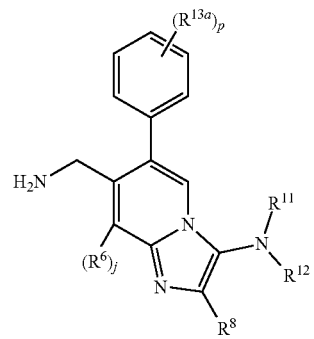

(XXV)

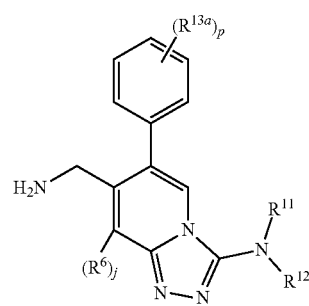

(XXVI)

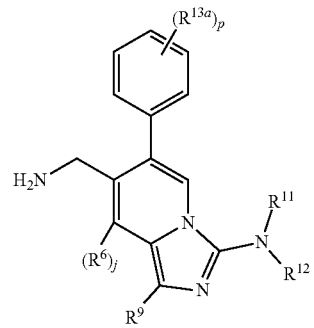

(XXVII)

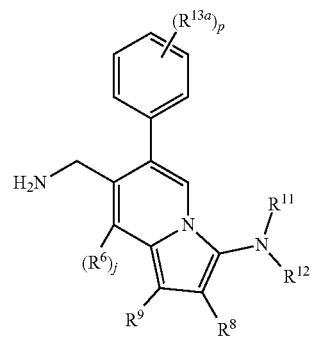

(XXVIII)

or, in each case, a pharmaceutically acceptable salt or prodrug thereof.

In compounds of the above Formulae (XXV to XXVIII), j is 0 or 1.

In compounds of the above Formulae, $R^{13a}$ is $R^{13}$. In a preferred embodiment the $R^{13a}$ substituents are independently from each other selected from halogen (preferably —Cl or —F) or $C_{1-6}$ alkyl (preferably methyl or ethyl) or $C_{1-6}$ alkoxy (preferably methoxy or ethoxy).

In compounds of the above Formulae, p is 0, 1, 2 or 3.

In compounds of the above Formulae, the phenyl group substituted with the $R^{13a}$ substituents is one of the following groups:

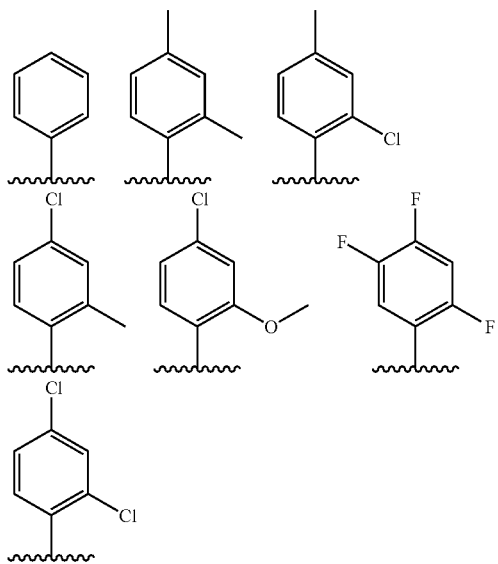

In other embodiments, one of a Cl or F atom shown in the above groups is exchanged for the other. Methyl and methoxy may be similarly exchanged.

In compounds of the above Formulae in a further embodiment $R^6$ is selected from halogen, trifluoromethyl, cyano, nitro, amino, hydroxy, 5- or 6-membered heterocycloalkyl, —$(CH_2)_k$-heterocycloalkyl, —C(O)-heterocycloalkyl, —C(O)—NH-heterocycloalkyl, —NH—C(O)—$C_{1-6}$alkyl, —NH—$(CH_2)_k$-heterocycloalkyl, $C_{1-6}$alkyl, $C_{1-6}$alkoxy, —NH—$C_{1-6}$alkyl, —N($C_{1-6}$ alkyl)($C_{1-6}$ alkyl), —NH—($C_{3-6}$ cycloalkyl), —N($C_{3-6}$ cycloalkyl)($C_{5-6}$ cycloalkyl), —$(CH_2)_k$—($C_{3-6}$ cycloalkyl), —$(CH_2)_k$-aryl (preferably substituted or unsubstituted phenyl), —NH—$(CH_2)_k$—$C_{3-6}$ cycloalkyl or —NH—$(CH_2)_k$-aryl, wherein the alkyl, cycloalkyl, heterocycloalkyl or aryl moieties can be substituted by 1, 2, 3 or 4 substituents selected from halogen, hydroxy, $C_{1-6}$ alkoxy, $C_{1-6}$ alkyl, —$CH_2$—$NH_2$, or amino. Wherein the heterocycloalkyl is preferably a 5- or 6-membered heterocycloalkyl (e.g.

The compounds of the above Formulae wherein $R^6$ is hydrogen.

The compounds of the above Formulae wherein $R^6$ is amino.

The compounds of the above Formulae wherein $R^6$ is amino, —NH—$C_{1-6}$ alkyl, —N($C_{1-6}$ alkyl)($C_{1-6}$ alkyl), —NH—($C_{3-6}$ cycloalkyl), $C_{1-6}$alkoxy, $C_{1-6}$alkyl, optionally substituted by halogen, hydroxy, $C_{1-6}$ alkoxy, $C_{1-6}$ alkyl, or amino.

In compounds of the above Formulae, $R^8$ and/or $R^9$ is often hydrogen or $C_{1-6}$ alkyl optionally substituted with 1, 2, 3, 4 or 5 $R^{13}$. In this case, the or each $R^{13}$ is often independently selected from hydroxy, halogen (e.g. fluorine or chlorine) or $C_{1-6}$ (e.g. $C_1$, $C_2$, $C_3$ or $C_4$) alkoxy.

In a preferred embodiment $R^8$ and/or $R^9$ is hydrogen.

With regard to Formulae (XXV) to (XXVIII), $R^{11}$ and $R^{12}$ may be each independently hydrogen or $C_{1-6}$ alkyl or —$(CH_2)_k$-carbocyclyl (e.g. —$(CH_2)_k$-cycloalkyl or —$(CH_2)_k$-aryl), or —$(CH_2)_k$-heterocyclyl, or —C(O)—$(CH_2)_k$-heterocyclyl, —C(O)—$(CH_2)_k$-cycloalkyl or —C(O)—$C_{1-6}$ alkyl, either of which is optionally substituted with 1, 2, 3, 4 or 5 $R^{13}$.

In particular, $R^{11}$ and $R^{12}$ may be each independently hydrogen or $C_{1-6}$ alkyl optionally substituted with 1, 2, 3, 4 or 5 substituents independently selected from —$OR^{14}$, —$C(O)R^{14}$ and —$C(O)OR^{14}$; wherein $R^{14}$ is usually hydrogen or selected from $C_{1-6}$ alkyl optionally substituted with 1, 2, 3, 4 or 5 $R^{13}$.

In a further embodiment $R^{11}$ may be hydrogen or $C_{1-6}$ alkyl optionally substituted with 1, 2, 3, 4 or 5 $R^{13}$ (preferably $R^{13}$ is then selected from halogen, cyano, amino, hydroxy and $C_{1-6}$ alkoxy), and $R^{12}$ may be hydrogen or $C_{1-6}$ alkyl or —$(CH_2)_k$-carbocyclyl (e.g. —$(CH_2)_k$-cycloalkyl or —$(CH_2)_k$-aryl), or —$(CH_2)_k$-heterocyclyl, or —C(O)—$(CH_2)_k$-heterocyclyl, —C(O)—$(CH_2)_k$-cycloalkyl or —C(O)—$C_{1-6}$ alkyl, either of which is optionally substituted with 1, 2, 3, 4 or 5 $R^{13}$. Typically, each $R^{13}$ is independently selected from oxo, halogen (e.g. fluorine, chlorine or bromine), hydroxy, cyano, amino, —C(O)OH, $C_{1-6}$ alkyl, $C_{1-6}$ alkoxy (e.g. $C_1$, $C_2$, $C_3$ or $C_4$ alkoxy), —C(O)—$C_{1-6}$ alkyl, —C(O)O—$C_{1-6}$ alkyl, —S(O)$_f$—$C_{1-6}$ alkyl, —NH($C_{1-6}$ alkyl) and —N($C_{1-6}$ alkyl)$_2$, benzyl, phenyl, wherein any $C_{1-6}$ alkyl group or aryl group, present is optionally substituted with 1, 2, 3, 4 or 5 substituents independently selected from halogen, cyano, amino, hydroxy and $C_{1-6}$ alkoxy.

In particular, $R^{11}$ may be hydrogen and $R^{12}$ may be each independently hydrogen or $C_{1-6}$ alkyl optionally substituted with 1, 2, 3, 4 or 5 substituents independently selected from —$OR^{14}$, —$C(O)R^{14}$ and —$C(O)OR^{14}$; wherein $R^{14}$ is usually hydrogen or selected from $C_{1-6}$ alkyl optionally substituted with 1, 2, 3, 4 or 5 $R^{13}$.

In a further embodiment $R^{11}$ may be hydrogen or $C_{1-6}$ alkyl optionally substituted with 1, 2, 3, 4 or 5 $R^{13}$ (preferably $R^{13}$ is then selected from halogen, cyano, amino, hydroxy and $C_{1-6}$ alkoxy), and $R^{12}$ may be hydrogen or $C_{1-6}$ alkyl or —$(CH_2)_k$-cycloalkyl or —$(CH_2)_k$-aryl, or —$(CH_2)_k$-heterocyclyl, or —C(O)—$(CH_2)_k$-heterocyclyl, —C(O)—$(CH_2)_k$-cycloalkyl or —C(O)—$C_{1-6}$ alkyl, either of which is optionally substituted with 1, 2, 3, 4 or 5 $R^{13}$. Typically, each $R^{13}$ is independently selected from oxo, halogen (e.g. fluorine, chlorine or bromine), hydroxy, cyano, amino, —C(O)OH, $C_{1-6}$ alkyl, $C_{1-6}$ alkoxy (e.g. $C_1$, $C_2$, $C_3$ or $C_4$ alkoxy), —C(O)—$C_{1-6}$ alkyl, —C(O)O—$C_{1-6}$ alkyl, —S(O)$_f$—$C_{1-6}$ alkyl, —NH ($C_{1-6}$ alkyl) and —N($C_{1-6}$ alkyl)$_2$, benzyl, phenyl, wherein any $C_{1-6}$ alkyl group or aryl group, present is optionally substituted with 1, 2, 3, 4 or 5 substituents independently selected from halogen, cyano, amino, hydroxy and $C_{1-6}$ alkoxy. When $R^{12}$ contains a heterocyclyl group it is in particular a 5- or 6-membered monocyclic heterocycloalkyl group (in particular piperidinyl, morpholinyl, tetrahydropyranyl, tetrahydrofuranyl, imidazolidinyl) or a 9- or 10-membered bicyclic heterocycloalkyl group, or 5- or 6-membered monocyclic heteroaryl group (in particular pyridinyl, furanyl, pyrimidinyl, pyrazinyl, imidazolyl, 1-methyl-1H-pyridinyl-2-one) or a 9- or 10-membered bicyclic heteroaryl group. When $R^{12}$ contains a cycloalkyl group it is in particular a $C_{3-6}$ cycloalkyl group (e.g. cyclopropyl, cyclobutyl, cyclopentyl, cyclohexyl) or a $C_{7-10}$ bicyclic cycloalkyl (e.g. adamantly, bicycloheptyl). When $R^{12}$ contains an aryl group it is in particular a phenyl group.

Alternatively, $R^{11}$ and $R^{12}$ taken together with the nitrogen atom to which they are attached may form heterocyclyl (e.g. heterocycloalkyl or heteroaryl) optionally substituted with 1, 2, 3, 4 or 5 $R^{13}$. Of particular mention are 5- or 6-membered heterocyclyl groups, especially 6-membered heterocyclyl groups, or a 9- or 10-membered ring, especially a 9-membered ring, which are optionally substituted with 1, 2, 3, 4 or 5 (e.g. 1, 2 or 3) $R^{13}$. In particular, $R^{11}$ and $R^{12}$ taken together with the attached nitrogen atom may form heterocycloalkyl (e.g. pyrrolidinyl, piperidinyl, piperazinyl, morpholinyl, thiomorpholinyl, or triazolopyrazinyl (e.g. [1,2,4]triazolo[4,3-a]

pyrazin-7-yl)) optionally substituted with 1, 2, 3, 4 or 5 (e.g. 1, 2, or 3) $R^{13}$. In this case, the heterocycloalkyl ring is often a 5- or 6-membered ring, especially a 6-membered ring or a 9- or 10-membered ring, especially a 9-membered ring. In particular each $R^{13}$ is independently selected from halogen, trifluoromethyl, cyano, nitro, a spiro group, amino, oxo, alkyl (preferably $C_{1-6}$ alkyl), —$(CH_2)_k$-heterocyclyl, —$(CH_2)_k$-aryl, $C_{1-6}$ alkoxy, —C(O)—$C_{1-6}$ alkyl, —C(O)—$(CH_2)_k$-cycloalkyl, —C(O)—$(CH_2)_k$-heterocyclyl, —C(O)O—$(CH_2)_k$-aryl, —C(O)O—$(C_{1-6}$ alkyl), —$(CH_2)_k$—C(O)-heterocyclyl, —$S(O)_2$—$(C_{1-6}$ alkyl), —NH—$(C_{1-6}$ alkyl), —N$(C_{1-6}$ alkyl)$(C_{1-6}$ alkyl), —C(O)NH—$(C_{1-6}$ alkyl), —C(O)N$(C_{1-6}$ alkyl)$(C_{1-6}$ alkyl). When $R^{13}$ contains a spiro group, a heterocyclyl group, a cycloalkyl group, an aryl group, or an alkyl group, such group is optionally substituted with 1, 2, 3, 4 or 5 substituents independently selected from halogen, cyano, oxo, amino, hydroxy, —C(O)—$C_{1-6}$ alkyl, $C_{1-6}$ alkyl and $C_{1-6}$ alkoxy. When $R^{13}$ contains a heterocyclyl group it is a 5- or 6-membered monocyclic heterocycloalkyl group (in particular piperidinyl, morpholinyl, tetrahydropyranyl, tetrahydrofuranyl, imidazolidinyl) or a 9- or 10-membered bicyclic heterocycloalkyl group, or 5- or 6-membered monocyclic heteroaryl group (in particular pyridinyl, furanyl, pyrimidinyl, pyrazinyl, imidazolyl, 1-methyl-1H-pyridinyl-2-one) or a 9- or 10-membered bicyclic heteroaryl group. When $R^{13}$ contains a cycloalkyl group it is in particular a $C_{3-6}$ cycloalkyl group e.g. cyclopropane, cyclobutane, cyclopentane, cyclohexane. When $R^{13}$ contains an aryl group it is in particular a phenyl group. When $R^{13}$ contains a spiro group it is in particular a 5-membered heterocyclic group (in particular oxazolan).

In a further embodiment when $R^{11}$ and $R^{12}$ taken together with the nitrogen atom to which they are attached form heterocyclyl the formed heterocyclyl can be selected from

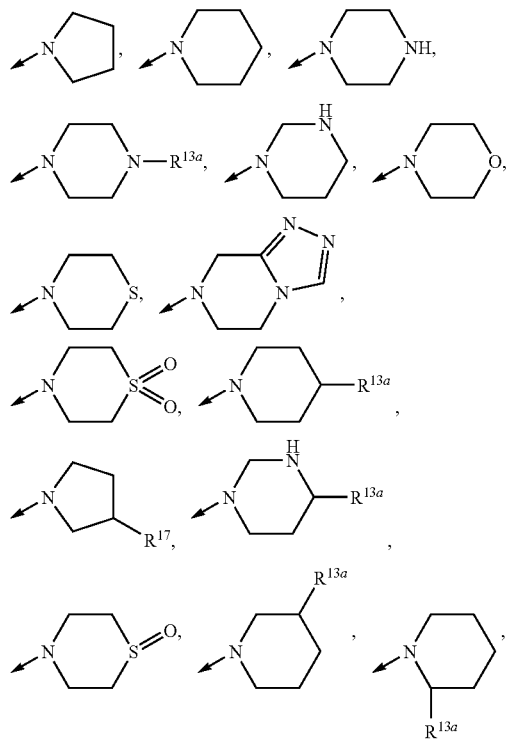

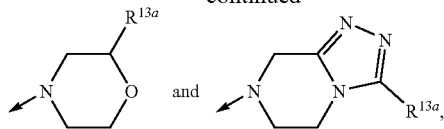

and can optionally be substituted with 1, 2 or 3 $R^{13}$ moieties preferably selected from halogen, oxo, trifluoromethyl, $C_{1-6}$ alkyl and $C_{1-6}$ alkoxy.

$R^{13a}$ is hydrogen or is $R^{13}$. $R^{13a}$ is preferably selected from hydrogen, halogen, trifluoromethyl, cyano, nitro, a spiro group, amino, oxo, alkyl (preferably $C_{1-6}$ alkyl), —$(CH_2)_k$-heterocyclyl, —$(CH_2)_k$-aryl, $C_{1-6}$ alkoxy, —C(O)—$C_{1-6}$ alkyl, —C(O)—$(CH_2)_k$-cycloalkyl, —C(O)—$(CH_2)_k$-heterocyclyl, —C(O)O—$(CH_2)_k$-aryl, —C(O)O—$(C_{1-6}$ alkyl), —$(CH_2)_k$—C(O)-heterocyclyl, —$S(O)_2$—$(C_{1-6}$ alkyl), —NH—$(C_{1-6}$ alkyl), —N$(C_{1-6}$ alkyl)$(C_{1-6}$ alkyl), —C(O)NH—$(C_{1-6}$ alkyl), —C(O)N$(C_{1-6}$ alkyl)$(C_{1-6}$ alkyl). When $R^{13a}$ contains a spiro group, a heterocyclyl group, a cycloalkyl group, an aryl group, or an alkyl group, such group is optionally substituted with 1, 2, 3, 4 or 5 substituents independently selected from halogen, cyano, oxo, amino, hydroxy, —C(O)—$C_{1-6}$alkyl, $C_{1-6}$ alkyl and $C_{1-6}$ alkoxy. When $R^{13a}$ contains a heterocyclyl group it is a 5- or 6-membered monocyclic heterocycloalkyl group (in particular piperidinyl, morpholinyl, tetrahydropyranyl, tetrahydrofuranyl, imidazolidinyl) or a 9- or 10-membered bicyclic heterocycloalkyl group, or 5- or 6-membered monocyclic heteroaryl group (in particular pyridinyl, furanyl, pyrimidinyl, pyrazinyl, imidazolyl, 1-methyl-1H-pyridinyl-2-one) or a 9- or 10-membered bicyclic heteroaryl group. When $R^{13}$ contains a cycloalkyl group it is in particular a $C_{3-6}$ cycloalkyl group e.g. cyclopropane, cyclobutane, cyclopentane, cyclohexane. When $R^{13a}$ contains an aryl group it is in particular a phenyl group. When $R^{13a}$ contains a spiro group it is in particular a 5-membered heterocyclic group (in particular oxazolan or azolan-2-one). When $R^{13a}$ is —$S(O)_2$—$(C_{1-6}$ alkyl) it is in particular —$S(O)_2$—$CH_3$ or —$S(O)_2$—$CH_2CH_3$.

In one family of compounds the only substituent is $R^{13a}$.

In a second family of compounds, $R^{13a}$ is different from hydrogen and the heterocyclyl is substituted by one or two substituents, selected independently from each other, from methyl, methoxy and oxo.

In a third family of compounds, $R^{13a}$ is hydrogen and the heterocyclyl is substituted by one or two substituents, selected independently from each other, from methyl, trifluoromethyl, methoxy and oxo.

In another embodiment, $R^{13a}$ is $R^{10}$; and $R^{12}$ is —C(O)$R^{10}$. In this case, $R^{11}$ may be hydrogen or $C_{1-6}$ alkyl optionally substituted with 1, 2, 3, 4 or 5 $R^{13}$; and $R^{12}$ may be —C(O)—$C_{1-6}$ alkyl, —C(O)—$(CH_2)_k$-carbocyclyl —C(O)—$(CH_2)_k$-heterocyclyl, any of which is optionally substituted with 1, 2, 3, 4 or 5 $R^{13}$. In particular, the carbocyclyl is a $C_5$ to $C_{12}$ cycloalkyl (e.g. cyclopentyl, cyclohexy, bicycloheptyl, adamantly), or a phenyl. In particular the heterocyclyl is a 5- or 6-membered monocyclic heterocyclyl (e.g. piperidinyl, piperazinyl, tetrahydropyranyl) or a 9- or 10-membered bicyclic hererocyclyl (e.g. tetrahydro-2H-pyridopyridazinyl).

Particular embodiments of Formula (XI) include the following compounds:

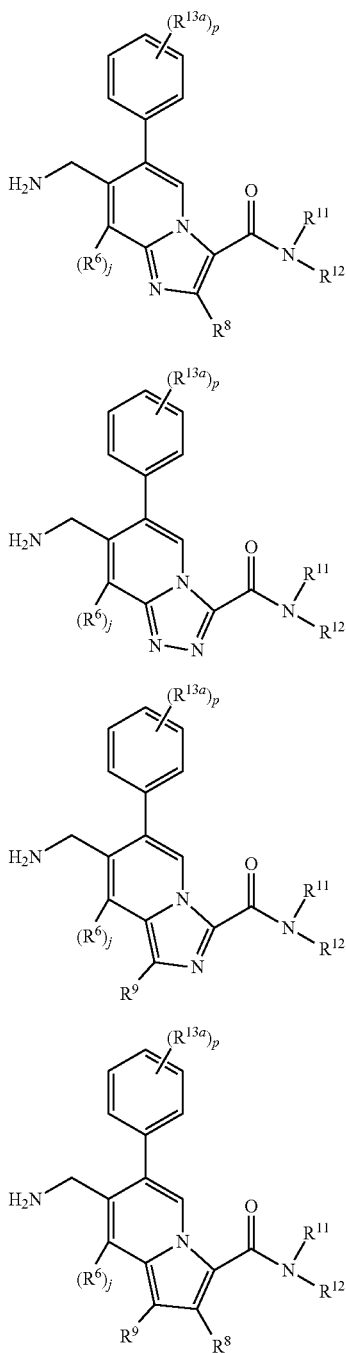

(XXIX)

(XXX)

(XXXI)

(XXXII)

or, in each case, a pharmaceutically acceptable salt or prodrug thereof.

In compounds of the above Formulae (XXIX to XXXII), j is 0 or 1.

In compounds of the above Formulae, $R^{13a}$ is $R^{13}$. In a preferred embodiment the $R^{13a}$ substituents are independently from each other selected from halogen (preferably —Cl or —F) or $C_{1-6}$ alkyl (preferably methyl or ethyl) or $C_{1-6}$ alkoxy (preferably methoxy or ethoxy).

In compounds of the above Formulae, p is 0, 1, 2 or 3.

In compounds of the above Formulae, the phenyl group substituted with the $R^{13a}$ substituents is one of the following groups:

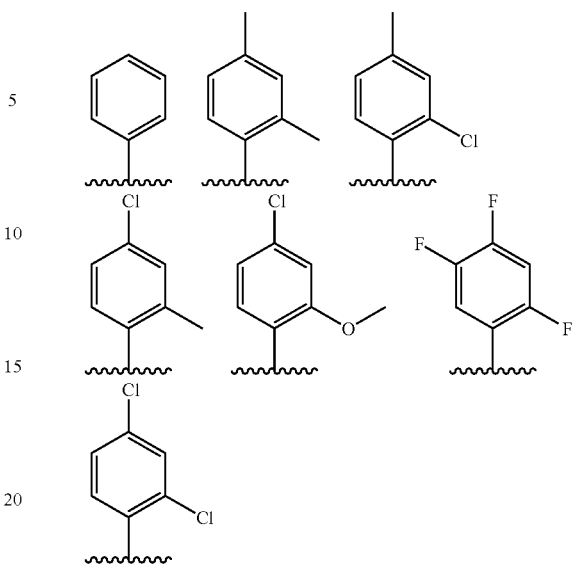

In other embodiments, one of a Cl or F atom shown in the above groups is exchanged for the other. Methyl and methoxy may be similarly exchanged.

In compounds of the above Formulae, $R^8$ and/or $R^9$ is often hydrogen or $C_{1-6}$ alkyl optionally substituted with 1, 2, 3, 4 or 5 $R^{13}$. In this case, the or each $R^{13}$ is often independently selected from hydroxy, halogen (e.g. fluorine or chlorine) or $C_{1-6}$ (e.g. $C_1$, $C_2$, $C_3$ or $C_4$) alkoxy.

In a preferred embodiment, $R^8$ and/or $R^9$ is hydrogen.

With regard to Formulae (XXIX) to (XXXII), $R^{11}$ and $R^{12}$ may be each independently hydrogen or $C_{1-6}$ alkyl or —$(CH_2)_k$-carbocyclyl (e.g. —$(CH_2)_k$-cycloalkyl or —$(CH_2)_k$-aryl), or —$(CH_2)_k$-heterocyclyl, or —C(O)—$(CH_2)_k$-heterocyclyl, —C(O)—$(CH_2)_k$-cycloalkyl or —C(O)—$C_{1-6}$ alkyl, either of which is optionally substituted with 1, 2, 3, 4 or 5 $R^{13}$.

In particular, $R^{11}$ and $R^{12}$ may be each independently hydrogen or $C_{1-6}$ alkyl optionally substituted with 1, 2, 3, 4 or 5 substituents independently selected from —$OR^{14}$, —C(O)$R^{14}$ and —C(O)$OR^{14}$; wherein $R^{14}$ is usually hydrogen or selected from $C_{1-6}$ alkyl optionally substituted with 1, 2, 3, 4 or 5 $R^{13}$.

In a further embodiment $R^{11}$ may be hydrogen or $C_{1-6}$ alkyl optionally substituted with 1, 2, 3, 4 or 5 $R^{13}$ (preferably $R^{13}$ is then selected from halogen, cyano, amino, hydroxy and Con alkoxy), and $R^{12}$ may be hydrogen or $C_{1-6}$ alkyl or —$(CH_2)_k$-carbocyclyl (e.g. —$(CH_2)_k$-cycloalkyl or —$(CH_2)_k$-aryl), or —$(CH_2)_k$-heterocyclyl, or —C(O)—$(CH_2)_k$-heterocyclyl, —C(O)—$(CH_2)_k$-cycloalkyl or —C(O)—$C_{1-6}$ alkyl, either of which is optionally substituted with 1, 2, 3, 4 or 5 $R^{13}$. Typically, each $R^{13}$ is independently selected from oxo, halogen (e.g. fluorine, chlorine or bromine), hydroxy, cyano, amino, —C(O)OH, $C_{1-6}$ alkyl, $C_{1-6}$ alkoxy (e.g. $C_1$, $C_2$, $C_3$ or $C_4$ alkoxy), —C(O)—$C_{1-6}$ alkyl, —C(O)O—$C_{1-6}$ alkyl, —S(O)$_l$—$C_{1-6}$ alkyl, —NH($C_{1-6}$ alkyl) and —N($C_{1-6}$ alkyl)$_2$, benzyl, phenyl, wherein any $C_{1-6}$ alkyl group or aryl group, present is optionally substituted with 1, 2, 3, 4 or 5 substituents independently selected from halogen, cyano, amino, hydroxy and $C_{1-6}$ alkoxy.

In particular, $R^{11}$ may be hydrogen and $R^{12}$ may be each independently hydrogen or $C_{1-6}$ alkyl optionally substituted with 1, 2, 3, 4 or 5 substituents independently selected from —OR$^{14}$, —C(O)R$^{14}$ and —C(O)OR$^{14}$; wherein R$^{14}$ is usually hydrogen or selected from C$_{1-6}$ alkyl optionally substituted with 1, 2, 3, 4 or 5 R$^{13}$.

In a further embodiment R$^{11}$ may be hydrogen or C$_{1-6}$ alkyl optionally substituted with 1, 2, 3, 4 or 5 R$^{13}$ (preferably R$^{13}$ is then selected from halogen, cyano, amino, hydroxy and C$_{1-6}$ alkoxy), and R$^{12}$ may be hydrogen or C$_{1-6}$ alkyl or —(CH$_2$)$_k$-cycloalkyl or —(CH$_2$)$_k$-aryl, or —(CH$_2$)$_k$-heterocyclyl, or —C(O)—(CH$_2$)$_k$-heterocyclyl, —C(O)—(CH$_2$)$_k$-cycloalkyl or —C(O)—C$_{1-6}$ alkyl, either of which is optionally substituted with 1, 2, 3, 4 or 5 R$^{13}$. Typically, each R$^{13}$ is independently selected from oxo, halogen (e.g. fluorine, chlorine or bromine), hydroxy, cyano, amino, —C(O)OH, C$_{1-6}$ alkyl, C$_{1-6}$ alkoxy (e.g. C$_1$, C$_2$, C$_3$ or C$_4$ alkoxy), —C(O)—C$_{1-6}$ alkyl, —C(O)O—C$_{1-6}$ alkyl, —S(O)$_t$—C$_{1-6}$ alkyl, —NH(C$_{1-6}$ alkyl) and —N(C$_{1-6}$ alkyl)$_2$, benzyl, phenyl, wherein any C$_{1-6}$ alkyl group or aryl group, present is optionally substituted with 1, 2, 3, 4 or 5 substituents independently selected from halogen, cyano, amino, hydroxy and C$_{1-6}$ alkoxy. When R$^{12}$ contains a heterocyclyl group it is in particular a 5- or 6-membered monocyclic heterocycloalkyl group (in particular piperidinyl, morpholinyl, tetrahydropyranyl, tetrahydrofuranyl, imidazolidinyl) or a 9- or 10-membered bicyclic heterocycloalkyl group, or 5- or 6-membered monocyclic heteroaryl group (in particular pyridinyl, furanyl, pyrimidinyl, pyrazinyl, imidazolyl, 1-methyl-1H-pyridinyl-2-one) or a 9- or 10-membered bicyclic heteroaryl group. When R$^{12}$ contains a cycloalkyl group it is in particular a C$_{3-6}$ cycloalkyl group (e.g. cyclopropyl, cyclobutyl, cyclopentyl, cyclohexyl) or a C$_{7-10}$ bicyclic cycloalkyl (e.g. adamantly, bicycloheptyl). When R$^{12}$ contains an aryl group it is in particular a phenyl group.

Alternatively, R$^{11}$ and R$^{12}$ taken together with the nitrogen atom to which they are attached may form heterocyclyl (e.g. heterocycloalkyl or heteroaryl) optionally substituted with 1, 2, 3, 4 or 5 R$^{13}$. Of particular mention are 5- or 6-membered heterocyclyl groups, especially 6-membered heterocyclyl groups, or a 9- or 10-membered ring, especially a 9-membered ring, which are optionally substituted with 1, 2, 3, 4 or 5 (e.g. 1, 2 or 3) R$^{13}$. In particular, R$^{11}$ and R$^{12}$ taken together with the attached nitrogen atom may form heterocycloalkyl (e.g. pyrrolidinyl, piperidinyl, piperazinyl, morpholinyl, thiomorpholinyl, or triazolopyrazinyl (e.g. [1,2,4]triazolo[4,3-a]pyrazin-7-yl)) optionally substituted with 1, 2, 3, 4 or 5 (e.g. 1, 2, or 3) R$^{13}$. In this case, the heterocycloalkyl ring is often a 5- or 6-membered ring, especially a 6-membered ring or a 9- or 10-membered ring, especially a 9-membered ring. In particular each R$^{13}$ is independently selected from halogen, trifluoromethyl, cyano, nitro, a spiro group, amino, oxo, alkyl (preferably C$_{1-6}$ alkyl), —(CH$_2$)$_k$-heterocyclyl, —(CH$_2$)$_k$-aryl, C$_{1-6}$ alkoxy, —C(O)—C$_{1-6}$ alkyl, —C(O)—(CH$_2$)$_k$-cycloalkyl, —C(O)—(CH$_2$)$_k$-heterocyclyl, —C(O)O—(CH$_2$)$_k$-aryl, —C(O)O—(C$_{1-6}$ alkyl), —(CH$_2$)$_k$—C(O)-heterocyclyl, —S(O)$_2$—(C$_{1-6}$ alkyl), —NH—(C$_{1-6}$ alkyl), —N(C$_{1-6}$ alkyl)(C$_{1-6}$ alkyl), —C(O)NH—(Con alkyl), —C(O)N(C$_{1-6}$ alkyl)(C$_{1-6}$ alkyl). When R$^{13}$ contains a spiro group, a heterocyclyl group, a cycloalkyl group, an aryl group, or an alkyl group, such group is optionally substituted with 1, 2, 3, 4 or 5 substituents independently selected from halogen, cyano, oxo, amino, hydroxy, —C(O)—C$_{1-6}$ alkyl, C$_{1-6}$ alkyl and C$_{1-6}$ alkoxy. When R$^{13}$ contains a heterocyclyl group it is a 5- or 6-membered monocyclic heterocycloalkyl group (in particular piperidinyl, morpholinyl, tetrahydropyranyl, tetrahydrofuranyl, imidazolidinyl) or a 9- or 10-membered bicyclic heterocycloalkyl group, or 5- or 6-membered monocyclic heteroaryl group (in particular pyridinyl, furanyl, pyrimidinyl, pyrazinyl, imidazolyl, 1-methyl-1H-pyridinyl-2-one) or a 9- or 10-membered bicyclic heteroaryl group. When R$^{13}$ contains a cycloalkyl group it is in particular a C$_{3-6}$ cycloalkyl group e.g. cyclopropane, cyclobutane, cyclopentane, cyclohexane. When R$^{13}$ contains an aryl group it is in particular a phenyl group. When R$^{13}$ contains a spiro group it is in particular a 5-membered heterocyclic group (in particular oxazolan).

In a further embodiment when R$^{11}$ and R$^{12}$ taken together with the nitrogen atom to which they are attached form heterocyclyl the formed heterocyclyl can be selected from

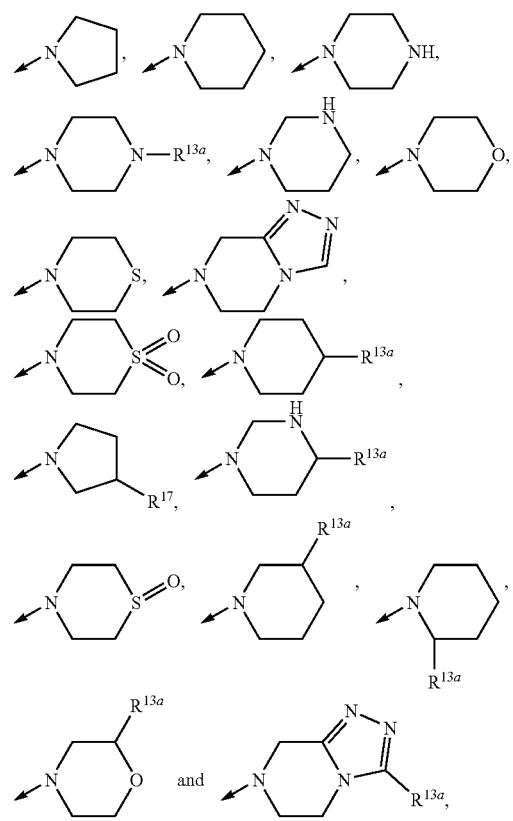

and can optionally be substituted with 1, 2 or 3 R$^{13}$ moieties preferably selected from oxo, trifluoromethyl, halogen, C$_{1-6}$ alkyl and C$_{1-6}$ alkoxy.

R$^{13a}$ is hydrogen or is R$^{13}$. R$^{13a}$ is preferably selected from hydrogen, halogen, trifluoromethyl, cyano, nitro, a spiro group, amino, oxo, alkyl (preferably C$_{1-6}$ alkyl), —(CH$_2$)$_k$-heterocyclyl, —(CH$_2$)$_k$-aryl, C$_{1-6}$ alkoxy, —C(O)—C$_{1-6}$ alkyl, —C(O)—(CH$_2$)$_k$-cycloalkyl, —C(O)—(CH$_2$)$_k$-heterocyclyl, —C(O)O—(CH$_2$)$_k$-aryl, —C(O)O—(C$_{1-6}$ alkyl), —(CH$_2$)$_k$—C(O)-heterocyclyl, —S(O)$_2$—(C$_{1-6}$ alkyl), —NH—(C$_{1-6}$ alkyl), —N(C$_{1-6}$ alkyl)(C$_{1-6}$ alkyl), —C(O)NH—(C$_{1-6}$ alkyl), —C(O)N(C$_{1-6}$ alkyl)(C$_{1-6}$ alkyl). When R$^{13a}$ contains a spiro group, a heterocyclyl group, a cycloalkyl group, an aryl group, or an alkyl group, such group is optionally substituted with 1, 2, 3, 4 or 5 substituents independently selected from halogen, cyano, oxo, amino, hydroxy, —C(O)—C$_{1-6}$ alkyl, C$_{1-6}$ alkyl and C$_{1-6}$ alkoxy. When R$^{13a}$ contains a heterocyclyl group it is a 5- or 6-membered monocyclic heterocycloalkyl group (in particular piperidinyl, morpholinyl, tetrahydropyranyl, tetrahydrofuranyl, imidazolidinyl) or a 9- or 10-membered bicyclic heterocycloalkyl group, or 5- or 6-membered monocyclic heteroaryl group (in particular pyridinyl, furanyl, pyrimidinyl, pyrazinyl, imidazolyl, 1-methyl-1H-pyridinyl-2-one) or a 9- or 10-membered bicyclic heteroaryl group. When $R^{13}$ contains a cycloalkyl group it is in particular a $C_{3-6}$ cycloalkyl group e.g. cyclopropane, cyclobutane, cyclopentane, cyclohexane. When $R^{13a}$ contains an aryl group it is in particular a phenyl group. When $R^{13a}$ contains a spiro group it is in particular a 5-membered heterocyclic group (in particular oxazolan or azolan-2-one). When $R^{13a}$ is —S(O)$_2$—(C$_{1-6}$ alkyl) it is in particular —S(O)$_2$—CH$_3$ or —S(O)$_2$—CH$_2$CH$_3$.

In one family of compounds the only substituent is $R^{13a}$.

In a second family of compounds, $R^{13a}$ is different from hydrogen and the heterocyclyl is substituted by one or two substituents, selected independently from each other, from methyl, methoxy and oxo.

In a third family of compounds, $R^{13a}$ is hydrogen and the heterocyclyl is substituted by one or two substituents, selected independently from each other, from methyl, trifluoromethyl, methoxy and oxo.

In a further embodiment $R^{11}$ may be hydrogen or $C_{1-6}$ alkyl optionally substituted with 1, 2, 3, 4 or 5 $R^{13}$ (preferably $R^{13}$ is then selected from halogen, cyano, amino, hydroxy and $C_{1-6}$ alkoxy), and $R^{12}$ may be hydrogen or $C_{1-6}$ alkyl or —(CH$_2$)$_k$-carbocyclyl (e.g. —(CH$_2$)$_k$-cycloalkyl or —(CH$_2$)$_k$-aryl), either of which is optionally substituted with 1, 2, 3, 4 or 5 $R^{13}$. Typically, each $R^{13}$ is independently selected from oxo, halogen (e.g. fluorine, chlorine or bromine), hydroxy, cyano, amino, —C(O)OH, $C_{1-6}$ alkyl, $C_{1-6}$ alkoxy (e.g. $C_1$, $C_2$, $C_3$ or $C_4$ alkoxy), —C(O)—$C_{1-6}$ alkyl, —C(O)O—$C_{1-6}$ alkyl, —S(O)$_l$—$C_{1-6}$ alkyl, —NH(C$_{1-6}$ alkyl) and —N(C$_{1-6}$ alkyl)$_2$, wherein any $C_{1-6}$ alkyl group present is optionally substituted with 1, 2, 3, 4 or 5 substituents independently selected from halogen, cyano, amino, hydroxy and $C_{1-6}$ alkoxy.

In particular, $R^{11}$ may be hydrogen and $R^{12}$ may be each independently hydrogen or $C_{1-6}$ alkyl optionally substituted with 1, 2, 3, 4 or 5 substituents independently selected from —OR$^{14}$, —C(O)R$^{14}$ and —C(O)OR$^{14}$; wherein $R^{14}$ is usually hydrogen or selected from $C_{1-6}$ alkyl optionally substituted with 1, 2, 3, 4 or 5 $R^{13}$.

In a further embodiment $R^{11}$ may be hydrogen or $C_{1-6}$ alkyl optionally substituted with 1, 2, 3, 4 or 5 $R^{13}$ (preferably $R^{13}$ is then selected from halogen, cyano, amino, hydroxy and $C_{1-6}$ alkoxy), and $R^{12}$ may be hydrogen or $C_{1-6}$ alkyl or —(CH$_2$)$_k$—C$_{3-6}$ cycloalkyl or —(CH$_2$)$_k$-phenyl, either of which is optionally substituted with 1, 2, 3, 4 or 5 $R^{13}$. Typically, each $R^{13}$ is independently selected from oxo, halogen (e.g. fluorine, chlorine or bromine), hydroxy, cyano, amino, —C(O)OH, $C_{1-6}$ alkyl, $C_{1-6}$ alkoxy (e.g. $C_1$, $C_2$, $C_3$ or $C_4$ alkoxy), —C(O)—$C_{1-6}$ alkyl, —C(O)O—$C_{1-6}$ alkyl, —S(O)$_l$—$C_{1-6}$ alkyl, —NH(C$_{1-6}$ alkyl) and —N(C$_{1-6}$ alkyl)$_2$, wherein any $C_{1-6}$ alkyl group present is optionally substituted with 1, 2, 3, 4 or 5 substituents independently selected from halogen, cyano, amino, hydroxy and $C_{1-6}$ alkoxy.

In another embodiment, $R^{11}$ is $R^{10}$; and $R^{12}$ is —C(O)R$^{10}$. In this case, $R^{11}$ may be hydrogen or $C_{1-6}$ alkyl optionally substituted with 1, 2, 3, 4 or 5 $R^{13}$; and $R^{12}$ may be —C(O)—C$_{1-6}$ alkyl, —C(O)—(CH$_2$)$_k$-carbocyclyl —C(O)—(CH$_2$)$_k$-heterocyclyl, any of which is optionally substituted with 1, 2, 3, 4 or 5 $R^{13}$. In particular, the carbocyclyl is a $C_5$ to $C_{12}$ cycloalkyl (e.g. cyclopentyl, cyclohexy, bicycloheptyl, adamantly), or a phenyl. In particular the heterocyclyl is a 5- or 6-membered monocyclic heterocyclyl (e.g. piperidinyl, piperazinyl, tetrahydropyranyl) or a 9- or 10-membered bicyclic hererocyclyl (e.g. tetrahydro-2H-pyridopyridazinyl). Typically, each $R^{13}$ is independently selected from oxo, halogen (e.g. fluorine, chlorine or bromine), hydroxy, cyano, amino, —C(O)OH, $C_{1-6}$ alkyl, $C_{1-6}$ alkoxy (e.g. $C_1$, $C_2$, $C_3$ or $C_4$ alkoxy), —C(O)—$C_{1-6}$ alkyl, —C(O)O—$C_{1-6}$ alkyl, —S(O)$_l$—$C_{1-6}$ alkyl, —NH(C$_{1-6}$ alkyl) and —N(C$_{1-6}$ alkyl)$_2$, wherein any $C_{1-6}$ alkyl group present is optionally substituted with 1, 2, 3, 4 or 5 substituents independently selected from halogen, cyano, amino, hydroxy and $C_{1-6}$ alkoxy.

Particular embodiments of Formula (XI) include the following compounds:

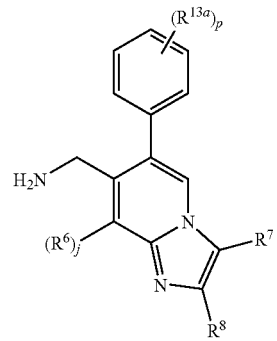

(XXXIII)

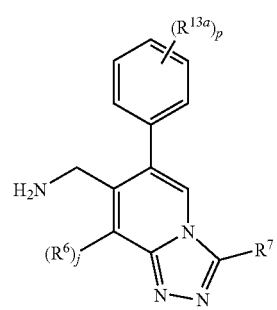

(XXXIV)

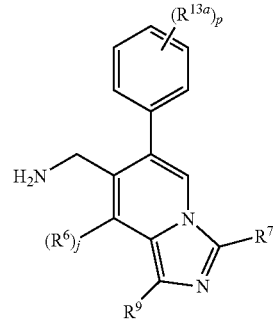

(XXXV)

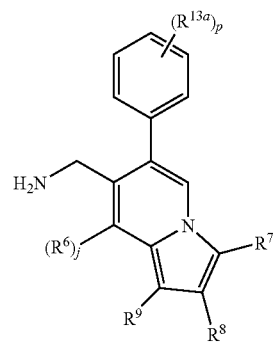

(XXXVI)

or, in each case, a pharmaceutically acceptable salt or prodrug thereof.

In compounds of the above Formulae (XXXIII to XXXVI), j is 0 or 1.

In compounds of the above Formulae, $R^{13a}$ is $R^{13}$. In a preferred embodiment the $R^{13a}$ substituents are independently from each other selected from halogen (preferably —Cl or —F) or $C_{1-6}$ alkyl (preferably methyl or ethyl) or $C_{1-6}$ alkoxy (preferably methoxy or ethoxy).

In compounds of the above Formulae, p is 0, 1, 2 or 3.

In compounds of the above Formulae, the phenyl group substituted with the $R^{13a}$ substituents is one of the following groups:

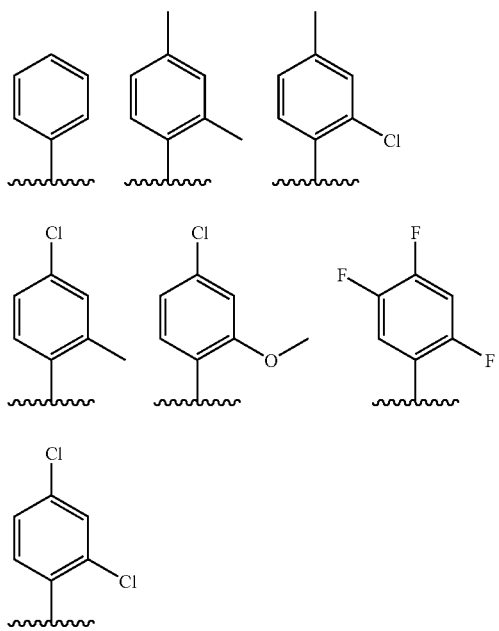

In other embodiments, one of a Cl or F atom shown in the above groups is exchanged for the other. Methyl and methoxy may be similarly exchanged.

In compounds of the above Formulae in a further embodiment $R^6$ is selected from halogen, trifluoromethyl, cyano, nitro, amino, hydroxy, 5- or 6-membered heterocycloalkyl, $C_{1-6}$alkyl, $C_{1-6}$alkoxy, —NH—$C_{1-6}$ alkyl, —N($C_{1-6}$ alkyl)$_2$, —NH—($C_{5-6}$ cycloalkyl), —(CH$_2$)$_k$—$C_{3-6}$ cycloalkyl or —(CH$_2$)$_k$-aryl (preferably substituted or unsubstituted phenyl), —NH—(CH$_2$)$_k$—$C_{3-6}$ cycloalkyl or —NH—(CH$_2$)$_k$-aryl, wherein the alkyl, cycloalkyl or aryl moieties can be substituted by halogen, hydroxy, $C_{1-6}$ alkoxy, $C_{1-6}$ alkyl, or amino.

In compounds of the above Formulae, $R^8$ and/or $R^9$ is often hydrogen or $C_{1-6}$ alkyl optionally substituted with 1, 2, 3, 4 or 5 $R^{13}$. In this case, the or each $R^{13}$ is often independently selected from hydroxy, halogen (e.g. fluorine or chlorine) or $C_{1-6}$ (e.g. $C_1$, $C_2$, $C_3$ or $C_4$) alkoxy.

In a preferred embodiment $R^8$ and/or $R^9$ is hydrogen.

In compounds of the above Formulae, $R^7$ is a 5- or 6-membered heterocyclyl group, especially a 5- or 6-membered heteroaryl groups, optionally substituted with 1, 2, 3, 4 or 5 $R^{13}$. In particular, $R^7$ may be imidazolyl, pyrazolyl, pyridinyl, pyrimidinyl, or pyrazinyl, any of which is optionally substituted with 1, 2 or 3 $R^{13}$. Typically, each $R^{13}$ is independently selected from oxo, halogen (e.g. fluorine, chlorine or bromine), hydroxy, cyano, amino, —C(O)OH, $C_{1-6}$ alkyl, $C_{1-6}$ alkoxy (e.g. $C_1$, $C_2$, $C_3$ or $C_4$ alkoxy), —C(O)—$C_{1-6}$ alkyl, —C(O)O—$C_{1-6}$ alkyl, —S(O)$_j$—CO$_{1-6}$ alkyl, —NH($C_{1-6}$ alkyl) and —N($C_{1-6}$ alkyl)$_2$, —C(O)—(CH$_2$)$_k$-heterocyclyl, —(CH$_2$)$_k$—C(O)-heterocyclyl, or a 5- or 6-membered heterocyclyl group (in particular piperidinyl, morpholinyl, thiomorpholinyl, tetrahydropyranyl), wherein any $C_{1-6}$ alkyl group present is optionally substituted with 1, 2, 3, 4 or 5 substituents independently selected from halogen, cyano, amino, hydroxyl, $C_{1-6}$ alkyl and $C_{1-6}$ alkoxy, and wherein the heterocyclyl group (which is in particular a 5- or 6-membered heterocyclyl group such as imidazolyl, pyridinyl, pyrimidinyl, pyrazinyl, piperidinyl, piperazinyl, morpholinyl, thiomorpholinyl or tetrahydropyranyl) is optionally substituted with 1, 2, 3, 4 or 5 substituents independently selected from halogen, cyano, oxo, amino, hydroxy, $C_{1-6}$ alkyl and $C_{1-6}$ alkoxy.

Examples of compounds of the invention include those shown below. It will of course be appreciated that where a salt is shown, this is merely an illustrative example and non-limiting and other forms may be contemplated. Each compound may, therefore, be in the form of the free compound, an acid or base addition salt, or a prodrug.

1

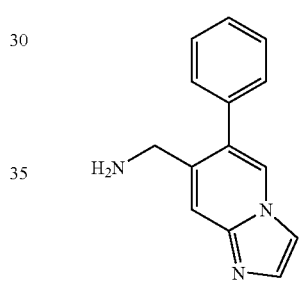

2a

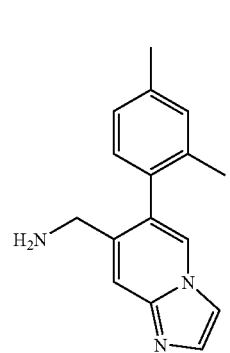

2b

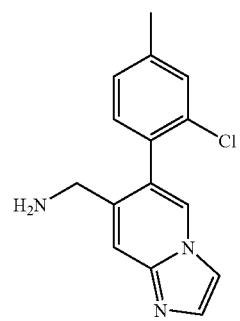

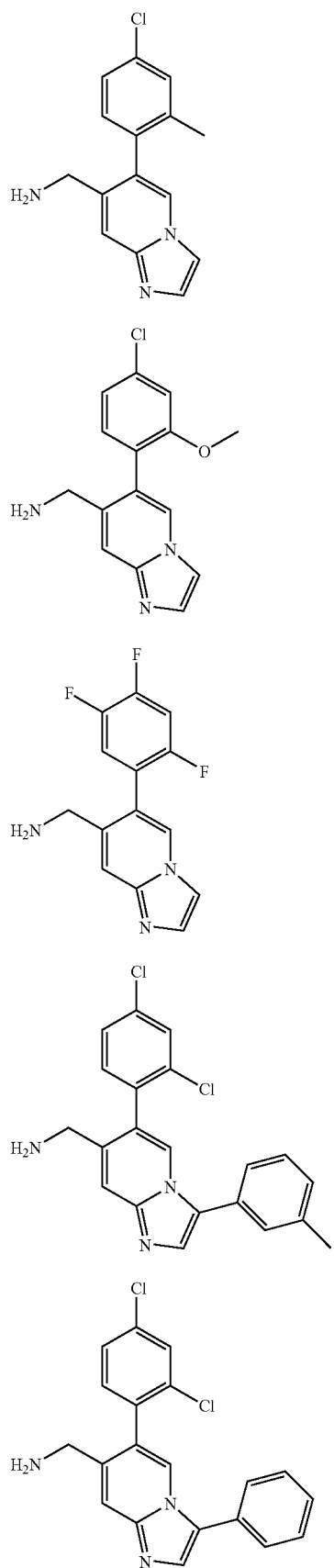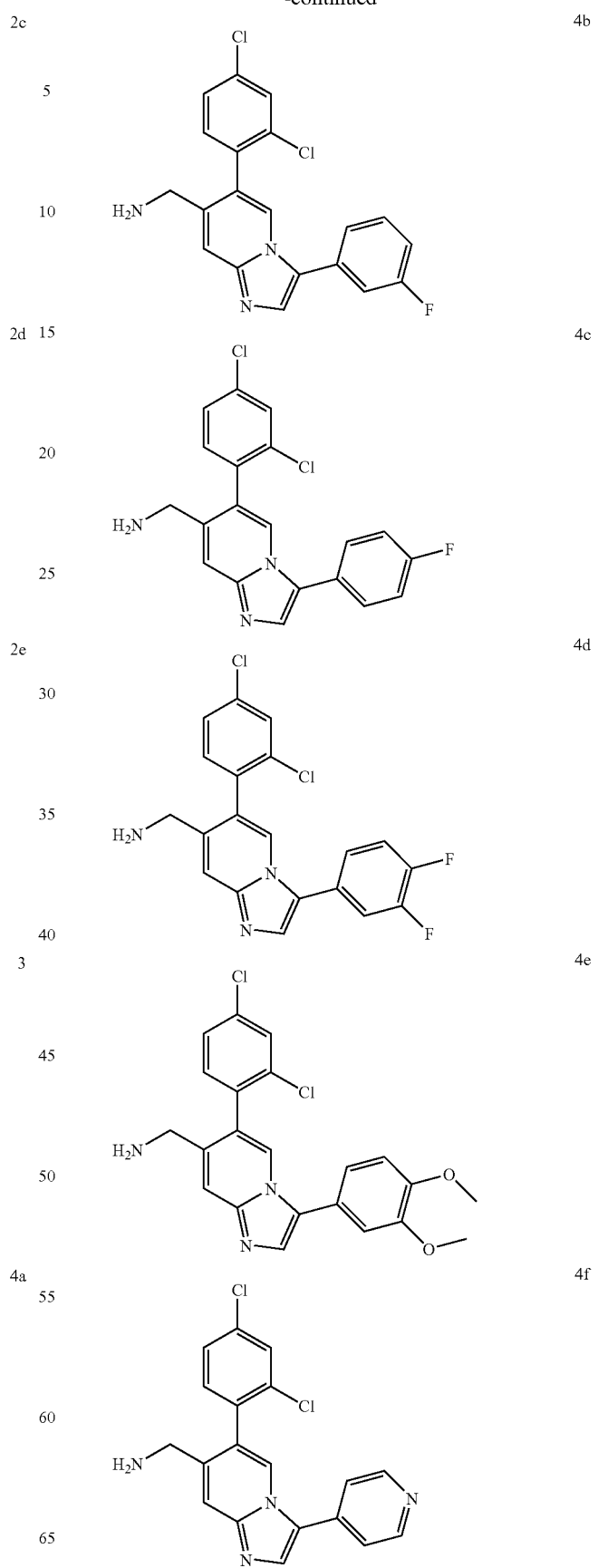

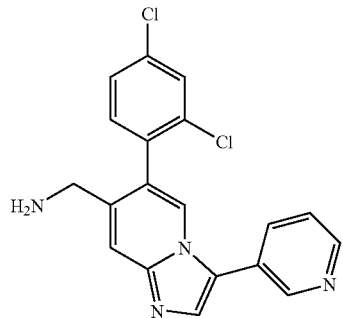
4g
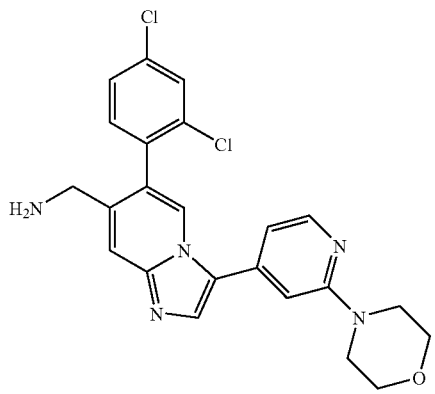
4k
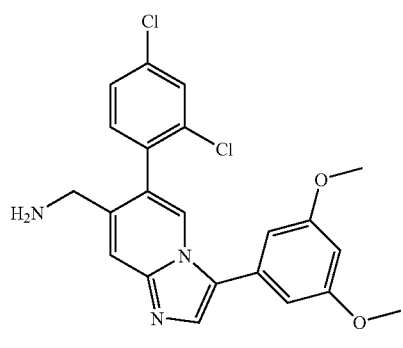
4h
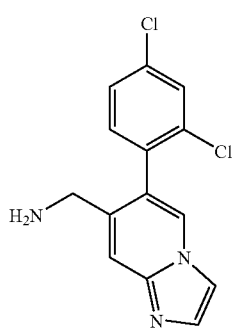
5
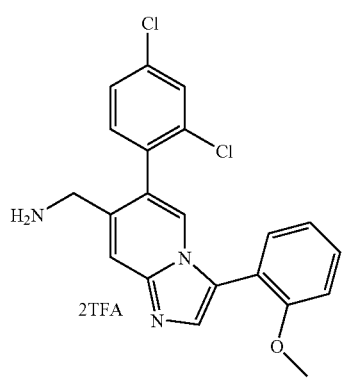
4i
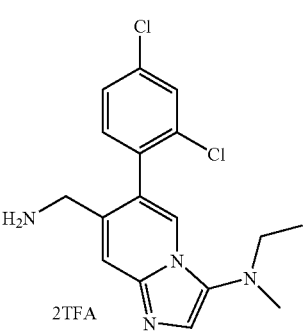
6
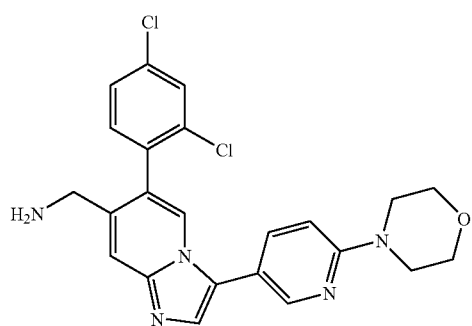
4j
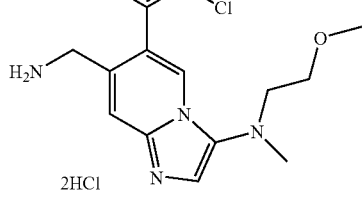
7

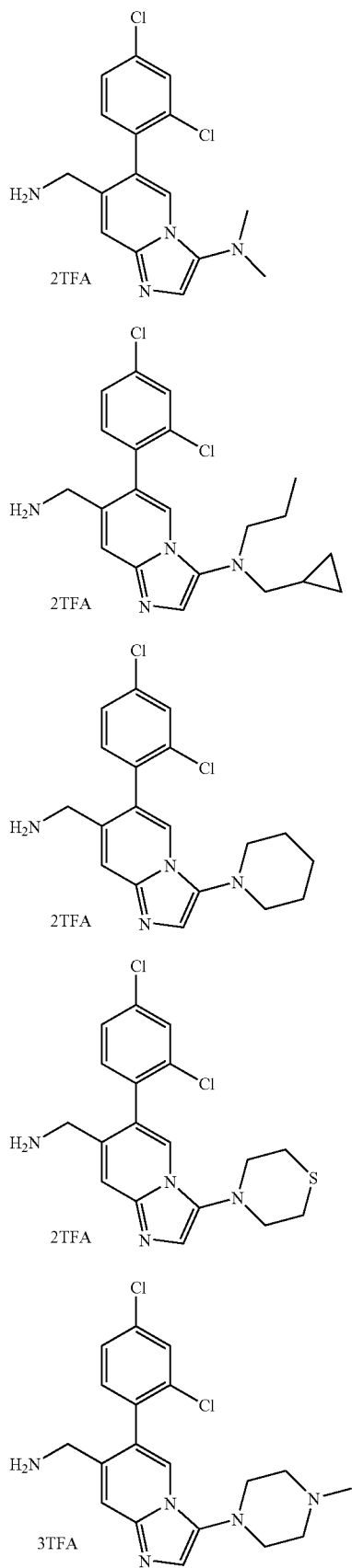
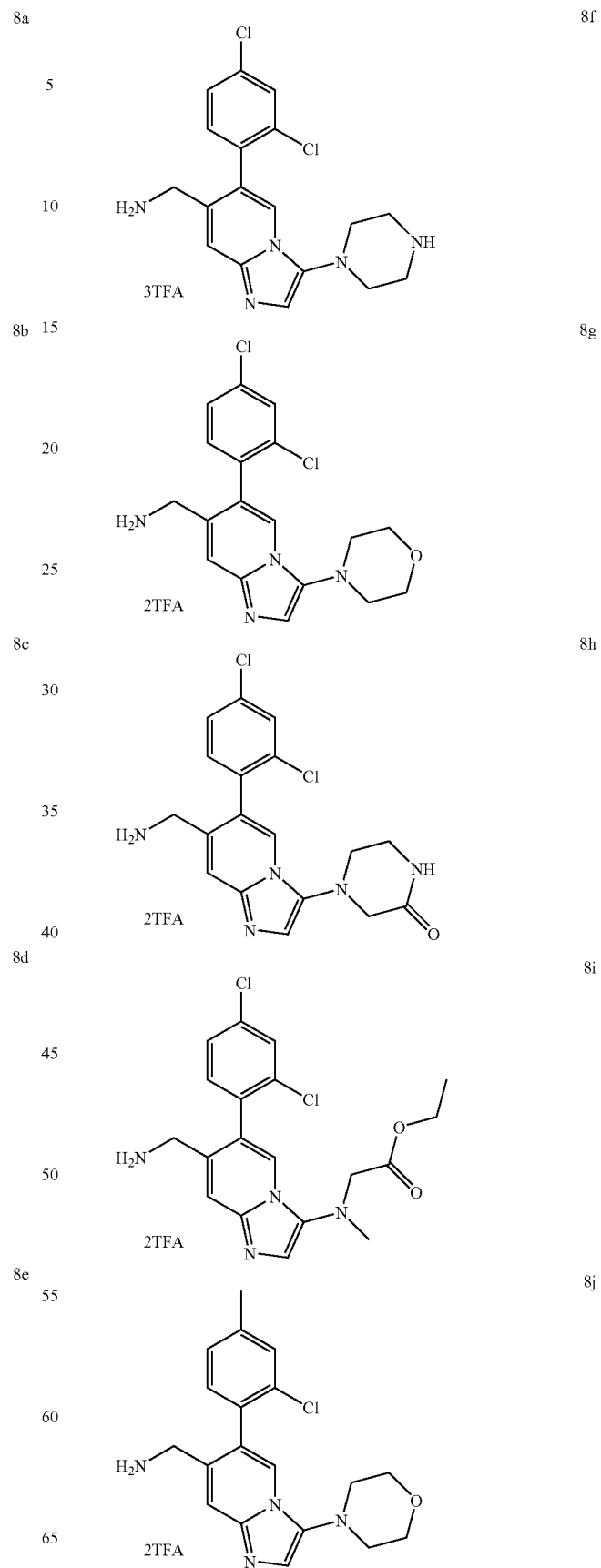

8k
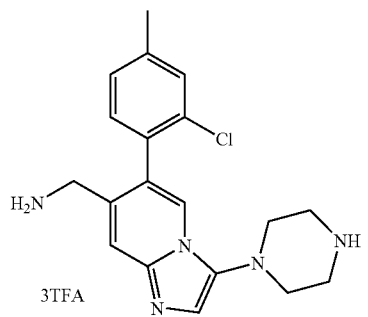
3TFA
8l
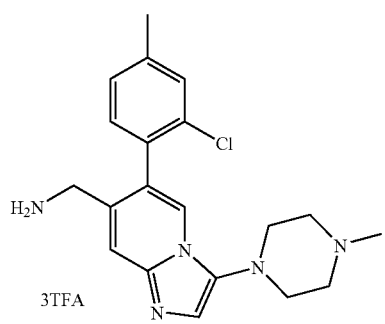
3TFA
8m
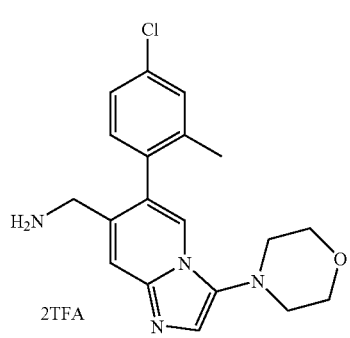
2TFA
8n
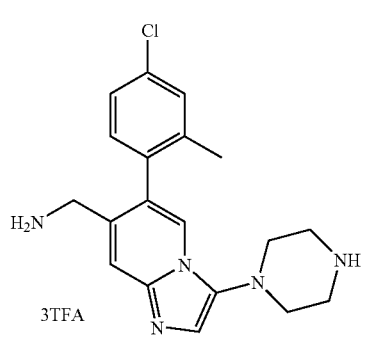
3TFA
8o
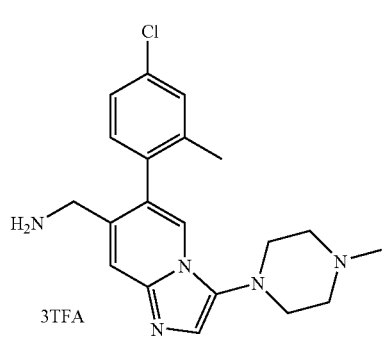
3TFA
8p
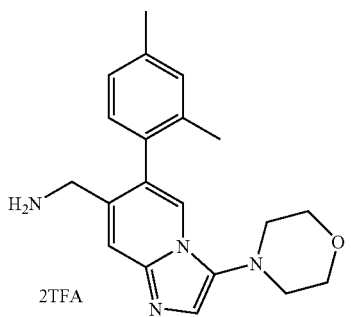
2TFA
8q
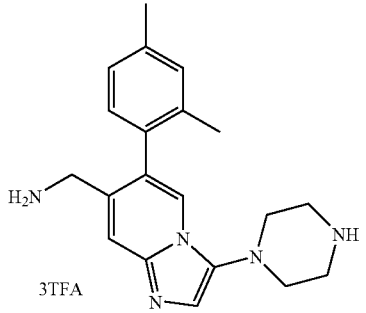
3TFA
8r
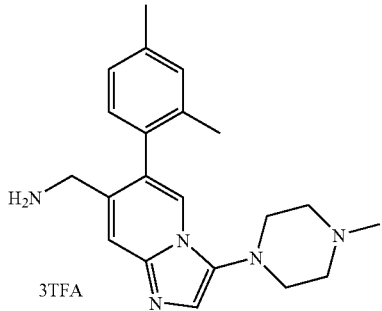
3TFA
8s
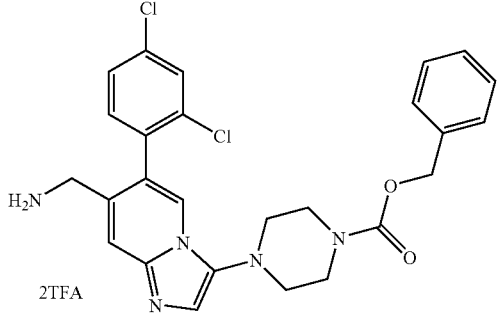
2TFA
8t
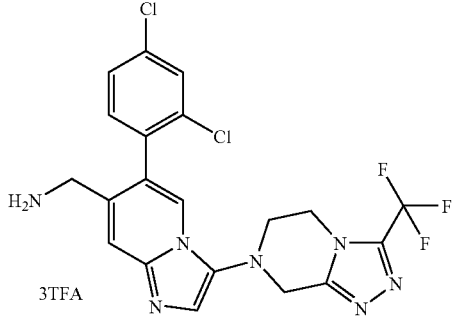
3TFA -continued
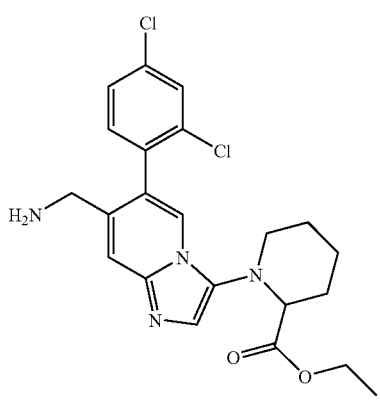
8u
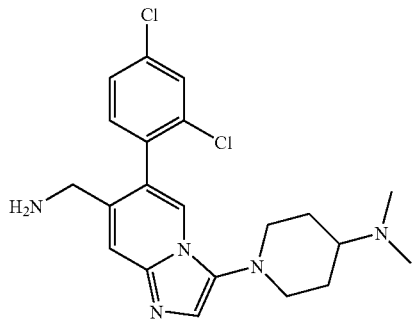
8y
8v
8z
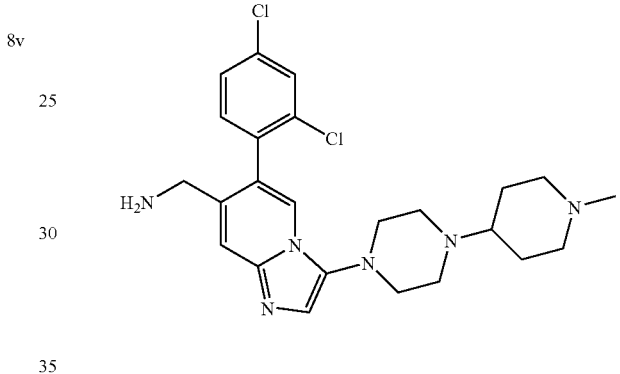
8w
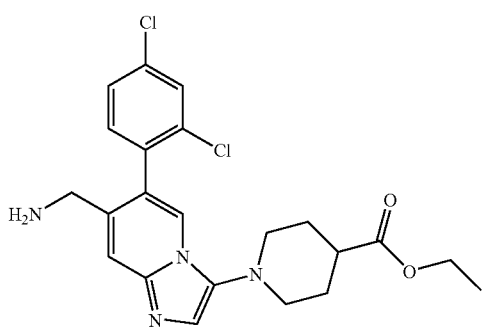
8a′
8x
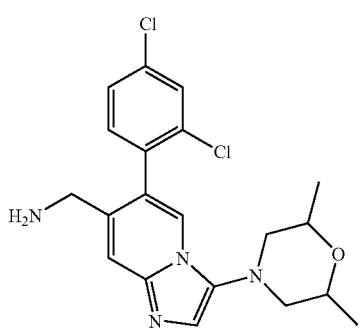
8b′

49
-continued
8c'
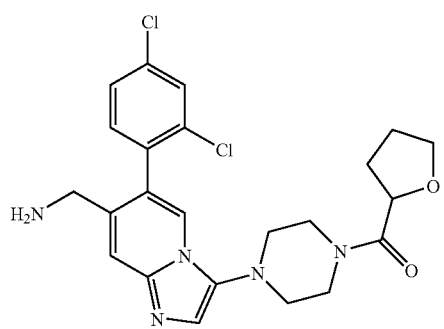
9
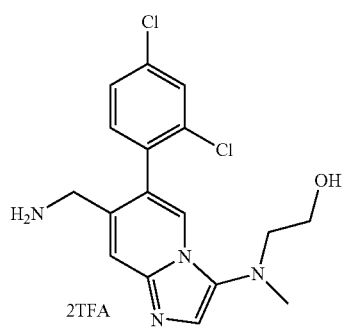
2TFA
10
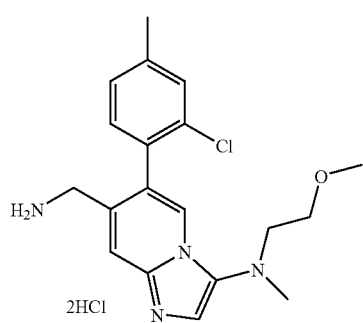
2HCl
11a
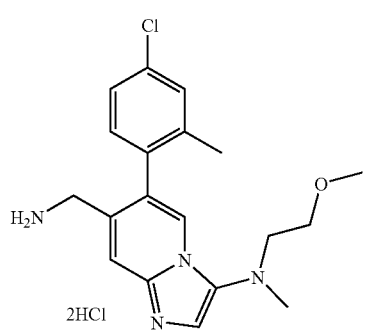
2HCl
11b
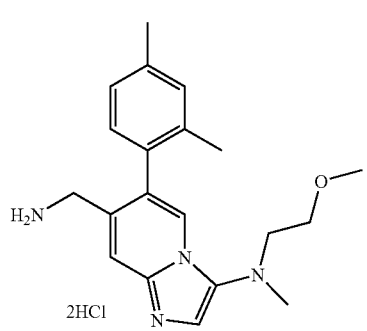
2HCl
50
-continued
5
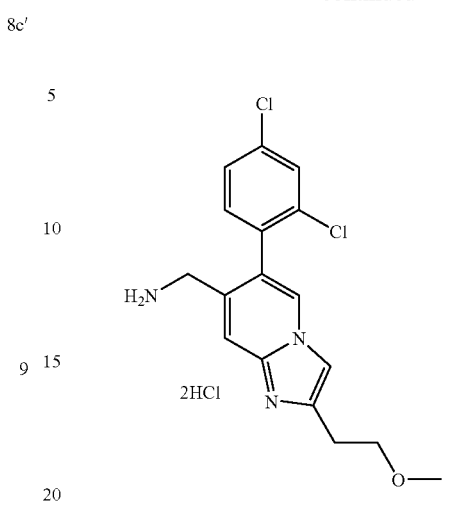
2HCl
12
13
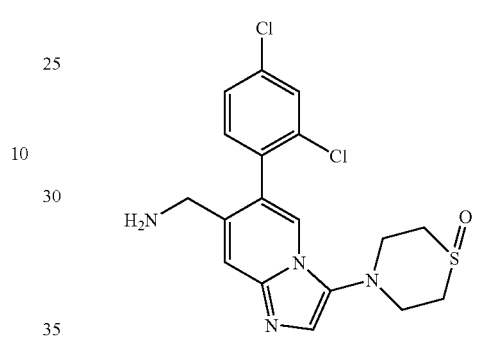
14
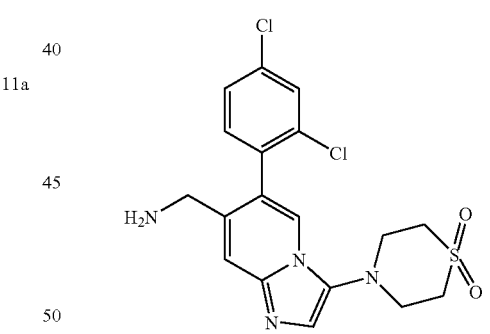
15
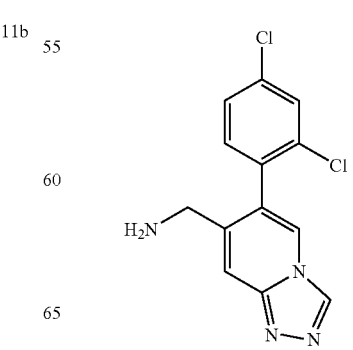

16
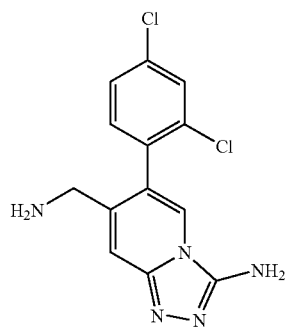
17
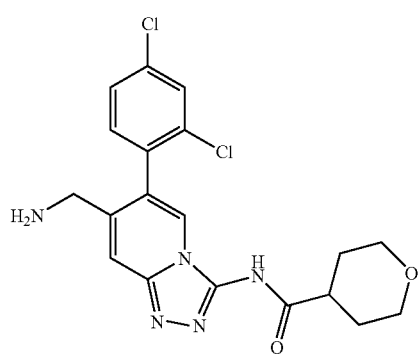
18a
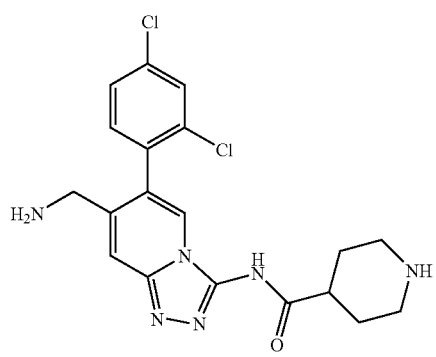
18b
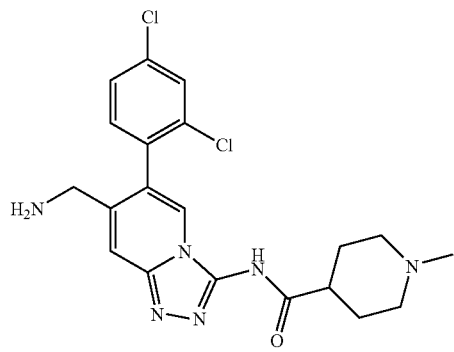
18c
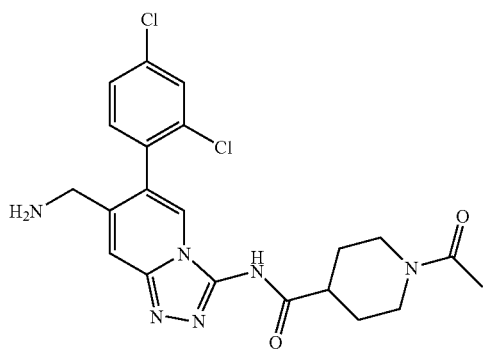
18d
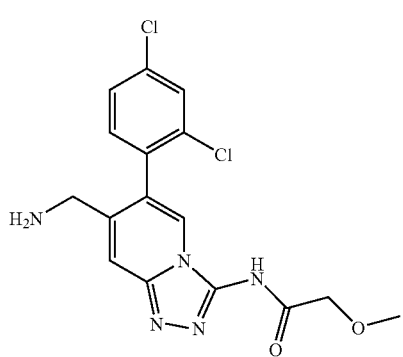
18e
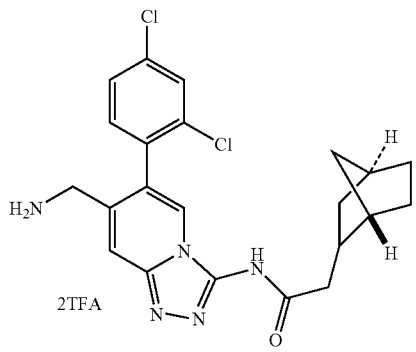
18f 18g
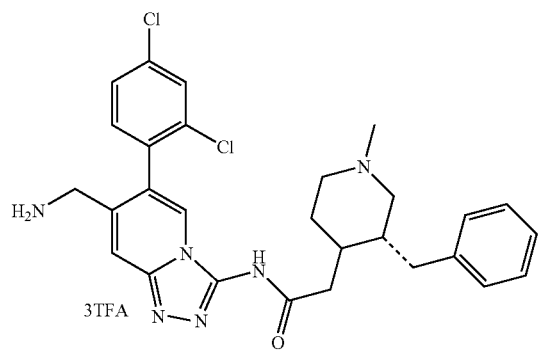
18h
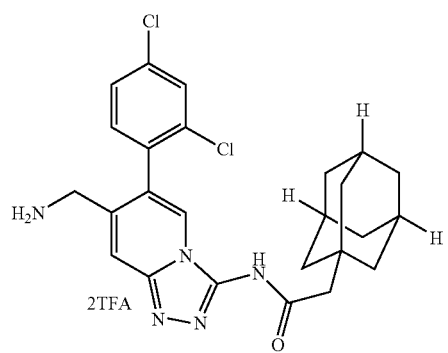
18i
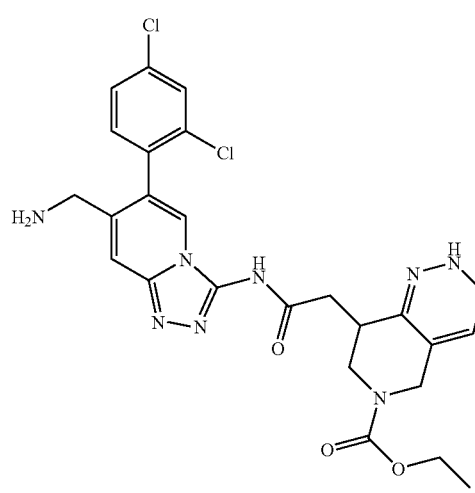
19
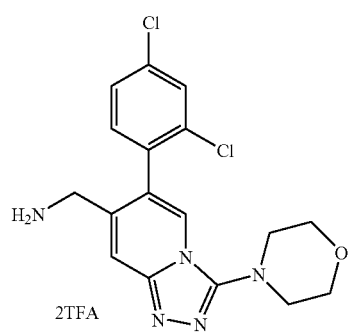
20
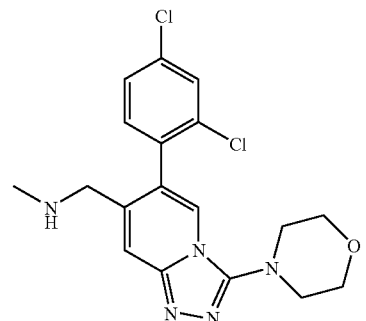
21a
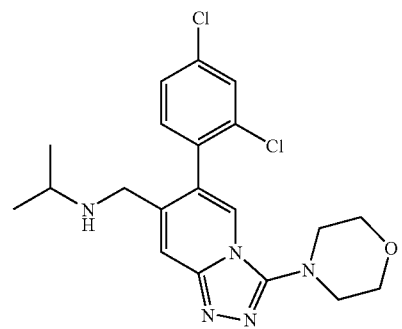
21b
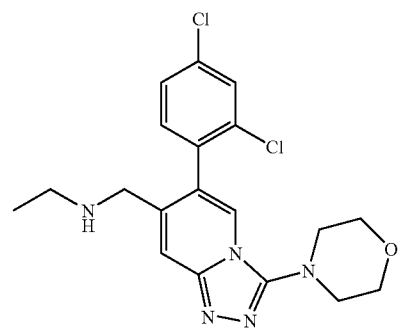
21c
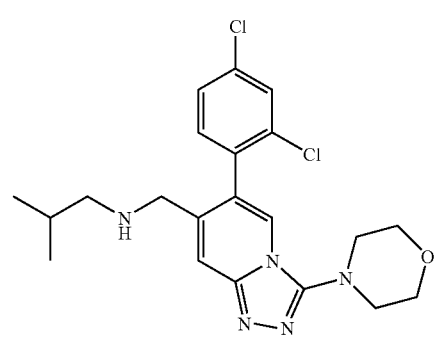
21d
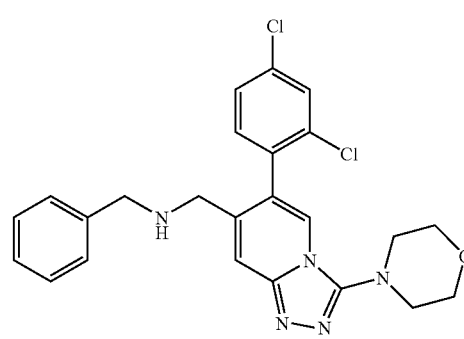

21e 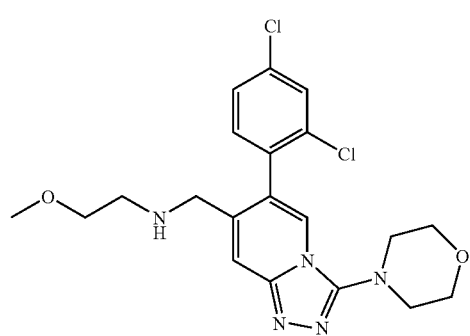
22 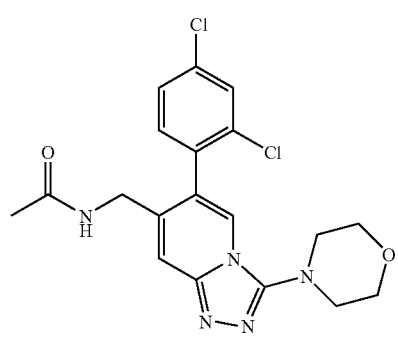
23 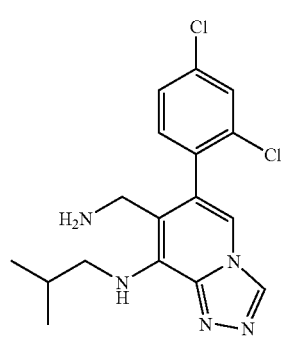
24a 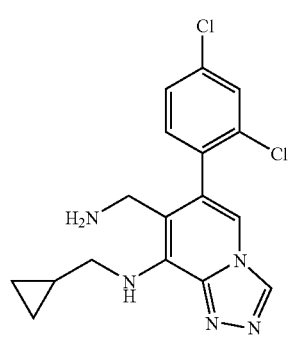
24b 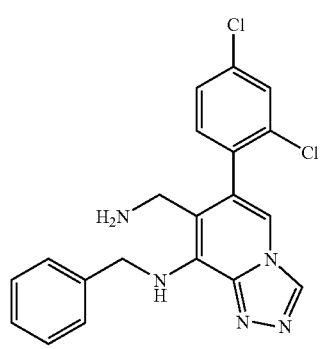
24c 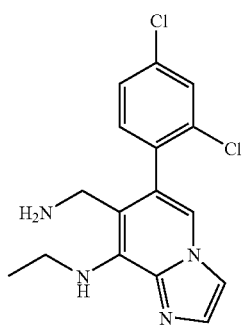
24d 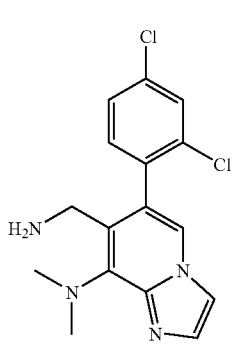
24e 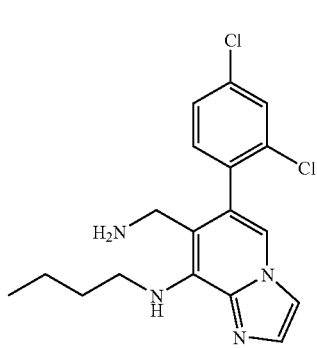
24f 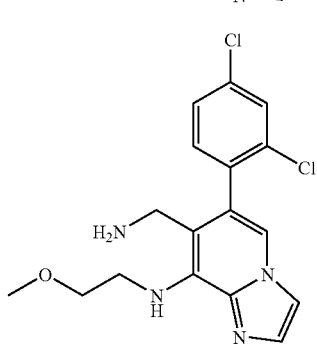
24g 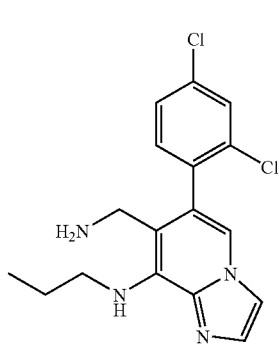

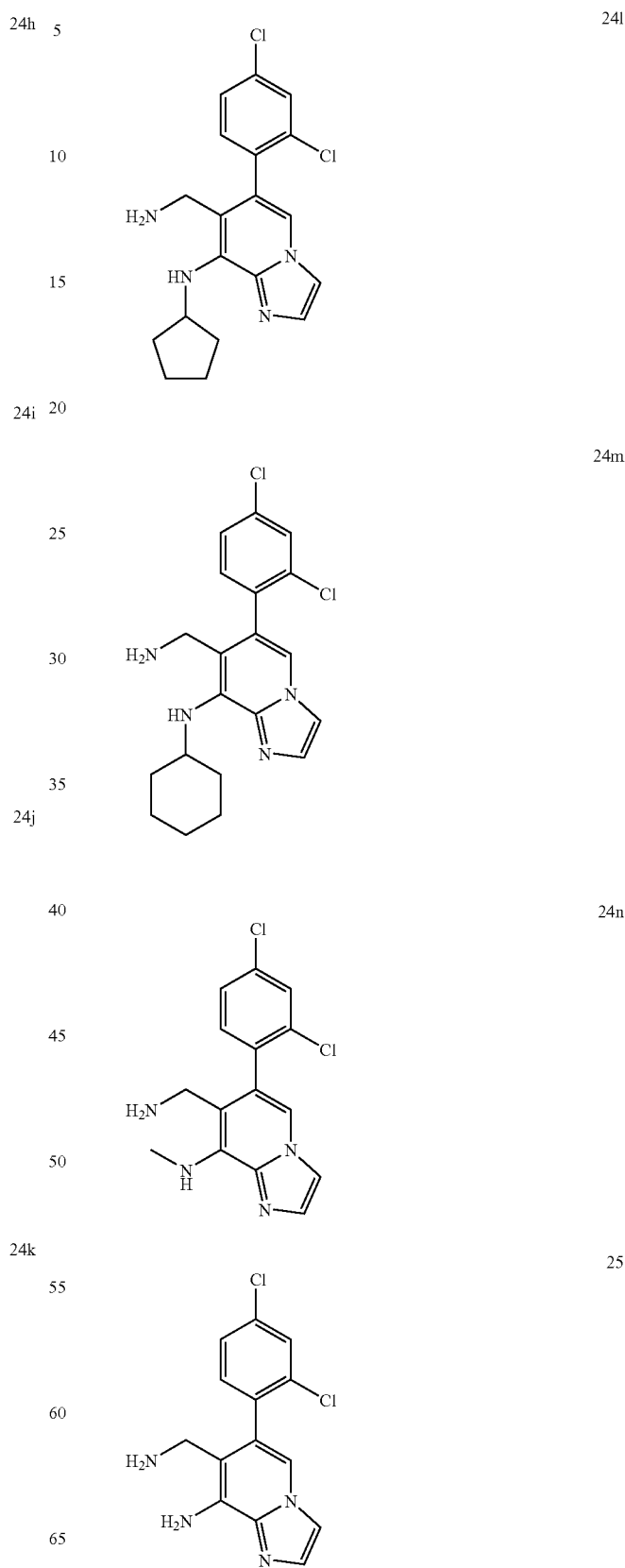

26
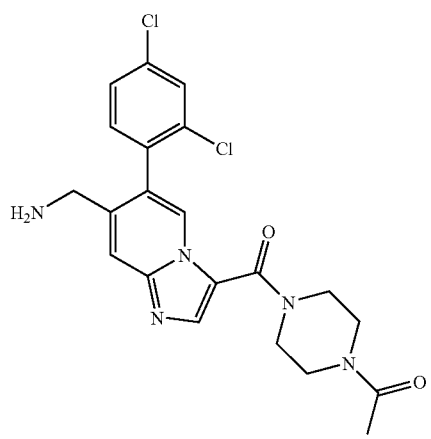
27a
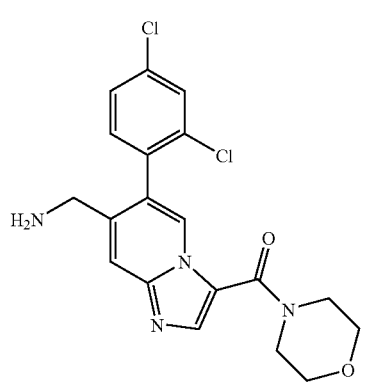
27b
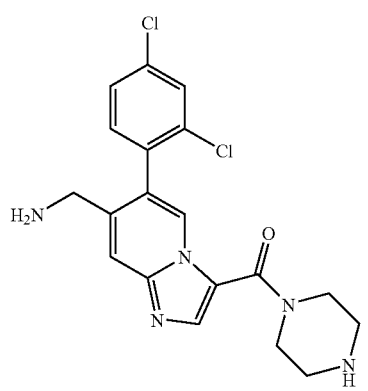
27c
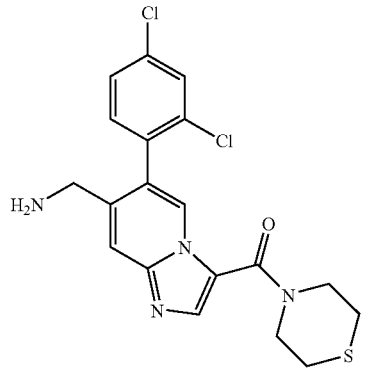
27d
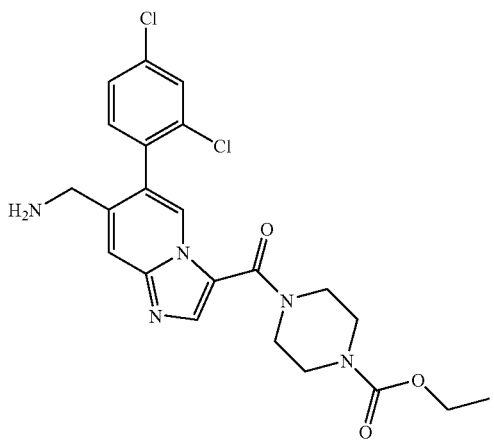
27e
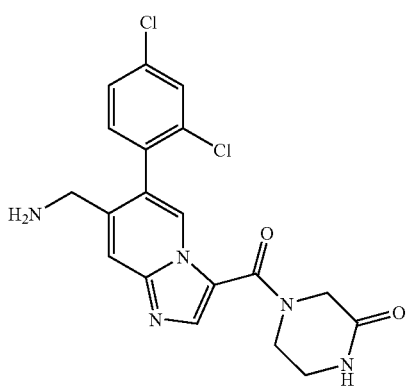
27f
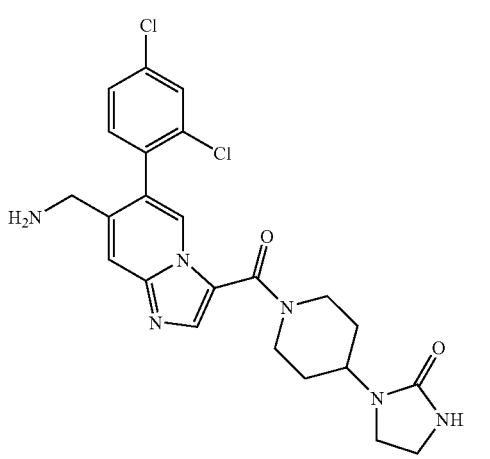

-continued
27g
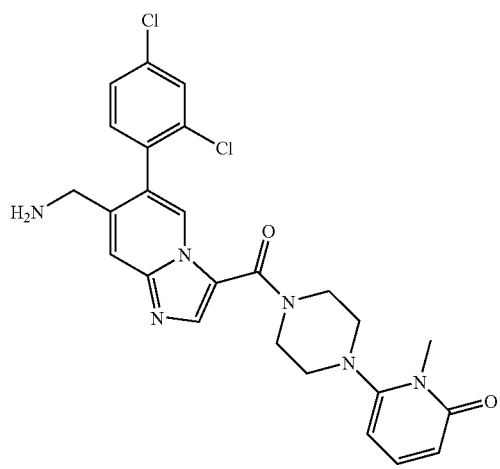
27j
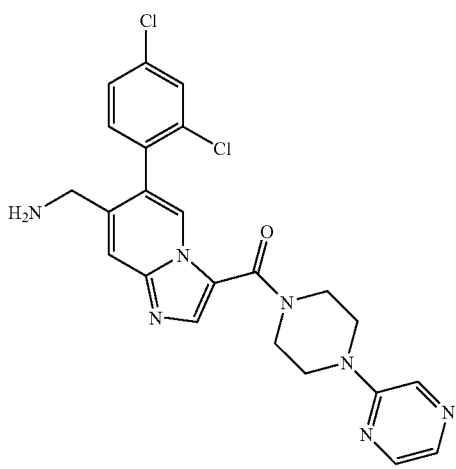
27h
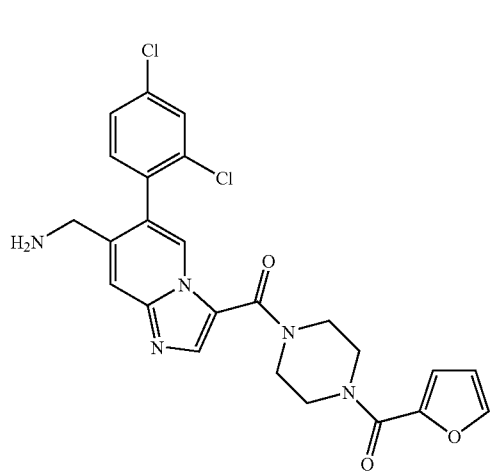
27k
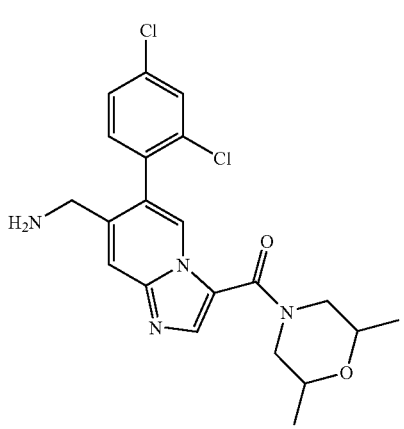
27i
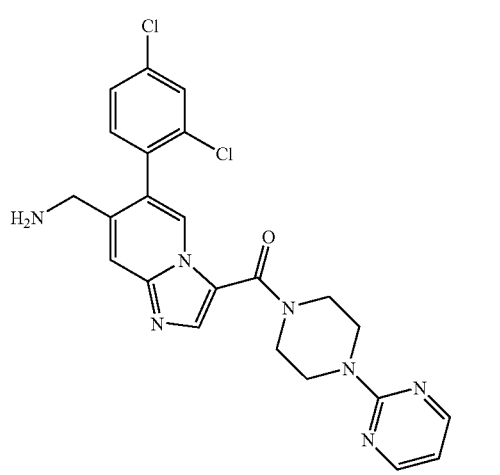
27l
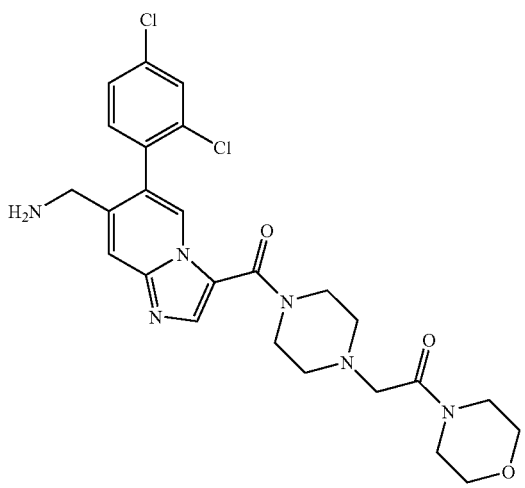

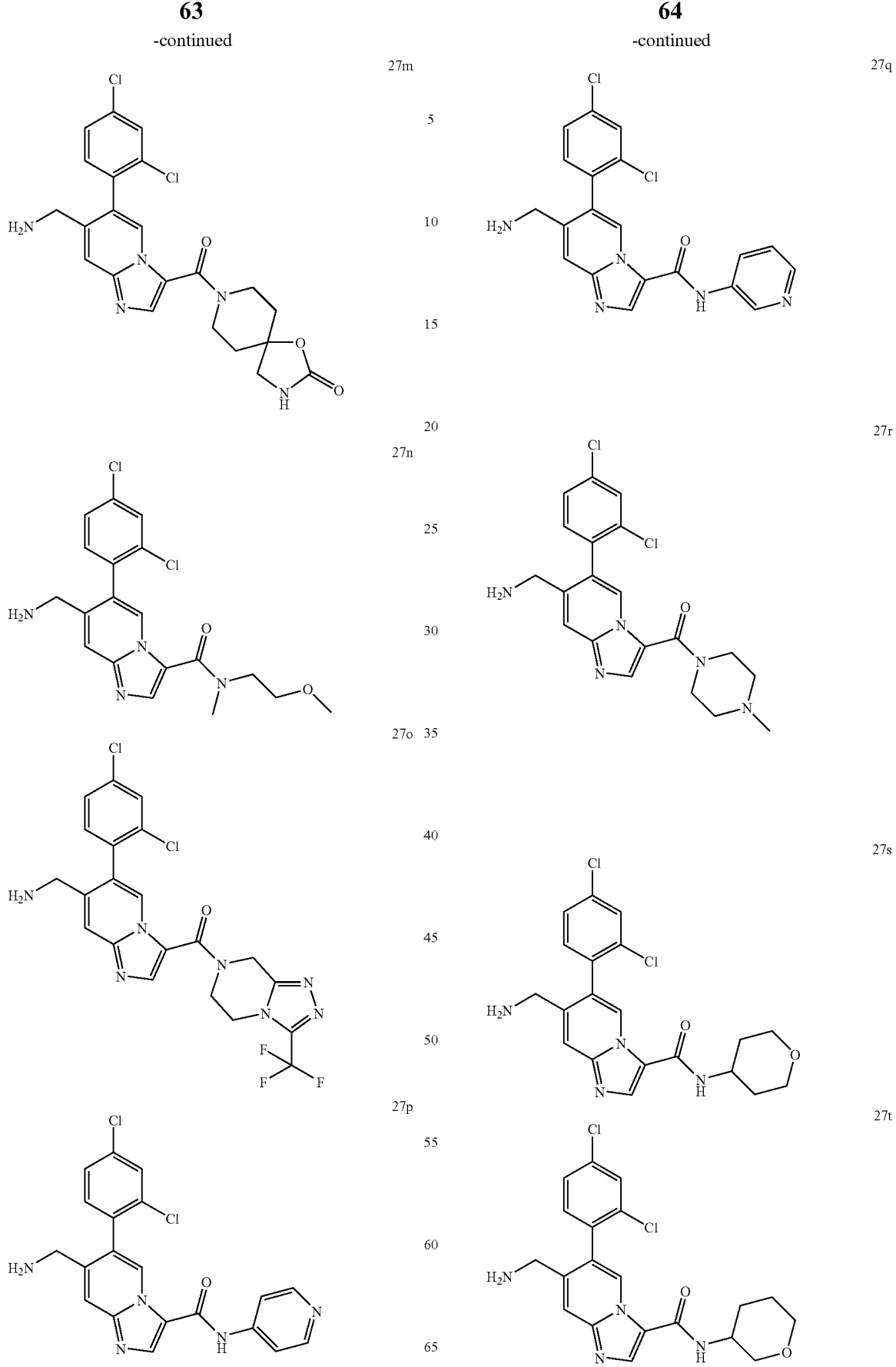

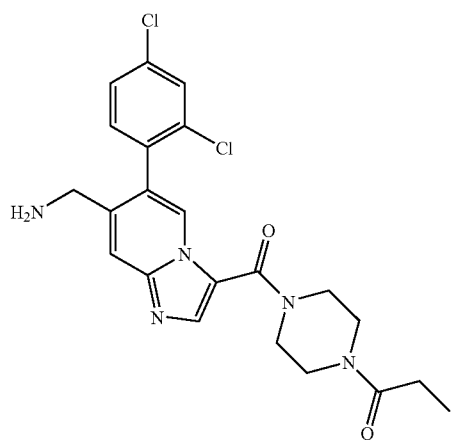
27u
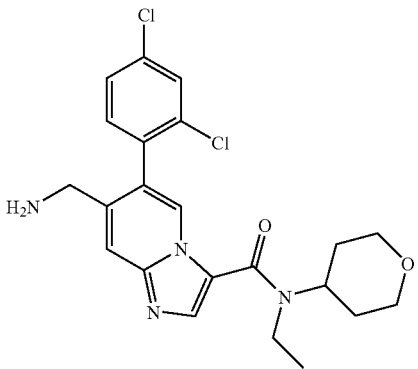
27y
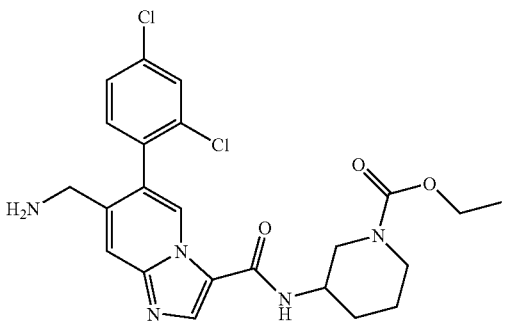
27v
27z
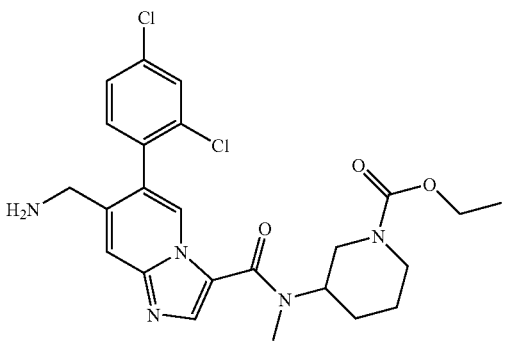
27w
27a'
27x
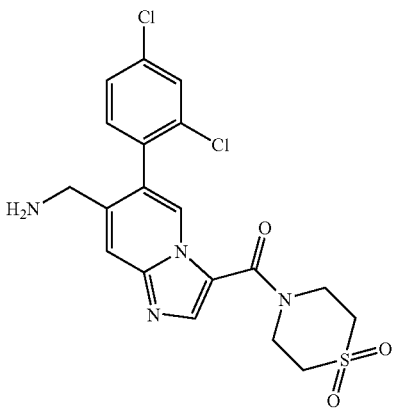
27b'

67
-continued
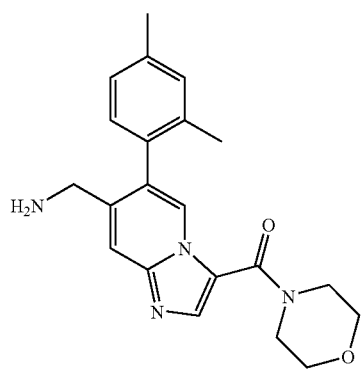
27c'
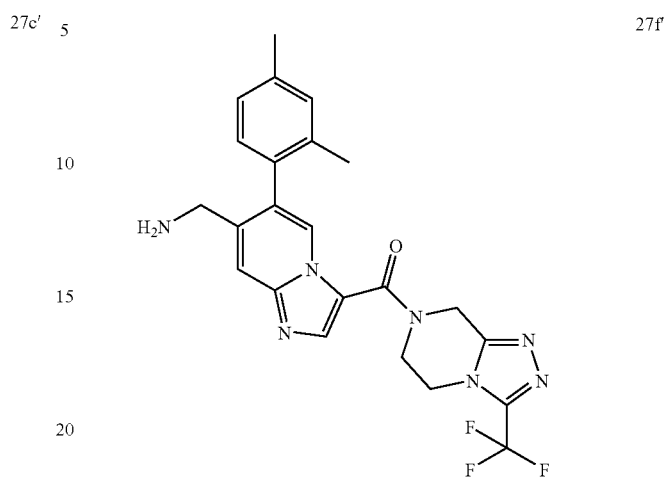
27d'
27e'
68
-continued
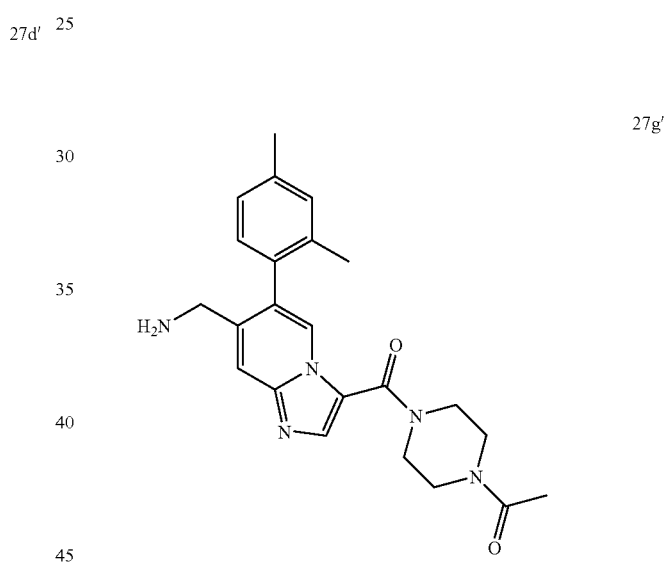
27f'
27g'
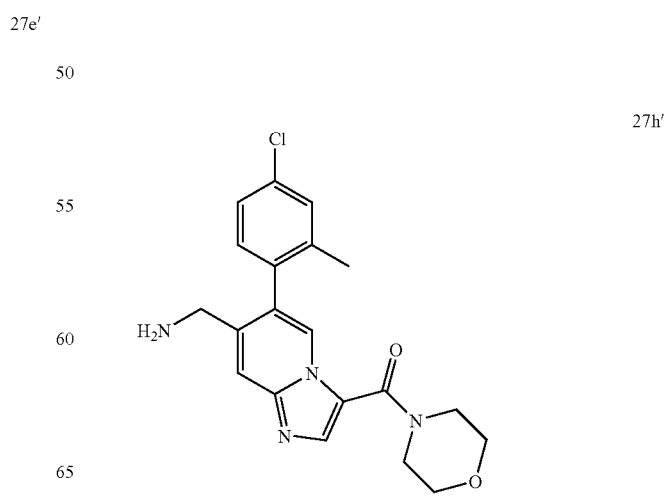
27h'

27i'
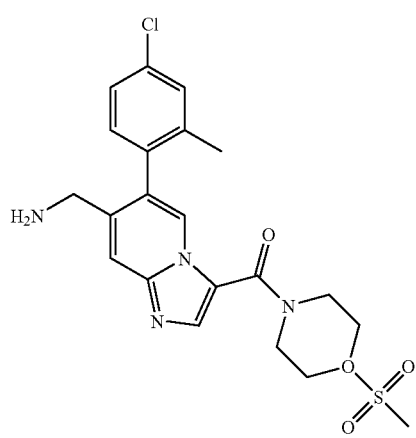
27j'
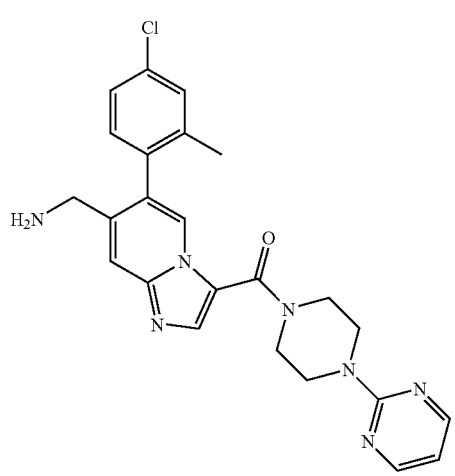
27k'
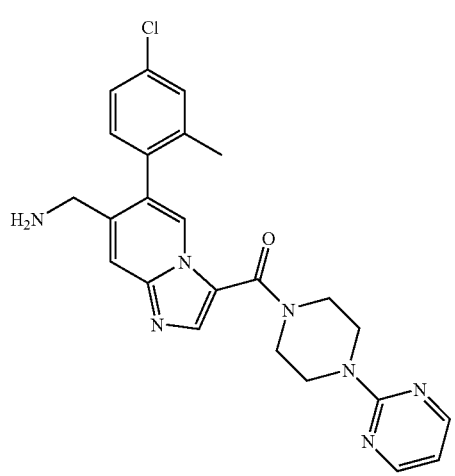
27l'
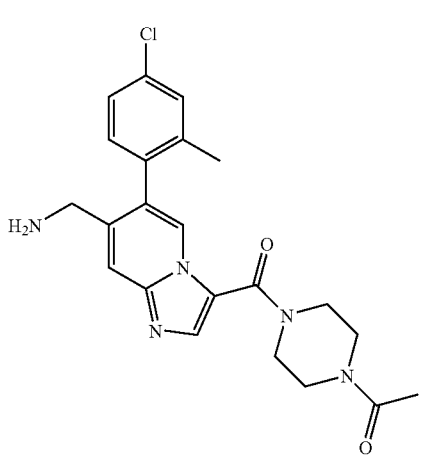
28
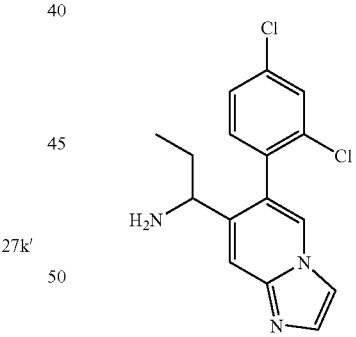
29
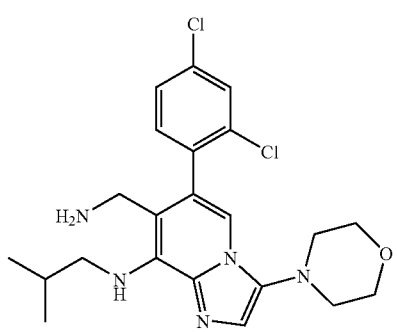
30

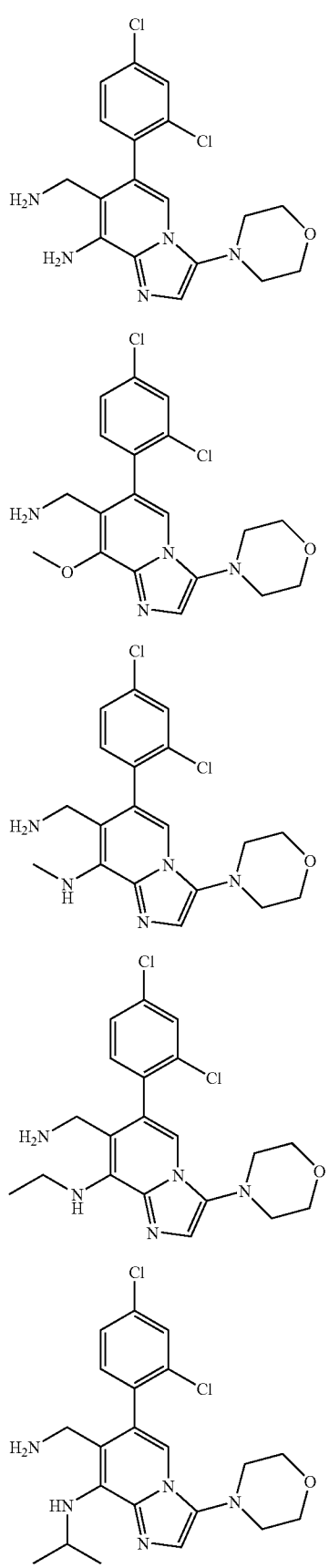
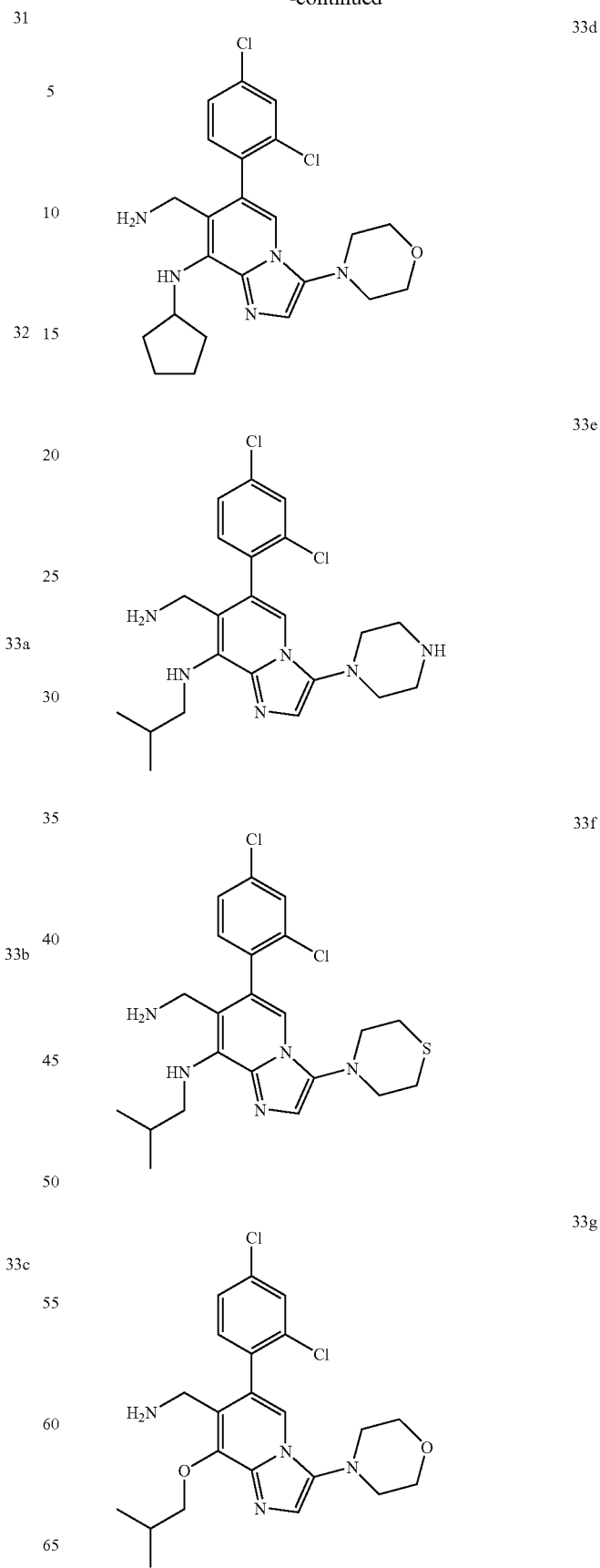

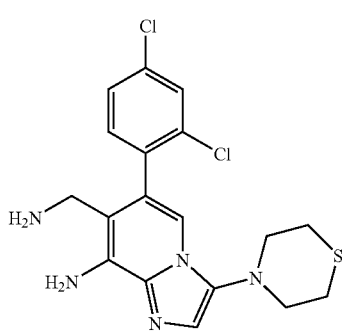
33h
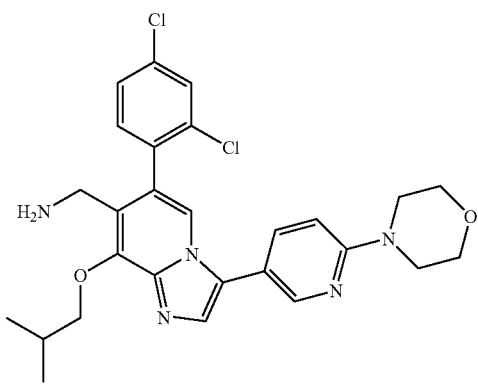
35
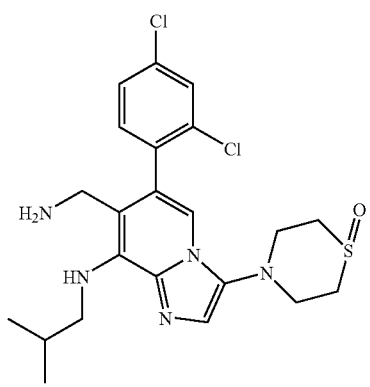
33i
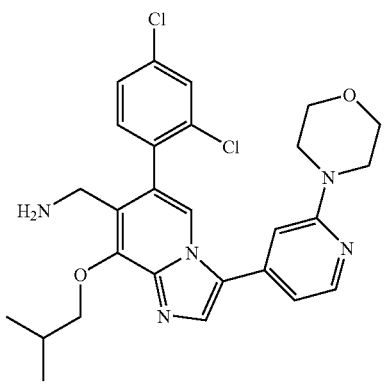
36
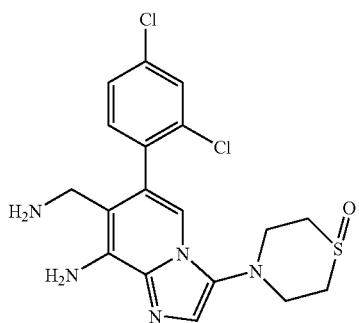
33j
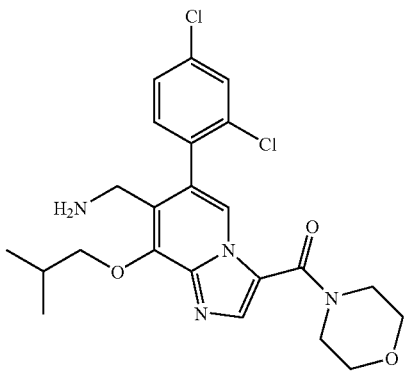
37
34
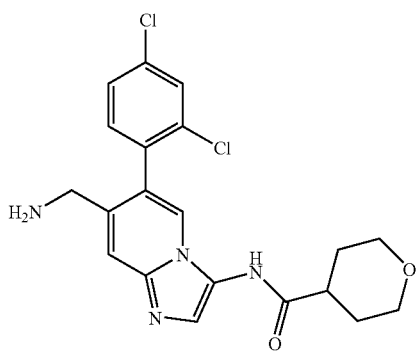
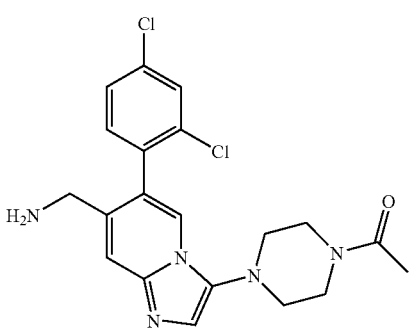
38

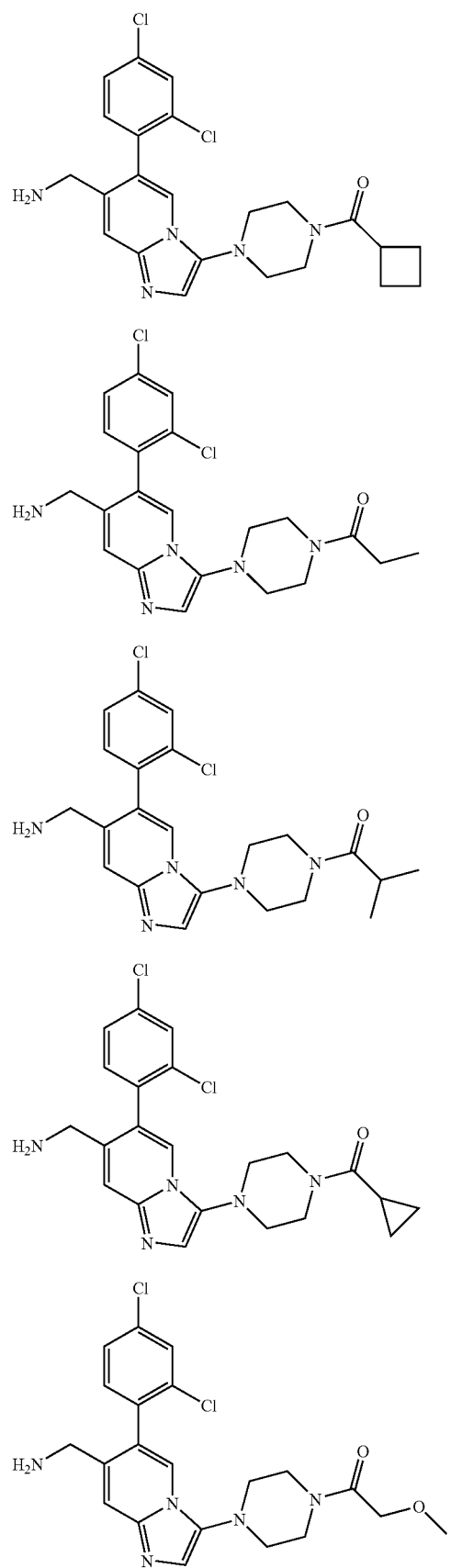
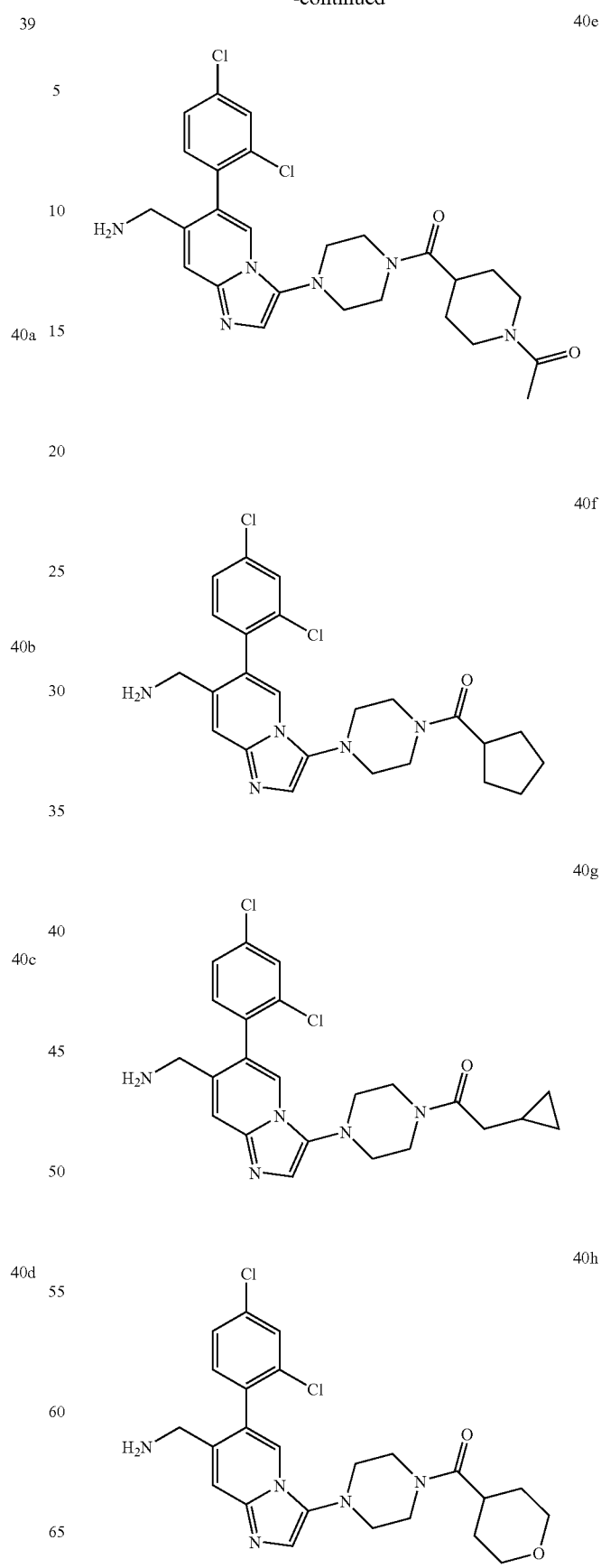

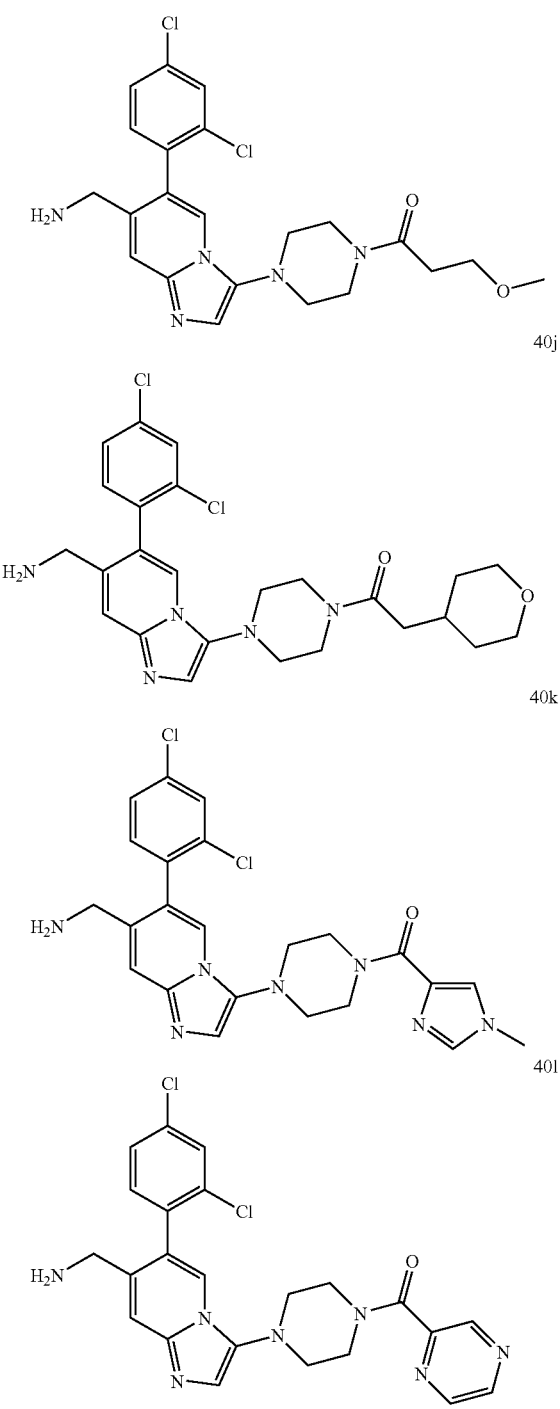

tical Sciences, 17th ed., Mack Publishing Company, Easton, Pa., US, 1985, p. 1418, the disclosure of which is hereby incorporated by reference; see also Stahl et al, Eds, "Handbook of Pharmaceutical Salts Properties Selection and Use", Verlag Helvetica Chimica Acta and Wiley-VCH, 2002.

The disclosure thus includes pharmaceutically-acceptable salts of the disclosed compounds wherein the parent compound is modified by making acid or base salts thereof. For example the conventional non-toxic salts or the quaternary ammonium salts which are formed, e.g. from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

The invention includes prodrugs for the active pharmaceutical species of the invention, for example in which one or more functional groups are protected or derivatised but can be converted in vivo to the functional group, as in the case of esters of carboxylic acids convertible in vivo to the free acid, or in the case of protected amines, to the free amino group. The term "prodrug," as used herein, represents in particular compounds which are rapidly transformed in vivo to the parent compound, for example, by hydrolysis in blood. A thorough discussion is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987; H Bundgaard, ed, Design of Prodrugs, Elsevier, 1985; and Judkins, et al. Synthetic Communications, 26(23), 43514367 (1996), each of which is incorporated herein by reference.

Prodrugs therefore include drugs having a functional group which has been transformed into a reversible derivative thereof. Typically, such prodrugs are transformed to the active drug by hydrolysis. As examples may be mentioned the following:

Compounds of the invention may be in the form of pharmaceutically acceptable salts. The pharmaceutically acceptable salts of the invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceu-

| Functional Group | Reversible derivative |
|---|---|
| Carboxylic acid | Esters, including e.g. acyloxyalkyl esters, amides |
| Alcohol | Esters, including e.g. sulfates and phosphates as well as carboxylic acid esters |
| Amine | Amides, carbamates, imines, enamines, |
| Carbonyl (aldehyde, ketone) | Imines, oximes, acetals/ketats, enol esters, oxazolidines and thiazoxolidines |

Prodrugs also include compounds convertible to the active drug by an oxidative or reductive reaction. As examples may be mentioned:

Oxidative Activation
N- and O-dealkylation
Oxidative deamination
N-oxidation
Epoxidation
Reductive activation
Azo reduction
Sulfoxide reduction
Disulfide reduction
Bioreductive alkylation
Nitro reduction.

Also to be mentioned as metabolic activations of prodrugs are nucleotide activation, phosphorylation activation and decarboxylation activation. For additional information, see "The Organic Chemistry of Drug Design and Drug Action", R B Silverman (particularly Chapter 8, pages 497 to 546), incorporated herein by reference.

The use of protecting groups is fully described in 'Protective Groups in Organic Chemistry', edited by J W F McOmie, Plenum Press (1973), and 'Protective Groups in Organic Synthesis', 2nd edition, T W Greene & P G M Wutz, Wiley-Interscience (1991).

Thus, it will be appreciated by those skilled in the art that, although protected derivatives of compounds of the disclosure may not possess pharmacological activity as such, they may be administered, for example parenterally or orally, and thereafter metabolised in the body to form compounds of the invention which are pharmacologically active. Such derivatives are therefore examples of "prodrugs". All prodrugs of the described compounds are included within the scope of the disclosure.

Many of the groups referred to or featured herein (especially those containing heteroatoms and conjugated bonds) can exist in tautomeric forms and all these tautomers are included in the scope of the disclosure. More generally, many species may exist in equilibrium, as for example in the case of organic acids and their counterpart anions; a reference herein to a species accordingly includes reference to all equilibrium forms thereof.

The compounds of the disclosure may also contain one or more asymmetric carbon atoms and may therefore exhibit optical and/or diastereoisomerism. All diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation, or by derivatisation, for example with a homochiral acid followed by separation of the diastereomeric derivatives by conventional means (e.g. HPLC, chromatography over silica). All stereoisomers are included within the scope of the disclosure.

Geometric isomers may also exist in the compounds of the present disclosure. The present disclosure contemplates the various geometric isomers and mixtures thereof resulting from the arrangement of substituents around a carbon-carbon double bond and designates such isomers as of the Z or E configuration, wherein the term "Z" represents substituents on the same side of the carbon-carbon double bond and the term "E" represents substituents on opposite sides of the carbon-carbon double bond.

The disclosure therefore includes all variant forms of the defined compounds, for example any tautomer or any pharmaceutically acceptable salt, ester, acid or other variant of the defined compounds and their tautomers as well as substances which, upon administration, are capable of providing directly or indirectly a compound as defined above or providing a species which is capable of existing in equilibrium with such a compound.

Synthesis

Scheme A illustrates a general method of preparing compounds of the invention:

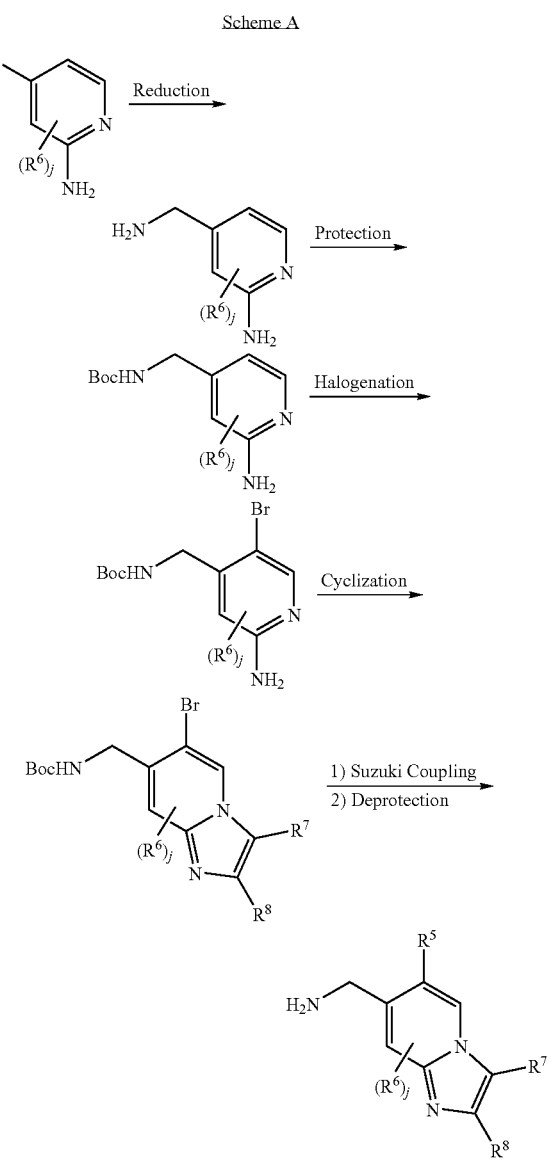

Scheme A

In Scheme A, reduction of the cyano group may be performed either by hydrogenolysis using Pd/C and hydrogen or using a $BH_3$-THF complex. Selective Boc-protection of the benzilic amine may be carried out by treatment with $Boc_2O$ in MeOH at 0° C. in the presence of triethylamine. Selective halogenation of the heteroaromatic system may be accomplished using standard procedures such as NBS in DMF, at low temperature or RT. The cyclization of appropriately functionalized 2-amino-pyridines may be performed by condensation of the adequate reagent including, but not limited to chloracetaldehyde, 1-chloro-4-methoxy-butan-2-one, 2-chloro-3-oxo-propionic acid ethyl ester, or a reagent generated by the condensation of benzotriazole, glyoxal, and any appropriate secondary amine, for example, as disclosed by Katritzky et al. (*J. Org. Chem.,* 2003, 68, 49354937 and *J. Org. Chem.,* 1990, 55, 3209-3213). The Suzuki coupling may be performed using an appropriate boronic acid and Pd(PPh$_3$)$_4$ as a catalyst in a mixture of DME and aqueous Na$_2$CO$_3$ under reflux conditions or by heating in a microwave oven. Finally, the Boc-protecting group may be removed by standard methods known in the art, such as using TFA in DCM or HCl in dioxane.

Scheme B illustrates an alternative method for preparing compounds of the invention:

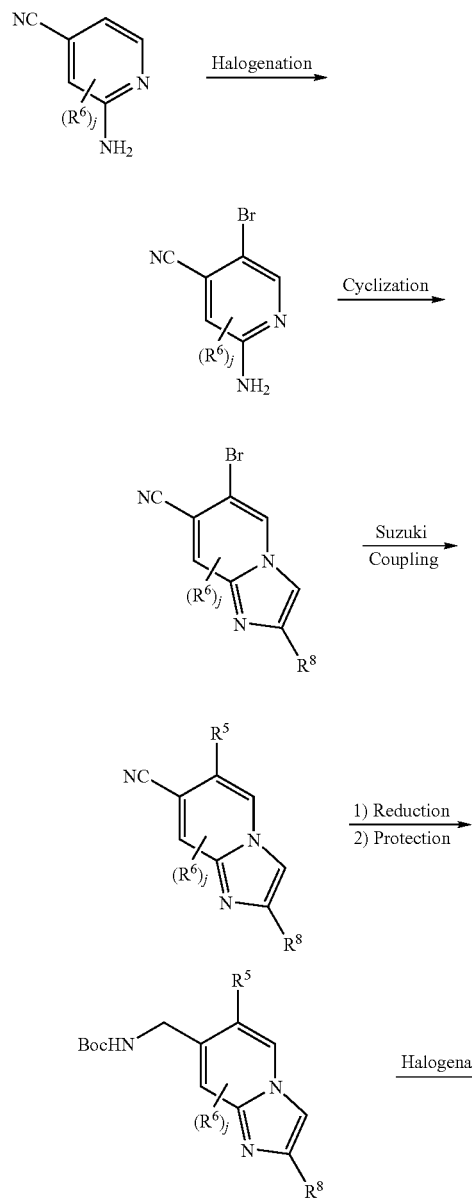

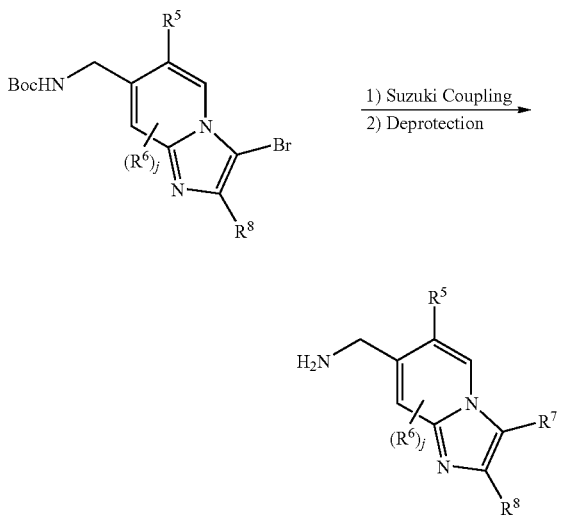

In Scheme B, selective bromation may be accomplished using standard procedures such as NBS in DMF at low temperature. As exemplified in the context of Scheme A, the imidazolo[1,2-a]pyridine moiety may be obtained by cyclization of the appropriate 2-amino-pyridine with the adequate reagent including, but not limited to chloracetaldehyde, 1-chloro-4-methoxy-butan-2-one, or a reagent generated by the condensation of benzotriazole, glyoxal, and any appropriate secondary amine as disclosed by Katritzky et al. (*J. Org. Chem.,* 2003, 68, 49354937 and *J. Org. Chem.,* 1990, 55, 3209-3213). The Suzuki coupling may be performed using the appropriate boronic acid and Pd(PPh$_3$)$_4$ as a catalyst in a mixture of DME and aqueous Na$_2$CO$_3$ under reflux conditions or by heating in a microwave oven. The cyano group may be reduced using a BH$_3$-THF complex and the benzilic amine may be Boc-protected as described in Scheme A. Selective halogenation of the imidazole part, followed by Suzuki coupling and Boc-deprotection may be performed using similar conditions as those described in respect of Scheme A.

Scheme C illustrates an alternative method for preparing compounds of the invention:

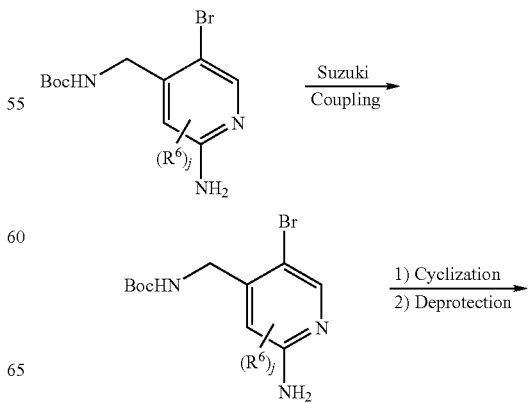

-continued

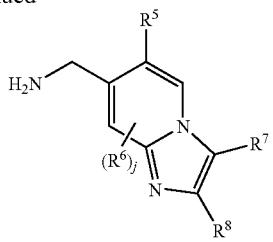

In Scheme C, Suzuki coupling on the appropriate 5-bromo-2-amino-pyridines may be performed prior to cyclization and Boc-deprotection, to give the functionalized imidazolo[1,2-a]pyridines. The conditions used are typically identical to those described in Scheme B.

Scheme D illustrates an alternative method for preparing compounds of the invention:

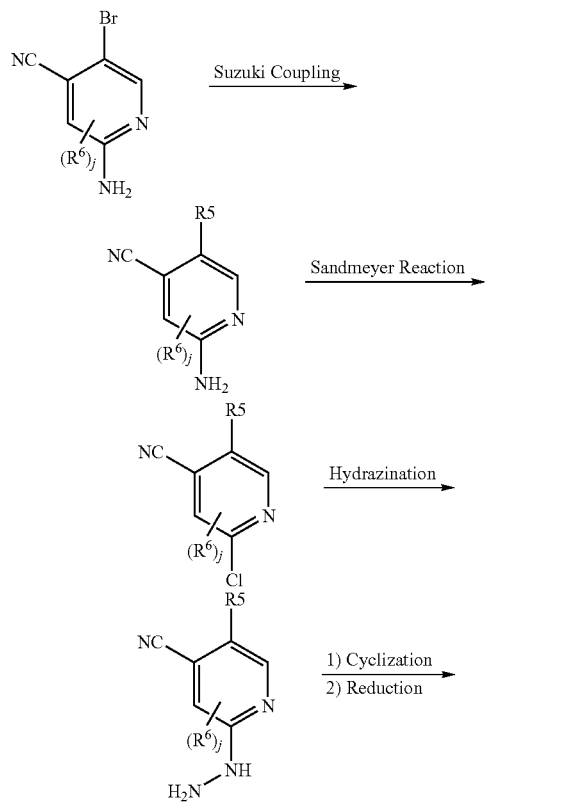

In Scheme D, the Suzuki coupling may be performed using an appropriate boronic acid and Pd(PPh$_3$)$_4$ as a catalyst in a mixture of DME and aqueous Na$_2$CO$_3$ under reflux conditions or by heating in a microwave oven. The Sandmeyer reaction may be carried out with NaNO$_2$ and HCl at low temperature or RT, or with tBuONO and CuCl$_2$ with exclusion of light. Hydrazination may be accomplished using standard procedures with hydrazine in EtOH or dioxane under reflux conditions. The cyclization of appropriately functionalized 2-hydrazino-pyridines may be performed by condensation of the adequate reagent including, but not limited to formic acid, or cyanogen bromide. The reduction of the cyano group may be performed using a BH$_3$-THF complex.

Scheme E illustrates an alternative method for preparing compounds of the invention:

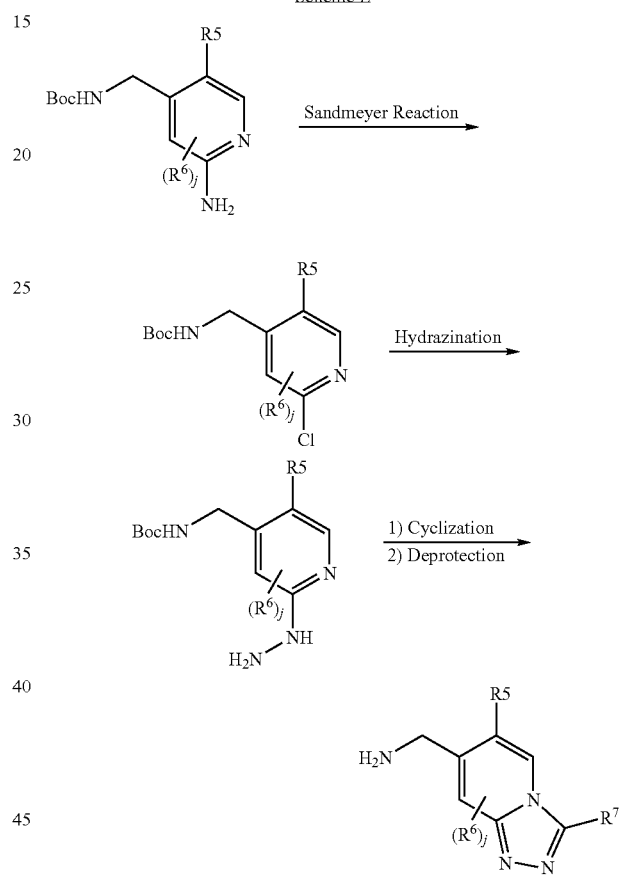

In Scheme E, the conditions used are typically identical to those described in Scheme D for the Sandmeyer reaction, the hydrazination and the cyclization, and in Scheme A for the deprotection.

Scheme F illustrates an alternative method for preparing compounds of the invention:

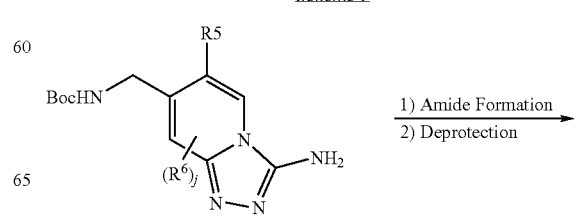

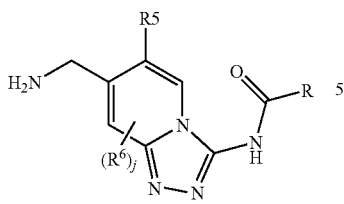

In Scheme F, amide bond may be formed from carboxylic acids by standard methods known in the art, such as using HATU as a coupling reagent. The Boc-deprotection may be performed using similar conditions as those described in respect of Scheme A. Scheme G illustrates an alternative method for preparing compounds of the invention:

Scheme G

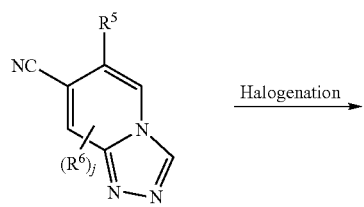

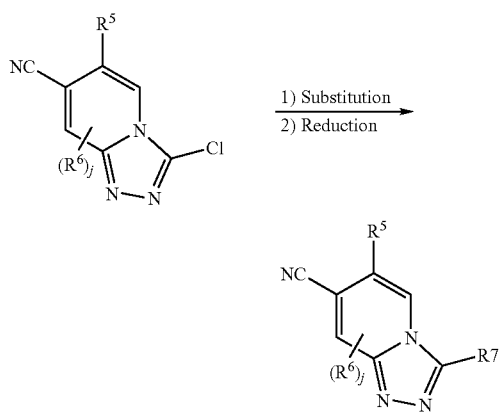

In Scheme G, selective chlorination may be accomplished using standard procedures such as NCS in DMF at 50° C. Substitution of the chlorine by primary or secondary amine may be performed at high temperature, neat or in an appropriate solvent. The reduction of the cyano group may be performed using similar conditions as those described in respect of Scheme D.

Scheme H illustrates an alternative method for preparing compounds of the invention:

Scheme H

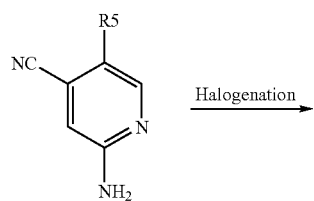

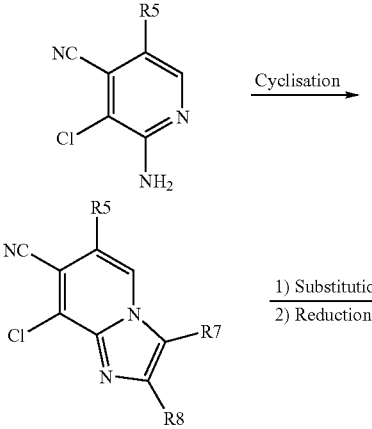

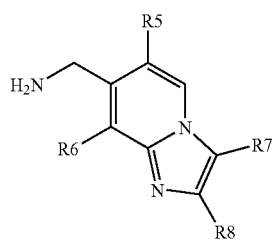

In Scheme H, selective chlorination may be accomplished using standard procedures such as NCS in DMF at 50° C. The cyclization of appropriately functionalized 2-amino-pyridines may be performed using similar conditions as those described in respect of Scheme A. Substitution of the chlorine by primary and secondary amine or alcools may be performed at high temperature in an appropriate solvent, using respectively the free amine and the alcoolat. The reduction of the cyano group may be performed using similar conditions as those described in respect of Scheme D.

Unless otherwise noted, all non-aqueous reactions in the above Schemes are usually carried out under an argon atmosphere with commercial dry solvents.

It will be understood that the processes detailed above and elsewhere herein are solely for the purpose of illustrating the invention and should not be construed as limiting. A process utilising similar or analogous reagents and/or conditions known to one skilled in the art may also be used to obtain a compound of the invention.

Any mixtures of final products or intermediates obtained can be separated on the basis of the physico-chemical differences of the constituents, in a known manner, into the pure final products or intermediates, for example by chromatography, distillation, fractional crystallisation, or by the formation of a salt if appropriate or possible under the circumstances.

Administration and Pharmaceutical Formulations

The compounds of the invention will normally be administered orally, intravenously, subcutaneously, buccally, rectally, dermally, nasally, tracheally, bronchially, by any other parenteral route, as an oral or nasal spray or via inhalation, The compounds may be administered in the form of pharmaceutical preparations comprising prodrug or active compound either as a free compound or, for example, a pharmaceutically acceptable non-toxic organic or inorganic acid or base addition salt, in a pharmaceutically acceptable dosage form. Depending upon the disorder and patient to be treated and the route of administration, the compositions may be administered at varying doses.

Typically, therefore, the pharmaceutical compounds of the invention may be administered orally or parenterally ("parenterally" as used herein, refers to modes of administration which include intravenous, intramuscular, intraperitoneal, intrasternal, subcutaneous and intraarticular injection and infusion) to a host to obtain an protease-inhibitory effect. In the case of larger animals, such as humans, the compounds may be administered alone or as compositions in combination with pharmaceutically acceptable diluents, excipients or carriers.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated and the condition and prior medical history of the patient being treated. However, it is within the skill of the art to start doses of the compound at levels lower than required for to achieve the desired therapeutic effect and to gradually increase the dosage until the desired effect is achieved.

In the treatment, prevention, control, amelioration, or reduction of risk of conditions which require inhibition of DPP-IV enzyme activity, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0 and 1000.0 milligrams of the active ingredient for the symptomatic adjustment of the dosage to the patient to be treated. The compounds may be administered on a regimen of 1 to 4 times per day, preferably once or twice per day. The dosage regimen may be adjusted to provide the optimal therapeutic response.

According to a further aspect of the invention there is thus provided a pharmaceutical composition including a compound of the invention, in admixture with a pharmaceutically acceptable adjuvant, diluent or carrier.

Pharmaceutical compositions of this invention for parenteral injection suitably comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants.

These compositions may also contain adjuvants such as preservative, wetting agents, emulsifying agents and dispersing agents. Prevention of the action of microorganisms may be ensured by the inclusion of various antibacterial and antifungal agents, for example, paraben, chlorobutanol or phenol sorbic acid. It may also be desirable to include isotonic agents such as sugars or sodium chloride, for example. Prolonged absorption of the injectable pharmaceutical form may be brought about by the inclusion of agents (for example aluminum monostearate and gelatin) which delay absorption.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are suitably made by forming microencapsule matrices of the drug in biodegradable polymers, for example polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations may also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use.

Solid dosage forms for oral administration include capsules, tablets, pills, powders and granules. In such solid dosage forms, the active compound is typically mixed with at least one inert, pharmaceutically acceptable excipient or carrier such as sodium citrate or dicalcium phosphate and/or one or more: a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycol, for example.

Suitably, oral formulations contain a dissolution aid. The dissolution aid is not limited as to its identity so long as it is pharmaceutically acceptable. Examples include nonionic surface active agents, such as sucrose fatty acid esters, glycerol fatty acid esters, sorbitan fatty acid esters (e.g. sorbitan trioleate), polyethylene glycol, polyoxyethylene hydrogenated castor oil, polyoxyethylene sorbitan fatty acid esters, polyoxyethylene alkyl ethers, methoxypolyoxyethylene alkyl ethers, polyoxyethylene alkylphenyl ethers, polyethylene glycol fatty acid esters, polyoxyethylene alkylamines, polyoxyethylene alkyl thioethers, polyoxyethylene polyoxypropylene copolymers, polyoxyethylene glycerol fatty acid esters, pentaerythritol fatty acid esters, propylene glycol monofatty acid esters, polyoxyethylene propylene glycol monofatty acid esters, polyoxyethylene sorbitol fatty acid esters, fatty acid alkylolamides, and alkylamine oxides; bile acid and salts thereof (e.g. chenodeoxycholic acid, cholic acid, deoxycholic acid, dehydrocholic acid and salts thereof, and glycine or taurine conjugate thereof); ionic surface active agents, such as sodium laurylsulfate, fatty acid soaps, alkylsulfonates, alkylphosphates, ether phosphates, fatty acid salts of basic amino acids; triethanolamine soap, and alkyl quaternary ammonium salts; and amphoteric surface active agents, such as betaines and aminocarboxylic acid salts.

The solid dosage forms of tablets, dragees, capsules, pills, and granules can be prepared with coatings and shells such as enteric coatings and other coatings well known in the pharmaceutical formulating art. They may optionally contain opacifying agents and may also be of a composition such that they release the active ingredient(s) only, or preferentially, in a certain part of the intestinal tract, and/or in delayed fashion. Examples of embedding compositions include polymeric substances and waxes.

The active compounds may also be in micro-encapsulated form, if appropriate, with one or more of the above-mentioned excipients.

The active compounds may be in finely divided form, for example it may be micronised.

Liquid dosage forms for oral administration include pharmaceutically acceptable emulsions, solutions, suspensions, syrups and elixirs. In addition to the active compounds, the liquid dosage forms may contain inert diluents commonly used in the art such as water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan and mixtures thereof. Besides inert diluents, the oral compositions may also include adjuvants such as wetting agents, emulsifying and suspending agents, sweetening, flavoring and perfuming agents. Suspensions, in addition to the active compounds, may contain suspending agents such as ethoxylated isostearyl alcohols, polyoxyethylene sorbitol and sorbitan esters, microcrystalline cellulose, aluminum metahydroxide, bentonite, agar-agar, and tragacanth and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolisable lipid capable of forming liposomes can be used. The present compositions in liposome form can contain, in addition to a compound of the present invention, stabilisers, preservatives, excipients and the like. The preferred lipids are the phospholipids and the phosphatidyl cholines (lecithins), both natural and synthetic. Methods to form liposomes are known in the art, for example, Prescott, Ed., Methods in Cell Biology, Volume XIV, Academic Press, New York, N.Y. (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants which may be required. Ophthalmic formulations, eye ointments, powders and solutions are also contemplated as being within the scope of this invention.

Advantageously, the compounds of the invention may be orally active, have rapid onset of activity and low toxicity.

The compounds of the invention may have the advantage that they are more efficacious, less toxic, longer acting, have a broader range of activity, more potent, produce fewer side effects, more easily absorbed than, or have other useful pharmacological properties over, compounds known in the prior art.

Combination Therapies

Compounds of the invention may be administered in combination with one or more therapeutic agents. Accordingly, the invention provides a pharmaceutical composition comprising an additional agent. The invention also provides a product comprising a compound of the invention and an agent; as a combined preparation for simultaneous, separate or sequential use in therapy.

In particular, a composition or product of the invention may further comprise a therapeutic agent selected from anti-diabetic agents, hypolipidemic agents, anti-obesity or appetite-regulating agents, anti-hypertensive agents, HDL-increasing agents, cholesterol absorption modulators, Apo-A1 analogues and mimetics, thrombin inhibitors, aldosterone inhibitors, inhibitors of platelet aggregation, estrogen, testosterone, selective estrogen receptor modulators, selective androgen receptor modulators, chemotherapeutic agents, and 5-HT$_3$ or 5-HT$_4$ receptor modulators; or pharmaceutically acceptable salts or prodrugs thereof.

Examples of anti-diabetic agents include insulin, insulin derivatives and mimetics; insulin secretagogues, for example sulfonylureas (e.g. glipizide, glyburide or amaryl); insulinotropic sulfonylurea receptor ligands, for example meglitinides (e.g. nateglinide or repaglinide); insulin sensitisers, for example protein tyrosine phosphatase-1B (PTP-1B) inhibitors (e.g. PTP-112); GSK3 (glycogen synthase kinase-3) inhibitors, for example SB-517955, SB-4195052, SB-216763, N,N-57-05441 or N,N-57-05445; RXR ligands, for example GW-0791 or AGN-194204; sodium-dependent glucose cotransporter inhibitors, for example T-1095; glycogen phosphorylase A inhibitors, for example BAY R3401; biguanides, for example metformin; alpha-glucosidase inhibitors, for example acarbose; GLP-1 (glucagon like peptide-1), GLP-1 analogues and mimetics, for example exendin-4; DPPIV (dipeptidyl peptidase IV) inhibitors, for example DPP728, LAF237 (vildagliptin), MK-0431, saxagliptin or GSK23A; AGE breakers; and thiazolidone derivatives, for example glitazone, pioglitazone, rosiglitazone or (R)-1-{4-[5-methyl-2-(4-trifluoromethyl-phenyl)-oxazol-4-ylmethoxy]-benzenesulfonyl}-2,3-dihydro-1H-indole-2-carboxylic acid (compound 4 of Example 19 of WO 031043985) or a non-glitazone type PPAR-agonist (e.g. GI-262570); or pharmaceutically acceptable salts or prodrugs thereof.

Examples of hypolipidemic agents include 3-hydroxy-3-methyl-glutaryl coenzyme A (HMG-CoA) reductase inhibitors, for example lovastatin, pitavastatin, simvastatin, pravastatin, cerivastatin, mevastatin, velostatin, fluvastatin, dalvastatin, atorvastatin, rosuvastatin or rivastatin; squalene synthase inhibitors; FXR (farnesoid X receptor) ligands;

LXR (liver X receptor) ligands; cholestyramine; fibrates; nicotinic acid; and aspirin; or pharmaceutically acceptable salts or prodrugs thereof.

Examples of anti-obesity/appetite-regulating agents include phentermine, leptin, bromocriptine, dexamphetamine, amphetamine, fenfluramine, dexfenfluramine, sibutramine, orlistat, dexfenfluramine, mazindol, phentermine, phendimetrazine, diethylpropion, fluoxetine, bupropion, topiramate, diethylpropion, benzphetamine, phenylpropanolamine or ecopipam, ephedrine, pseudoephedrine and cannabinoid receptor antagonists (rimonaban); or pharmaceutically acceptable salts or prodrugs thereof.

Examples of anti-hypertensive agents include loop diuretics, for example ethacrynic acid, furosemide or torsemide; diuretics, for example thiazide derivatives, chlorithiazide, hydrochlorothiazide or amiloride; angiotensin converting enzyme (ACE) inhibitors, for example benazepril, captopril, enalapril, fosinopril, lisinopril, moexipril, perinodopril, quinapril, ramipril or trandolapril; Na-K-ATPase membrane pump inhibitors, for example digoxin; neutralendopeptidase (NEP) inhibitors, for example thiorphan, terteo-thiorphan or SQ29072; ECE inhibitors, for example SLV306; dual ACE/NEP inhibitors, for example omapatrilat, sampatrilat or fasidotril; angiotensin II antagonists, for example candesartan, eprosartan, irbesartan, losartan, telmisartan or valsartan; renin inhibitors, for example aliskiren, terlakiren, ditekiren, RO-66-1132 or RO-66-1168; b-adrenergic receptor blockers, for example acebutolol, atenolol, betaxolol, bisoprolol, metoprolol, nadolol, propranolol, sotalol or timolol; inotropic agents, for example digoxin, dobutamine or milrinone; calcium channel blockers, for example amlodipine, bepridil, diltiazem, felodipine, nicardipine, nimodipine, nifedipine, nisoldipine or verapamil; aldosterone receptor antagonists; and aldosterone synthase inhibitors; or pharmaceutically acceptable salts or prodrugs thereof.

Examples of cholesterol absorption modulators include Zetia® and KT6-971, or pharmaceutically acceptable salts or prodrugs thereof.

Examples of aldosterone inhibitors include anastrazole, fadrazole and eplerenone, or pharmaceutically acceptable salts or prodrugs thereof.

Examples of inhibitors of platelet aggregation include aspirin or clopidogrel bisulfate, or pharmaceutically acceptable salts or prodrugs thereof.

Examples of chemotherapeutic agents include compounds decreasing the protein kinase activity, for example PDGF receptor tyrosine kinase inhibitors (e.g. imatinib or 4-methyl-N-[3-(4-methyl-imidazol-1-yl)-5-trifluoromethyl-phenyl]-3-(4-pyridin-3-yl-pyrimidin-2-ylamino)-benzamide), or pharmaceutically acceptable salts or prodrugs thereof.

Examples of 5-$HT_3$ or 5-$HT_4$ receptor modulators include tegaserod, tegaserod hydrogen maleate, cisapride or cilansetron, or pharmaceutically acceptable salts or prodrugs thereof.

The weight ratio of the compound of the present invention to the further active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200.

Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

Use

Compounds of the invention may be useful in the therapy of a variety of diseases and conditions.

In particular, compounds of the invention may be useful in the treatment or prevention of a disease or condition selected from non-insulin-dependent diabetes mellitus, arthritis, obesity, allograft transplantation, osteoporosis, heart failure, impaired glucose metabolism or impaired glucose tolerance, neurodegenerative diseases (for example Alzheimer's disease or Parkinson disease), cardiovascular or renal diseases (for example diabetic cardiomyopathy, left or right ventricular hypertrophy, hypertrophic medial thickening in arteries and/or in large vessels, mesenteric vasculature hypertrophy or mesanglial hypertrophy), neurodegenerative or cognitive disorders, hyperglycemia, insulin resistance, lipid disorders, dyslipidemia, hyperlipidemia, hypertriglyceridemia, hypercholesterolemia, low HDL levels, high LDL levels, atherosclerosis, vascular restenosis, irritable bowel syndrome, inflammatory bowel disease (e.g. Crohn's disease or ulcerative colitis), pancreatitis, retinopathy, nephropathy, neuropathy, syndrome X, ovarian hyperandrogenism (polycystic ovarian syndrome), type 2 diabetes, growth hormone deficiency, neutropenia, neuronal disorders, tumor metastasis, benign prostatic hypertrophy, gingivitis, hypertension and osteoporosis.

The compounds may also be useful in producing a sedative or anxiolytic effect, attenuating post-surgical catabolic changes or hormonal responses to stress, reducing mortality and morbidity after myocardial infarction, modulating hyperlipidemia or associated conditions; and lowering VLDL, LDL or Lp(a) levels.

EXAMPLES

The following Examples illustrate the invention.
Abbreviations:
AcOEt ethyl acetate
$BH_3$.THF borane tetrahydrofuran complex
$Boc_2O$ di-tert-butyl dicarbonate
BrCN cyanogen bromide
$CHCl_3$ chloroform
$CuCl_2$ copper(II) chloride
DCE 1,2-dichloroethane
DCM dichloromethane
DIPEA N,N-diisopropylethylamine
DMAP 4-dimethylaminopyridine
DME 1,2-dimethoxyethane
DMF N,N-dimethylformamide
DMSO dimethylsulfoxide
EtMgBr ethylmagnesium bromide
$Et_3N$ triethylamine
$Et_2O$ diethylether
EtOH ethanol
h hour
HATU O-(7-azabenzotriazol-1-yl)-N,N,N',N'-tetramethyluronium hexafluorophosphate
HCl hydrochloric acid
$HNO_3$ nitric acid
HPLC high pressure liquid chromatography
$H_2SO_4$ sulfuric acid
KOH potassium hydroxide
$LiBH_4$ lithium borohydride
LiOH lithium hydroxide mCPBA 3-chloroperbenzoic acid
MeCN acetonitrile
MeOH methanol
MnO$_2$ manganese(IV) oxide
MS mass spectroscopy
MW microwave
Na$_2$CO$_3$ sodium carbonate
NaH sodium hydride
NaHCO$_3$ sodium hydrogencarbonate
NaIO$_4$ sodium (meta)periodate
NaNO$_2$ sodium nitrite
NaOH sodium hydroxide
NaOMe sodium methoxide
Na$_2$SO$_4$ sodium sulfate
NBS N-bromosuccinimide
NCS N-chlorosuccinimide
NH$_3$ ammonia
NH$_4$Cl ammonium chloride
Pd/C palladium over charcoal
PdCl$_2$(PPh$_3$)$_2$ dichloro-bis-triphenylphosphinepalladium(II)
Pd(PPh$_3$)$_4$ tetrakis(triphenylphosphine)palladium
R$_F$ retention factor
RT room temperature
SiO$_2$ silica
SnCl$_2$ tin(II) chloride
TBAF tetrabutylammonium fluoride
TBME tert-butyl-methylether
tBuOH tert-butanol
tBuONO tert-butyl nitrite
TFA trifluoroacetic acid
THF tetrahydrofuran
TLC thin layer chromatography
ZnBr$_2$ zinc bromide
prep-HPLC preparative high pressure liquid chromatography; *Waters system.* Column: reversed phase SunFire™ Prep (100×30 mm), C18 OBD, 5 μM. Gradient elution (CH$_3$CN/water with 0.1% TFA), generally product obtained as a TFA salt after lyophilization.
HPLC Conditions:
$^A$t$_{Ret}$: retention time [min] for System A: Linear gradient 5-100% CH$_3$CN and H$_2$O (0.1% TFA) in 4 min+0.5 min 100% CH$_3$CN; PDA MaxPlot detection (210.0 nm to 400.0 nm), flow rate 3 ml/min at 35° C. Column: Sunfire™ (4.6×20 mm) C18, 3.5 μm.

Example 1

C-(6-Phenyl-imidazo[1,2-a]pyridin-7-yl)-methylamine

Compound 1 was prepared according to Scheme 1;

Scheme 1

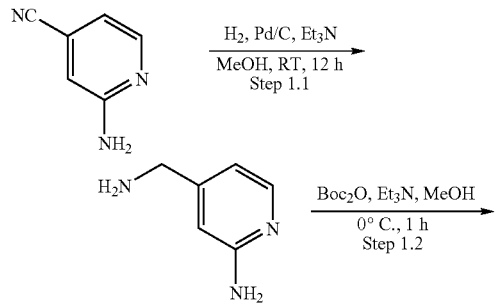

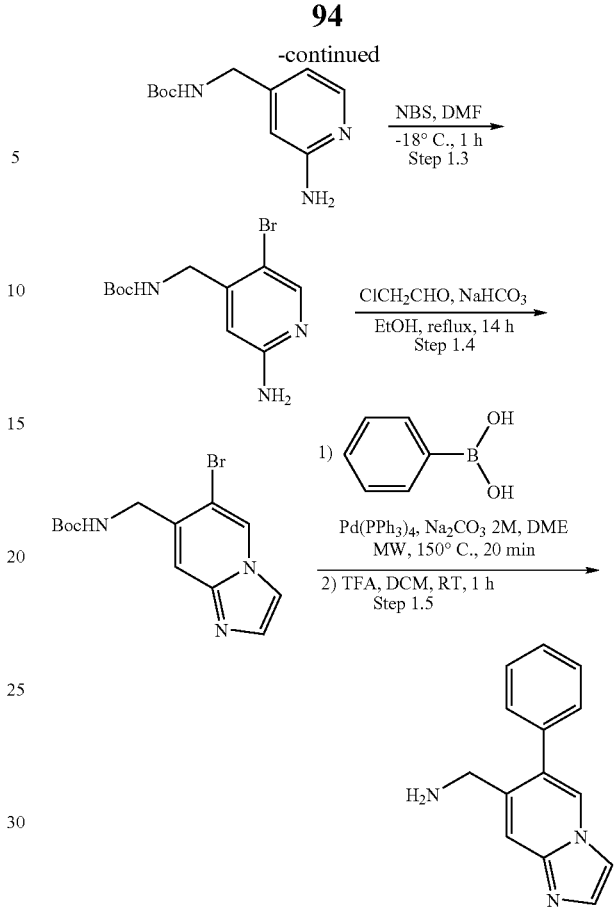

Step 1.1:4-Aminomethyl-pyridin-2-ylamine.

In a sealed flask, a well stirred mixture of 2-amino-isonicotinonitrile (12.6 g, 106.0 mmol), Et$_3$N (98 mL) and Pd/C 10% (15.0 g) in EtOH (400 mL) was placed under an H$_2$ atmosphere (50 psi) and hydrogenated at RT for 12 h. The catalyst was filtered through a Celite pad and washed with MeOH. The filtrate was concentrated to dryness to yield the title compound (11.6 g, 94.2 mmol, 89%) as a white solid, which was used without further purification. MS: 122 [M−1]$^+$; HPLC: $^A$t$_{Ret}$=0.16.

Step 1.2: (2-Amino-pyridin-4-ylmethyl)-carbamic acid tert-butyl ester

To a solution of 4-aminomethyl-pyridin-2-ylamine (11.36 g, 92.2 mmol) and Et$_3$N (16.7 mL, 120.0 mmol) in MeOH (150 mL) was added a solution of Boc$_2$O (20.2 g, 92.2 mmol) in MeOH (20 mL) at 0° C. The reaction mixture was stirred at 0° C. for 1 h and concentrated under vacuum. The residue was dissolved in AcOEt (800 mL) and washed with water (200 mL) and brine (100 mL). The organic layer was dried over Na$_2$SO$_4$, filtered, and evaporated to dryness to yield the crude title compound (17.55 g) as a yellow foam, which was used without further purification. MS: 224 [M+1]$^+$; HPLC: $^A$t$_{Ret}$=0.88.

Step 1.3: (2-Amino-5-bromo-pyridin-4-ylmethyl)-carbamic acid tert-butyl ester

A solution of crude (2-amino-pyridin-4-ylmethyl)-carbamic acid tertbutyl ester (17.55 g) in DMF (50 mL) was cooled to −18° C. (ice/MeOH bath), treated with NBS (12.6 g, 70.7 mmol), and stirred at −18° C. for 1 h. The reaction mixture was diluted in AcOEt (800 mL) and washed with water (2×100 mL) and brine (50 mL). The organic layer was dried over Na$_2$SO$_4$, filtered and evaporated. The residue was purified by Combi-Flash Companion™ (Isco Inc.) column chromatography (SiO$_2$; gradient elution, hexane/DCM/TBME 100:10:1→TBME 100%) to yield the title compound (13.95 g, 46.2 mmol, 50% for 2 steps) as a pale yellow solid. MS: 303 [M+1]$^+$ HPLC: $^A$t$_{Ret}$=1.10; TLC: RF 0.18 (hexane/DCM/TBME 1:1:2).

Step 1.4: (6-Bromo-imidazo[1,2-a]pyridin-7-ylmethyl)-carbamic acid tert-butyl ester A mixture of (2-amino-5-bromo-pyridin-4-ylmethyl)-carbamic acid tert-butyl ester (1.0 g, 3.3 mmol), NaHCO$_3$ (474 mg, 5.6 mmol) and chloracetaldehyde (2.2 mL, 15.0 mmol) was vigorously stirred and refluxed for 14 h. The reaction mixture was cooled to RT, concentrated under vacuum and the remaining residue was suspended in DCM and brine. The aqueous layer was separated and extracted with DCM (5×), and the combined organic fractions were dried over Na$_2$SO$_4$, filtered, and evaporated. The residue was purified by Combi-Flash Companion™ (Isco Inc.) column chromatography (SiO$_2$; gradient elution, hexane/DCM/TBME 10:10:1→1:1:18) to yield the title compound (860 mg, 2.6 mmol, 79%) as a pale yellow solid. MS: 327 [M+1]$^+$; HPLC: $^A$t$_{Ret}$=1.07; TLC: R$_F$ 0.16 (hexane/DCM/TBME 1:1:2).

Step 1.5

(1) In a sealed tube, a mixture of (6-bromo-imidazo[1,2-a]pyridin-7-ylmethyl)-carbamic acid tert-butyl ester (40 mg, 0.12 mmol), phenylboronic acid (22 mg, 0.18 mmol), Pd(PPh$_3$)$_4$ (7 mg, 0.006 mmol) and Na$_2$CO$_3$ (2.0 M solution in water, 0.21 mL) in DME (0.50 mL) was heated at 150° C. for 20 min in a microwave oven. The reaction mixture was cooled to RT, filtered through a Florisil pad and the filter cake was washed with AcOEt. The filtrate was dried over Na$_2$SO$_4$, filtered, and evaporated.

(2) The residue was dissolved in DCM (2 mL) and TFA (1 mL) and the solution was stirred at RT for 1 h. The reaction mixture was concentrated to dryness and the remaining residue purified by reverse phase prep-HPLC (Waters system) to give the title compound (2TFA salt, 15 mg, 0.033 mmol, 28% for 2 steps) as a white solid. MS: 224 [M+1]$^+$; HPLC: $^A$t$_{Ret}$=0.44.

Example 2

Compounds 2a to 2e were obtained analogously to Example 1, using various phenylboronic acid derivatives in Step 1.5. The compounds are of the following general formula:

| Compound | Name | R$^5$ | HPLC $^A$t$_{Ret}$ [min] | MS [M + 1]$^+$ |
|---|---|---|---|---|
| 2a | C-[6-(2,4-Dimethyl-phenyl)-imidazo[1,2-a]pyridin-7-yl]-methylamine | 2,4-dimethylphenyl | 0.78 | 252 |
| 2b | C-[6-(2-Chloro-4-methyl-phenyl)-imidazo[1,2-a]pyridin-7-yl]-methylamine | 2-chloro-4-methylphenyl | 0.80 | 272 |
| 2c | C-[6-(4-Chloro-2-methyl-phenyl)-imidazo[1,2-a]pyridin-7-yl]-methylamine | 4-chloro-2-methylphenyl | 0.83 | 272 |
| 2d | C-[6-(4-Chloro-2-methoxy-phenyl)-imidazo[1,2-a]pyridin-7-yl]-methylamine | 4-chloro-2-methoxyphenyl | 0.81 | 288 |

-continued
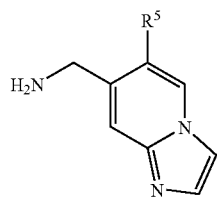
| Compound | Name | R[5] | HPLC $^A t_{Ret}$ [min] | MS [M + 1]+ |
|---|---|---|---|---|
| 2e | C-[6-(2,4,5-Trifluoro-phenyl)-imidazo[1,2-a]pyridin-7-yl]-methylamine | (2,4,5-trifluorophenyl) | 0.57 | 278 |
Example 3
C-[6-(2,4-Dichloro-phenyl)-3-m-tolyl-imidazo[1,2-a]pyridin-7-yl]-methylamine
Compound 3 was prepared according to Scheme 2:
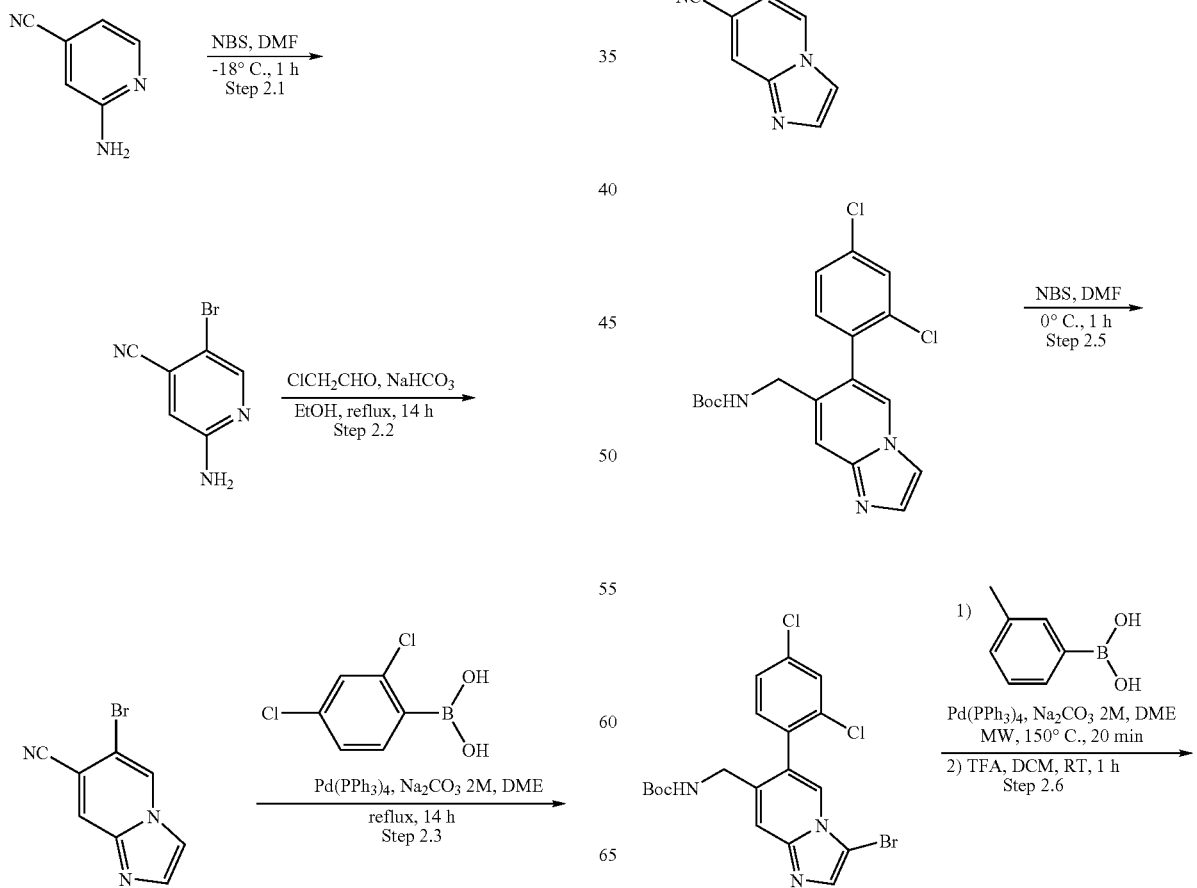

-continued

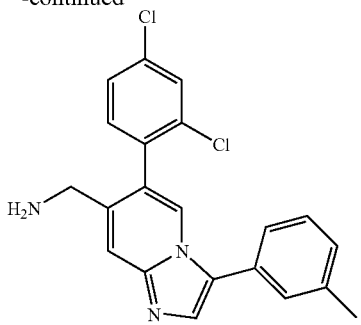

Step 2.1: 2-Amino-5-bromo-isonicotinonitrile

A solution of 2-amino-isonicotinonitrile (10.0 g, 83.9 mmol) in DMF (20 mL) was cooled to −18° C. (ice/MeOH bath), treated with NBS (16.5 g, 92.3 mmol), and stirred at −18° C. for 1 h. The reaction mixture was diluted in AcOEt (500 mL) and washed with water (200 mL). The aqueous phase was separated and extracted with AcOEt (2×500 ml). The combined organic fractions were dried over $Na_2SO_4$, filtered and evaporated. The residue was purified by Combi-Flash Companion™ (Isco Inc.) column chromatography ($SiO_2$; gradient elution, [hexane/DCM 1:1]/TBME 98:2→6:4) to yield the title compound (13.0 g, 65.6 mmol, 78%) as a pale yellow solid. MS: 199 $[M+1]^+$; HPLC: $^At_{Ret}=1.13$; TLC: RF 0.39 (hexane/DCM/TBME 1:1:2).

Step 2.2: 6-Bromo-imidazo[1,2-a]pyridine-7-carbonitrile

A mixture of 2-amino-5-bromo-isonicotinonitrile (5.0 g, 25.3 mmol), $NaHCO_3$ (3.6 g, 42.9 mmol) and chloracetaldehyde (17.0 mL, 114.0 mmol) in EtOH (160 mL) was vigorously stirred and refluxed for 14 h. The reaction mixture was cooled to RT, concentrated under vacuum and the remaining residue was suspended in DCM (500 mL) and brine (100 mL). The aqueous layer was separated and extracted with DCM (5×), and the combined organic fractions were dried over $Na_2SO_4$, filtered, and evaporated. The residue was purified by Combi-Flash Companion™ (Isco Inc.) column chromatography ($SiO_2$; gradient elution, [hexane/DCM 1:1]/TBME 95:5→3:7) to yield the title compound (2.97 g, 13.4 mmol, 53%) as an orange solid. MS: 223 $[M+1]^+$; HPLC: $^At_{Ret}=0.54$; TLC: $R_F$ 0.17 (hexane/DCM/TBME 1:1:2).

Step 2.3: 6-(2,4-Dichloro-phenyl)-imidazo[1,2-a]pyridine-7-carbonitrile

A mixture of 6-bromo-imidazo[1,2-a]pyridine-7-carbonitrile (1.5 g, 6.8 mmol), 2,4-dichloro-benzeneboronic acid (1.9 g, 10.1 mmol), $Pd(PPh_3)_4$ (390 mg, 0.34 mmol) and $Na_2CO_3$ (2.0 M solution in water, 12 mL) in OME (30 mL) was refluxed for 14 h under an inert atmosphere of argon. The reaction mixture was cooled to RT, diluted in AcOEt (200 mL) and washed with water (200 mL). The organic layer was dried over $Na_2SO_4$, filtered, and evaporated. The residue was purified by Combi-Flash Companion™ (isco Inc.) column chromatography ($SiO_2$; gradient elution, [hexane/DCM 1:1]/TBME 95:5→1:1) to yield the title compound (750 mg, 2.6 mmol, 39%) as an orange foam. MS: 289 $[M+1]^+$; HPLC: $^At_{Ret}=1.50$; TLC: $R_F$ 0.16 ([hexane/DCM 1:1]/TBME 3:7).

Step 2.4: [6-(2,4-Dichloro-phenyl)-imidazo[1,2-a]pyridin-7-ylmethyl]-carbamic acid tert-butyl ester (1) In a sealed flask, a solution of 6-(2,4-dichloro-phenyl)-imidazo[1,2-a]pyridine-7-carbonitrile (750 mg, 2.6 mmol) in THF (20 mL) was cautiously added to well stirred $BH_3$.THF complex (1.0 M solution in THF, 13 mL, 13.0 mmol) at 0° C. The reaction mixture was heated at 40° C. for 1 h and cooled to RT. MeOH (large excess) and Amberlyst 15 (35 g) were successively added and the resulting mixture was shaken at RT for 30 min. The resin was filtered, washed with MeOH (500 mL), and the desired compound was released with ammonia (1.0 M solution in MeOH, 1.2 L). The $NH_3$-MeOH fraction was evaporated to yield the crude C-[6-(2,4-dichloro-phenyl)-imidazo[1,2-a]pyridin-7-yl]-methylamine (778 mg) as a yellow oil.

(2) To a solution of the crude (778 mg) and $Et_3N$ (0.47 mL, 3.4 mmol) in MeOH (20 mL) was added a solution of $Boc_2O$ (599 mg, 2.7 mmol) in MeOH (2 mL) at RT. The reaction mixture was stirred at RT for 1 h and concentrated under vacuum. The residue was dissolved in AcOEt (125 mL) and washed with a 0.5 M aqueous HCl solution (2×50 mL) and brine (50 mL). The organic layer was dried over $Na_2SO_4$, filtered, and evaporated to dryness to yield the crude title compound (671 mg, 1.7 mmol, 66%) as a brownish foam, which was used without further purification. MS: 393 $[M+1]^+$; HPLC: $^At_{Ret}=1.70$.

Step 2.5: [3-Bromo-6-(2,4-dichloro-phenyl)-imidazo[1,2-a]pyridin-7-ylmethyl]-carbamic acid tert-butyl ester A solution of [6-(2,4-dichloro-phenyl)-imidazo[1,2-a]pyridin-7-ylmethyl]-carbamic acid tert-butyl ester (543 mg, 1.38 mmol) in DMF (5 mL) was cooled to 0° C., treated with NBS (222 mg, 1.25 mmol), and stirred at 0° C. for 1 h. The reaction mixture was diluted in AcOEt and washed with water and brine. The organic layer was dried over $Na_2SO_4$, filtered and evaporated. The residue was purified by Combi-Flash Companion™ (Isco Inc.) column chromatography ($SiO_2$; gradient elution, [hexane/DCM 1:1]/TBME 95:5→6:4) to yield the title compound (435 mg, 0.92 mmol, 67%) as a beige foam. MS: 472 $[M+1]^+$; HPLC: $^At_{Ret}=1.93$; TLC: $R_F$ 0.50 (hexane/DCM/TBME 1:1:2).

Step 2.6

(1) In a sealed tube, a mixture of [3-bromo-6-(2,4-dichloro-phenyl)-imidazo[1,2-a]pyridin-7-ylmethyl]-carbamic acid tert-butyl ester (40 mg, 0.08 mmol), m-tolylboronic acid (17 mg, 0.13 mmol), $Pd(PPh_3)_4$ (5 mg, 0.004 mmol) and $Na_2CO_3$ (2.0 M solution in water, 0.15 mL) in DME (0.50 mL) was heated at 150° C. for 20 min in a microwave oven. The reaction mixture was cooled to RT, filtered through a Florisil pad and the filter cake was washed with AcOEt. The filtrate was dried over $Na_2SO_4$, filtered, and evaporated to dryness.

(2) The residue was dissolved in DCM (2 mL) and TFA (1 mL) and the solution was stirred at RT for 1 h. The reaction mixture was concentrated to dryness and the remaining residue purified by reverse phase prep-HPLC (Waters system) to give the title compound (2TFA salt, 24 mg, 0.039 mmol, 49% for 2 steps) as a white solid. MS: 383 $[M+1]^+$; HPLC: $^At_{Ret}=1.45$.

Example 4

Compounds 4a to 4k were obtained analogously to Example 3, using various phenylboronic acid derivatives in Step 2.6. The compounds are of the following general formula:

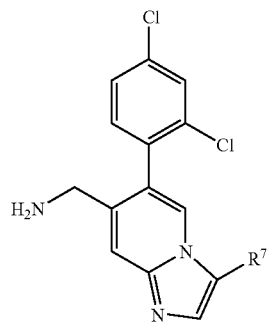

| Compound | Name | R⁷ | HPLC $^A t_{Ret}$ [min] | MS [M + 1]⁺ |
|---|---|---|---|---|
| 4a | C-[6-(2,4-Dichloro-phenyl)-3-phenyl-imidazo[1,2-a]pyridin-7-yl]-methylamine | phenyl | 1.19 | 369 |
| 4b | C-[6-(2,4-Dichloro-phenyl)-3-(3-fluoro-phenyl)-imidazo[1,2-a]pyridin-7-yl]-methylamine | 3-fluorophenyl | 1.40 | 387 |
| 4c | C-[6-(2,4-Dichloro-phenyl)-3-(4-fluoro-phenyl)-imidazo[1,2-a]pyridin-7-yl]-methylamine | 4-fluorophenyl | 1.37 | 387 |
| 4d | C-[6-(2,4-Dichloro-phenyl)-3-(3,4-difluoro-phenyl)-imidazo[1,2-a]pyridin-7-yl]-methylamine | 3,4-difluorophenyl | 1.44 | 405 |
| 4e | C-[6-(2,4-Dichloro-phenyl)-3-(3,4-dimethoxy-phenyl)-imidazo[1,2-a]pyridin-7-yl]-methylamine | 3,4-dimethoxyphenyl | 1.30 | 429 |
| 4f | C-[6-(2,4-Dichloro-phenyl)-3-pyridin-4-yl-imidazo[1,2-a]pyridin-7-yl]-methylamine | pyridin-4-yl | 0.83 | 370 |
| 4g | C-[6-(2,4-Dichloro-phenyl)-3-pyridin-3-yl-imidazo[1,2-a]pyridin-7-yl]-methylamine | pyridin-3-yl | 0.91 | 370 |
| 4h | C-[6-(2,4-Dichloro-phenyl)-3-(3,5-dimethoxy-phenyl)-imidazo]1,2-a]pyridin-7-yl)-methylamine | 3,5-dimethoxyphenyl | 1.44 | 429 |
| 4i | C-[6-(2,4-Dichloro-phenyl)-3-(2-methoxy-phenyl)-imidazo[1,2-a]pyridin-7-yl]-methylamine | 2-methoxyphenyl | 1.20 | 399 |

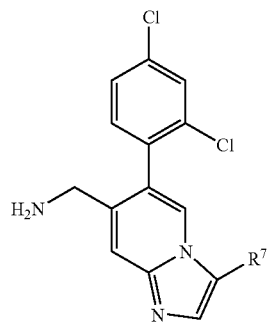

| Compound | Name | R⁷ | HPLC $^At_{Ret}$ [min] | MS [M + 1]⁺ |
|---|---|---|---|---|
| 4j | C-[6-(2,4-Dichloro-phenyl)-3-(6-morpholin-4-yl-pyridin-3-yl)-imidazo[1,2-a]pyridin-7-yl]-methylamine | | 1.06 | 454 |
| 4k | C-[6-(2,4-Dichloro-phenyl)-3-(2-morpholin-4-yl-pyridin-4-yl)-imidazo[1,2-a]pyridin-7-yl]-methylamine | | 0.98 | 454 |

Example 5

C-[6-(2,4-Dichloro-phenyl)-imidazo[1,2-a]pyridin-7-yl]-methylamine

A solution of [6-(2,4-dichloro-phenyl)-imidazo[1,2-a]pyridin-7-ylmethyl]-carbamic acid tert-butyl ester (30 mg, 0.07 mmol) in DCM (2 mL) and TFA (1 mL) was stirred at RT for 30 min, then concentrated to dryness. The remaining residue was purified by reverse phase prep-HPLC (Waters system) to give the title compound (2 TFA salt, 19 mg, 0.037 mmol, 52%) as a white solid. MS: 293 [M+1]⁺; HPLC: $^At_{Ret}$=0.84.

Example 6

[7-Aminomethyl-6-(2,4-dichloro-phenyl)-imidazo[1,2-a]pyridin-3-yl]-ethyl-methyl-amine Compound 6 was prepared according to Scheme 3:

Scheme 3

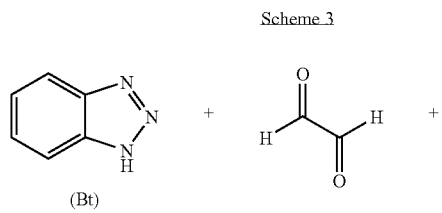

a)

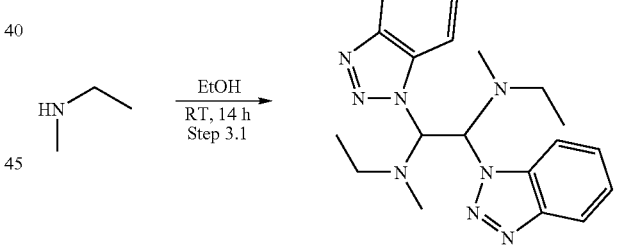

b)

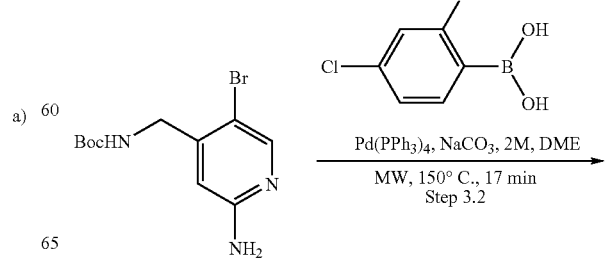

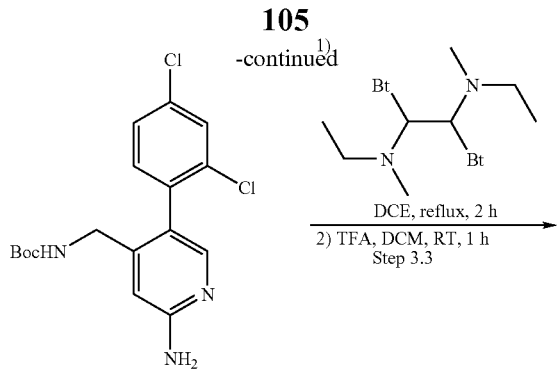

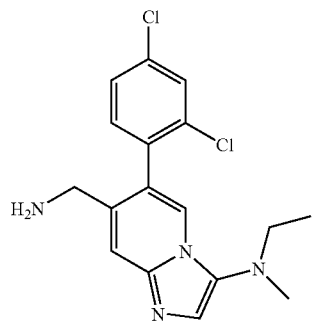

Step 3.1: 1,2-Bis-benzotriazol-1-yl-N,N'-diethyl-N,N'-dimethyl-ethane-1,2-diamine According to the procedure published by Katritzky and al. (*J. Org. Chem.*, 1990, 55, 3209-3213), a mixture of ethyl-methyl-amine (0.10 mL, 1.2 mmol) and 1H-benzotriazole (144 mg, 1.2 mmol) in EtOH (2 mL) was stirred at RT for 5 min. Glyoxal (40 wt. % in water, 0.07 mL, 0.6 mmol) was then added, the mixture was stirred at RT for 14 h and evaporated to dryness to give the crude title compound as a brown oil which was used without further purification.

Step 3.2: [2-amino-5-(2,4-dichloro-phenyl)-pyridin-4-ylmethyl]-carbamic acid tert-butyl ester In a sealed tube, a mixture of (2-amino-5-bromo-pyridin-4-ylmethyl)-carbamic acid tert-butyl ester (4.48 g, 14.8 mmol, prepared according to Example 1, Step 1.3), 2,4-dichloro-benzeneboronic acid (4.24 g, 22.2 mmol), Pd(PPh$_3$)$_4$ (855 mg, 0.74 mmol) and Na$_2$CO$_3$ (2.0 M solution in water, 26 mL, 52.0 mmol) in DME (50 mL) was heated at 150° C. for 17 min in a microwave oven. The reaction mixture was cooled to RT, diluted in AcOEt and washed with water. The organic layer was dried over Na$_2$SO$_4$, filtered and evaporated. The residue was purified by Combi-Flash Companion™ (Isco Inc.) column chromatography (SiO$_2$; gradient elution, [hexane/DCM 1:1]/TBME 95:5→100% TBME) to yield the title compound (3.2 g, 8.7 mmol, 59%) as a white solid. MS: 368 [M−1]$^+$; HPLC: $^A$t$_{Ret}$=1.69.

Step 3.3

(1) A mixture of [2-amino-5-(2,4-dichloro-phenyl)-pyridin-4-ylmethyl]-carbamic acid tert-butyl ester (50 mg, 0.14 mmol) and 1,2-bis-benzotriazol-1-yl-N,N'-diethyl-N,N'-dimethyl-ethane-1,2-diamine (51 mg, 0.14 mmol) in DCE (1.5 mL) was refluxed for 2 h, then cooled to RT. Powdered KOH (29.2 mg, 0.45 mmol) was added, the mixture was stirred at RT for 30 min and filtered. The solid was washed with CHCl$_3$ and the filtrate was concentrated to dryness. The remaining residue was purified by reverse phase prep-HPLC (Waters system) to give the Boc-protected intermediate (TFA salt) as a white solid. MS: 450 [M+1]$^+$; HPLC: $^A$t$_{Ret}$=2.00.

(2) The Boc-protected compound was dissolved in DCM (2 mL) and TFA (1 mL) and the solution was stirred at RT for 1 h. The reaction mixture was concentrated to dryness and the remaining residue purified by reverse phase prep-HPLC (Waters system) to give the title compound (2TFA salt, 23 mg, 0.040 mmol, 29% for 2 steps) as a white solid. MS: 350 [M+1]$^+$; HPLC: $^A$t$_{Ret}$=1.27.

Example 7

[7-Aminomethyl-6-(2,4-dichloro-phenyl)-imidazo[1,2-a]pyridin-3-yl]-(2-methoxy-ethyl)-methyl-amine (1) The TFA salt was obtained analogously to Example 6 from [2-amino-5-(2,4-dichloro-phenyl)-pyridin-4-ylmethyl]-carbamic acid tert-butyl ester (50 mg, 0.14 mmol) and 1,2-bis-benzotriazol-1-yl-N,N'-bis-(2-methoxy-ethyl)-N,N'-dimethyl-ethane-1,2-diamine (59.5 mg, 0.14 mmol) and subsequent Boc-deprotection and reverse phase prep-HPLC (Waters system) purification.

(2) The TFA salt was dissolved in HCl (2.0 M solution in dioxane), stirred for 5 min at RT, and evaporated to dryness (the sequence was performed twice). The remaining residue was dissolved in t-BuOH and lyophilized to give the HCl salt of the title compound (2HCl salt, 34 mg, 0.075 mmol, 55% for 2 steps) as an off-white solid. MS: 380 [M+1]$^+$; HPLC: $^A$t$_{Ret}$=1.19.

Example 8

Compounds 8a to 8c' were obtained as TFA or HCl salts, using procedures analogous to those of Examples 6 and 7. Adequate boronic acid was used for the Suzuki coupling and adequate freshly prepared bis-benzotriazol-1,2-diamine was used for the cyclization step.

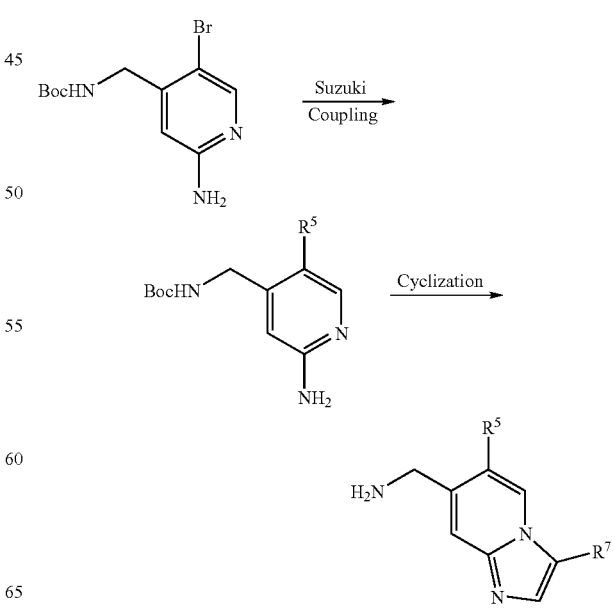

| Compound | Name | R⁵ | R⁷ | HPLC ᴬt_Ret [min] | MS [M + 1]⁺ |
|---|---|---|---|---|---|
| 8a | [7-Aminomethyl-6-(2,4-dichloro-phenyl)-imidazo[1,2-a]pyridin-3-yl]-dimethyl-amine | 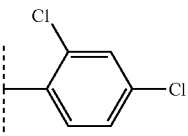 |  | 1.14 | 336 |
| 8b | [7-Aminomethyl-6-(2,4-dichloro-phenyl)-imidazo[1,2-a]pyridin-3-yl]-cyclopropylmethyl-propyl-amine | 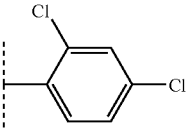 | 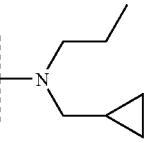 | 1.63 | 404 |
| 8c | C-[6-(2,4-Dichloro-phenyl)-3-piperidin-1-yl-imidazo[1,2-a]pyridin-7-yl]methylamine | 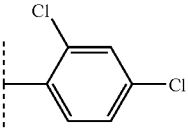 | 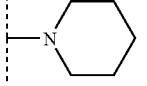 | 1.39 | 376 |
| 8d | C-[6-(2,4-Dichloro-phenyl)-3-thiomorpholin-4-yl-imidazo[1,2-a]pyridin-7-yl]-methylamine | 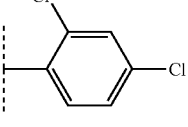 | 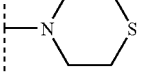 | 1.30 | 394 |
| 8e | C-[6-(2,4-Dichloro-phenyl)-3-(4-methyl-piperazin-1-yl)-imidazo[1,2-a]pyridin-7-yl]-methylamine | 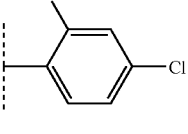 | 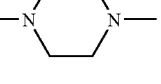 | 0.74 | 391 |
| 8f | C-[6-(2,4-Dichloro-phenyl)-3-piperazin-1-yl-imidazo[1,2-a]pyridin-7-yl]-methylamine | 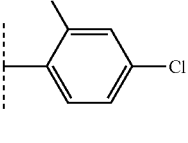 | 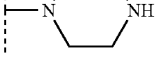 | 0.71 | 377 |
| 8g | C-[6-(2,4-Dichloro-phenyl)-3-morpholin-4-yl-imidazo[1,2-a]pyridin-7-yl]-methylamine | 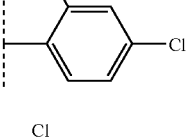 | 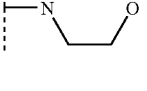 | 1.09 | 378 |
| 8h | 4-[7-Aminomethyl-6-(2,4-dichloro-phenyl)-imidazo[1,2-a]pyridin-3-yl]-piperazin-2-one | 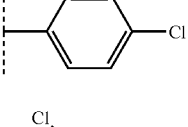 | 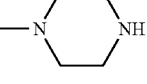 | 0.88 | 391 |
| 8i | {[7-Aminomethyl-6-(2,4-dichloro-phenyl)-imidazo[1,2-a]pyridin-3-yl]-methyl-amino}-acetic acid ethyl ester | 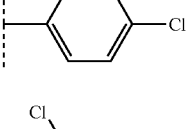 | 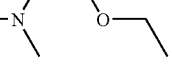 | 1.29 | 408 |
| 8j | C-[6-(2-Chloro-4-methyl-phenyl)-3-morpholin-4-yl-imidazo[1,2-a]pyridin-7-yl]-methylamine | 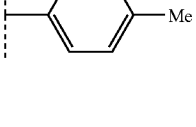 | 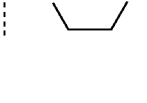 | 1.04 | 357 |

-continued

| Compound | Name | R⁵ | R⁷ | HPLC $^At_{Ret}$ [min] | MS [M + 1]⁺ |
|---|---|---|---|---|---|
| 8k | C-[6-(2-Chloro-4-methyl-phenyl)-3-piperazin-1-yl-imidazo[1,2-a]pyridin-7-yl]-methylamine | 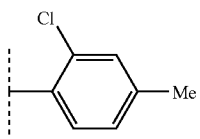 | 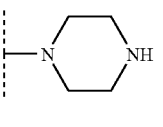 | 0.65 | 356 |
| 8l | C-[6-(2-Chloro-4-methyl-phenyl)-3-(4-methyl-piperazin-1-yl)-imidazo[1,2-a]pyridin-7-yl]-methylamine | 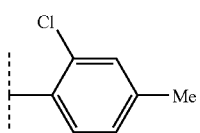 | 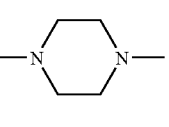 | 0.68 | 370 |
| 8m | C-[6-(4-Chloro-2-methyl-phenyl)-3-morpholin-4-yl-imidazo[1,2-a]pyridin-7-yl]-methylamine | 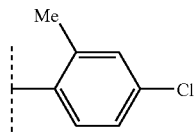 | 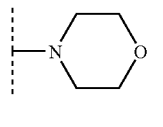 | 1.08 | 357 |
| 8n | C-[6-(4-Chloro-2-methyl-phenyl)-3-piperazin-1-yl-imidazo[1,2-a]pyridin-7-yl]-methylamine | 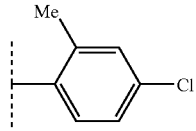 | 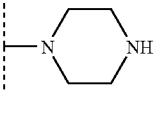 | 0.69 | 356 |
| 8o | C-[6-(4-Chloro-2-methyl-phenyl)-3-(4-methyl-piperazin-1-yl)-imidazo[1,2-a]pyridin-7-yl]-methylamine | 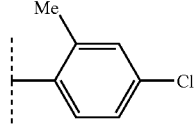 | 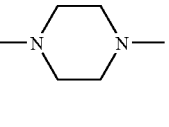 | 0.73 | 370 |
| 8p | C-[6-(2,4-Dimethyl-phenyl)-3-morpholin-4-yl-imidazo[1,2-a]pyridin-7-yl]-methylamine | 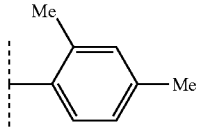 | 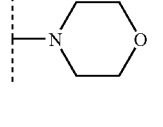 | 1.05 | 337 |
| 8q | C-[6-(2,4-Dimethyl-phenyl)-3-piperazin-1-yl-imidazo[1,2-a]pyridin-7-yl]-methylamine | 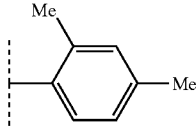 | 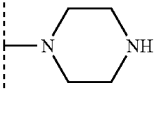 | 0.64 | 336 |
| 8r | C-[6-(2,4-Dimethyl-phenyl)-3-(4-methyl-piperazin-1-yl)-imidazo[1,2-a]pyridin-7-yl]-methylamine | 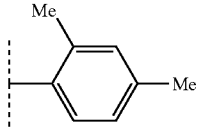 | 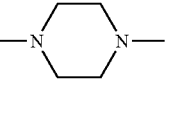 | 0.67 | 350 |
| 8s | 4-[7-Aminomethyl-6-(2,4-dichloro-phenyl)-imidazo[1,2-a]pyridin-3-yl]-piperazin-1-carboxylic acid benzyl ester | 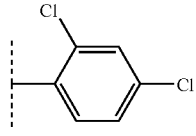 | 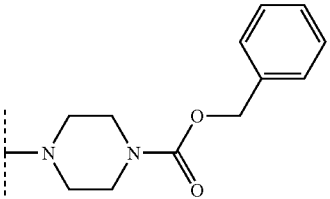 | 1.38 | 511 |
| 8t | C-[6-(2,4-Dichloro-phenyl)-3-(3-trifluoromethyl-5,6-dihydro-8H-[1,2,4]triazolo[4,3-a]pyrazin-7-yl)-imidazo[1,2-a]pyridin-7-yl]-methylamine | 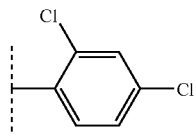 | 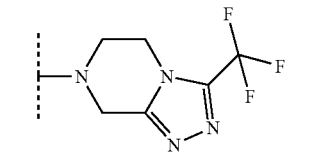 | 1.03 | 483 |

-continued

| Compound | Name | R⁵ | R⁷ | HPLC $^A t_{Ret}$ [min] | MS [M + 1]⁺ |
|---|---|---|---|---|---|
| 8u | 1-[7-Aminomethyl-6-(2,4-dichloro-phenyl)-imidazo[1,2-a]pyridin-3-yl]-piperidine-2-carboxylic acid ethyl ester | 2,4-dichlorophenyl | piperidin-1-yl-2-carboxylic acid ethyl ester | 1.54 | 448 |
| 8v | 1-[7-Aminomethyl-6-(2,4-dichloro-phenyl)-imidazo[1,2-a]pyridin-3-yl]-piperidine-3-carboxylic acid ethyl ester | 2,4-dichlorophenyl | piperidin-1-yl-3-carboxylic acid ethyl ester | 1.48 | 448 |
| 8w | 1-[7-Aminomethyl-6-(2,4-dichloro-phenyl)-imidazo[1,2-a]pyridin-3-yl]-piperidine-4-carboxylic acid ethyl ester | 2,4-dichlorophenyl | piperidin-1-yl-4-carboxylic acid ethyl ester | 1.46 | 448 |
| 8x | C-[6-(2,4-Dichloro-phenyl)-3-(2,6-dimethyl-morpholin-4-yl)-imidazo[1,2-a]pyridin-7-yl]-methylamine | 2,4-dichlorophenyl | 2,6-dimethyl-morpholin-4-yl | 1.32 | 406 |
| 8y | {1-[7-Aminomethyl-6-(2,4-dichloro-phenyl)-imidazo[1,2-a]pyridin-3-yl]-piperidin-4-yl}-dimethyl-amine | 2,4-dichlorophenyl | 4-dimethylamino-piperidin-1-yl | 0.82 | 419 |
| 8z | C-{6-(2,4-Dichloro-phenyl)-3-[4-(1-methyl-piperidin-4-yl)-piperazin-1-yl]-imidazo[1,2-a]pyridin-7-yl}-methylamine | 2,4-dichlorophenyl | 4-(1-methyl-piperidin-4-yl)-piperazin-1-yl | 0.72 | 474 |
| 8a' | 2-{4-[7-Aminomethyl-6-(2,4-dichloro-phenyl)-imidazo[1,2-a]pyridin-3-yl]-piperazin-1-yl}-1-morpholin-4-yl-ethanone | 2,4-dichlorophenyl | 4-(2-morpholin-4-yl-2-oxo-ethyl)-piperazin-1-yl | 0.78 | 504 |
| 8b' | C-{6-(2,4-Dichloro-phenyl)-3-[4-(4-methoxy-phenyl)-piperazin-1-yl]-imidazo[1,2-a]pyridin-7-yl}-methylamine | 2,4-dichlorophenyl | 4-(4-methoxyphenyl)-piperazin-1-yl | 1.31 | 483 |
| 8c' | {4-[7-Aminomethyl-6-(2,4-dichloro-phenyl)-imidazo[1,2-a]pyridin-3-yl]-piperazin-1-yl}-(tetrahydro-furan-2-yl)-methanone | 2,4-dichlorophenyl | 4-(tetrahydrofuran-2-carbonyl)-piperazin-1-yl | 1.12 | 475 |

Example 9

2-{[7-Aminomethyl-6-(2,4-dichloro-phenyl)-imidazo[1,2-a]pyridin-3-yl]-methyl-amino}-ethanol

Compound 9 was obtained by the following procedure.

(1) A mixture of [2-amino-5-(2,4-dichloro-phenyl)-pyridin-4-ylmethyl]-carbamic acid tert-butyl ester (100 mg, 0.27 mmol) and 1,2-bis-benzotriazol-1-yl-N,N'-bis-[2-(tert-butyl-diphenyl-silanyloxy)-ethyl]-N,N'-dimethyl-ethane-1,2-diamine (241 mg, 0.27 mmol) in DCE (3 mL) was refluxed for 2 h then cooled to RT. The reaction mixture was diluted in DCM (40 mL) and washed with a 2.0 M aqueous KOH solution (10 mL). The organic layer was dried over $Na_2SO_4$, filtered and evaporated. The remaining residue was purified by reverse phase prep-HPLC (Waters system) to give the Boc-protected intermediate (TFA salt, 43 mg, 19%) as a white solid. MS: 704 [M+1]$^+$; HPLC: $^At_{Ret}$=2.92.

(2) The Boc-protected compound (43 mg, 0.053 mmol) was dissolved in THF (0.1 mL), and TBAF (1.0 M solution in THF, 0.11 mL, 0.11 mmol) was added. The reaction mixture was stirred at RT for 2 h and evaporated to dryness. The remaining residue was dissolved in DCM (2 mL) and TFA (1 mL) and the solution was stirred at RT for 30 min. The reaction mixture was concentrated to dryness and the residue purified by reverse phase prep-HPLC (Waters system) to give the title compound as a white solid (2TFA salt, 22 mg, 0.037 mmol, 70%). MS: 366 [M+1]$^+$; HPLC: $^At_{Ret}$=0.96.

Example 10

[7-Aminomethyl-6-(2-chloro-4-methyl-phenyl)-imidazo[1,2-a]pyridin-3-yl]-(2-methoxy-ethyl)-methyl-amine

Compound 10 was prepared according to Scheme 4:

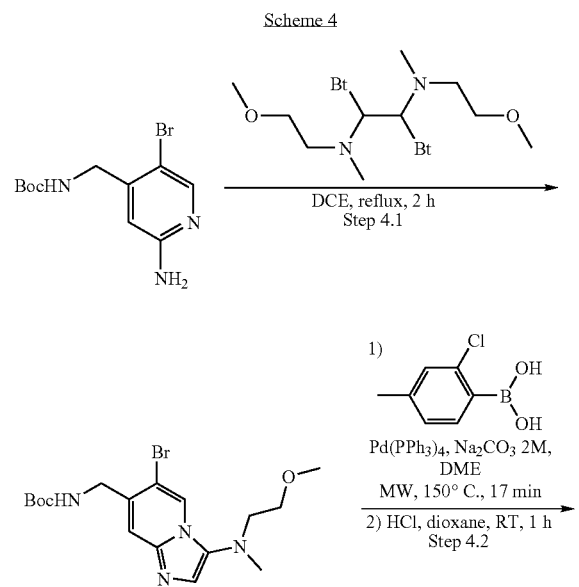

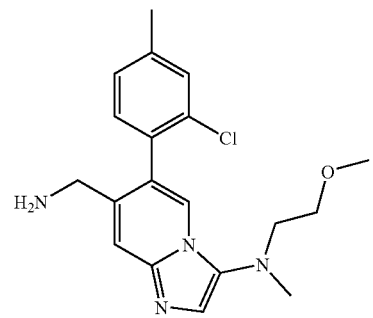

Step 4.1: [{6-Bromo-3-[(2-methoxy-ethyl)-methyl-amino]-imidazo[1,2-a]pyridin-7-ylmethyl}-carbamic acid tert-butyl ester The cyclization was carried out as described for Example 6 from (2-amino-5-bromo-pyridin-4-ylmethyl)-carbamic acid tert-butyl ester (600 mg, 2.0 mmol, prepared according to Example 1, Step 1.3) and 1,2-bis-benzotriazol-1-yl-N,N'-bis-(2-methoxy-ethyl)-N,N'-dimethyl-ethane-1,2-diamine (871 mg, 2.0 mmol, prepared according to Example 6, Step 3.1). After the work-up, the crude was purified by Combi-Flash Companion™ (Isco Inc.) column chromatography ($SiO_2$; gradient elution, [hexane/DCM 1:1]/TBME (containing 0.5% of a 7.0 M solution of $NH_3$ in MeOH) 1:0→0:1) to yield the title compound (546 mg, 1.32 mmol, 67%) as a brownish oil. MS: 414 [M−1]$^+$; HPLC: $^At_{Ret}$=1.40; TLC—$R_F$ 0.15 (hexane/DCM/TBME (containing 0.5% of a 7.0 M solution of $NH_3$ in MeOH) 1:1:2).

Step 4.2

(1) The Suzuki coupling was carried out as described for Example 1 from {6-bromo-3-[(2-methoxy-ethyl)-methyl-amino]-imidazo[1,2-a]pyridin-7-ylmethyl}-carbamic acid tert-butyl ester (60 mg, 0.15 mmol), 2-chloro-4-methylphenylboronic acid (29.7 mg, 0.17 mmol), Pd(PPh$_3$)$_4$ (8.4 mg, 0.007 mmol) and $Na_2CO_3$ (2.0 M solution in water, 0.25 mL, 0.5 mmol) in DME (0.5 mL). After the work-up, the remaining residue was purified by reverse phase prep-HPLC (Waters system) to give the Boc-protected intermediate (TFA salt). MS: 459 [M+1]$^+$; HPLC: $^At_{Ret}$=1.89.

(2) The Boc-protected intermediate was dissolved in a 2.0 M HCl solution in dioxane (2 mL), stirred at RT for 1 h, and evaporated to dryness. The remaining residue was dissolved in t-BuOH and lyophilized to give the title compound (2HCl salt, 29 mg, 0.067 mmol, 45% for 2 steps) as a redish solid. MS: 359 [M+1]$^+$; HPLC: $^At_{Ret}$=1.13.

Example 11

Compounds 11a and 11b were obtained analogously to Example 10, using various phenylboronic acid derivatives in Step 4.2. The compounds are of the following general formula:

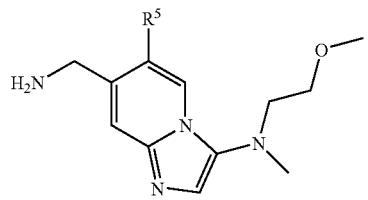

| Compound | Name | R⁵ | HPLC $^A t_{Ret}$ [min] | MS [M + 1]⁺ |
|---|---|---|---|---|
| 11a | [7-Aminomethyl-6-(4-chloro-2-methyl-phenyl)-imidazo[1,2-a]pyridin-3-yl]-(2-methoxy-ethyl)-methyl-amine | 2-Me, 4-Cl phenyl | 1.17 | 359 |
| 11b | [7-Aminomethyl-6-(2,4-dimethyl-phenyl)-imidazo[1,2-a]pyridin-3-yl]-(2-methoxy-ethyl)-methyl-amine | 2-Me, 4-Me phenyl | 1.13 | 339 |

Example 12

C-[6-(2,4-Dichloro-phenyl)-2-(2-methoxy-ethyl)-imidazo[1,2-a]pyridin-7-yl]-methylamine Compound 12 was prepared according to Scheme 5:

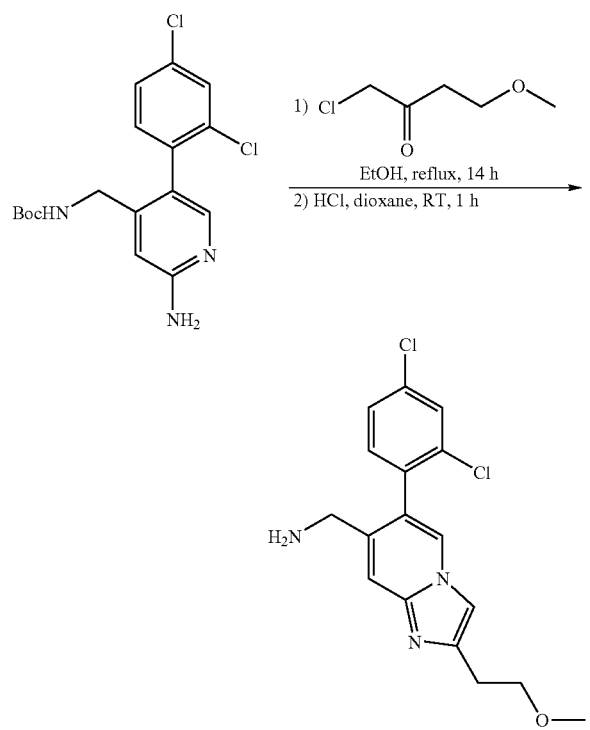

Scheme 5

(1) In a sealed tube, a mixture of [2-amino-5-(2,4-dichloro-phenyl)-pyridin-4-ylmethyl]-carbamic acid tert-butyl ester (50 mg, 0.14 mmol, prepared according to Example 6, Step 3.2), 1-chloro-4-methoxy-butan-2-one (37.1 mg, 0.27 mmol, prepared according to a published procedure: M. Okahara and al., *J. Org. Chem.*, 1988, 53, 2737-2740), and NaHCO₃ (19.4 mg, 0.23 mmol) in EtOH (1 mL) was heated at 75° C. for 14 h. The reaction mixture was cooled to RT and concentrated, then the residue was diluted in DCM (20 mL) and washed with brine (10 mL). The aqueous layer was extracted with DCM (2×) and the combined organic fractions were dried over Na₂SO₄, filtered, and evaporated. The remaining residue was purified by reverse phase prep-HPLC (Waters system) to give the Boc-protected intermediate (TFA salt). MS: 450 [M+1]⁺; HPLC: $^A t_{Ret}$=1.79.

(2) The Boc-protected intermediate was dissolved in a 2.0 M HCl solution in dioxane (2 mL), stirred at RT for 1 h, and evaporated to dryness. The remaining residue was dissolved in t-BuOH and lyophilized to give the title compound (2HCl salt, 21 mg, 0.050 mmol, 36% for 2 steps) as an off-white solid. MS: 351 [M+1]⁺; HPLC: $^A t_{Ret}$=0.96.

Example 13

C-[6-(2,4-Dichloro-phenyl)-3-(1-oxo-1lambda*4*-thiomorpholin-4-yl)-imidazo[1,2-a]pyridin-7-yl]-methylamine Compound 13 was obtained by the following procedure.

(1) A solution of [6-(2,4-dichloro-phenyl)-3-thiomorpholin-4-yl-imidazo[1,2-a]pyridin-7-ylmethyl]-carbamic acid tert-butyl ester (50 mg, 0.10 mmol, prepared according to Example 6, Step 3.3) in a mixture of EtOH (5 mL) and water (1 mL) was cooled to 0° C. (ice bath), then NaIO₄ (22.7 mg, 0.105 mmol) was added. The reaction mixture was slowly warmed to RT and stirred for 14 h. The suspension was diluted in AcOEt (30 mL) then washed successively with water (10 mL) and brine (10 mL). The organic layer was dried over Na₂SO₄, filtered, and evaporated to give the crude Boc-protected intermediate.

(2) The Boc-protected intermediate was dissolved in DCM (2 mL) and TFA (1 mL) and the solution was stirred at RT for 30 min. The reaction mixture was concentrated to dryness and the remaining residue purified by reverse phase prep-HPLC (Waters system) to give the title compound (2TFA salt, 29.5 mg, 0.046 mmol, 46% for 2 steps) as a white solid. MS: 410 [M+1]⁺; HPLC: $^A t_{Ret}$=0.95.

Example 14

C-[6-(2,4-Dichloro-phenyl)-3-(1,1-dioxo-1lambda*6*-thiomorpholin-4-yl)-imidazo[1,2-a]pyridin-7-yl]-methylamine Compound 14 was obtained by the following procedure.

(1) A solution of [6-(2,4-dichloro-phenyl)-3-thiomorpholin-4-yl-imidazo[1,2-a]pyridin-7-ylmethyl]-carbamic acid tert-butyl ester (50 mg, 0.10 mmol, prepared according to Example 6, Step 3.3) in DCM (7 mL) was cooled to 0° C. (ice bath), then mCPBA (52.5 mg, 0.30 mmol) was added. The reaction mixture was slowly warmed to RT, stirred for 14 h, and diluted in DCM (20 mL). The mixture was washed successively with a saturated aqueous NaHCO₃ solution (10 mL) and brine (10 mL). The organic layer was dried over Na₂SO₄, filtered, and evaporated to give the crude Boc-protected intermediate.

(2) The Boc-protected intermediate was dissolved in DCM (2 mL) and TFA (1 mL) and the solution was stirred at RT for 30 min. The reaction mixture was concentrated to dryness and the remaining residue purified by reverse phase prep-HPLC (Waters system) to give the title compound (2TFA salt, 13.5 mg, 0.021 mmol, 21% for 2 steps) as a white solid. MS: 426 [M+1]⁺; HPLC: $^A t_{Ret}$=0.70.

Example 15

C-[6-(2,4-Dichloro-phenyl)-[1,2,4]triazolo[4,3-a]pyridin-7-yl]-methylamine

Compound 15 was prepared according to Scheme 6:

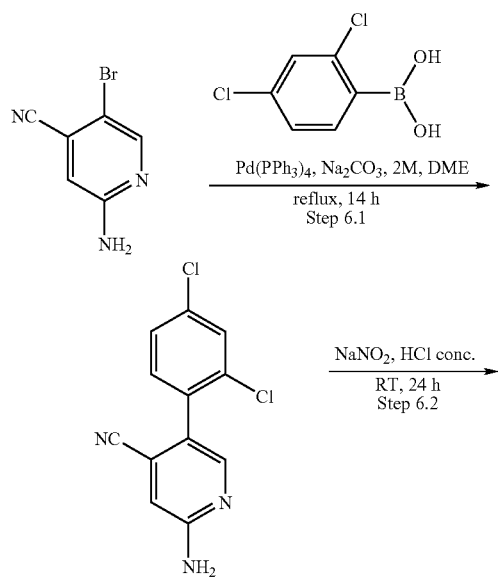

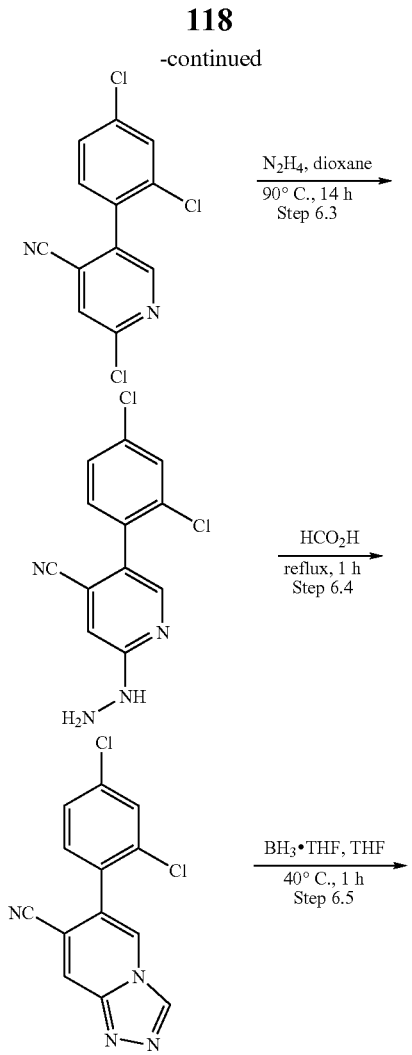

Step 6.1: 2-Amino-5-(2,4-dichloro-phenyl)-isonicotinonitrile.

A mixture of 2-amino-5-bromo-isonicotinonitrile (1.0 g, 5.1 mmol, prepared according to Example 3, Step 2.1), 2,4-dichloro-benzeneboronic acid (1.45 g, 7.6 mmol), Pd(PPh₃)₄ (292 mg, 0.25 mmol) and Na₂CO₃ (2.0 M solution in water, 8.8 mL) in DME (10 mL) was refluxed for 2 h under an inert atmosphere of argon. The reaction mixture was cooled to RT, diluted in AcOEt and washed with water. The organic layer was dried over Na₂SO₄, filtered, and evaporated. The residue was purified by Combi-Flash Companion™ (Isco Inc.) column chromatography (SiO₂; gradient elution, [hexane/DCM 1:1]/TBME 95:5→3:7) to yield the title compound (880 mg, 3.3 mmol, 66%). MS: 264 [M+1]⁺; HPLC: $^At_{Ret}$=1.73; TLC: R_F 0.31 (hexane/DCM/TBME 1:1:2).

Step 6.2: 2-Chloro-5-(2,4-dichloro-phenyl)-isonicotinonitrile.

A mixture of 2-amino-5-(2,4-dichloro-phenyl)-isonicotinonitrile (880 mg, 3.3 mmol) in HCl conc. (15 mL) was vigorously stirred and cooled to −15° C. (ice/MeOH bath). NaNO$_2$ (4.6 g, 66.7 mmol) was carefully added, then the reaction mixture was slowly warmed to RT and stirred for 24 h. The formed precipitate was filtered, washed with water, and purified by Combi-Flash Companion™ (Isco Inc.) column chromatography (SiO$_2$; gradient elution, [hexane/DCM 1:1]/ TBME 95:5→5:95) to yield the title compound (453 mg, 1.6 mmol, 48%). MS: 284 [M+1]⁺; HPLC: $^At_{Ret}$=2.70.

Step 6.3: 5-(2,4-Dichloro-phenyl)-2-hydrazino-isonicotinonitrile.

A solution of 2-chloro-5-(2,4-dichloro-phenyl)-isonicotinonitrile (453 mg, 1.6 mmol) and hydrazine monohydrate (7.76 mL, 160 mmol) in dioxane (9 mL) was heated at 90° C. and stirred for 14 h. The reaction mixture was cooled to RT, poured into water (50 mL) and extracted with AcOEt (3×25 mL). The combined organic fractions were dried over Na$_2$SO$_4$, filtered, and evaporated to provide the crude title compound (520 mg, quant.) as a yellow solid, which was used without further purification. MS: 279 [M+1]⁺; HPLC: $^At_{Ret}$=1.44.

Step 6.4: 6-(2,4-Dichloro-phenyl)-[1,2,4]triazolo[4,3-a]pyridine-7-carbonitrile.

A solution of the crude 5-(2,4-dichloro-phenyl)-2-hydrazino-isonicotinonitrile (520 mg) in formic acid (15 mL) was stirred and refluxed for 1 h. The reaction mixture was concentrated under vacuum, then the remaining residue was diluted in AcOEt (50 mL) and washed with a 2.0 M aqueous NaHCO$_3$ solution (2×25 mL). The organic layer was dried over Na$_2$SO$_4$, filtered, and evaporated. The residue was purified by Combi-Flash Companion™ (Isco Inc.) column chromatography (SiO$_2$; gradient elution, DCM→DCM/MeOH 7:3) to yield the title compound (397 mg, 1.37 mmol, 86% over 2 steps). MS: 289 [M+1]⁺; HPLC: $^At_{Ret}$=1.79; TLC: R_F 0.41 (DCM/MeOH 95:5).

Step 6.5.

In a sealed flask, a solution of 6-(2,4-dichloro-phenyl)-[1,2,4]triazolo[4,3-a]pyridine-7-carbonitrile (50 mg, 0.164 mmol) in THF (0.5 mL) was cooled to 0° C. (ice bath) then treated with BH$_3$.THF complex (1.0 M solution in THF, 0.82 mL, 0.82 mmol). The reaction mixture was heated at 40° C. for 1 h, cooled to RT, and diluted in MeOH (large excess). The mixture was concentrated under vacuum, and the remaining residue was suspended in 2.0 M HCl, and shaken for 15 min. After evaporation to dryness, the remaining residue was purified by reverse phase prep-HPLC (Waters system) to give the title compound (2TFA salt, 1.9 mg, 0.004 mmol, 2%) as a white solid. MS: 293 [M+1]⁺; HPLC: $^At_{Ret}$=0.95.

Example 16

7-Aminomethyl-6-(2,4-dichloro-phenyl)-[1,2,4]triazolo[4,3-a]pyridin-3-ylamine Compound 16 was prepared according to Scheme 7:

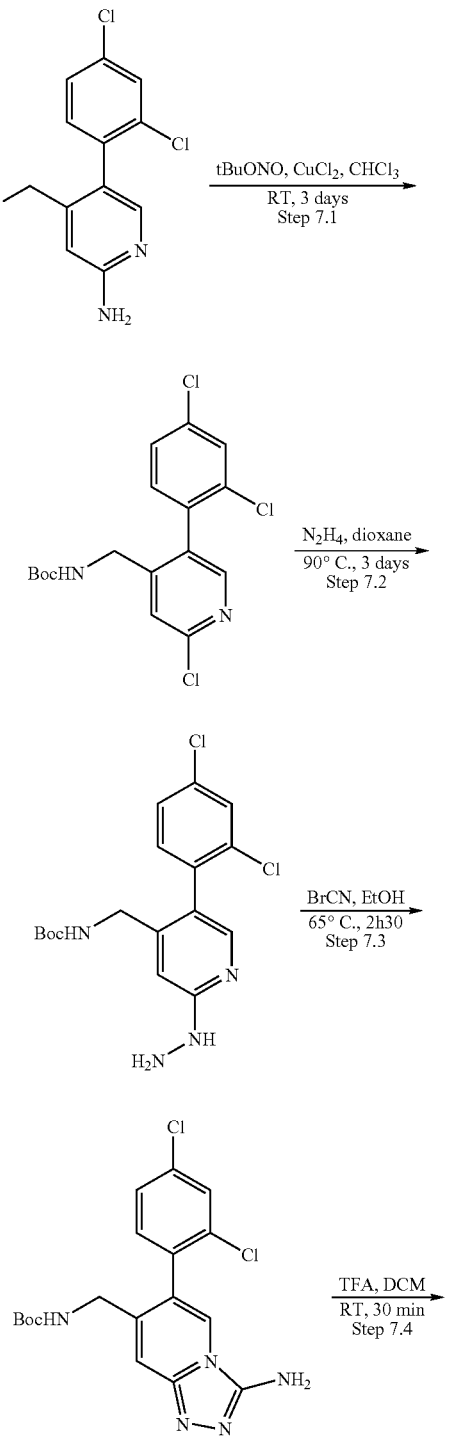

Scheme 7

-continued

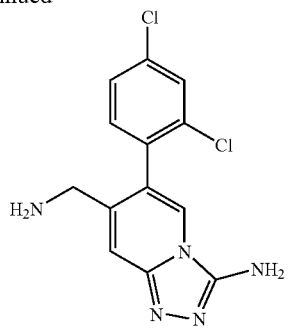

Step 7.1: [2-Chloro-5-(2,4-dichloro-phenyl)-pyridin-4-ylmethyl]-carbamic acid tert-butyl ester.

A mixture of [2-amino-5-(2,4-dichloro-phenyl)-pyridin-4-ylmethyl]-carbamic acid tert-butyl ester (1.78 g, 4.82 mmol, prepared according to Example 6, Step 3.2), tBuONO (1.05 mL, 8.0 mmol), and CuCl$_2$ (1.01 g, 7.51 mmol) in CHCl$_3$ (6 mL) was stirred at RT for 3 days with exclusion of light. The reaction mixture was concentrated under vacuum, then the remaining residue was suspended in a 2.0 M aqueous Na$_2$CO$_3$ solution (200 mL) and extracted with AcOEt (2×100 mL). The combined organic fractions were dried over Na$_2$SO$_4$, filtered, and evaporated. The residue was purified by Combi-Flash Companion™ (Isco Inc.) column chromatography (SiO$_2$; gradient elution, [hexane/DCM 1:1]/TBME 95:5→4:6) to yield the title compound (1.17 g, 3.0 mmol, 62%) as a colorless solid. MS: 388 [M+1]$^+$; HPLC: $^At_{Ret}$=2.89; TLC: R$_F$ 0.36 ([hexane/DCM 1:1]/TBME 95:5).

Step 7.2: [5-(2,4-Dichloro-phenyl)-2-hydrazino-pyridin-4-ylmethyl]-carbamic acid tert-butyl ester.

A solution of [2-chloro-5-(2,4-dichloro-phenyl)-pyridin-4-ylmethyl]-carbamic acid ted-butyl ester (1.17 g, 3.0 mmol) and hydrazine monohydrate (14.6 mL, 300 mmol) in dioxane (8 mL) was heated at 90° C. and stirred for 3 days. The reaction mixture was cooled to RT, poured into AcOEt (200 mL) and washed with a 2.0 M aqueous Na$_2$CO$_3$ solution (2×100 mL). The organic layer was dried over Na$_2$SO$_4$, filtered, and evaporated to provide the crude title compound (1.66 g, quant.), which was used without further purification. HPLC: $^At_{Ret}$=1.61.

Step 7.3: [3-Amino-6-(2,4-dichloro-phenyl)-[1,2,4]triazolo[4,3-a]pyridin-7-ylmethyl]-carbamic acid tert-butyl ester.

A mixture of the crude [5-(2,4-dichloro-phenyl)-2-hydrazino-pyridin-4-ylmethyl]-carbamic acid tert-butyl ester (1.66 g) and BrCN (638 mg, 6.0 mmol) in EtOH (40 mL) was heated at 65° C. and stirred for 2 h30. The reaction mixture was cooled to RT, poured into AcOEt (100 mL) and washed with a 2.0 M aqueous Na$_2$CO$_3$ solution (2×50 mL). The organic layer was dried over Na$_2$SO$_4$, filtered, and evaporated. The residue was purified by Combi-Flash Companion™ (Isco Inc.) column chromatography (SiO$_2$; gradient elution, DCM/MeOH 95:5→4:6) to yield the title compound (908 mg, 2.22 mmol, 74% over 2 steps) as a brownish solid. MS: 408 [M+1]$^+$; HPLC: $^At_{Ret}$=1.62; TLC: R$_F$ 0.16 (DCM/MeOH 95:5).

Step 7.4.

[3-Amino-6-(2,4-dichloro-phenyl)-[1,2,4]triazolo[4,3-a]pyridin-7-ylmethyl]-carbamic acid tert-butyl ester (17 mg, 0.042 mmol) was dissolved in DCM (2 mL) and TFA (1 mL) and the solution was stirred at RT for 30 min. The reaction mixture was concentrated to dryness and the remaining residue purified by reverse phase prep-HPLC (Waters system) to give the title compound (2TFA salt, 5.7 mg, 0.011 mmol, 26%) as a white solid. MS: 308 [M+1]$^+$; HPLC: $^At_{Ret}$=0.77.

Example 17

Tetrahydro-pyran-4-carboxylic acid [7-aminomethyl-6-(2,4-dichloro-phenyl)-[1,2,4]triazolo[4,3-a]pyridin-3-yl]-amide Compound 17 was prepared according to Scheme 8:

Scheme 8

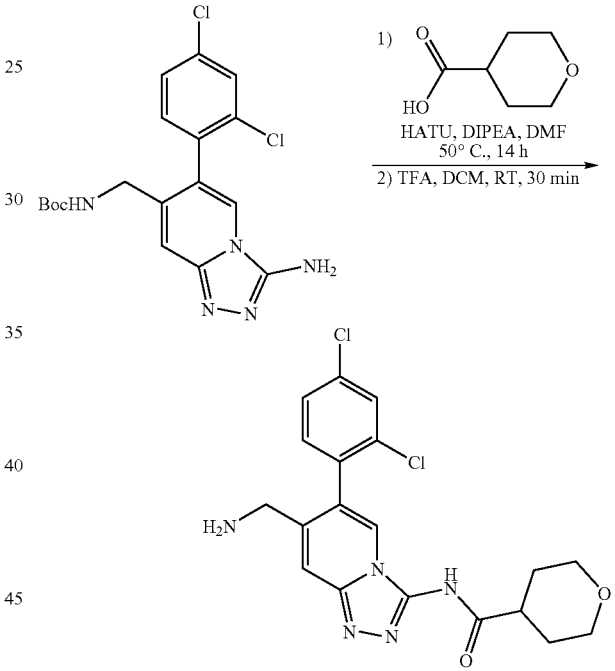

(1) To a solution of [3-amino-6-(2,4-dichloro-phenyl)-[1,2,4]triazolo[4,3-a]pyridin-7-ylmethyl]-carbamic acid tert-butyl ester (30 mg, 0.073 mmol, prepared according to Example 16, Step 7.3), tetrahydro-pyran-4-carboxylic acid (15.3 mg, 0.118 mmol) and DIPEA (0.031 mL, 0.220 mmol) in DMF (0.5 mL) was added HATU (41.9 mg, 0.110 mmol) at RT. The reaction mixture was heated at 50° C. for 2 h, then poured into AcOEt (10 mL) and washed with a 2.0 M aqueous Na$_2$CO$_3$ solution (2×5 mL) and brine (5 mL). The organic layer was dried over Na$_2$SO$_4$, filtered, and evaporated to give the crude Boc-protected intermediate.

(2) The Boc-protected intermediate was dissolved in DCM (2 mL) and TFA (1 mL) and the solution was stirred at RT for 30 min. The reaction mixture was concentrated to dryness and the remaining residue purified by reverse phase prep-HPLC (Waters system) to give the title compound (2TFA salt, 21.4 mg, 0.033 mmol, 45% for 2 steps) as a white solid. MS: 420 [M+1]$^+$; HPLC: $^At_{Ret}$=1.11.

Example 18

Compounds 18a to 18i were obtained analogously to Example 17, using various carboxylic acid derivatives. The compounds are of the following general formula:

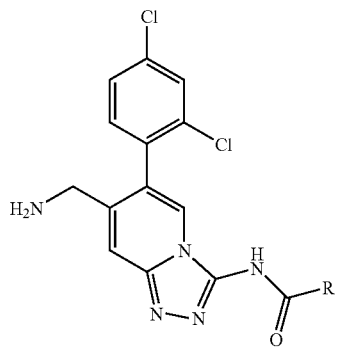

| Compound | Name | R | HPLC $^A t_{Ret}$ [min] | MS $[M + 1]^+$ |
|---|---|---|---|---|
| 18a | Piperidine-4-carboxylic acid [7-aminomethyl-6-(2,4-dichloro-phenyl)-[1,2,4]triazolo[4,3-a]pyridin-3-yl]-amide | piperidine | 0.81 | 419 |
| 18b | 1-Methyl-piperidine-4-carboxylic acid [7-aminomethyl-6-(2,4-dichloro-phenyl)-[1,2,4]triazolo[4,3-a]pyridin-3-yl]-amide | N-methyl piperidine | 0.82 | 433 |
| 18c | 1-Acetyl-piperidine-4-carboxylic acid [7-aminomethyl-6-(2,4-dichloro-phenyl)-[1,2,4]triazolo[4,3-a]pyridin-3-yl]-amide | N-acetyl piperidine | 1.09 | 461 |
| 18d | N-[7-Aminomethyl-6-(2,4-dichloro-phenyl)-[1,2,4]triazolo[4,3-a]pyridin-3-yl]-2-methoxy-acetamide | methoxymethyl | 1.10 | 380 |
| 18e | N-[7-Aminomethyl-6-(2,4-dichloro-phenyl)-[1,2,4]triazolo[4,3-a]pyridin-3-yl]-3-methoxy-propionamide | methoxyethyl | 1.13 | 394 |
| 18f | N-[7-Aminomethyl-6-(2,4-dichloro-phenyl)-[1,2,4]triazolo[4,3-a]pyridin-3-yl]-2-bicyclo[2.2.1]hept-2-yl-acetamide | norbornyl methyl | 1.70 | 444 |
| 18g | N-[7-Aminomethyl-6-(2,4-dichloro-phenyl)-[1,2,4]triazolo[4,3-a]pyridin-3-yl]-2-((R)-3-benzyl-1-methyl-piperidin-4-yl)-acetamide | (R)-3-benzyl-1-methyl-piperidin-4-yl methyl | 1.22 | 537 |

-continued

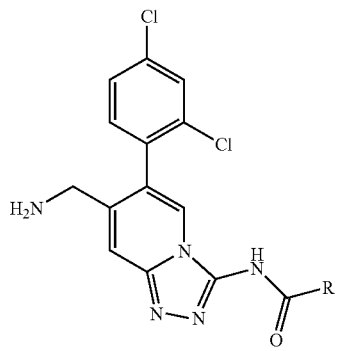

| Compound | Name | R | HPLC $^A t_{Ret}$ [min] | MS $[M + 1]^+$ |
|---|---|---|---|---|
| 18h | 2-Adamantan-1-yl-N-[7-aminomethyl-6-(2,4-dichloro-phenyl)-[1,2,4]triazolo[4,3-a]pyridin-3-yl]-acetamide | | 1.86 | 484 |
| 18i | 8-{[7-Aminomethyl-6-(2,4-dichloro-phenyl)-[1,2,4]triazolo[4,3-a]pyridin-3-ylcarbamoyl]-methyl}-3-oxo-3,5,7,8-tetrahydro-2H-pyrido[4,3-c]pyridazine-6-carboxylic acid ethyl ester NVP-BJV736-Al-1 | | 1.21 | 571 |

Example 19

C-[6-(2,4-Dichloro-phenyl)-3-morpholin-4-yl-[1,2,4]triazolo[4,3-a]pyridin-7-yl]-methylamine Compound 19 was prepared according to Scheme 9:

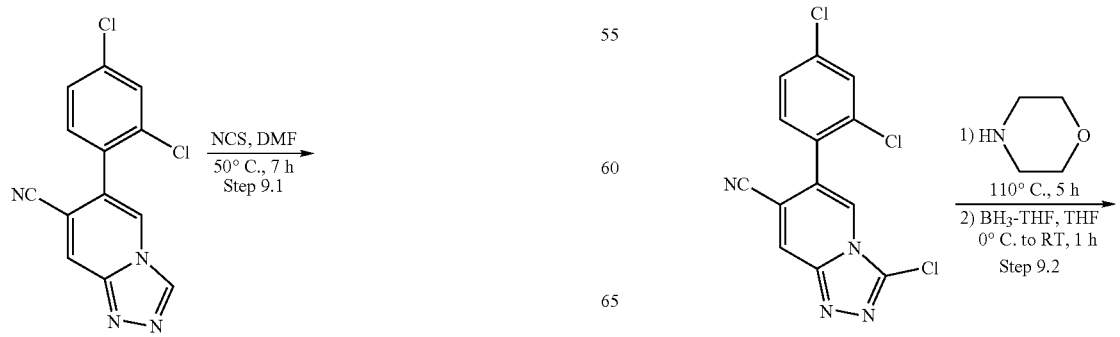

127

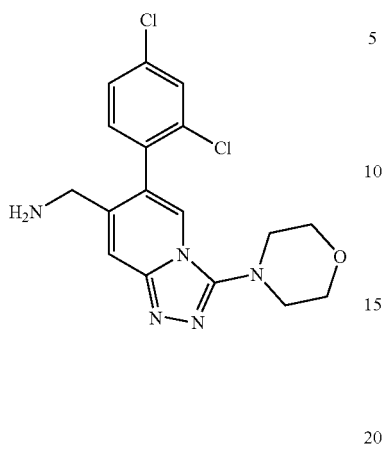

Step 9.1: [3-Chloro-6-(2,4-dichloro-phenyl)-[1,2,4]triazolo[4,3-a]pyridine-7-carbonitrile.

A mixture of 6-(2,4-dichloro-phenyl)-[1,2,4]triazolo[4,3-a]pyridine-7-carbonitrile (397 mg, 1.37 mmol, prepared according to Example 15, Step 6.4) and NCS (275 mg, 2.06 mmol) in DMF (8 mL) was heated at 50° C. and stirred for 7 h. The reaction mixture was diluted in AcOEt (50 mL) and washed with water (2×25 mL). The organic layer was dried over $Na_2SO_4$, filtered, and evaporated to give the crude title compound (466 mg, quant.). MS: 323 [M+1]$^+$; HPLC: $^At_{Ret}$=2.11.

Step 9.2.

(1) A solution of the crude [3-chloro-6-(2,4-dichloro-phenyl)-[1,2,4]triazolo[4,3-a]pyridine-7-carbonitrile (50 mg, 0.148 mmol) in morpholine (1.2 mL) was heated at 110° C. and stirred for 5 h. The reaction mixture was concentrated in vacuum, the remaining residue was suspended in water (10 mL) and extracted with AcOEt (3×5 mL). The combined organic fractions were dried over $Na_2SO_4$, filtered, and evaporated to give the crude 6-(2,4-dichloro-phenyl)-3-morpholin-4-yl-[1,2,4]triazolo[4,3-a]pyridine-7-carbonitrile, which was used without further purification. MS: 374 [M+1+]; HPLC: $^At_{Ret}$=1.94.

(2) In a sealed flask, a solution of the crude 6-(2,4-dichloro-phenyl)-3-morpholin-4-yl-[1,2,4]triazolo[4,3-a]pyridine-7-carbonitrile in THF (1 mL) was cooled to 0° C. (ice bath) then treated with $BH_3$.THF complex (1.0 M solution in THF, 0.73 mL, 0.73 mmol). The reaction mixture was heated at 40° C. for 1 h, cooled to RT, and diluted in MeOH (large excess). The mixture was concentrated under vacuum, and the remaining residue was suspended in 2.0 M HCl, and shaken for 15 min. After evaporation to dryness, the remaining residue was purified by reverse phase prep-HPLC (Waters system) to give the title compound (2TFA salt, 5 mg, 0.008 mmol, 5%) as a white solid. MS: 378 [M+1]$^+$; HPLC: $^At_{Ret}$=1.15.

128

Example 20

[6-(2,4-Dichloro-phenyl)-3-morpholin-4-yl-imidazo[1,2-a]pyridin-7-ylmethyl]-methylamine Compound 20 was prepared according to Scheme 10:

Scheme 10

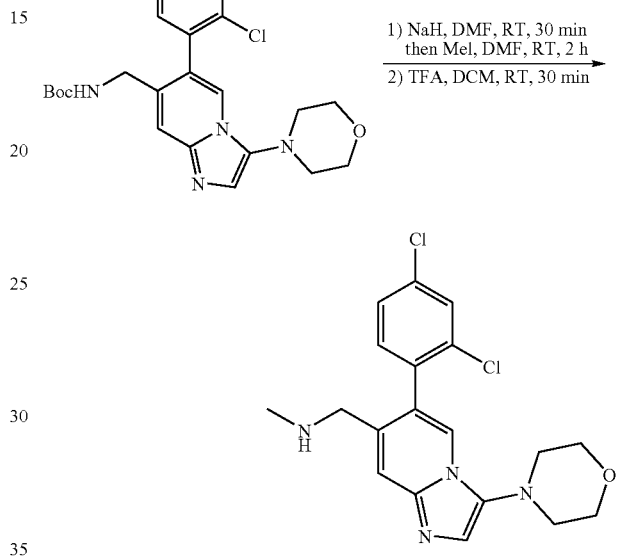

1) NaH, DMF, RT, 30 min then MeI, DMF, RT, 2 h
2) TFA, DCM, RT, 30 min (1) A solution of [6-(2,4-dichloro-phenyl)-3-morpholin-4-yl-imidazo[1,2-a]pyridin-7-ylmethyl]-carbamic acid tert-butyl ester (20 mg, 0.042 mmol, prepared according to Example 6, Step 3.3) in DMF (0.5 mL) was treated with NaH (60% in mineral oil, 2.0 mg, 0.050 mmol) and stirred at RT for 30 min. MeI (0.003 mL, 0.050 mmol) was added and the mixture was stirred at RT for 2 h. The reaction mixture was poured into water (10 mL) and extracted with DCM (20 mL). The organic layer was dried over $Na_2SO_4$, filtered, and evaporated to dryness to yield the crude Boc-protected intermediate.

2) The Boc-protected intermediate was dissolved in DCM (1 mL), TFA (1 mL) was added and the solution was stirred at RT for 30 min. The reaction mixture was concentrated to dryness and the remaining residue purified by reverse phase prep-HPLC (Waters system) to give the title compound as a TFA salt.

(3) The TFA salt was dissolved in HCl (1.25 M solution in MeOH), stirred for 5 min at RT, and evaporated to dryness (the sequence was performed 3 times). The remaining residue was dissolved in water and lyophilized to give the HCl salt of the title compound (2HCl salt, 13 mg, 0.028 mmol, 70%). MS: 392 [M+1]$^+$; HPLC: $^At_{Ret}$=1.26.

Example 21

Compounds 21a to 21e were obtained analogously to Example 20, using various alkyl halides. The compounds are of the following general formula:

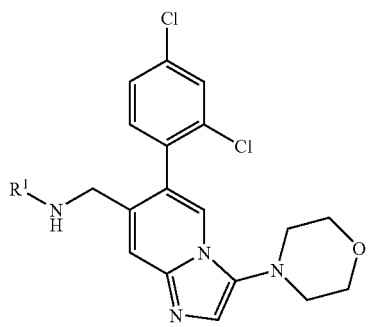

| Compound | Name | R¹ | HPLC $^A t_{Ret}$ [min] | MS [M + 1]⁺ |
|---|---|---|---|---|
| 21a | [6-(2,4-Dichloro-phenyl)-3-morpholin-4-yl-imidazo[1,2-a]pyridin-7-ylmethyl]-isopropyl-amine | isopropyl | 1.16 | 420 |
| 21b | [6-(2,4-Dichloro-phenyl)-3-morpholin-4-yl-imidazo[1,2-a]pyridin-7-ylmethyl]-ethyl-amine | ethyl | 1.11 | 406 |
| 21c | [6-(2,4-Dichloro-phenyl)-3-morpholin-4-yl-imidazo[1,2-a]pyridin-7-ylmethyl]-isobutyl-amine | isobutyl | 1.27 | 434 |
| 21d | Benzyl-[6-(2,4-dichloro-phenyl)-3-morpholin-4-yl-imidazo[1,2-a]pyridin-7-ylmethyl]-amine | benzyl | 1.39 | 467 |
| 21e | [6-(2,4-Dichloro-phenyl)-3-morpholin-4-yl-imidazo[1,2-a]pyridin-7-ylmethyl]-(2-methoxy-ethyl)-amine | 2-methoxyethyl | 1.16 | 436 |

Example 22

N-[6-(2,4-Dichloro-phenyl)-3-morpholin-4-yl-imidazo[1,2-a]pyridin-7-ylmethyl]-acetamide Compound 22 was prepared according to Scheme 11:

Scheme 11

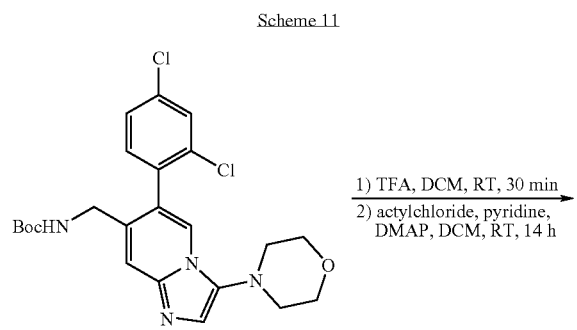

1) TFA, DCM, RT, 30 min
2) actylchloride, pyridine, DMAP, DCM, RT, 14 h

-continued

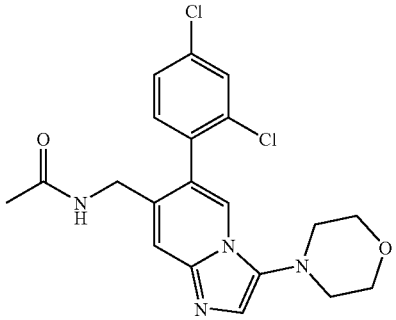

1) A solution of [6-(2,4-dichloro-phenyl)-3-morpholin-4-yl-imidazo[1, 2-a]pyridin-7-ylmethyl]-carbamic acid tert-butyl ester (30 mg, 0.063 mmol, prepared according to Example 6, Step 3.3) in DCM (1 mL) and TFA (1 mL) was stirred at RT for 30 min. The reaction mixture was concentrated to dryness, the remaining residue was diluted in AcOEt and washed with a 2.0 M Na$_2$CO$_3$ solution in water (2×). The organic layer was dried over Na$_2$SO$_4$, filtered and evaporated to give the crude benzylic amine intermediate which was used in the next step without further purification.

(2) To a solution of the previously obtained benzylic amine in DCM (0.5 mL) were added successively pyridine (0.015 mL, 0.189 mmol), DMAP (0.8 mg, 0.006 mmol) and acetyl chloride (0.005 ml, 0.075 mmol) at RT. The reaction mixture was stirred for 14 h then concentrated to dryness and the remaining residue was purified by reverse phase prep-HPLC (Waters system) to give the title compound (TFA salt, 11.7 mg, 0.022 mmol, 35% for 2 steps). MS: 420 [M+1]$^+$; HPLC: $^A$t$_{Ret}$=1.34.

Example 23

[7-Aminomethyl-6-(2,4-dichloro-phenyl)-imidazo[1,2-a]pyridin-8-yl]-isobutyl-amine Compound 23 was prepared according to Scheme 12:

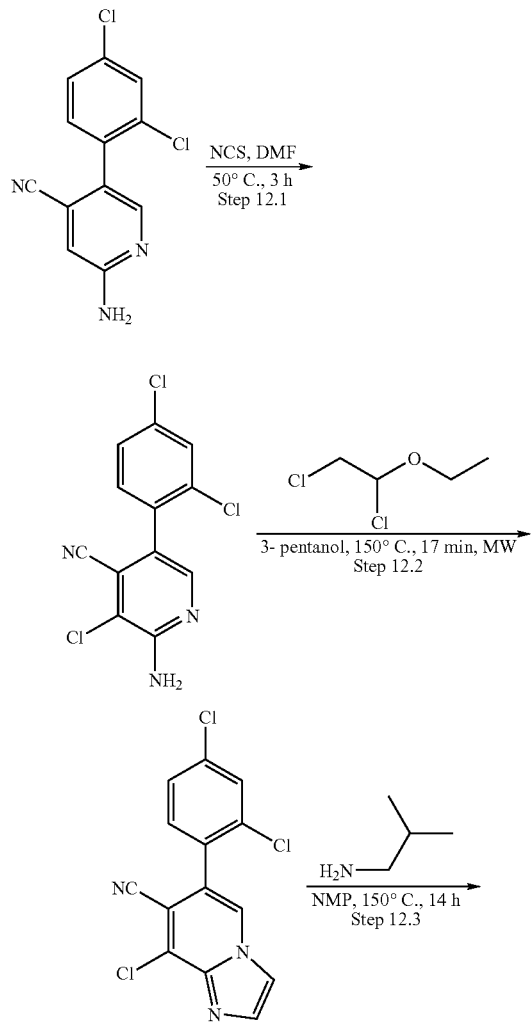

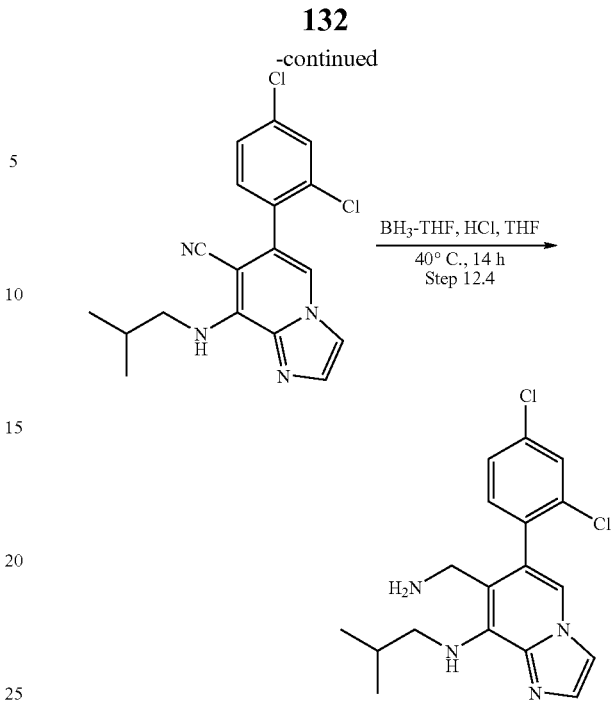

Step 12.1: 2-Amino-3-chloro-5-(2,4-dichloro-phenyl)-isonicotinonitrile.

A mixture of 2-amino-5-(2,4-dichloro-phenyl)-isonicotinonitrile (300 mg, 1.14 mmol, prepared according to Example 15, Step 6.1) and NCS (159 mg, 1.19 mmol) in DMF (4 mL) was stirred and heated at 50° C. for 3 h. The reaction mixture was cooled to RT, poured into AcOEt (40 mL) and washed with water (10 mL). The organic layer was dried over Na$_2$SO$_4$, filtered and evaporated. The residue was purified by Combi-Flash Companion™ (Isco Inc.) column chromatography (SiO$_2$; gradient elution, hexane/TBME 95:5→100% TBME) to yield the title compound (310 mg, 0.99 mmol, 87%) as a yellow solid. MS: 296 [M−1]$^+$; HPLC: $^A$t$_{Ret}$=2.43; TLC: R$_F$ 0.33 (hexane/TBME 1:1).

Step 12.2: 8-Chloro-6-(2,4-dichloro-phenyl)-imidazo[1,2-a]pyridine-7-carbonitrile.

In a sealed tube, a mixture of 2-amino-3-chloro-5-(2,4-dichloro-phenyl)-isonicotinonitrile (285 mg, 0.96 mmol) and 1,2-dichloro-1-ethoxy-ethane (0.64 mL, 5.25 mmol) was heated at 150° C. for 17 min under microwave irradiation. The reaction mixture was cooled to RT, poured into AcOEt (75 mL) and washed with a 2.0 M Na$_2$CO$_3$ solution in water (2×25 mL). The organic layer was dried over Na$_2$SO$_4$, filtered and evaporated. The residue was purified by Combi-Flash Companion™ (Isco Inc.) column chromatography (SiO$_2$; gradient elution, [hexane/DCM 1:1]/TBME 95:5→3:7) to yield the title compound (185 mg, 0.57 mmol, 60%) as a brownish solid. MS: 322 [M+1]$^+$; HPLC: $^A$t$_{Ret}$=2.17; TLC: R$_F$ 0.13 (hexane/DCM/TBME 1:1:2).

Step 12.3: 6-(2,4-Dichloro-phenyl)-8-isobutylamino-imidazo[1,2-a]pyridine-7-carbonitrile.

In a sealed tube, a mixture of 8-chloro-6-(2,4-dichloro-phenyl)-imidazo[1,2-a]pyridine-7-carbonitrile (20 mg, 0.062 mmol) and isobutylamine (0.037 mL, 0.37 mmol) was heated at 150° C. for 14 h. The reaction mixture was cooled to RT, poured into AcOEt (5 mL) and washed with a 2.0 M $Na_2CO_3$ solution in water (2×2 mL). The organic layer was dried over $Na_2SO_4$, filtered and evaporated. The residue was purified by Combi-Flash Companion™ (Isco Inc.) column chromatography ($SiO_2$; gradient elution, [hexane/DCM 1:1]/TBME 95:5→8:2) to yield the title compound (19.1 mg, 0.053 mmol, 85%) as a reddish solid. MS: 359 [M+1]$^+$; HPLC: $^At_{Ret}$=2.61; TLC: $R_F$ 0.64 (hexane/DCM/TBME 1:1:2).

Step 12.4.

In a sealed flask, a solution of 6-(2,4-dichloro-phenyl)-8-isobutylamino-imidazo[1,2-a]pyridine-7-carbonitrile (19.1 mg, 0.053 mmol) in THF (0.5 mL) was cooled to 0° C. (ice bath), treated with $BH_3$.THF complex (1.0 M solution in THF, 0.48 mL, 0.48 mmol) and heated at 40° C. After 1 h, the reaction was not complete according to HPLC. 4.0 M HCl in dioxane (2 drops) and additional $BH_3$.THF complex (1.0 M solution in THF, 0.16 mL, 0.16 mmol) were added, then the reaction mixture was heated at 40° C. for 14 h, cooled to 0° C., and diluted in MeOH (large excess). The resulting mixture was concentrated under vacuum, and the remaining residue was dissolved in TFA. After evaporation to dryness, the remaining residue was purified by reverse phase prep-HPLC (Waters system) to give the title compound (2TFA salt, 7.6 mg, 0.013 mmol, 24%). MS: 363 [M+1]$^+$; HPLC: $^At_{Ret}$=1.47.

Example 24

Compounds 24a to 24n were obtained analogously to Example 23, using various amines in Step 12.3. The compounds are of the following general formula:

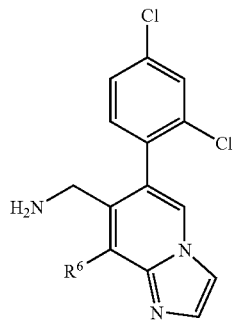

| Compound | Name | R$^6$ | HPLC $^At_{Ret}$ [min] | MS [M + 1]$^+$ |
|---|---|---|---|---|
| 24a | [7-Aminomethyl-6-(2,4-dichloro-phenyl)-imidazo[1,2-a]pyridin-8-yl]-cyclopropylmethyl-amine | | 1.18 | 361 |
| 24b | [7-Aminomethyl-6-(2,4-dichloro-phenyl)-imidazo[1,2-a]pyridin-8-yl]-benzyl-amine | | 1.31 | 397 |
| 24c | [7-Aminomethyl-6-(2,4-dichloro-phenyl)-imidazo[1,2-a]pyridin-8-yl]-ethyl-amine | | 1.03 | 335 |
| 24d | [7-Aminomethyl-6-(2,4-dichloro-phenyl)-imidazo[1,2-a]pyridin-8-yl]-dimethyl-amine | | 0.91 | 335 |
| 24e | [7-Aminomethyl-6-(2,4-dichoro-phenyl)-imidazo[1,2-a]pyridin-8-yl]-butyl-amine | | 1.28 | 363 |
| 24f | [7-Aminomethyl-6-(2,4-dichloro-phenyl)-imidazo[1,2-a]pyridin-8-yl]-(2-methoxy-ethyl)-amine | | 1.01 | 365 |

-continued

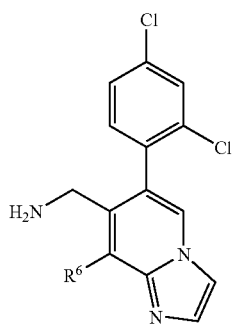

| Compound | Name | R⁶ | HPLC $^A t_{Ret}$ [min] | MS [M + 1]⁺ |
|---|---|---|---|---|
| 24g | [7-Aminomethyl-6-(2,4-dichloro-phenyl)-imidazo[1,2-a]pyridin-8-yl]-propyl-amine | propyl-NH- | 1.16 | 349 |
| 24h | 2-[7-Aminomethyl-6-(2,4-dichloro-phenyl)-imidazo[1,2-a]pyridin-8-ylamino]-ethanol | HO-CH₂CH₂-NH- | 0.91 | 351 |
| 24i | C-[6-(2,4-Dichloro-phenyl)-8-piperidin-1-yl-imidazo[1,2-a]pyridin-7-yl]-methylamine | piperidin-1-yl | 1.05 | 375 |
| 24j | C-[6-(2,4-Dichloro-phenyl)-8-morpholin-4-yl-imidazo[1,2-a]pyridin-7-yl]-methylamine | morpholin-4-yl | 0.93 | 377 |
| 24k | C-[6-(2,4-Dichloro-phenyl)-8-pyrrolidin-1-yl-imidazo[1,2-a]pyridin-7-yl]-methylamine | pyrrolidin-1-yl | 1.03 | 361 |
| 24l | [7-Aminomethyl-6-(2,4-dichloro-phenyl)-imidazo[1,2-a]pyridin-8-yl]-cyclopentyl-amine | cyclopentyl-NH- | 1.29 | 375 |
| 24m | [7-Aminomethyl-6-(2,4-dichloro-phenyl)-imidazo[1,2-a]pyridin-8-yl]-cyclohexyl-amine | cyclohexyl-NH- | 1.36 | 389 |
| 24n | [7-Aminomethyl-6-(2,4-dichloro-phenyl)-imidazo[1,2-a]pyridin-8-yl]-methyl-amine | CH₃-NH- | 0.97 | 321 |

Example 25

7-Aminomethyl-6-(2,4-dichloro-phenyl)-imidazo[1,2-a]pyridin-8-ylamine

Compound 25 was prepared according to Scheme 13:

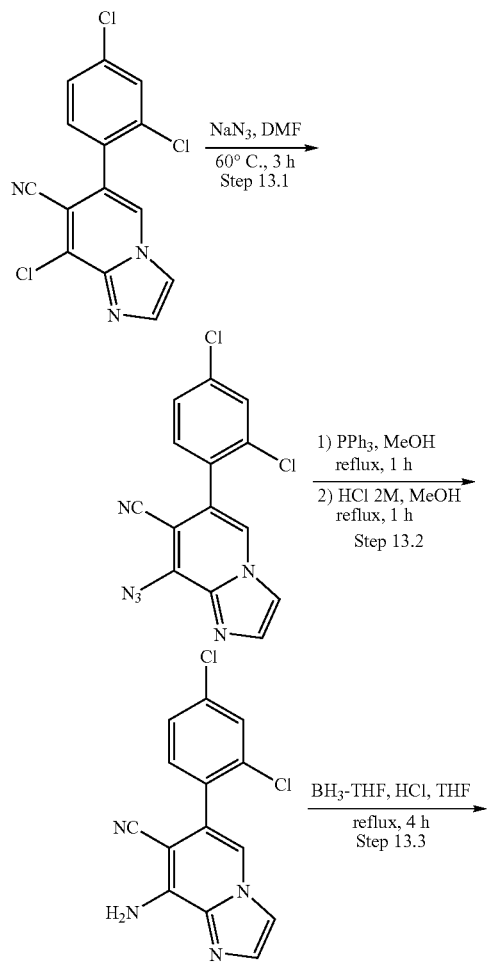

Step 13.1: 8-Azido-6-(2,4-dichloro-phenyl)-imidazo[1,2-a]pyridine-7-carbonitrile.

A mixture of 8-chloro-6-(2,4-dichloro-phenyl)-imidazo[1,2-a]pyridine-7-carbonitrile (80 mg, 0.25 mmol, prepared according to Example 23, Step 12.2) and sodium azide (81 mg, 1.24 mmol) in DMF (1 mL) was stirred and heated at 60° C. for 3 h. The reaction mixture was cooled to RT, poured into AcOEt and washed successively with water and brine. The organic layer was dried over $Na_2SO_4$, filtered and evaporated to yield the crude title compound (77.4 mg, 0.24 mmol, 95%) as a brownish solid, which was used in the next step without further purification. MS: 329 [M+1]$^+$; HPLC: $^At_{Ret}$=2.56.

Step 13.2: 8-Amino-6-(2,4-dichloro-phenyl)-imidazo[1,2-a]pyridine-7-carbonitrile.

A mixture of crude 8-azido-6-(2,4-dichloro-phenyl)-imidazo[1,2-a]pyridine-7-carbonitrile (68 mg, 0.21 mmol) and triphenylphosphine (83.7 mg, 0.32 mmol) in MeOH (2.5 mL) was stirred and refluxed for 1 h. 2 M HCl in water (1 mL) was added and the reaction mixture was further refluxed for 1 h. The reaction mixture was cooled to RT, concentrated under vacuum and the remaining residue was dissolved in water. The aqueous solution was basified to pH 12 by the addition of 2 M NaOH in water. The resulting slurry was extracted with DCM (2×) and the combined organic fractions were dried over $Na_2SO_4$, filtered and evaporated. The remaining residue was dissolved in hot MeOH, then the solution was slowly cooled to RT and the formed precipitate was filtered and washed with cold MeOH to yield the title compound (32.5 mg, 0.11 mmol, 52%) as a brownish solid. MS: 303 [M+1]$^+$; HPLC: $^At_{Ret}$=1.72.

Step 13.3.

To a solution of 8-amino-6-(2,4-dichloro-phenyl)-imidazo[1,2-a]pyridine-7-carbonitrile (32.5 mg, 0.11 mmol) in THF (1 mL) was added a $BH_3$.THF complex (1.0 M solution in THF, 0.43 mL, 0.43 mmol) followed by 4 M HCl in dioxane (2 drops). The reaction mixture was stirred and refluxed for 4 h, then cooled to 0° C. (ice bath) and poured into MeOH. The mixture was concentrated under vacuum, then the remaining residue was dissolved in TFA, evaporated to dryness and purified by reverse phase prep-HPLC (Waters system) to give the title compound (2TFA salt, 35.7 mg, 0.067 mmol, 62%). MS: 307 [M+1]$^+$; HPLC: $^At_{Ret}$=0.99.

Example 26

1-{4-[7-Aminomethyl-6-(2,4-dichloro-phenyl)-imidazo[1,2-a]pyridine-3-carbonyl]-piperazin-1-yl}-ethanone Compound 26 was prepared according to Scheme 14:

Scheme 14

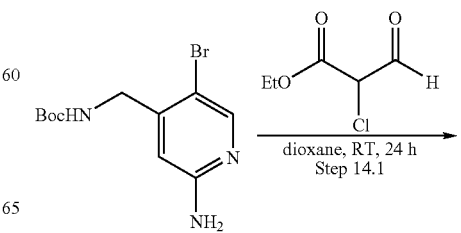

139
-continued

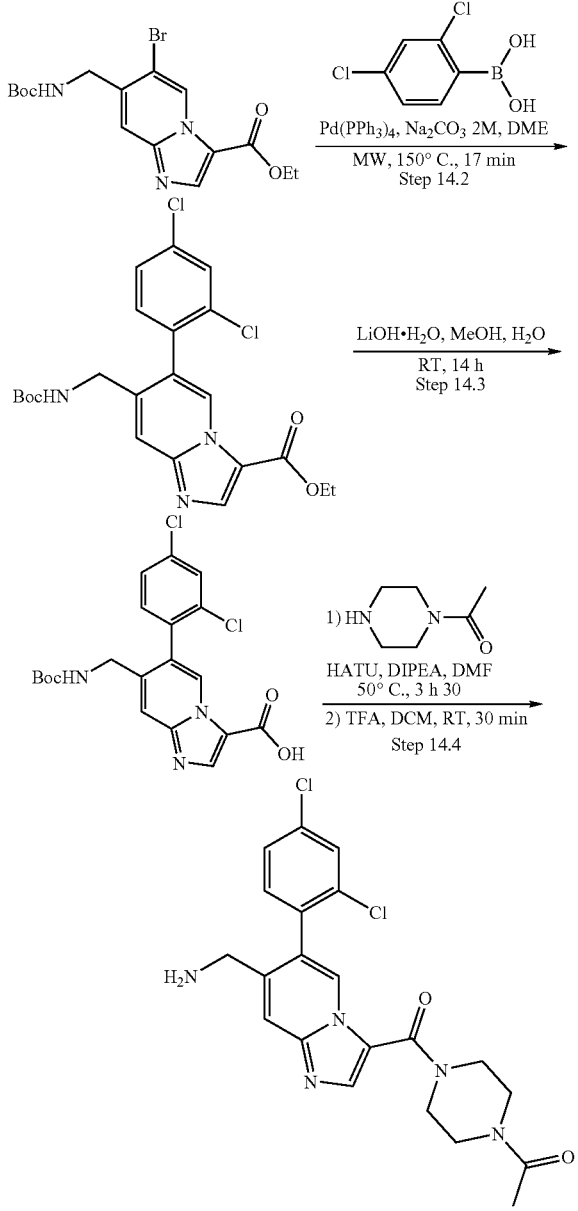

Step 14.1: 6-Bromo-7-(tert-butoxycarbonylamino-methyl)-imidazo[1,2-a]pyridine-3-carboxylic acid ethyl ester.

A solution of (2-amino-5-bromo-pyridin-4-ylmethyl)-carbamic acid tert-butyl ester (3.5 g, 11.6 mmol, prepared according to Example 1, Step 1.3) and freshly prepared 2-chloro-3-oxo-propionic acid ethyl ester (8.97 g, 59.6 mmol, prepared according to a patented procedure U.S. Pat. No. 5,559,158-A1) in dioxane (60 mL) was stirred at RT for 14 h. The reaction mixture was diluted in AcOEt (400 mL) and washed with a 2.0 M aqueous $Na_2CO_3$ solution (2×200 mL). The organic layer was dried over $Na_2SO_4$, filtered, and evaporated. The residue was purified by Combi-Flash Companion™ (Isco Inc.) column chromatography (SiO$_2$; gradient elution, [hexane/DCM 1:1]/TBME 95:5→2:8) to yield the title compound (1.31 g, 4.83 mmol, 41%) as a light yellow solid. MS: 398 [M+1]$^+$; HPLC: $^A$t$_{Ret}$=1.85; TLC: R$_F$ 0.47 (hexane/DCM/TBME 1:1:2).

140

Step 14.2: 7-(tert-Butoxycarbonylamino-methyl)-6-(2,4-dichloro-phenyl)-imidazo[1,2-a]pyridine-3-carboxylic acid ethyl ester.

In a sealed tube, a mixture of 6-bromo-7-(tert-butoxycarbonylamino-methyl)-imidazo[1,2-a]pyridine-3-carboxylic acid ethyl ester (1.4 g, 3.52 mmol), 2,4-dichloro-benzeneboronic acid (1.01 g, 5.29 mmol), Pd(PPh$_3$)$_4$ (203 mg, 0.18 mmol) and $Na_2CO_3$ (2.0 M solution in water, 6.2 mL) in DME (20 mL) was heated at 150° C. for 17 min under microwave irradiation. The reaction mixture was cooled to RT, diluted in AcOEt (400 mL) and washed with a 2.0 M aqueous $Na_2CO_3$ solution (2×200 mL). The organic layer was dried over $Na_2SO_4$, filtered, and evaporated. The residue was purified by Combi-Flash Companion™ (Isco Inc.) column chromatography (SiO$_2$; gradient elution, [hexane/DCM 1:1]/TBME 95:5→2:8) to yield the title compound (1.39 g, 2.81 mmol, 80%). MS: 464 [M+1]$^+$; HPLC: $^A$t$_{Ret}$=2.31; TLC: RF 0.47 (hexane/DCM/TBME 1:1:2).

Step 14.3: 7-(tert-Butoxycarbonylamino-methyl)-6-(2,4-dichloro-phenyl)-imidazo[1,2-a]pyridine-3-carboxylic acid.

To a suspension of 7-(tert-butoxycarbonylamino-methyl)-6-(2,4-dichloro-phenyl)-imidazo[1,2-a]pyridine-3-carboxylic acid ethyl ester (1.39 g, 2.99 mmol) in MeOH (24 mL) and water (12 mL) was added LiOH.H$_2$O (377 mg, 8.98 mmol) in one portion. The slurry was stirred at RT for 14 h then the clear solution was acidified to pH 5 by the addition of 2.0 M HCl in water. The resulting precipitate was filtered, the solid washed with water and dried under vacuum to yield the title compound (1.25 g, 2.76 mmol, 92%) as a colorless solid, which was used in the next step without further purification. MS: 436 [M+1]$^+$; HPLC: $^A$t$_{Ret}$=1.76.

Step 14.4.

(1) To a mixture of 7-(tert-butoxycarbonylamino-methyl)-6-(2,4-dichloro-phenyl)-imidazo[1,2-a]pyridine-3-carboxylic acid (50 mg, 0.115 mmol), 1-piperazin-1-yl-ethanone (16.2 mg, 0.126 mmol) and DIPEA (0.040 mL, 0.229 mmol) in DMF (0.8 mL) was added HATU (47.9 mg, 0.126 mmol) at RT. The reaction mixture was heated at 50° C. for 3 h30, then poured into AcOEt (20 mL) and washed successively with a 2.0 M aqueous $Na_2CO_3$ solution (2×10 mL) and brine (10 mL). The organic layer was dried over $Na_2SO_4$, filtered, and evaporated to give the crude Boc-protected intermediate.

(2) The Boc-protected intermediate was dissolved in DCM (2 mL), TFA (1 mL) was added and the solution was stirred at RT for 30 min. The reaction mixture was concentrated to dryness and the remaining residue purified by reverse phase prep-HPLC (Waters system) to give the title compound as a TFA salt.

(3) The TFA salt was dissolved in HCl (1.25 M solution in MeOH), stirred for 5 min at RT, and evaporated to dryness (the sequence was performed 3 times). The remaining residue was dissolved in water and lyophilized to give the HCl salt of the title compound (2HCl salt, 39.8 mg, xmmol, 67%) as a yellow solid. MS: 446 [M+1]$^+$; HPLC: $^A$t$_{Ret}$=1.06.

Example 27

Compounds 27a to 27l' were obtained as TFA or HCl salts, analogously to Example 26, using various boronic acid in Step 14.2 and various amines in Step 14.4. The compounds are of the following general formula:

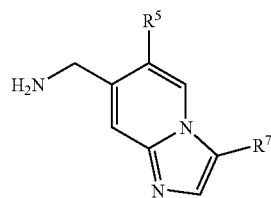

| Compound | Name | R⁵ | R⁷ | HPLC $^A t_{Ret}$ [min] | MS [M + 1]⁺ |
|---|---|---|---|---|---|
| 27a | [7-Aminomethyl-6-(2,4-dichloro-phenyl)-imidazo[1,2-a]pyridin-3-yl]-morpholin-4-yl-methanone | 2,4-diCl-phenyl | morpholine-C(O)- | 1.58 | 405 |
| 27b | [7-Aminomethyl-6-(2,4-dichloro-phenyl)-imidazo[1,2-a]pyridin-3-yl]-piperazin-1-yl-methanone | 2,4-diCl-phenyl | piperazine-C(O)- | 0.81 | 404 |
| 27c | [7-Aminomethyl-6-(2,4-dichloro-phenyl)-imidazo[1,2-a]pyridin-3-yl]-thiomorpholin-4-yl-methanone | 2,4-diCl-phenyl | thiomorpholine-C(O)- | 1.30 | 421 |
| 27d | 4-[7-Aminomethyl-6-(2,4-dichloro-phenyl)-imidazo[1,2-a]pyridine-3-carbonyl]-piperazine-1-carboxylic acid ethyl ester | 2,4-diCl-phenyl | 4-(ethoxycarbonyl)piperazine-C(O)- | 1.33 | 476 |
| 27e | 4-[7-Aminomethyl-6-(2,4-dichloro-phenyl)-imidazo[1,2-a]pyridine-3-carbonyl]-piperazin-2-one | 2,4-diCl-phenyl | 3-oxopiperazine-C(O)- | 0.95 | 418 |
| 27f | 1-{1-[7-Aminomethyl-6-(2,4-dichloro-phenyl)-imidazo[1,2-a]pyridine-3-carbonyl]-piperidin-4-yl}-imidazolin-2-one | 2,4-diCl-phenyl | 4-(2-oxoimidazolidin-1-yl)piperidine-C(O)- | 1.08 | 487 |
| 27g | 6-{4-[7-Aminomethyl-6-(2,4-dichloro-phenyl)-imidazo[1,2-a]pyridine-3-carbonyl]-piperazin-1-yl}-1-methyl-1H-pyridin-2-one | 2,4-diCl-phenyl | 4-(1-methyl-6-oxo-1,6-dihydropyridin-2-yl)piperazine-C(O)- | 1.22 | 511 |

-continued

| Compound | Name | R⁵ | R⁷ | HPLC $^A t_{Ret}$ [min] | MS [M + 1]⁺ |
|---|---|---|---|---|---|
| 27h | [7-Aminomethyl-6-(2,4-dichloro-phenyl)-imidazo[1,2-a]pyridin-3-yl]-[4-(furan-2-carbonyl)-piperazin-1-yl]-methanone | 2,4-dichlorophenyl | 4-(furan-2-carbonyl)-piperazin-1-yl carbonyl | 1.26 | 498 |
| 27i | [7-Aminomethyl-6-(2,4-dichloro-phenyl)-imidazo[1,2-a]pyridin-3-yl]-(4-pyrimidin-2-yl-piperazin-1-yl)-methanone | 2,4-dichlorophenyl | 4-pyrimidin-2-yl-piperazin-1-yl carbonyl | 1.26 | 482 |
| 27j | [7-Aminomethyl-6-(2,4-dichloro-phenyl)-imidazo[1,2-a]pyridin-3-yl]-(2,3,5,6-tetrahydro-[1,2']bipyrazinyl-4-yl)-methanone | 2,4-dichlorophenyl | 4-pyrazin-2-yl-piperazin-1-yl carbonyl | 1.24 | 482 |
| 27k | [7-Aminomethyl-6-(2,4-dichloro-phenyl)-imidazo[1,2-a]pyridin-3-yl]-(2,6-dimethyl-morpholin-4-yl)-methanone | 2,4-dichlorophenyl | 2,6-dimethyl-morpholin-4-yl carbonyl | 1.30 | 433 |
| 27l | 2-{4-[7-Aminomethyl-6-(2,4-dichloro-phenyl)-imidazo[1,2-a]pyridine-3-carbonyl]-piperazin-1-yl}-1-morpholin-4-yl-ethanone | 2,4-dichlorophenyl | 4-(2-morpholin-4-yl-2-oxo-ethyl)-piperazin-1-yl carbonyl | 0.92 | 531 |
| 27m | 8-[7-Aminomethyl-6-(2,4-dichloro-phenyl)-imidazo[1,2-a]pyridine-3-carbonyl]-1-oxa-3,8-diaza-spiro[4.5]decan-2-one | 2,4-dichlorophenyl | 1-oxa-3,8-diaza-spiro[4.5]decan-2-one-8-yl carbonyl | 1.07 | 474 |

-continued

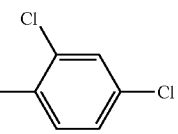

| Compound | Name | R⁵ | R⁷ | HPLC ᴬt_Ret [min] | MS [M + 1]⁺ |
|---|---|---|---|---|---|
| 27n | 7-Aminomethyl-6-(2,4-dichloro-phenyl)-imidazo[1,2-a]pyridine-3-carboxylic acid (2-methoxy-ethyl)-methyl-amide | 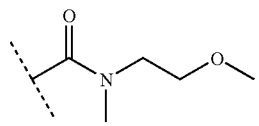 | 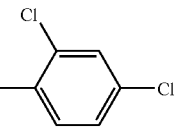 | 1.14 | 407 |
| 27o | [7-Aminomethyl-6-(2,4-dichloro-phenyl)-imidazo[1,2-a]pyridin-3-yl]-(3-trifluoromethyl-5,6-dihydro-8H-[1,2,4]triazolo[4,3-a]pyrazin-7-yl)-methanone | 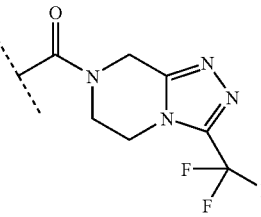 | 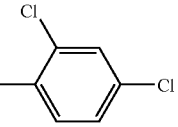 | 1.32 | 510 |
| 27p | 7-Aminomethyl-6-(2,4-dichloro-phenyl)-imidazo[1,2-a]pyridine-3-carboxylic acid pyridin-4-ylamide | 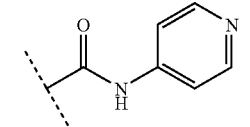 | 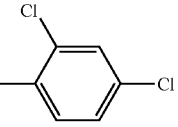 | 1.05 | 412 |
| 27q | 7-Aminomethyl-6-(2,4-dichloro-phenyl)-imidazo[1,2-a]pyridine-3-carboxylic acid pyridin-3-ylamide | 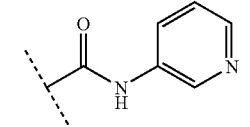 | 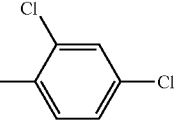 | 1.03 | 412 |
| 27r | [7-Aminomethyl-6-(2,4-dichloro-phenyl)-imidazo[1,2-a]pyridin-3-yl]-(4-methyl-piperazin-1-yl)-methanone | 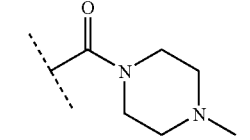 | 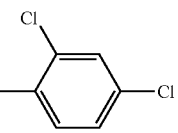 | 0.84 | 418 |
| 27s | 7-Aminomethyl-6-(2,4-dichloro-phenyl)-imidazo[1,2-a]pyridine-3-carboxylic acid (tetrahydro-pyran-4-yl)-amide | 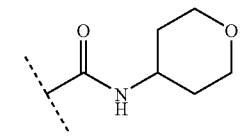 | 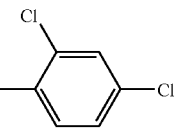 | 1.21 | 419 |
| 27t | 7-Aminomethyl-6-(2,4-dichloro-phenyl)-imidazo[1,2-a]pyridine-3-carboxylic acid (tetrahydro-pyran-3-yl)-amide | 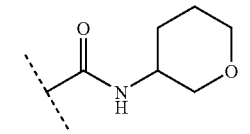 | 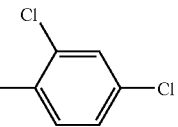 | 1.25 | 419 |
| 27u | 1-{4-[7-Aminomethyl-6-(2,4-dichloro-phenyl)-imidazo[1,2-a]pyridine-3-carbonyl]-piperazin-1-yl}-propan-1-one | 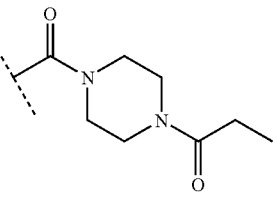 | | 1.16 | 460 |

-continued

| Compound | Name | R⁵ | R⁷ | HPLC $^A t_{Ret}$ [min] | MS [M + 1]⁺ |
|---|---|---|---|---|---|
| 27v | [7-Aminomethyl-6-(2,4-dichloro-phenyl)-imidazo[1,2-a]pyridin-3-yl]-(4-methanesulfonyl-piperazin-1-yl)-methanone | 2,4-dichlorophenyl | 4-methanesulfonyl-piperazin-1-yl carbonyl | 1.18 | 482 |
| 27w | 4-[7-Aminomethyl-6-(2,4-dichloro-phenyl)-imidazo[1,2-a]pyridine-3-carbonyl]-piperazine-1-carboxylic acid dimethylamide | 2,4-dichlorophenyl | 4-(dimethylcarbamoyl)-piperazin-1-yl carbonyl | 1.17 | 475 |
| 27x | 7-Aminomethyl-6-(2,4-dichloro-phenyl)-imidazo[1,2-a]pyridine-3-carboxylic acid methyl-(tetrahydro-pyran-4-yl)-amide | 2,4-dichlorophenyl | N-methyl-N-(tetrahydropyran-4-yl) carbamoyl | 1.17 | 433 |
| 27y | 7-Aminomethyl-6-(2,4-dichloro-phenyl)-imidazo[1,2-a]pyridine-3-carboxylic acid ethyl-(tetrahydro-pyran-4-yl)-amide | 2,4-dichlorophenyl | N-ethyl-N-(tetrahydropyran-4-yl) carbamoyl | 1.28 | 447 |
| 27z | 3-{[7-Aminomethyl-6-(2,4-dichloro-phenyl)-imidazo[1,2-a]pyridine-3-carbonyl]-amino}-piperidine-1-carboxylic acid ethyl ester | 2,4-dichlorophenyl | 1-(ethoxycarbonyl)piperidin-3-ylaminocarbonyl | 1.45 | 490 |
| 27a' | 3-{[7-Aminomethyl-6-(2,4-dichloro-phenyl)-imidazo[1,2-a]pyridine-3-carbonyl]-methyl-amino}-piperidine-1-carboxylic acid ethyl ester | 2,4-dichlorophenyl | N-methyl-N-[1-(ethoxycarbonyl)piperidin-3-yl] carbamoyl | 1.42 | 504 |

-continued

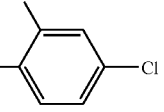

| Compound | Name | R⁵ | R⁷ | HPLC $^A t_{Ret}$ [min] | MS [M + 1]⁺ |
|---|---|---|---|---|---|
| 27b' | [7-Aminomethyl-6-(2,4-dichloro-phenyl)-imidazo[1,2-a]pyridin-3-yl]-(1,1-dioxo-1lambda*6*-thiomorpholin-4-yl)-methanone | 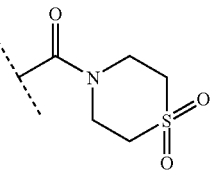 | 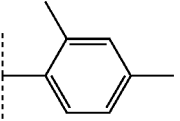 | 1.11 | 453 |
| 27c' | [7-Aminomethyl-6-(2,4-dimethyl-phenyl)-imidazo[1,2-a]pyridin-3-yl]-morpholin-4-yl-methanone | 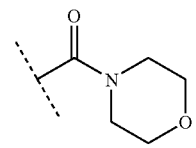 | 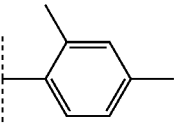 | 1.34 | 365 |
| 27d' | [7-Aminomethyl-6-(2,4-dimethyl-phenyl)-imidazo[1,2-a]pyridin-3-yl]-(4-methanesulfonyl-piperazin-1-yl)-methanone | 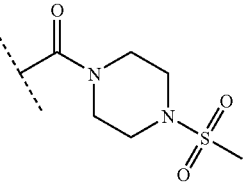 | 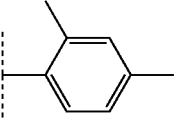 | 1.11 | 442 |
| 27e' | [7-Aminomethyl-6-(2,4-dimethyl-phenyl)-imidazo[1,2-a]pyridin-3-yl]-(4-pyrimidin-2-yl-piperazin-1-yl)-methanone | 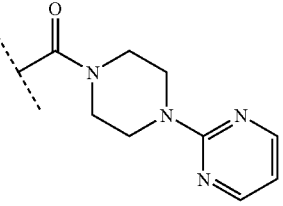 | 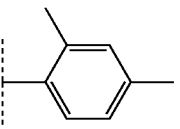 | 1.19 | 442 |
| 27f' | [7-Aminomethyl-6-(2,4-dimethyl-phenyl)-imidazo[1,2-a]pyridin-3-yl]-(3-trifluoromethyl-5,6-dihydro-8H-[1,2,4]triazolo[4,3-a]pyrazin-7-yl)-methanone | 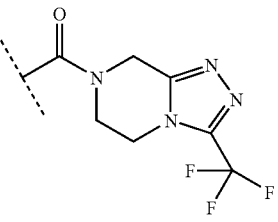 | 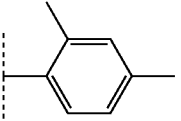 | 1.22 | 470 |
| 27g' | 1-{4-[7-Aminomethyl-6-(2,4-dimethyl-phenyl)-imidazo[1,2-a]pyridine-3-carbonyl]-piperazin-1-yl}-ethanone | 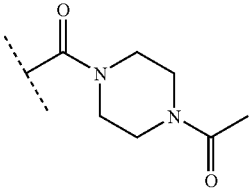 | | 0.97 | 406 |

-continued

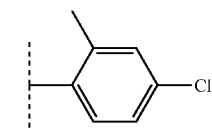

| Compound | Name | R⁵ | R⁷ | HPLC $^A t_{Ret}$ [min] | MS [M + 1]⁺ |
|---|---|---|---|---|---|
| 27h' | [7-Aminomethyl-6-(4-chloro-2-methyl-phenyl)-imidazo[1,2-a]pyridin-3-yl]-morpholin-4-yl-methanone | 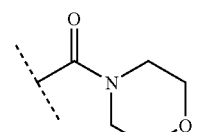 | 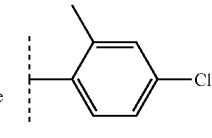 | 1.09 | 385 |
| 27i' | [7-Aminomethyl-6-(4-chloro-2-methyl-phenyl)-imidazo[1,2-a]pyridin-3-yl]-(4-methanesulfonyl-piperazin-1-yl)-methanone | 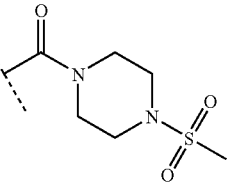 | 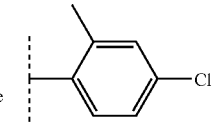 | 1.16 | 462 |
| 27j' | [7-Aminomethyl-6-(4-chloro-2-methyl-phenyl)-imidazo[1,2-a]pyridin-3-yl]-(4-pyrimidin-2-yl-piperazin-1-yl)-methanone | 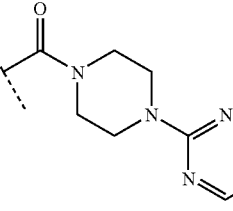 | 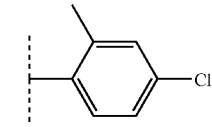 | 1.24 | 462 |
| 27k' | [7-Aminomethyl-6-(4-chloro-2-methyl-phenyl)-imidazo[1,2-a]pyridin-3-yl]-(3-trifluoromethyl-5,6-dihydro-8H-[1,2,4]triazolo[4,3-a]pyrazin-7-yl)-methanone | 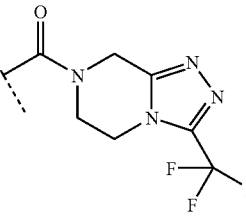 | 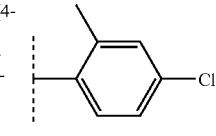 | 1.31 | 490 |
| 27l' | 1-{4-[7-Aminomethyl-6-(4-chloro-2-methyl-phenyl)-imidazo[1,2-a]pyridine-3-carbonyl]-piperazin-1-yl}-ethanone | 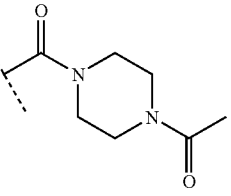 | | 1.03 | 426 |

Example 28

1-[6-(2,4-Dichloro-phenyl)-imidazo[1,2-a]pyridin-7-yl]-ethylamine

Compound 28 was prepared according to Scheme 15:

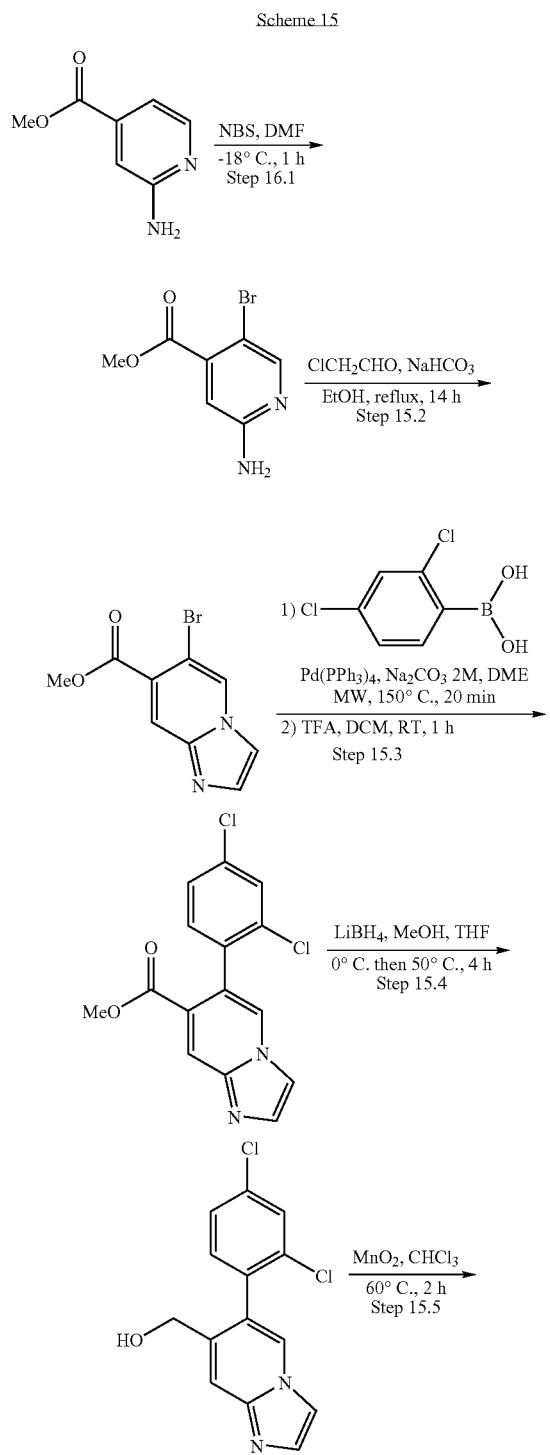

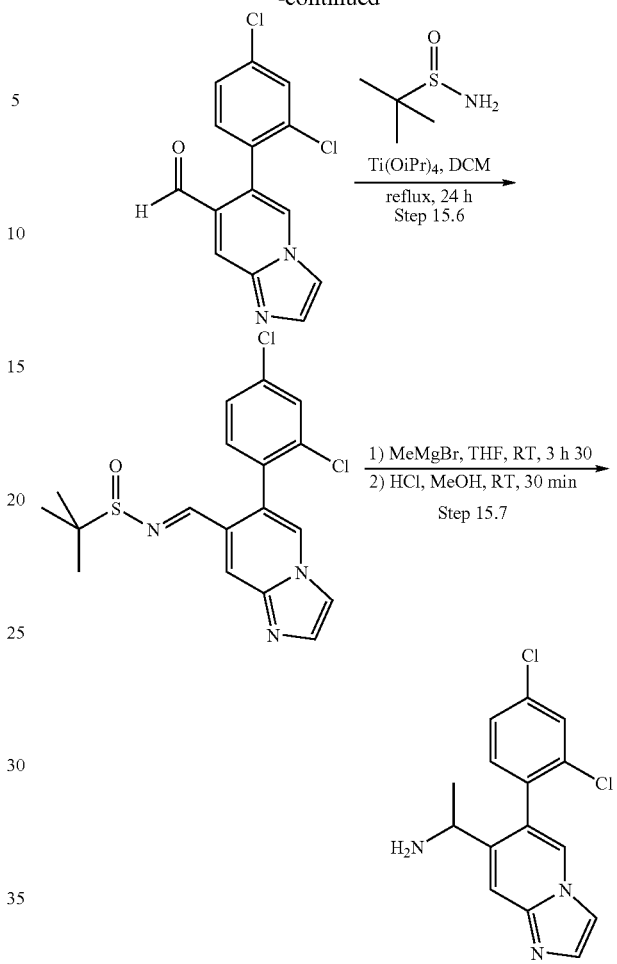

Step 15.1: 2-Amino-5-bromo-isonicotinic acid methyl ester.

A solution of 2-amino-isonicotinic acid methyl ester (5.58 g, 36.7 mmol) in DMF (56 mL) was cooled to −18° C. (ice/MeOH bath), treated with NBS (7.21 g, 38.5 mmol), and stirred at −18° C. for 1 h. The reaction mixture was diluted in AcOEt (500 mL) and washed with water (2×250 mL). The organic layer was dried over $Na_2SO_4$, filtered and evaporated to yield the crude title compound (3.0 g, 13.0 mmol, 35%) as a yellow solid, which was used in the next step without further purification. MS: 231 [M+1]$^+$; HPLC: $^A t_{Ret}$=0.70.

Step 15.2: 6-Bromo-imidazo-[1,2-a]pyridine-7-carboxylic acid methyl ester.

A mixture of 2-amino-5-bromo-isonicotinic acid methyl ester (500 mg, 2.16 mmol), $NaHCO_3$ (309 mg, 3.68 mmol) and chloracetaldehyde (1.16 mL, 9.8 mmol) in EtOH (15 mL) was vigorously stirred and refluxed for 14 h. The reaction mixture was cooled to RT, concentrated under vacuum and the remaining residue was suspended in AcOEt (100 mL). The organic fraction was washed with water (2×50 mL), then dried over $Na_2SO_4$, filtered, and evaporated. The residue was purified by Combi-Flash Companion™ (Isco Inc.) column chromatography ($SiO_2$; gradient elution, [hexane/DCM 1:1]/TBME 95:5-100% TBME) to yield the title compound (505 mg, 1.98 mmol, 91%). MS: 255 [M+1]$^+$; HPLC: $^A t_{Ret}$=0.58 TLC: $R_F$ 0.16 (hexane/DCM/TBME 1:1:2).

Step 15.3: 6-(2,4-Dichloro-phenyl)-imidazo[1,2-a]pyridine-7-carboxylic acid methyl ester.

In a sealed tube, a mixture of 6-bromo-imidazo[1,2-a]pyridine-7-carboxylic acid methyl ester (505 mg, 1.98 mmol), 2,4-dichlorobenzeneboronic acid (416 mg, 2.18 mmol), Pd(PPh$_3$)$_4$ (114 mg, 0.10 mmol) and Na$_2$CO$_3$ (2.0 M solution in water, 3.5 mL) in DME (5 mL) was heated at 150° C. for 17 min in a microwave oven. The reaction mixture was cooled to RT, poured into AcOEt and washed with water. The organic layer was dried over Na$_2$SO$_4$, filtered, and evaporated. The remaining residue was purified by Combi-Flash Companion™ (Isco Inc.) column chromatography (SiO$_2$; gradient elution, [hexane/DCM 1:1]/TBME 95:5→100% TBME) to yield the title compound (488 mg, 1.52 mmol, 77%). MS: 321 [M+1]$^+$; HPLC: $^A$t$_{Ret}$=1.43; TLC: R$_F$ 0.16 (hexane/DCM/TBME 1:1:2).

Step 15.4: [6-(2,4-Dichloro-phenyl)-imidazo[1,2-a]pyridin-7-yl]-methanol.

A solution of 6-(2,4-dichloro-phenyl)-imidazo[1,2-a]pyridine-7-carboxylic acid methyl ester (394 mg, 1.23 mmol) and MeOH (0.15 mL, 3.68 mmol) in THF (8 mL) was cooled to 0° C. (ice bath) then LiBH$_4$ (2 M solution in THF, 1.8 mL, 3.6 mmol) was added dropwise and the resulting mixture was heated at 50° C. and stirred for 4 h. The reaction mixture was cooled to RT, quenched by the addition of a saturated NH$_4$Cl solution in water, diluted in water and extracted with AcOEt (2×). The combined organic fractions were dried over Na$_2$SO$_4$, filtered and evaporated to dryness. The remaining residue was purified by Combi-Flash Companion™ (Isco Inc.) column chromatography (SiO$_2$; gradient elution, DCM/MeOH 99:1→8.2) to yield the title compound (156 mg, 0.53 mmol, 43%). MS: 293 [M+1]$^+$; HPLC: $^A$t$_{Ret}$=1.20, TLC: R$_F$ 0.20 (DCM/MeOH 95:5).

Step 15.5: 6-(2,4-Dichloro-phenyl)-imidazo[1,2-a]pyridine-7-carbaldehyde.

A mixture of [6-(2,4-dichloro-phenyl)-imidazo[1,2-a]pyridin-7-yl]-methanol (125 mg, 0.43 mmol) and MnO$_2$ (371 mg, 4.27 mmol) in CHCl$_3$ (2 mL) was stirred at 60° C. for 2 h, then cooled to RT and filtered through a Celite pad. The solid was washed with AcOEt and the filtrate was evaporated to dryness to give the crude title compound (104 mg, 0.36 mmol, 84%) which was used in the next step without further purification. HPLC: $^A$t$_{Ret}$=1.22.

Step 15.6: 2-Methyl-propane-2-sulfinic acid 1-[6-(2,4-dichloro-phenyl)-imidazo-[1,2-a]pyridin-7-yl]-meth-(E)-ylideneamide.

To a solution of 6-(2,4-dichloro-phenyl)-imidazo[1,2-a]pyridine-7-carbaldehyde (104 mg, 0.36 mmol) in DCM (5 mL) were successively added 2-methyl-2-propane-sulfinamide (47.6 mg, 0.39 mmol) and titanium tetraisopropoxide (0.21 mL, 0.72 mmol) at RT, then the mixture was heated at 45° C. and stirred for 14 h. The reaction mixture was cooled to RT, quenched by the successive addition of MeOH (2 mL) and several drops of a saturated NaHCO$_3$ solution in water. The resulting precipitate was filtered through a Na$_2$SO$_4$ pad, the solid was washed with AcOEt and the filtrate was evaporated to dryness. The remaining residue was purified by Combi-Flash Companion™ (Isco Inc.) column chromatography (SiO$_2$; gradient elution, [hexane/DCM 1:1]/TBME 95:5→100% TBME) to yield the title compound (101 mg, 0.26 mmol, 72%). MS: 394 [M+1]$^+$; HPLC: $^A$t$_{Ret}$=1.58; TLC: R$_F$ 0.33 (hexane/DCM/TBME 1:1:6).

Step 15.7.

(1) To a solution of 2-methyl-propane-2-sulfinic acid 1-[6-(2,4-dichloro-phenyl)-imidazo[1,2-a]pyridin-7-yl]-meth-(E)-ylideneamide (20 mg, 0.045 mmol) in anhydrous THF (0.5 mL) was added methylmagnesium bromide (3 M solution in Et$_2$O, 0.045 mL, 0.14 mmol) at RT. The reaction mixture was stirred for 3 h30 then poured into a saturated solution of NH$_4$Cl in water and extracted with AcOEt. The organic layer was dried over Na$_2$SO$_4$, filtered and evaporated to dryness to give the crude 2-methyl-propane-2-sulfinic acid {1-[6-(2,4-dichloro-phenyl)-imidazo[1,2-a]pyridin-7-yl]-ethyl}-amide intermediate.

(2) The previously obtained intermediate was dissolved in a 1.25 M HCl solution in MeOH (2 mL) at RT, the resulting solution was stirred for 30 min then evaporated to dryness. The remaining residue was purified by reverse phase prep-HPLC (Waters system) to give the title compound (2TFA salt, 8.6 mg, 0.016 mmol, 36% for 2 steps). MS: 306 [M+1]$^+$; HPLC: $^A$t$_{Ret}$=0.75 and 0.92 (two different conformers).

Example 29

1-[6-(2,4-Dichloro-phenyl)-imidazo[1,2-a]pyridin-7-yl]-propylamine

The title compound was obtained analogously to Example 28 from 2-methyl-propane-2-sulfinic acid 1-[6-(2,4-dichloro-phenyl)-imidazo[1,2-a]pyridin-7-yl]-meth-(E)-ylideneamide (101 mg, 0.26 mmol, prepared according to Example 28, Step 15.6) and ethylmagnesium bromide (1M THF solution, 0.77 mL, 0.77 mmol), followed by subsequent sulfonamide deprotection and reverse phase prep-HPLC (Waters system) purification (58.2 mg, 0.158 mmol, 62% for 2 steps). MS: 320 [M+1]$^+$; HPLC: $^A$t$_{Ret}$=0.87 and 1.05 (two different conformers).

Example 30

[7-Aminomethyl-6-(2,4-dichloro-phenyl)-3-morpholin-4-yl-imidazo[1,2-a]pyridin-8-yl]-isobutyl-amine Compound 30 was prepared according to Scheme 16:

Scheme 16

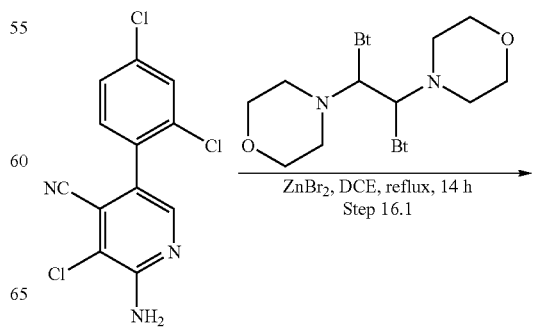

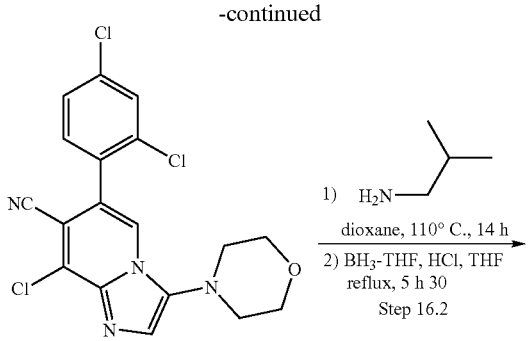

1) H₂N-CH₂CH(CH₃)₂
dioxane, 110° C., 14 h
2) BH₃-THF, HCl, THF
reflux, 5 h 30
Step 16.2

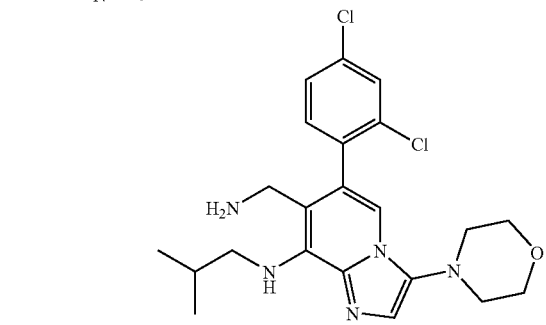

Step 16.1: 8-Chloro-6-(2,4-dichloro-phenyl)-3-morpholin-4-yl-imidazo[1,2-a]pyridine-7-carbonitrile.

A well stirred mixture of 2-amino-3-chloro-5-(2,4-dichloro-phenyl)-isonicotinonitrile (312 mg, 1.05 mmol, prepared according to Example 23, Step 12.1), ZnBr₂ (588 mg, 2.61 mmol) and (1,2-bis-benzotriazol-1-yl-1,2-bis-morpholin-4-yl-ethyl)-12-diamine (1.14 g, 2.62 mmol, freshly prepared according to Example 6, Step 3.1) in DCE (6 mL) was refluxed for 14 h, then cooled to RT and diluted into DCM (100 mL). The resulting slurry was filtered through a Celite pad and the filter cake washed with DCM. The filtrate was washed with a 2M KOH solution in water (3×50 mL), dried over Na₂SO₄, filtered and evaporated to dryness. The remaining residue was purified by Combi-Flash Companion™ (Isco Inc.) column chromatography (SiO₂; gradient elution, [hexane/DCM 1:1]/[TBME/MeOH—NH₃ 98:2] 95:5→4:6) to yield the title compound (167 mg, 0.41 mmol, 39%). MS: 407 [M+1]⁺; HPLC: $^A t_{Ret}$=2.40; TLC: $R_F$ 0.24 (DCM/hexane/MeOH containing 1% MeOH—NH₃ 1/1/2).

Step 16.2.

(1) In a sealed tube, a solution of 8-chloro-6-(2,4-dichloro-phenyl)-3-morpholin-4-yl-imidazo[1,2-a]pyridine-7-carbonitrile (30 mg, 0.074 mmol) and isobutylamine (0.044 mL, 0.44 mmol) in dioxane (1 mL) was heated at 110° C. for 14 h. The reaction mixture was cooled to RT, then frozen at −44° C. (dry ice) and lyophilized to give the crude 6-(2,4-dichloro-phenyl)-8-isobutylamino-3-morpholin-4-yl-imidazo[1,2-a]pyridine-7-carbonitrile intermediate. HPLC: $^A t_{Ret}$=2.77.

(2) To a solution of the previously obtained crude intermediate in THF (1 mL) were added slowly a 1M BH₃ solution in THF (0.29 mL, 0.29 mmol) followed by 2 drops of a 4M HCl solution in dioxane. The reaction mixture was refluxed for 2 h then cooled to RT and additional 1M BH₃ solution in THF (0.29 mL, 0.29 mmol) followed by 2 drops of a 4M HCl solution in dioxane were added. The reaction mixture was refluxed for further 3 h30, then cooled to RT and poured carefully into MeOH at 0° C. The resulting solution was concentrated to dryness, the remaining residue was dissolved in TFA, and evaporated under vacuum. The remaining residue was purified by reverse phase prep-HPLC (Waters system) to give the title compound (2TFA salt, 20 mg, 0.030 mmol, 40%). MS: 448 [M+1]⁺; HPLC: $^A t_{Ret}$=1.38.

Example 31

7-Aminomethyl-6-(2,4-dichloro-phenyl)-3-morpholin-4-yl-imidazo[1,2-a]pyridin-8-ylamine Compound 31 was prepared according to Scheme 17:

Scheme 17

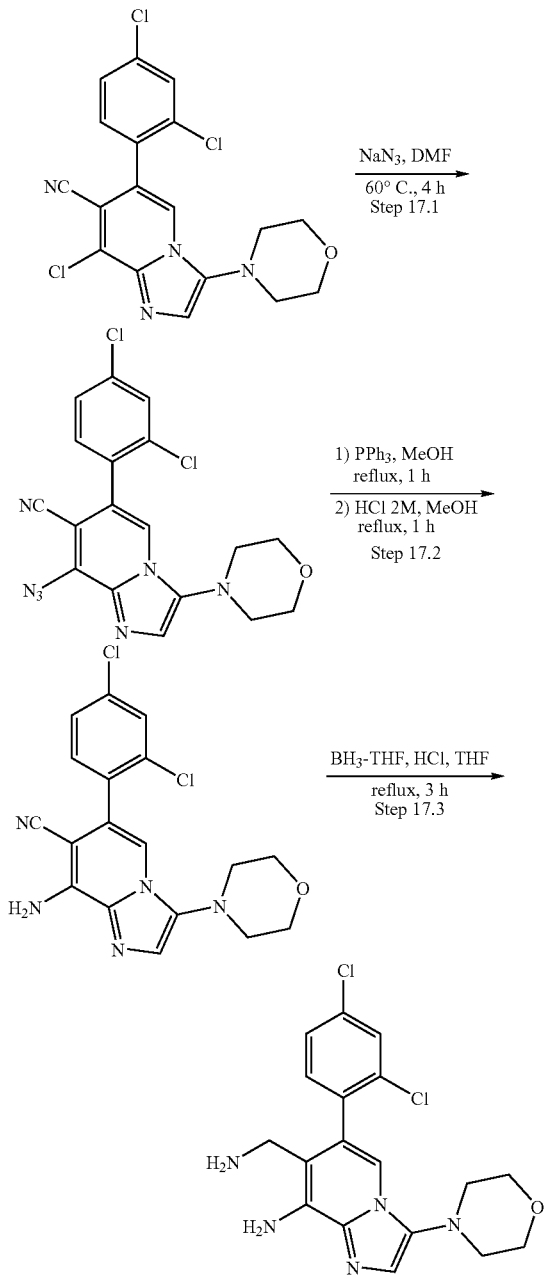

Step 17.1: 8-Azido-6-(2,4-dichloro-phenyl)-3-morpholin-4-yl-imidazo[1,2-a]pyridine-7-carbonitrile.

A mixture of 8-chloro-6-(2,4-dichloro-phenyl)-3-morpholin-4-yl-imidazo[1,2-a]pyridine-7-carbonitrile (135 mg, 0.33 mmol, prepared according to Example 30, Step 16.1) and sodium azide (108 mg, 1.66 mmol) in DMF (1 mL) was heated at 60° C. and stirred for 4 h. The reaction mixture was cooled to RT, poured into AcOEt and washed successively with water and brine. The organic layer was dried over $Na_2SO_4$, filtered and evaporated to dryness to yield the crude title compound (144 mg, 0.33 mmol, quant.) as a brownish solid, which was used in the next step without further purification. HPLC: $^At_{Ret}$=2.77.

Step 17.2: 8-Amino-6-(2,4-dichloro-phenyl)-3-morpholin-4-yl-imidazo[1,2-a]pyridine-7-carbonitrile.

A mixture of crude 8-azido-6-(2,4-dichloro-phenyl)-3-morpholin-4-yl-imidazo[1,2-a]pyridine-7-carbonitrile (144 mg, 0.33 mmol) and triphenylphosphine (133 mg, 0.51 mmol) in MeOH (4 mL) was stirred and refluxed for 1 h. 2M HCl in water (1 mL) was added and the reaction mixture was further refluxed for 1 h. The reaction mixture was cooled to RT, concentrated under vacuum and the remaining residue was dissolved in water. The aqueous solution was basified to pH 12 by the addition of a 2M NaOH solution in water. The resulting slurry was extracted with DCM (3×) and the combined organic fractions were dried over $Na_2SO_4$, filtered and evaporated. The remaining residue was purified by Combi-Flash Companion™ (Isco Inc.) column chromatography ($SiO_2$; gradient elution, DCM/MeOH 99:1→92:8) to yield the title compound (112 mg, 0.29 mmol, 87%). MS: 388 [M+1]$^+$; HPLC: $^At_{Ret}$=1.91; TLC: $R_F$ 0.56 (DCM/MeOH 95:5).

Step 17.3.

To a solution of 8-amino-6-(2,4-dichloro-phenyl)-3-morpholin-4-yl-imidazo[1,2-a]pyridine-7-carbonitrile (112 mg, 0.29 mmol) in THF (4 mL) was added a $BH_3$.THF complex (1.0 M solution in THF, 1.2 mL, 1.2 mmol) followed by a 4M HCl solution in dioxane (2 drops). The reaction mixture was stirred and refluxed for 3 h, then cooled to 0° C. (ice bath) and poured into MeOH. The mixture was concentrated under vacuum, the remaining residue was dissolved in a 2M HCl solution in water, and the mixture was washed with $Et_2O$ (2×). The aqueous layer was frozen and lyophilized. The remaining residue was purified by recrystallization in a mixture of MeOH/AcOEt to yield the title compound (2HCl salt, 36 mg, 0.077 mmol, 27%). MS: 392 [M+1]$^+$; HPLC: $^At_{Ret}$=1.13.

Example 32

C-[6-(2,4-Dichloro-phenyl)-8-methoxy-3-morpholin-4-yl-imidazo[1,2-a]pyridin-7yl]-methylamine Compound 32 was prepared according to Scheme 18:

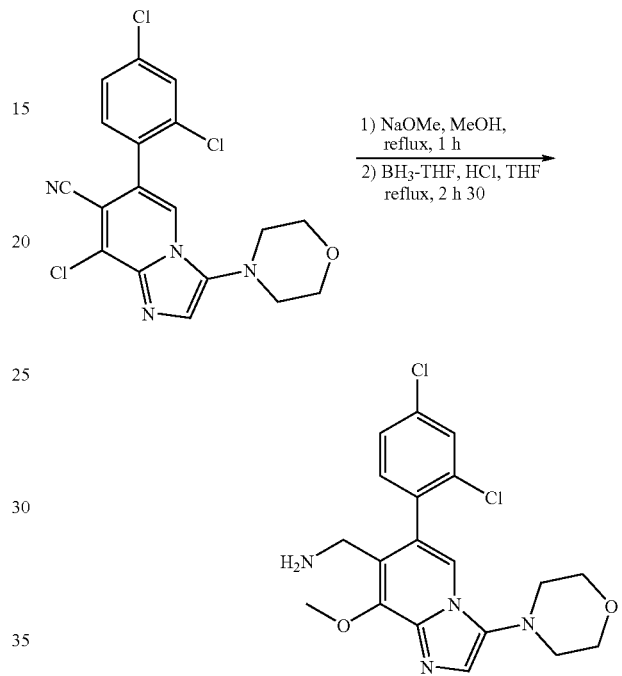

Scheme 18

A mixture of 8-chloro-6-(2,4-dichloro-phenyl)-3-morpholin-4-yl-imidazo[1,2-a]pyridine-7-carbonitrile (20 mg, 0.05 mmol, prepared according to Example 30, Step 16.1) and NaOMe (8.2 mg, 0.15 mmol) in MeOH (0.5 mL) was refluxed and stirred for 1 h. The reaction mixture was cooled to RT, poured into water (20 ml) and extracted with DCM (3×10 mL). The combined organic fractions were dried over $Na_2SO_4$, filtered, and evaporated. The remaining residue was dissolved in THF and a $BH_3$.THF complex (1.0 M solution in THF, 0.2 mL, 0.2 mmol) followed by a 4M HCl solution in dioxane (2 drops) were added. The reaction mixture was stirred and refluxed for 2 h30, then cooled to 0° C. (ice bath) and poured into MeOH. The resulting solution was evaporated to dryness and the remaining residue was purified by reverse phase prep-HPLC (Waters system) to give the title compound (2TFA salt, 3.3 mg, 0.005 mmol, 9% for 2 steps). MS: 407 [M+1]$^+$; HPLC: $^At_{Ret}$=1.09.

Example 33

Compounds 33a to 33j were obtained analogously to Example 30, using the adequate cyclization reagent in Step 16.1 and various amines in Step 16.2, or analogously to Example 32, using various sodium alkoxydes, or analogously to Example 31 from the adequate starting material. The compounds are of the following general formula:

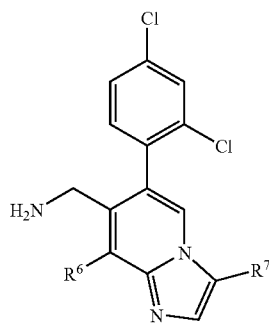

| Compound | Name | R⁶ | R⁷ | HPLC $^At_{Ret}$ [min] | MS [M + 1]⁺ |
|---|---|---|---|---|---|
| 33a | [7-Aminomethyl-6-(2,4-dichloro-phenyl)-3-morpholin-4-yl-imidazo[1,2-a]pyridin-8-yl]-methyl-amine | CH₃-NH- | morpholin-4-yl | 1.13 | 406 |
| 33b | [7-Aminomethyl-6-(2,4-dichloro-phenyl)-3-morpholin-4-yl-imidazo[1,2-a]pyridin-8-yl]-ethyl-amine | Et-NH- | morpholin-4-yl | 1.21 | 420 |
| 33c | [7-Aminomethyl-6-(2,4-dichloro-phenyl)-3-morpholin-4-yl-imidazo[1,2-a]pyridin-8-yl]-isopropyl-amine | iPr-NH- | morpholin-4-yl | 1.26 | 434 |
| 33d | [7-Aminomethyl-6-(2,4-dichloro-phenyl)-3-morpholin-4-yl-imidazo[1,2-a]pyridin-8-yl]-cyclopentyl-amine | cyclopentyl-NH- | morpholin-4-yl | 1.39 | 460 |
| 33e | [7-Aminomethyl-6-(2,4-dichloro-phenyl)-3-piperazin-1-yl-imidazo[1,2-a]pyridin-8-yl]-isobutyl-amine | iBu-NH- | piperazin-1-yl | 1.38 | 447 |
| 33f | [7-Aminomethyl-6-(2,4-dichloro-phenyl)-3-thiomorpholin-4-yl-imidazo[1,2-a]pyridin-8-yl]-isobutyl-amine | iBu-NH- | thiomorpholin-4-yl | 1.56 | 464 |
| 33g | C-[6-(2,4-Dichloro-phenyl)-8-isobutoxy-3-morpholin-4-yl-imidazo[1,2-a]pyridin-7-yl]-methylamine | iBu-O- | morpholin-4-yl | 1.35 | 449 |
| 33h | 7-Aminomethyl-6-(2,4-dichloro-phenyl)-3-thiomorpholin-4-yl-imidazo[1,2-a]pyridin-8-ylamine | H₂N- | thiomorpholin-4-yl | 1.35 | 408 |
| 33i(*) | [7-Aminomethyl-6-(2,4-dichloro-phenyl)-3-(1-oxo-1lambda*4*-thiomorpholin-4-yl)-imidazo[1,2-a]pyridin-8-yl]-isobutyl-amine | iBu-NH- | 1-oxo-thiomorpholin-4-yl | 1.21 | 480 |

-continued

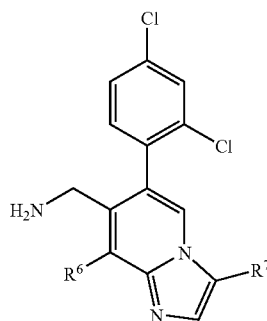

| Compound | Name | R⁶ | R⁷ | HPLC $^At_{Ret}$ [min] | MS [M + 1]⁺ |
|---|---|---|---|---|---|
| 33j(*) | 7-Aminomethyl-6-(2,4-dichloro-phenyl)-3-(1-oxo-1lambda*4*-thiomorpholin-4-yl)-imidazo[1,2-a]pyridin-8-ylamine | H₂N— | —N⌒S=O | 0.96 | 424 |

(*)Compounds 33i and 33j were obtained respectively from 33f and 33h using the following procedure.

A solution of [7-aminomethyl-6-(2,4-dichloro-phenyl)-3-thiomorpholin-4-yl-imidazo[1,2-a]pyridin-8-yl]-isobutyl-amine (30 mg, 0.065 mmol) in EtOH (3 mL) was treated with NaIO₄ mg, 0.136 mmol) at 0° C., warmed to RT before water (0.6 mL) was added. The reaction mixture was stirred at RT for 24 h then poured into AcOEt (20 mL) and washed successively with water (10 mL) and brine (10 mL). The organic layer was dried over Na₂SO₄, filtered, and evaporated to dryness. The remaining residue was purified by reverse phase prep-HPLC (Waters system) to give the title compound (2TFA salt, 2.3 mg, 0.003 mmol, 5%). MS: 480 [M+1]⁺; HPLC: $^At_{Ret}$=1.21.

Example 34

Tetrahydro-pyran-4-carboxylic acid [7-aminomethyl-6-(2,4-dichloro-phenyl)-imidazo[1,2-a]pyridin-3-yl]-amide Compound 34 was prepared according to Scheme 19:

Scheme 19

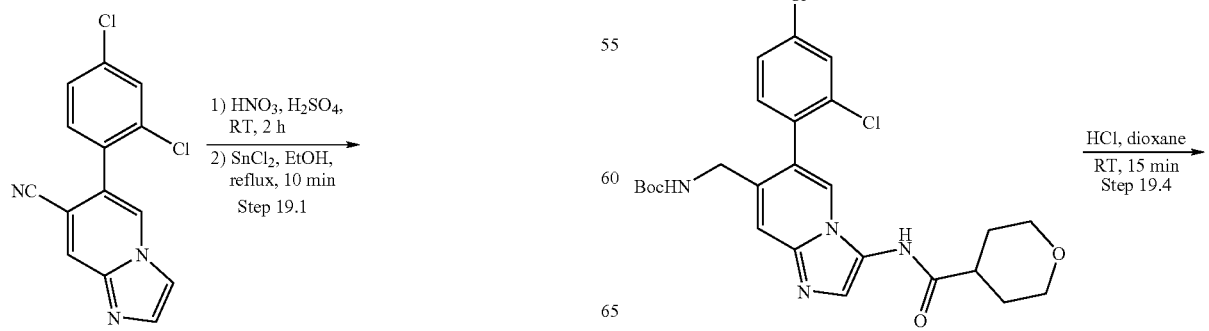

-continued

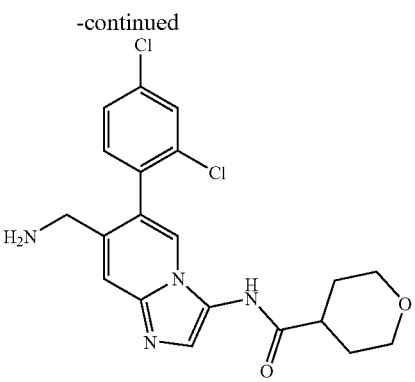

Step 19.1: 3-Amino-6-(2,4-dichloro-phenyl)-imidazo[1,2-a]pyridine-7-carbonitrile.

(1) To a solution of 6-(2,4-dichloro-phenyl)-imidazo[1,2-a]pyridine-7-carbonitrile (3.07 g, 6.10 mmol, prepared according to Example 3, Step 2.3) in concentrated $H_2SO_4$ (55 mL) was added a freshly prepared mixture of fuming $HNO_3$ in $H_2SO_4$ (1:2, v/v, 2.55 mL) at RT. The reaction mixture was stirred at RT for 2 h then cautiously added to cold water (300 mL) and extracted with DCM (5×). The combined organic fractions were dried over $Na_2SO_4$, filtered, and evaporated to dryness to give the crude 6-(2,4-dichloro-phenyl)-3-nitro-imidazo[1,2-a]pyridine-7-carbonitrile as a brown solid (533 mg). MS: 333 [M+1]$^+$; HPLC: $^At_{Ret}$=1.57.

(2) A mixture of the previously obtained 6-(2,4-dichloro-phenyl)-3-nitro-imidazo[1,2-a]pyridine-7-carbonitrile and Tin(II) chloride dihydrate (3.61 g, 15.7 mmol) in absolute EtOH (10 mL) was refluxed for 10 min, then cooled to RT and concentrated under vacuum. The residue was suspended into a 2M NaOH solution in water (100 mL) and extracted with DCM (4×50 mL). The combined organic fractions were washed with brine, dried over $Na_2SO_4$, filtered, and evaporated to dryness. The remaining residue was purified by Combi-Flash Companion™ (Isco Inc.) column chromatography (SiO$_2$; gradient elution, DCM/MeOH—$NH_3$ 99:1→95:5) to yield the title compound (517 mg, 1.71 mmol, 28% for 2 steps). HPLC: $^At_{Ret}$=1.34; TLC: R$_F$ 0.47 (DCM/7N $NH_3$ in MeOH 95:5).

Step 19.2: [3-Amino-6-(2,4-dichloro-phenyl)-imidazo[1,2-a]pyridin-7-ylmethyl]-carbamic acid tert-butyl ester.

(1) A solution of 3-amino-6-(2,4-dichloro-phenyl)-imidazo[1,2-a]pyridine-7-carbonitrile (517 mg, 1.71 mmol) in anhydrous THF (10 mL) was cooled to 0° C. (ice bath), treated with a 1M $BH_3$ solution in THF (8.5 mL, 8.5 mmol) and stirred at 40° C. for 1 h. The reaction mixture was cooled to 0° C. (ice bath), quenched by the cautious addition of MeOH until gas evolution ceased and concentrated to dryness. The residue was suspended into a 2M HCl solution in water, stirred at RT for 10 min and evaporated to dryness. The resulting HCl salt was suspended into a 2M NaOH solution in water then extracted with DCM and AcOEt. The combined organic fractions were dried over $Na_2SO_4$, filtered, and evaporated under vacuum to give the crude 7-aminomethyl-6-(2,4-dichloro-phenyl)-imidazo[1,2-a]pyridin-3-ylamine (277 mg). HPLC: $^At_{Ret}$=0.81.

(2) To a solution of the crude 7-aminomethyl-6-(2,4-dichloro-phenyl)-imidazo[1,2-a]pyridin-3-ylamine (277 mg) in MeOH (2.5 ml) were successively added Et$_3$N (0.24 mL, 1.70 mmol) and a solution of Boc$_2$O (197 mg, 0.90 mmol) in MeOH (2.5 mL). The reaction mixture was stirred at RT for 30 min and concentrated under vacuum. The residue was dissolved in AcOEt, washed with a 2M $Na_2CO_3$ solution in water, dried over $Na_2SO_4$, filtered, and evaporated to dryness to yield the crude title compound (327 mg, 0.80 mmol, 47% for 2 steps) as an orange solid, which was used in the next step without further purification. An analytical sample was purified by Combi-Flash Companion™ (Isco Inc.) column chromatography (SiO$_2$; gradient elution, DCM/MeOH—$NH_3$ 99:1→94:6) to give pure material as a white solid. MS: 407 [M+1]$^+$; HPLC: $^At_{Ret}$=1.57.

Step 19.3: {6-(2,4-Dichloro-phenyl)-3-[(tetrahydro-pyran-4-carbonyl)-amino]-imidazo[1,2-a]pyridin-7-ylmethyl}-carbamic acid tert-butyl ester.

To a mixture of [3-amino-6-(2,4-dichloro-phenyl)-imidazo[1,2-a]pyridin-7-ylmethyl]-carbamic acid tert-butyl ester (100 mg, 0.25 mmol), tetrahydro-pyran-4-arboxylic acid (192 mg, 1.47 mmol) and DIPEA (0.52 mL, 2.95 mmol) in DMF (3 mL) was added HATU (560 mg, 1.47 mmol) at RT. The reaction mixture was heated at 80° C. and stirred for 24 h, then poured into AcOEt (50 mL) and washed with a 2.0 M aqueous $Na_2CO_3$ solution (2×25 mL). The organic layer was dried over $Na_2SO_4$, filtered, and evaporated to dryness. The remaining residue was purified by Combi-Flash Companion™ (Isco Inc.) column chromatography (SiO$_2$; gradient elution, DCM/MeOH 99:1→84:16) to yield the title compound (79.5 mg, 0.153 mmol, 62%). MS: 519 [M+1]$^+$; HPLC: $^At_{Ret}$=1.49; TLC: R$_F$ 0.14 (DCM/MeOH 95:5).

Step 19.4.

To a solution of {6-(2,4-dichloro-phenyl)-3-[(tetrahydro-pyran-4-carbonyl)-amino]-imidazo[1,2-a]pyridin-7-ylmethyl}-carbamic acid tert-butyl ester (79.5 mg, 0.153 mmol) in dioxane (3 mL) was added a 4M HCl solution in dioxane (2 mL) and the mixture was stirred at RT for 15 min. The formed precipitate was filtered and dried under vacuum to yield the title compound (2HCl salt, 58 mg, 0.118 mmol, 48%) as a brownish solid. MS: 419 [M+1]$^+$; HPLC: $^At_{Ret}$=0.83.

Example 35

C-[6-(2,4-Dichloro-phenyl)-8-isobutoxy-3-(6-morpholin-4-yl-pyridin-3-yl)-imidazol-[1,2-a]pyridin-7-yl]-methylamine Compound 35 was prepared according to Scheme 20:

Scheme 20

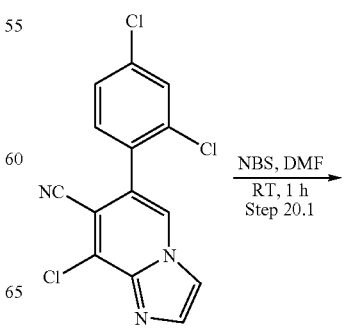

NBS, DMF
RT, 1 h
Step 20.1

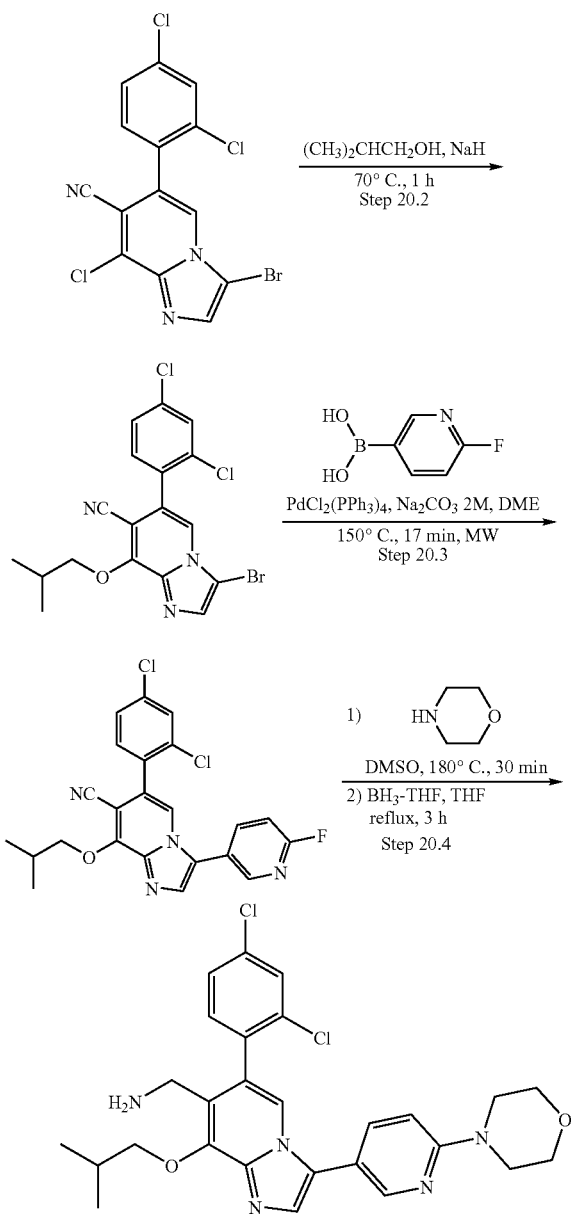

Step 20.1: 3-Bromo-8-chloro-6-(2,4-dichloro-phenyl)-imidazo[1,2-a]pyridine-7-carbonitrile.

A solution of 8-chloro-6-(2,4-dichloro-phenyl)-imidazo[1,2-a]pyridine-7-carbonitrile (1.5 g, 4.65 mmol, prepared according to Example 23, Step 12.2) in DMF (19 mL) was treated with NBS (910 mg, 5.12 mmol) at RT and stirred for 1 h. The reaction mixture was diluted in AcOEt and washed with water. The organic layer was dried over $Na_2SO_4$, filtered and evaporated to yield the crude title compound (1.92 g, 4.65 mmol, quant.), which was used in the next step without further purification. MS: 400 [M+1]$^+$; HPLC: $^At_{Ret}$=2.67.

Step 20.2: 3-Bromo-6-(2,4-dichloro-phenyl)-8-isobutoxy-imidazo[1,2-a]pyridine-7-carbonitrile.

NaH (60% in mineral oil, 149 mg, 3.7 mmol) was carefully added to 2-methyl-1-propanol (10 mL) at 0° C. (ice bath). The mixture was stirred at RT for 10 min before 3-bromo-8-chloro-6-(2,4-dichloro-phenyl)-imidazo[1,2-a]pyridine-7-carbonitrile (500 mg, 1.25 mmol) was added in one portion. The reaction mixture was heated at 70° C. and stirred for 1 h, then cooled to RT and poured into water (100 mL). The formed slurry was extracted successively with DCM (2×50 mL) and AcOEt (50 mL), and the combined organic fractions were dried over $Na_2SO_4$, filtered, and evaporated to dryness. The remaining residue was purified by Combi-Flash Companion™ (Isco Inc.) column chromatography ($SiO_2$; gradient elution, hexane/TBME 95.5→100% TBME) to yield the title compound (348 mg, 0.79 mmol, 63%). MS: 438 [M+1]$^+$; HPLC: $^At_{Ret}$=3.36; TLC: $R_F$ 0.81 (hexane/TBME 1:1).

Step 20.3: 6-(2,4-Dichloro-phenyl)-3-(6-fluoro-pyridin-3-yl)-8-isobutoxy-imidazo[1,2-a]pyridine-7-carbonitrile.

In a sealed tube, a mixture of 3-bromo-6-(2,4-dichloro-phenyl)-8-isobutoxy-imidazo[1,2-a]pyridine-7-carbonitrile (115 mg, 0.25 mmol), 2-fluoro-5-pyridine-boronic acid (38.4 mg, 0.27 mmol), $PdCl_2(PPh_3)_2$ (8.7 mg, 0.01 mmol) and $Na_2CO_3$ (2.0 M solution in water, 0.43 mL) in DME (1 mL) was heated at 150° C. for 17 min in a microwave oven. The reaction mixture was cooled to RT, diluted in AcOEt (20 mL) and washed with water (2×10 mL). The organic layer was dried over $Na_2SO_4$, filtered, and evaporated to dryness. The remaining residue was purified by Combi-Flash Companion™ (Isco Inc.) column chromatography ($SiO_2$; gradient elution, hexane/TBME 95:5→7:3) to yield the title compound (64 mg, 0.14 mmol, 56%) as a white solid. MS: 455 [M+1]$^+$; HPLC: $^At_{Ret}$=3.14; TLC: $R_F$ 0.34 (hexane/TBME 1:1).

Step 20.4.

(1) A mixture of 6-(2,4-dichloro-phenyl)-3-(6-fluoro-pyridin-3-yl)-8-isobutoxy-imidazo[1,2-a]pyridine-7-carbonitrile (64 mg, 0.14 mmol) and morpholine (0.06 mL, 0.70 mmol) in DMSO (1 mL) was heated at 180° C. and stirred for 30 min. The reaction mixture was cooled to RT, diluted in AcOEt (20 mL) and washed with water (2×10 ml). The organic layer was dried over $Na_2SO_4$, filtered, and evaporated to dryness to yield the crude 6-(2,4-dichloro-phenyl)-8-isobutoxy-3-(6-morpholin-4-yl-pyridin-3-yl)-imidazo[1,2-a]pyridine-7-carbonitrile intermediate (67.8 mg) as a brown solid.

(2) To a solution of the crude intermediate (67.8 mg) in anhydrous THF (1 mL) in THF was slowly added a $BH_3$·THF complex (1.0 M solution in THF, 0.56 mL, 0.56 mmol) at RT. The reaction mixture was stirred and refluxed for 3 h, then cooled to RT and quenched by the careful addition of MeOH until gas evolution ceased. The resulting solution was concentrated under vacuum then a 2M HCl solution in water was added and the formed slurry was evaporated to dryness. The remaining residue was purified by reverse phase prep-HPLC (Waters system) to give the title compound (2TFA salt, 7.3 mg, 0.010 mmol, 7% for 2 steps). MS: 526 [M+1]$^+$; HPLC: $^At_{Ret}$=1.42.

Example 36

C-[6-(2,4-Dichloro-phenyl)-8-isobutoxy-3-(2-morpholin-4-yl-pyridin-4-yl)-imidazo[1,2-a]pyridin-7-yl]-methylamine Compound 36 was prepared according to Scheme 21:

Scheme 21

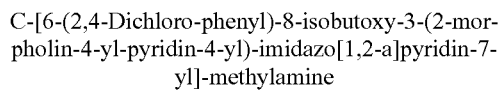

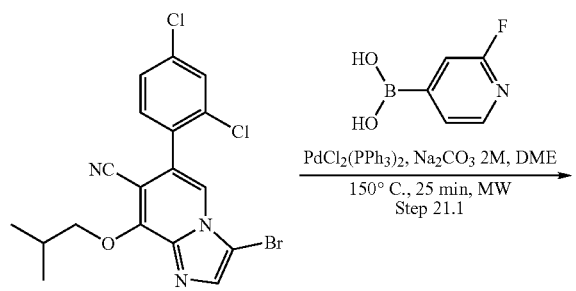

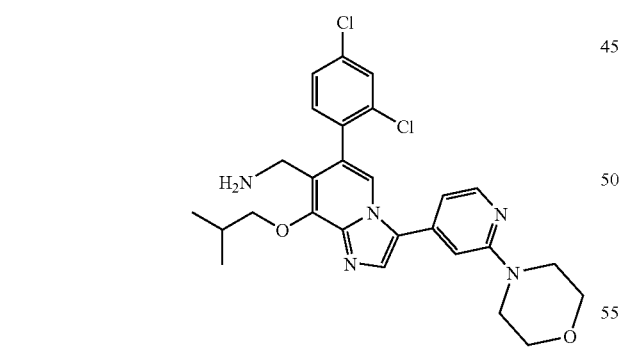

Step 21.1: 6-(2,4-Dichloro-phenyl)-3-(2-fluoro-pyridin-4-yl)-8-isobutoxy-imidazo[1,2-a]pyridine-7-carbonitrile.

In a sealed tube, a mixture of 3-bromo-6-(2,4-dichlorophenyl)-8-isobutoxy-imidazo[1,2-a]pyridine-7-carbonitrile (115 mg, 0.25 mmol, prepared according to Example 35, Step 20.2), 2-fluoro-4-pyridine-boronic acid (45.3 mg, 0.32 mmol), PdCl$_2$(PPh$_3$)$_2$ (9.6 mg, 0.014 mmol) and Na$_2$CO$_3$ (2.0 M solution in water, 0.43 mL) in DME (1 mL) was heated at 150° C. for 25 min in a microwave oven. The reaction mixture was cooled to RT, diluted in AcOEt (20 mL) and washed with water (2×10 mL). The organic layer was dried over Na$_2$SO$_4$, filtered, and evaporated to dryness. The remaining residue was purified by Combi-Flash Companion™ (Isco Inc.) column chromatography (SiO$_2$; gradient elution, hexane/TBME 95:5→6:4) to yield the title compound (46.6 mg, 0.10 mmol, 41%) as a white solid. MS: 455 [M+1]$^+$; HPLC: $^At_{Ret}$=3.18; TLC: R$_F$ 0.25 (hexane/TBME 1:1).

Step 21.2.

(1) A mixture of 6-(2,4-dichloro-phenyl)-3-(2-fluoro-pyridin-4-yl)-8-isobutoxy-imidazo[1,2-a]pyridine-7-carbonitrile (46.6 mg, 0.10 mmol) and morpholine (0.045 mL, 0.51 mmol) in DMSO (0.8 mL) was heated at 180° C. and stirred for 30 min. The reaction mixture was cooled to RT, diluted in AcOEt (20 mL) and washed with water (2×10 ml). The organic layer was dried over Na$_2$SO$_4$, filtered, and evaporated to dryness to yield the crude 6-(2,4-dichloro-phenyl)-8-isobutoxy-3-(2-morpholin-4-yl-pyridin-4-yl)-imidazo[1,2-a]pyridine-7-carbonitrile intermediate.

(2) To a solution of the crude intermediate in anhydrous THF (1 mL) in THF was slowly added a BH$_3$.THF complex (1.0 M solution in THF, 0.41 mL, 0.41 mmol) at RT. The reaction mixture was stirred and refluxed for 3 h, then cooled to RT and quenched by the careful addition of MeOH until gas evolution ceased. The resulting solution was concentrated under vacuum then a 2M HCl solution in water was added and the formed slurry was evaporated to dryness. The remaining residue was purified by reverse phase prep-HPLC (Waters system) to give the title compound (2TFA salt, 8.1 mg, 0.011 mmol, 10% for 2 steps). MS: 526 [M+1]$^+$; HPLC: $^At_{Ret}$=1.36.

Example 37

[7-Aminomethyl-6-(2,4-dichloro-phenyl)-8-isobutoxy-imidazo[1,2-a]pyridin-3-yl]-morpholin-4-yl-methanone Compound 37 was prepared according to Scheme 22:

Scheme 22

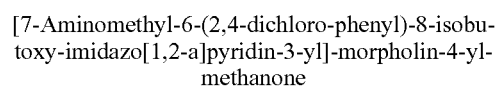

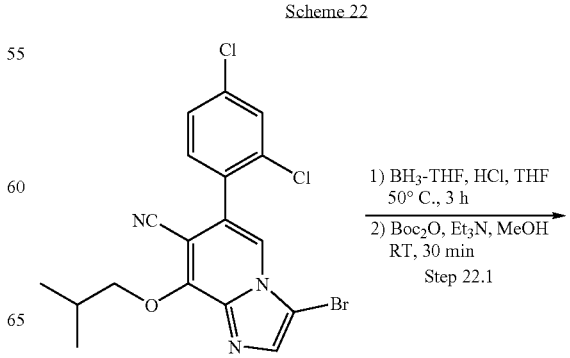

-continued

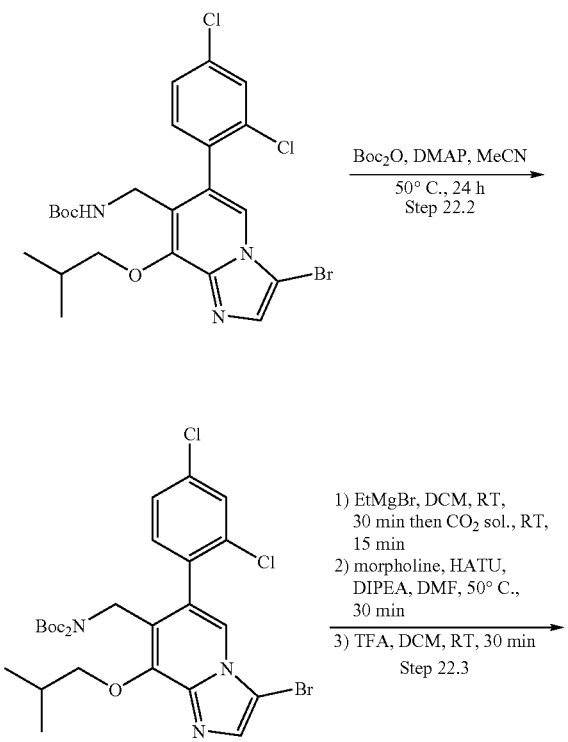

Step 22.1: [3-Bromo-6-(2,4-dichloro-phenyl)-8-isobutoxy-imidazo[1,2-a]pyridin-7-ylmethyl]-carbamic acid tert-butyl ester.

(1) To a solution of 3-bromo-6-(2,4-dichloro-phenyl)-8-isobutoxy-imidazo[1,2-a]pyridine-7-carbonitrile (477 mg, 1.0 mmol, prepared according to Example 35, Step 20.2) in anhydrous THF (12 mL) were added a $BH_3$.THF complex (1.0 M solution in THF, 4.5 mL, 4.5 mmol) followed by a 4M HCl solution in dioxane (10 drops) at RT. The reaction mixture was heated at 50° C. and stirred for 3 h, then cooled to 0° C. (ice bath), quenched by the cautious addition of a 2M HCl solution in water (10 mL) and poured into water (100 mL). The aqueous mixture was washed with $Et_2O$ (2×30 mL) then basified to pH 10 by the addition of a 2M $Na_2CO_3$ solution in water and extracted with DCM (2×30 mL). The combined organic fractions were dried over $Na_2SO_4$, filtered, and evaporated to dryness to yield the crude C-[3-bromo-6-(2,4-dichloro-phenyl)-8-isobutoxy-imidazo[1,2-a]pyridin-7-yl]-methylamine intermediate.

(2) To a solution of the crude intermediate in MeOH (3 mL) were successively added $Et_3N$ (0.28 mL, 1.99 mmol) and $Boc_2O$ (239.1 mg, 1.10 mmol) at RT. The reaction mixture was stirred for 30 min then concentrated under vacuum and the resulting residue was dissolved in AcOEt and washed successively with a 2M $Na_2CO_3$ solution in water and brine. The organic layer was dried over $Na_2SO_4$, filtered, and evaporated to dryness. The remaining residue was purified by Combi-Flash Companion™ (Isco Inc.) column chromatography ($SiO_2$; gradient elution, hexane/TBME 95:5→1:1) to yield the title compound (80.1 mg, 0.15 mmol, 15%) as a white solid. MS: 542 [M+1]$^+$; HPLC: $^At_{Ret}$=3.24, TLC: $R_F$ 0.77 (hexane/TBME 1:1).

Step 22.2: [3-Bromo-6-(2,4-dichloro-phenyl)-8-isobutoxy-imidazo[1,2-a]pyridin-7-ylmethyl]-carbamic acid bis-tert-butyl ester.

A solution of [3-bromo-6-(2,4-dichloro-phenyl)-8-isobutoxy-imidazo[1,2-a]pyridin-7-ylmethyl]-carbamic acid tert-butyl ester (80 mg, 0.15 mmol), DMAP (7.2 mg, 0.059 mmol) and $Boc_2O$ (354 mg, 1.62 mmol) in MeCN (1 mL) was heated at 50° C. and stirred for 24 h. The reaction mixture was cooled to RT, concentrated under vacuum, diluted in AcOEt (20 mL) and washed with a 2M $Na_2CO_3$ solution in water (2×10 mL). The organic layer was dried over $Na_2SO_4$, filtered, and evaporated to dryness. The remaining residue was purified by Combi-Flash Companion™ (Isco Inc.) column chromatography ($SiO_2$; isocratic, hexane/TBME 95:5) to yield the title compound (74 mg, 0.12 mmol, 78%). MS: 642 [M+1]$^+$; HPLC: $^At_{Ret}$=3.79; TLC: $R_F$ 0.83 (hexane/TBME 1:1).

Step 22.3.

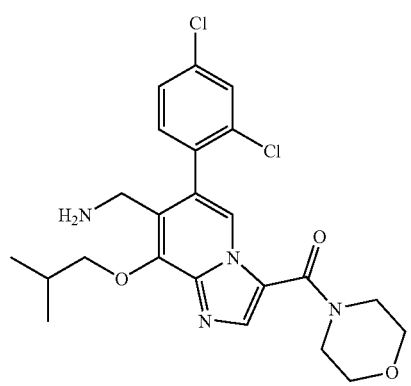

(1) To a solution of [3-bromo-6-(2,4-dichloro-phenyl)-8-isobutoxy-imidazo[1,2-a]pyridin-7-ylmethyl]-carbamic acid bis-tert-butyl ester (64 mg, 0.10 mmol) in DCM (1 mL) was added dropwise EtMgBr (1M THF solution, 0.99 mL, 0.99 mmol) at RT. The clear solution was stirred for 30 min before a large excess of dry ice was added in one portion. The heavy slurry was stirred until the temperature raised to RT (15 min) then diluted in DCM (20 mL) and washed with water (10 mL). The organic layer was concentrated under vacuum, dissolved in AcOEt (20 mL) and washed with a saturated aqueous $NH_4Cl$ solution (2×10 mL). The aqueous phase was reextracted with AcOEt (2×10 mL) and the combined organic fractions were dried over Na₂SO₄, filtered, and evaporated to dryness to yield the crude carboxylic acid intermediate (50 mg).

(2) To a mixture of the crude carboxylic acid intermediate (50 mg), morpholine (0.010 mL, 0.11 mmol) and DIPEA (0.035 mL, 0.20 mmol) in DMF (0.5 mL) was added HATU (41.6 mg, 0.11 mmol) at RT. The reaction mixture was heated at 50° C. and stirred for 30 min, then poured into AcOEt (10 mL) and washed with a 2.0 M aqueous Na₂CO₃ solution (2×5 mL). The organic layer was dried over Na₂SO₄, filtered, and evaporated to dryness. The remaining residue was dissolved in DCM (2 mL) and TFA (1 mL) and the solution was stirred at RT for 30 min. The reaction mixture was concentrated to dryness and the remaining residue purified by reverse phase prep-HPLC (Waters system) to give the title compound (2TFA salt, 11.4 mg, 0.016 mmol, 16% for 3 steps) as a white solid. MS: 477 [M+1]⁺; HPLC: $^A t_{Ret}$=1.57.

Example 38

1-{4-[7-Aminomethyl-6-(2,4-dichloro-phenyl)-imidazo[1,2-a]pyridin-3-yl]-piperazin-1-yl}-ethanone Compound 38 was prepared according to Scheme 23:

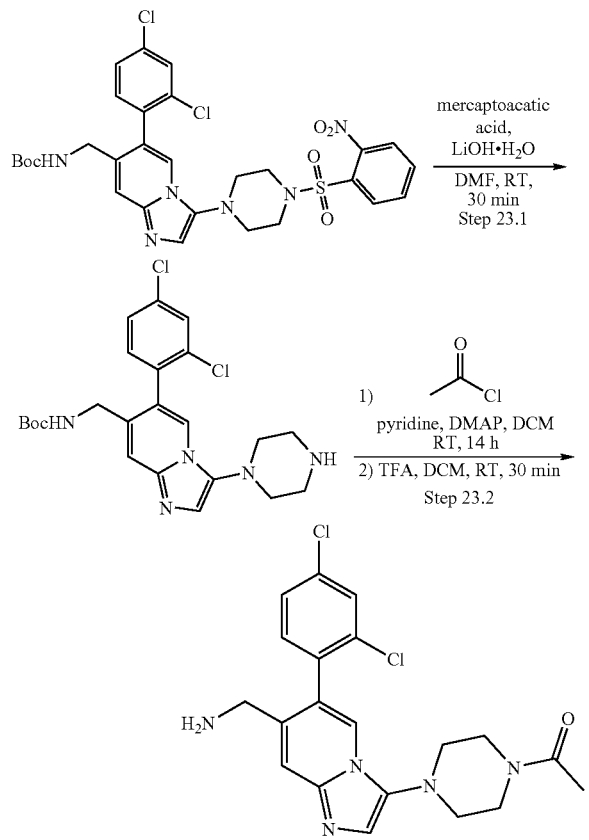

Step 23.1: [6-(2,4-Dichloro-phenyl)-3-piperazin-1-yl-imidazo[1,2-a]pyridin-7-ylmethyl]-carbamic acid tert-butyl ester.

A mixture of {6-(2,4-dichloro-phenyl)-3-[4-(2-nitro-benzenesulfonyl)-piperazin-1-yl]-imidazo[1,2-a]pyridin-7-ylmethyl}-carbamic acid tert-butyl ester (2.9 g, 4.38 mmol, prepared following the procedure described for Example 6, Step 3.3 using the adequate cyclisation reagent), LiOH·H₂O (1.11 g, 26.3 mmol) and mercaptoacetic acid (0.94 mL, 13.2 mmol) in DMF (20 mL) was stirred at RT for 30 min then poured into a saturated aqueous NaHCO₃ solution (200 mL) and extracted with AcOEt (4×200 mL). The combined organic fractions were washed with brine (100 mL), dried over Na₂SO₄, filtered and evaporated to dryness. The remaining residue was purified by Combi-Flash CompanionT™ (Isco Inc.) column chromatography (SiO₂; gradient elution, DCM/[DCM/MeOH—NH₃ 9:1]95:5→100% [DCM/MeOH—NH₃ 9:1]) to yield the title compound (1.61 g, 3.38 mmol, 77%) as a yellow foam. MS: 477 [M+1]⁺; HPLC: $^A t_{Ret}$=1.45; TLC: R$_F$ 0.33 (DCM/MeOH—NH₃ 9:1).

Step 23.2.

To a solution of [6-(2,4-dichloro-phenyl)-3-piperazin-1-yl-imidazo[1,2-a]pyridin-7-ylmethyl]-carbamic acid tert-butyl ester (30 mg, 0.06 mmol) in DCM (0.5 mL) were added successively acetyl chloride (6 mg, 0.07 mmol), pyridine (0.015 mL, 0.19 mmol) and DMAP (1 mg, 0.006 mmol). The reaction mixture was stirred at RT for 14 h then evaporated to dryness. The resulting residue was dissolved in DCM (2 mL) then TFA (1 mL) was added and the mixture was stirred at RT for 30 min. The reaction mixture was concentrated to dryness and the remaining residue purified by reverse phase prep-HPLC (Waters system) to give the title compound (2TFA salt, 22 mg, 0.034 mmol, 57% for 2 steps) as a white solid. MS: 419 [M+1]⁺; HPLC: $^A t_{Ret}$=1.00.

Example 39

1-{4-[7-Aminomethyl-6-(2,4-dichloro-phenyl)-imidazo[1,2-a]pyridin-3-yl]-piperazin-1-yl}-ethanone To a mixture of [6-(2,4-dichloro-phenyl)-3-piperazin-1-yl-imidazo[1,2-a]pyridin-7-ylmethyl]-carbamic acid tert-butyl ester (30 mg, 0.06 mmol, prepared according to Example 38, Step 23.1), cyclobutanecarboxylic acid (0.007 mL, 0.07 mmol) and NMM (0.035 mL, 0.32 mmol) in DMF (0.5 mL) was added HATU (35.9 mg, 0.095 mmol). The reaction mixture was stirred at RT for 14 h, then poured into AcOEt (20 mL) and washed with a 2.0 M aqueous Na₂CO₃ solution (10 mL) and brine (10 mL). The organic layer was dried over Na₂SO₄, filtered, and evaporated to dryness. The remaining residue was dissolved in DCM (2 mL) and TFA (1 mL) and the solution was stirred at RT for 30 min. The reaction mixture was concentrated to dryness and the remaining residue purified by reverse phase prep-HPLC (Waters system) to give the title compound (2TFA salt, 20 mg, 0.029 mmol, 46% for 2 steps). MS: 459 [M+1]⁺; HPLC: $^A t_{Ret}$=1.29.

Example 40

Compounds 40a to 40l were obtained analogously to Examples 38 and 39, using the adequate acyl chloride or carboxylic acid in Step 23.2. The compounds are of the following general formula:

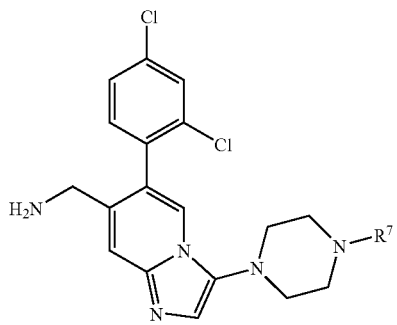

| Compound | Name | R⁷ | HPLC $^A t_{Ret}$ [min] | MS [M + 1]⁺ |
|---|---|---|---|---|
| 40a | 1-{4-[7-Aminomethyl-6-(2,4-dichloro-phenyl)-imidazo[1,2-a]pyridin-3-yl]-piperazin-1-yl}-propan-1-one | | 1.10 | 433 |
| 40b | 1-{4-[7-Aminomethyl-6-(2,4-dichloro-phenyl)-imidazo[1,2-a]pyridin-3-yl]-piperazin-1-yl}-2-methyl-propan-1-one | | 1.20 | 447 |
| 40c | {4-[7-Aminomethyl-6-(2,4-dichloro-phenyl)-imidazo[1,2-a]pyridin-3-yl]-piperazin-1-yl}-cyclopropyl-methanone | | 1.14 | 445 |
| 40d | 1-{4-[7-Aminomethyl-6-(2,4-dichloro-phenyl)-imidazo[1,2-a]pyridin-3-yl]-piperazin-1-yl}-2-methoxy-ethanone | | 1.02 | 449 |
| 40e | 1-(4-{4-[7-Aminomethyl-6-(2,4-dichloro-phenyl)-imidazo[1,2-a]pyridin-3-yl]piperazine-1-carbonyl}-piperidin-1-yl)-ethanone | | 1.09 | 530 |
| 40f | {4-[7-Aminomethyl-6-(2,4-dichloro-phenyl)-imidazo[1,2-a]pyridin-3-yl]-piperidin-1-yl}-cyclopentyl-methanone | | 1.33 | 473 |
| 40g | 1-{4-[7-Aminomethyl-6-(2,4-dichloro-phenyl)-imidazo[1,2-a]pyridin-3-yl]-piperazin-1-yl}-2-cyclopropyl-ethanone | | 1.21 | 459 |
| 40h | {4-[7-Aminomethyl-6-(2,4-dichloro-phenyl)-imidazo[1,2-a]pyridin-3-yl]-piperazin-1-yl}-(tetrahydro-pyran-4-yl)-methanone | | 1.11 | 489 |

-continued

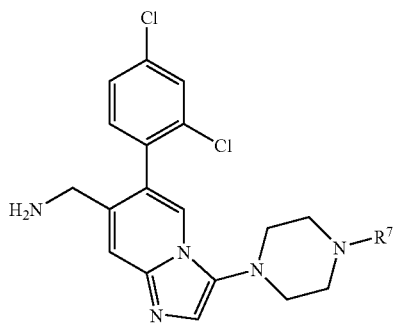

| Compound | Name | R⁷ | HPLC $\Delta t_{Ret}$ [min] | MS [M + 1]⁺ |
|---|---|---|---|---|
| 40i | 1-{4-[7-Aminomethyl-6-(2,4-dichloro-phenyl)-imidazo[1,2-a]pyridin-3-yl]-piperazin-1-yl}-3-methoxy-propan-1-one | | 1.09 | 463 |
| 40j | 1-{4-[7-Aminomethyl-6-(2,4-dichloro-phenyl)-imidazo[1,2-a]pyridin-3-yl]-piperazin-1-yl}-2-(tetrahydro-pyran-4-yl)-ethanone | | 1.16 | 503 |
| 40k | {4-[7-Aminomethyl-6-(2,4-dichloro-phenyl)-imidazo[1,2-a]pyridin-3-yl]-piperazin-1-yl}-(1-methyl-1H-imidazol-4-yl)-methanone | | 0.91 | 485 |
| 40l | {4-[7-Aminomethyl-6-(2,4-dichloro-phenyl)-imidazo[1,2-a]pyridin-3-yl]-piperazin-1-yl}-pyrazin-2-yl-methanone | | 1.08 | 483 |

Example 41

Activity Assay

Some of Compounds 1 to 40 were tested for their inhibitory activity to human DPP-IV.

Materials

Human DPP-IV consisting of amino acids 39 to 766 followed by a C-terminal Streptavidin-tag was expressed using the baculovirus system and purified to >80% purity. The enzyme was stored in 25 mM Tris buffer, pH 9.0, containing 300 mM NaCl at −80° C.

The fluorogenic substrates H-Gly-Pro-AMC was purchased from Bachem AG (Bubendorf, Switzerland). The substrate was kept as a 5 mM stock solution in DMSO at −20° C. All other chemicals were purchased from Sigma (Buchs, Switzerland).

The assay buffer for the DPP-IV reaction was 25 mM Tris/HCl, pH 7.5, containing 140 mM NaCl, 10 mM KCl and 0.05% (w/v) CHAPS.

Compound and Liquid Handling

The test compounds were dissolved in 90% DMSO/10% H2O (v/v). Serial dilutions of the compounds from 3 mM to 0.03 µM in 90% DMSO/10% H2O (v/v) followed by a 1:33.3 dilution in assay buffer was done in 96-well polypropylene plates using a CyBio Dilus 8-channel pipettor (CyBio AG, Jena, Germany) with tip change after each pipetting step. The compound solutions as well as the substrate and the enzyme solutions were transferred to the assay plates (384-well black Cliniplate; cat. no. 95040020 Labsystems Oy, Finland) by means of a CyBi-Well 96-channel pipettor (CyBio AG, Jena, Germany).

Kinetic Measurements

Enzyme kinetics were measured by mixing 10 µl of a 3-fold concentrated substrate solution in assay buffer (final substrate concentration was 10 µM) with 10 µl of the corresponding compound solution. The reactions were initiated by addition of 10 µl of a 3-fold concentrated solution of the enzyme in assay buffer. Final enzyme (active site) concentrations in the assay was 10 µM for DPP-IV. Fluorescence product (AMC) formation was monitored for 1 hour at room temperature at 35 second intervals by measuring the fluorescence emission at 500 nm using an exitation wavelength of 350 nm in a TECAN Ultra fluorescence reader (TECAN, Maennedorf, Switzerland). The fluorescence in each well was excited by one flash per measurement. The Origin software package (Origin 7.5 Mircocal, Northampton, Mass., USA) was used to generate all graphs and to perform the IC50 calculations.

Results

The inhibitory activities ($IC_{50}$ values) of the compounds to human DPP-IV were found to be 7.7 μM or less and in many cases 0.1 μM or less. In the case of exemplary compounds, their $IC_{50}$ values were found to be between 7.7 μM and 0.007 μM. Table 1 shows the inhibitory activity ($IC_{50}$ values) of representative compounds to human DPP-4.

| Example | $IC_{50}$ (μM) |
| --- | --- |
| 7 | 0.023 |
| 4d | 0.023 |
| 18b | 0.025 |
| 27a | 0.022 |

The invention claimed is:

1. A compound of Formula (I):

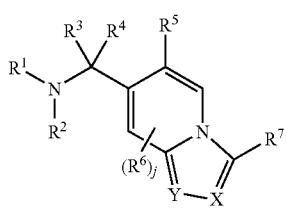

(I)

wherein

X is =C($R^8$)—;

Y is =N—;

$R^1$ and $R^2$ are each independently selected from $R^{10}$, —$OR^{10}$, —C(O)$R^{10}$, —C(O)O$R^{10}$ and —S(O)$_l R^{10}$;

$R^3$ and $R^4$ are each independently hydrogen or $R^{13}$; or $R^3$ and $R^4$ taken together with the carbon atom to which they are attached form carbocyclyl or heterocyclyl, either of which is optionally substituted with 1, 2, 3, 4 or 5 $R^{13}$;

$R^5$ is aryl or heteroaryl, either of which is optionally substituted with 1, 2, 3, 4 or 5 $R^{13}$;

$R^6$ is selected from halogen, trifluoromethyl, cyano, nitro, $R^{10}$, —$OR^{10}$, —C(O)$R^{10}$, —C(O)O$R^{10}$, —OC(O)$R^{10}$, —S(O)$_l R^{11}$, —N($R^{11}$)($R^{12}$) and —C(O)N($R^{11}$)($R^{12}$);

$R^7$, $R^8$ and $R^9$ are each independently selected from hydrogen, halogen and moieties comprising from 1 to 30 plural valent atoms selected from C, N, O and S; for example $R^7$, $R^8$ and $R^9$ are each independently selected from halogen, trifluoromethyl, cyano, nitro, $R^{10}$, —$OR^{10}$, —C(O)$R^{10}$, —C(O)O$R^{10}$, —OC(O)$R^{10}$, —S(O)$_l R^{11}$, —N($R^{11}$)($R^{12}$) and —C(O)N($R^{11}$)($R^{12}$);

$R^{10}$ is hydrogen, hydrocarbyl optionally substituted with 1, 2, 3, 4 or 5 $R^{13}$; or —(CH$_2$)$_k$-heterocyclyl optionally substituted with 1, 2, 3, 4 or 5 $R^{13}$;

$R^{11}$ and $R^{12}$ are each independently selected from $R^{10}$, —$OR^{10}$, —C(O)$R^{10}$, —C(O)O$R^{10}$, —(CH$_2$)$_k$—$R^{10}$, —C(O)—(CH$_2$)$_k$—$R^{10}$ and —S(O)$_l R^{10}$; or $R^{11}$ and $R^{12}$ taken together with a nitrogen atom to which they are attached form heterocyclyl optionally substituted with 1, 2, 3, 4 or 5 $R^{13}$;

each $R^{13}$ is independently selected from halogen, trifluoromethyl, cyano, nitro, oxo, =N$R^{14}$, —O$R^{14}$, —C(O)$R^{14}$, —C(O)O$R^{14}$, —OC(O)$R^{14}$, —S(O)$_l R^{14}$, —N($R^{14}$) $R^{15}$, —C(O)N($R^{14}$)$R^{15}$ and $R^{16}$;

$R^{14}$ and $R^{15}$ are each independently hydrogen or $R^{16}$;

$R^{16}$ is selected from a spiro group, hydrocarbyl, —(CH$_2$)$_k$-hydrocarbyl, —(CH$_2$)$_k$-heterocyclyl and —(CH$_2$)$_k$—C(O)heterocyclyl, either of which is optionally substituted with 1, 2, 3, 4 or 5 substituents independently selected from halogen, cyano, oxo, amino, hydroxy, —C(O)—C$_{1-6}$ alkyl, C$_{1-6}$ alkyl and $_{1-6}$ alkoxy;

j is 0, 1 or 2;

k is 0, 1, 2, 3, 4, 5 or 6; and l is 0, 1, or 2;

or a pharmaceutically acceptable salt thereof.

2. The compound according to claim 1, wherein;

$R^{11}$ and $R^{12}$ are each independents selected from $R^{10}$, —$OR^{10}$, —C(O)$R^{10}$, —C(O)O$R^{10}$ and —S(O)$_l R^{10}$; or $R^{11}$ and $R^{12}$ taken together with a nitrogen atom to which they are attached form heterocyclyl optionally substituted with 1, 2, 3, 4 or 5 $R^{13}$; and $R^{16}$ is selected from hydrocarbyl and —(CH$_2$)$_k$-heterocyclyl, either of which is optionally substituted with 1, 2, 3, 4 or 5 substituents independents selected from halogen, cyano, amino, hydroxy, C$_{1-6}$ alkyl and C$_{1-6}$ alkoxy;

or a pharmaceutically acceptable salt thereof.

3. The compound according to claim 1, which is of the Formula (II):

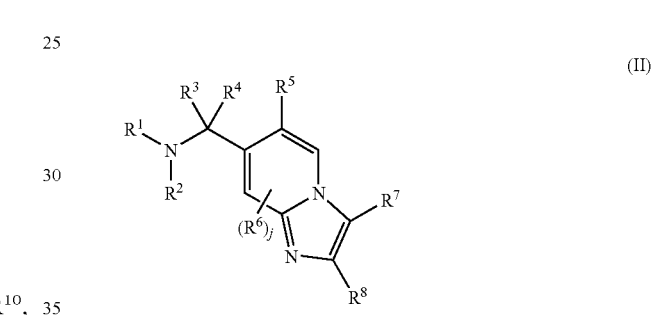

(II)

or a pharmaceutically acceptable salt thereof.

4. The compound according to claim 3, wherein $R^8$ is hydrogen.

5. The compound according to claim 1, wherein $R^1$ and $R^2$ are each independently selected from hydrogen, C$_{1-6}$ alkyl optionally substituted with 1, 2, 3, 4 or 5 $R^{13}$, and —(CH$_2$)$_k$-carbocyclyl optionally substituted with 1, 2, 3, 4 or 5 $R^{13}$.

6. The compound according to claim 5, wherein $R^1$ and $R^2$ are each hydrogen.

7. The compound according to claim 1, wherein $R^3$ and $R^4$ are each independently selected from hydrogen, C$_{1-6}$ alkyl optionally substituted with 1, 2, 3, 4 or 5 $R^{13}$, and —(CH$_2$)$_k$-carbocyclyl optionally substituted with 1, 2, 3, 4 or 5 $R^{13}$.

8. The compound according to claim 7, wherein $R^3$ and $R^4$ are each hydrogen.

9. The compound according to claim 1, wherein $R^1$, $R^2$, $R^3$ and $R^4$ are each hydrogen.

10. The compound according to claim 1, wherein $R^5$ is aryl optionally substituted with 1, 2, 3, 4 or 5 $R^{13}$.

11. The compound according to claim 10, wherein $R^5$ is phenyl optionally substituted with 1, 2, 3, 4 or 5 $R^{13}$.

12. The compound according to claim 11, wherein $R^5$ is phenyl optionally substituted with 1, 2 or 3 substituents independents selected from halogen, cyano, amino, hydroxy, C$_{1-6}$ alkyl and C$_{1-6}$ alkoxy.

13. The compound according to claim 12, wherein $R^5$ is phenyl comprising substituents at the 2- and 4- positions, wherein the substituents are independently selected from halogen, methyl and methoxy.

14. The compound according to claim 13, wherein $R^5$ is 2,4-dichlorophenyl.

15. The compound according to claim 1, selected from:
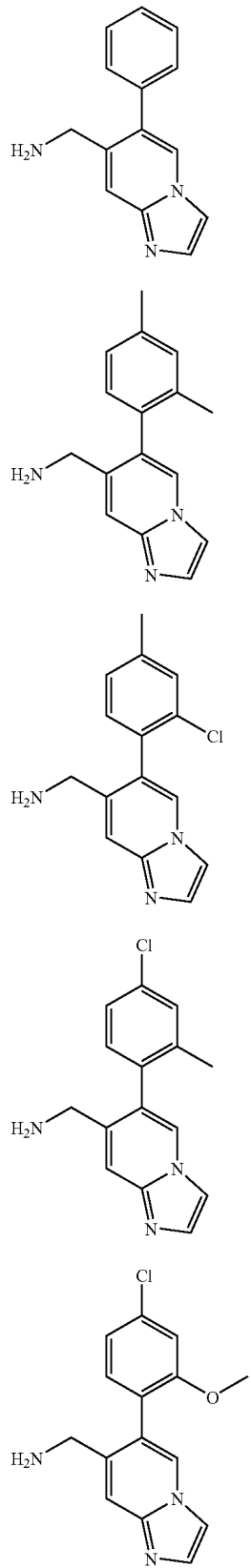
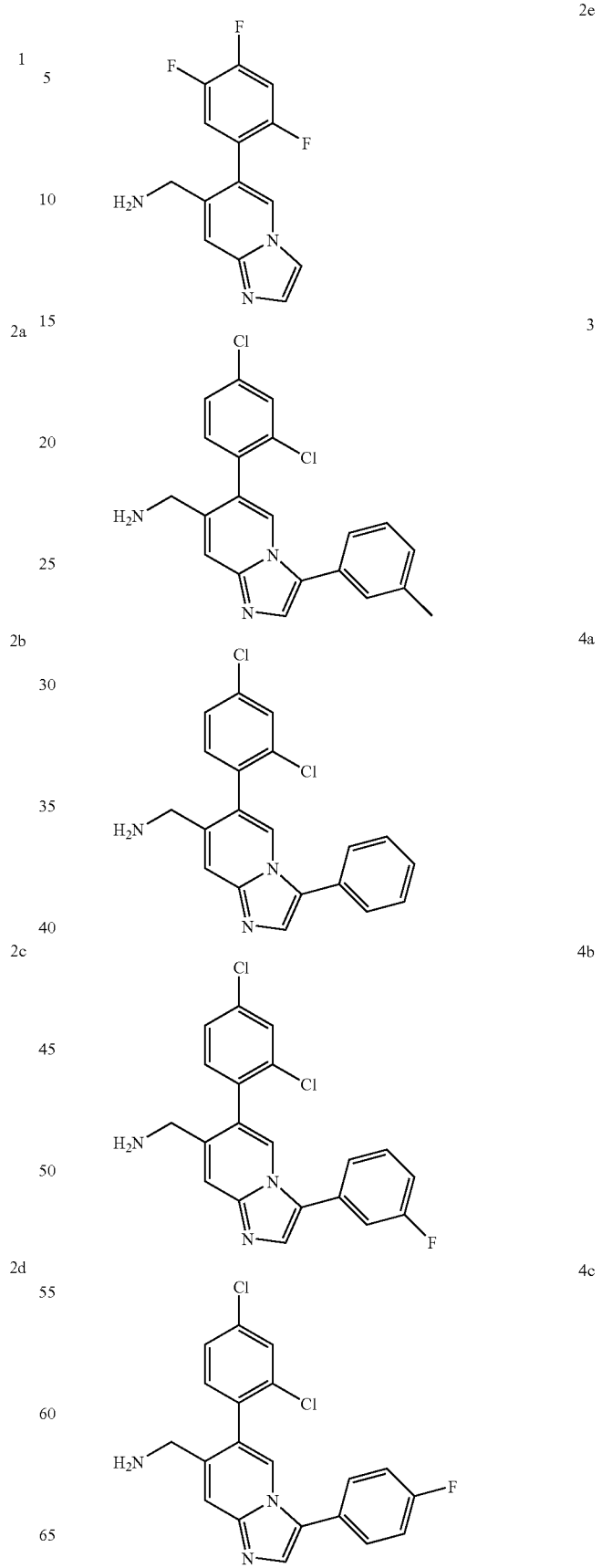

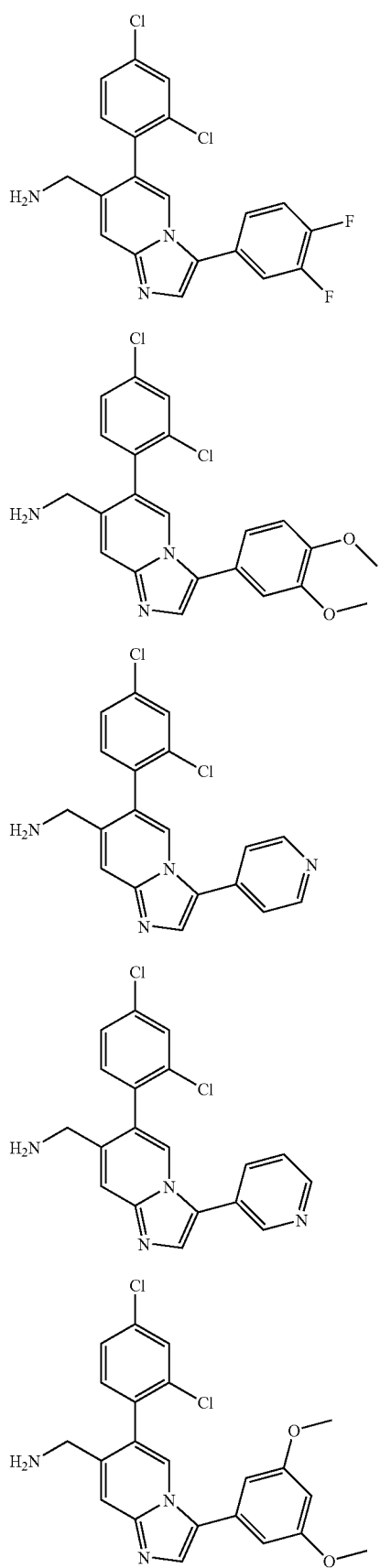
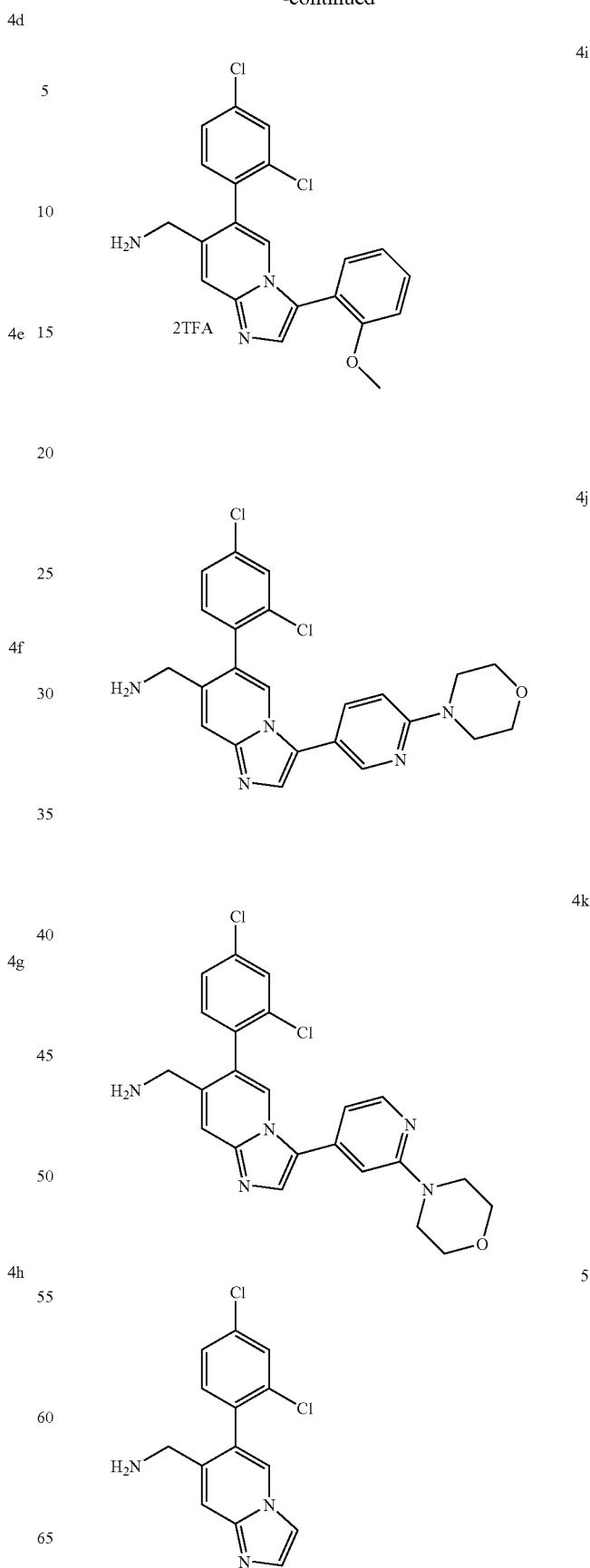

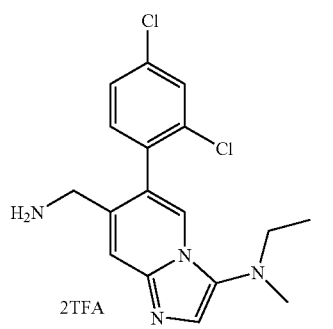
6
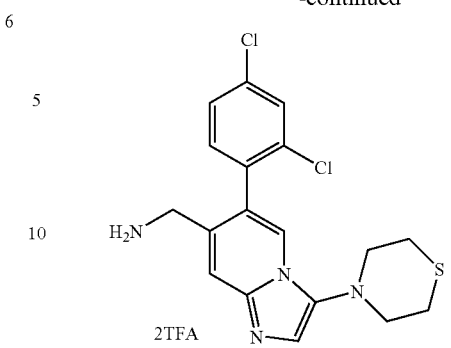
8d
7
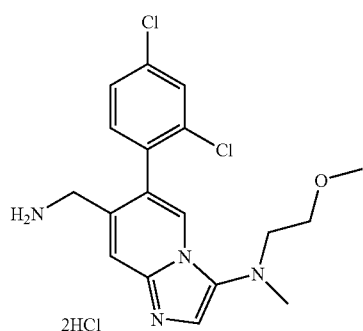
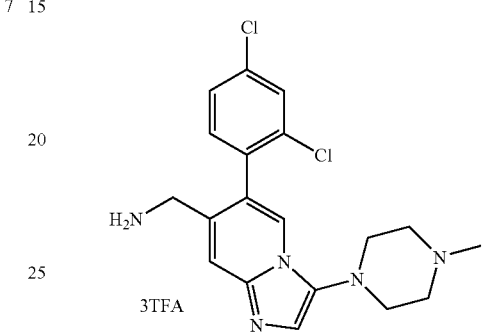
8e
8a
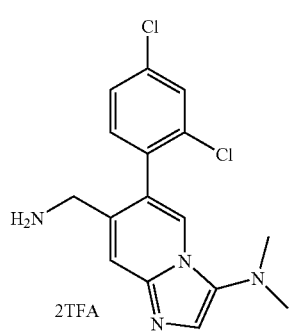
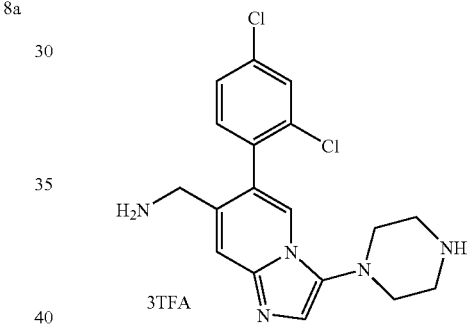
8f
8b
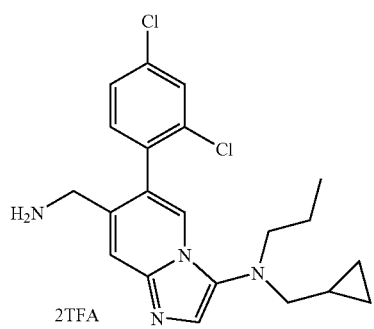
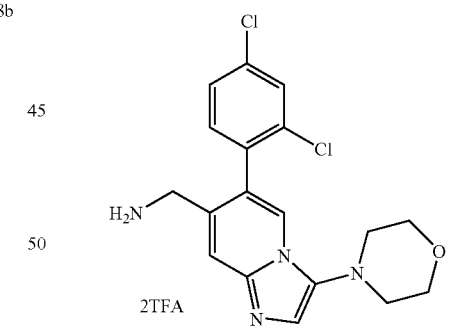
8g
8c
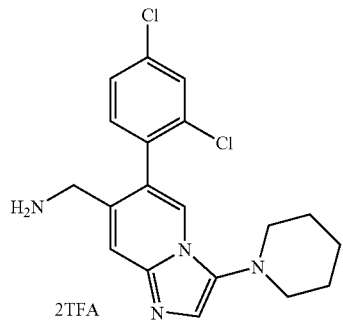
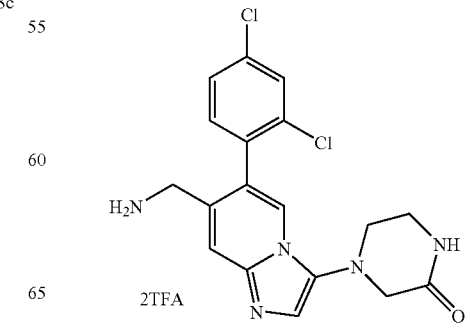
8h -continued
8i
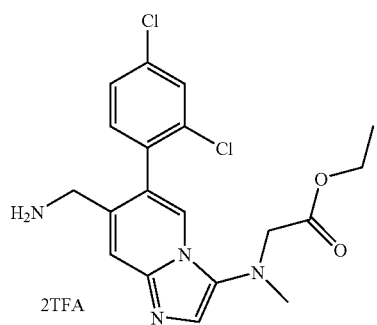
8j
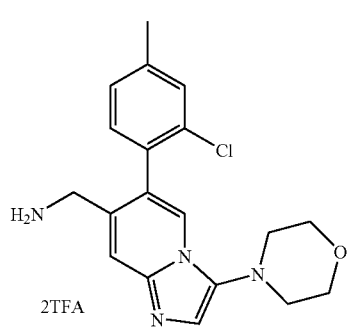
8k
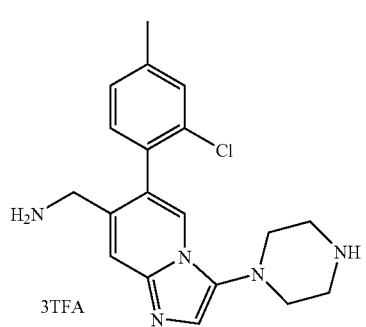
8l
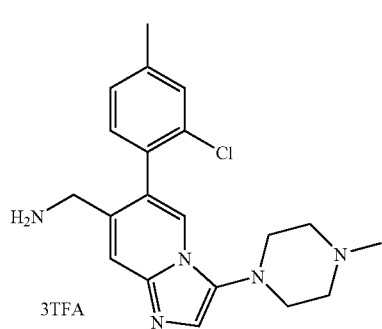
8m
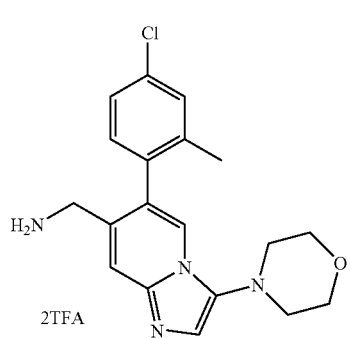
-continued
8n
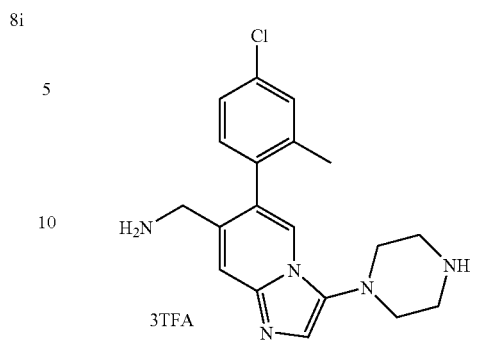
8o
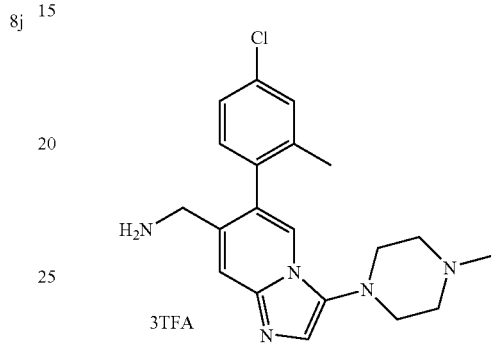
8p
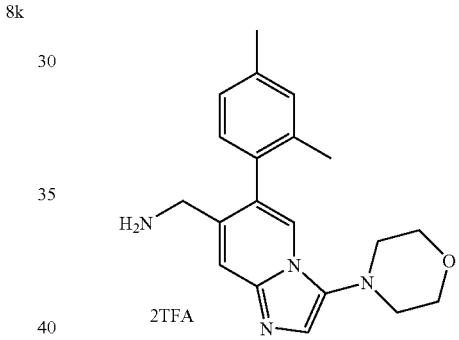
8q
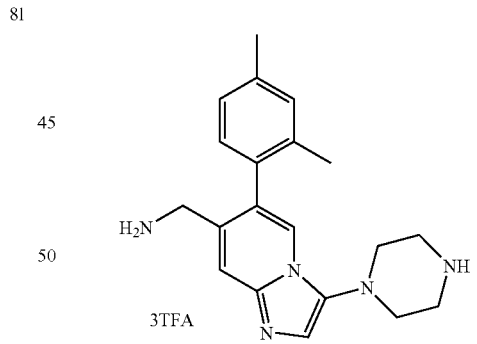
8r
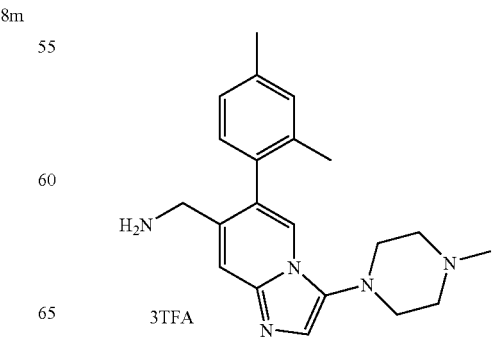

| 189 -continued | | 190 -continued | |
|---|---|---|---|
| 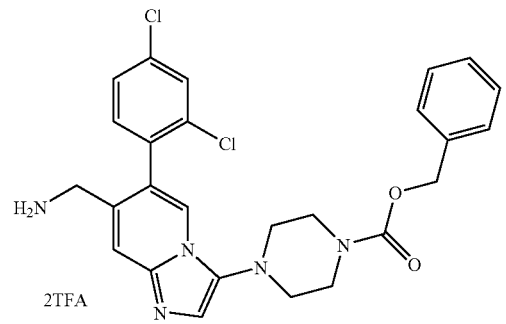 | 8s | 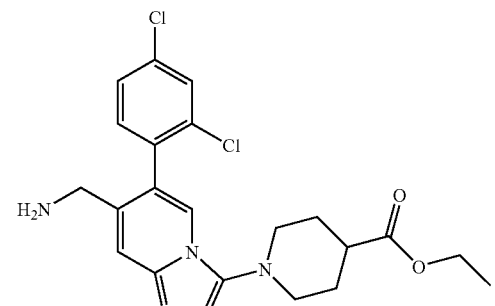 | 8w |
| 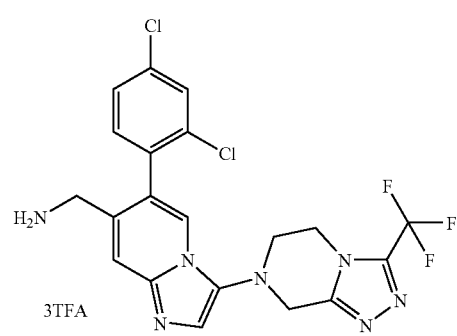 | 8t | 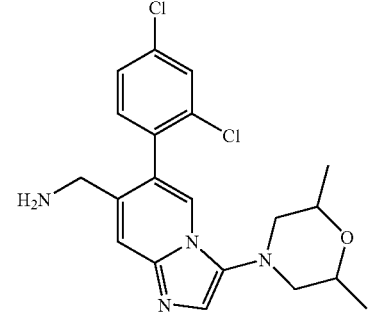 | 8x |
| 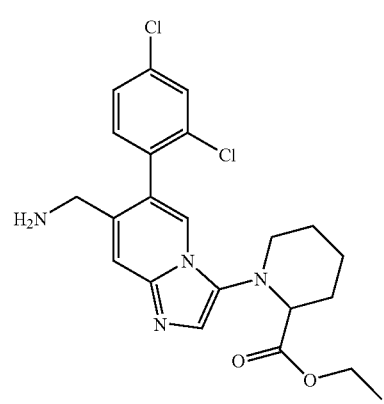 | 8u | 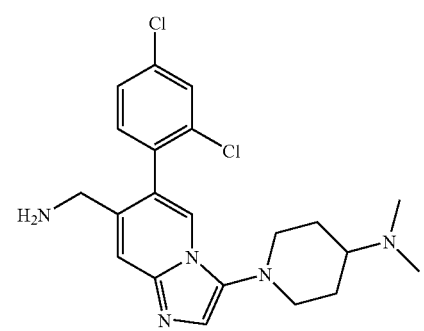 | 8y |
| 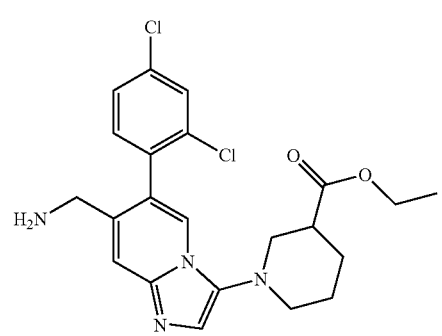 | 8v | 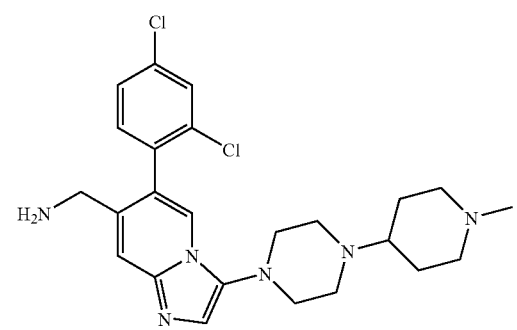 | 8z |
| | | 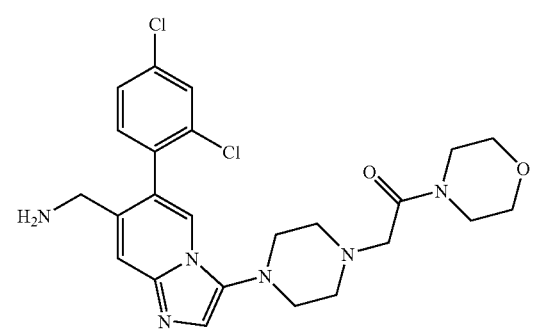 | 8a' |

-continued
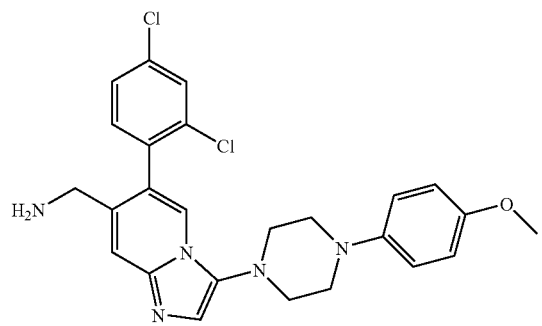
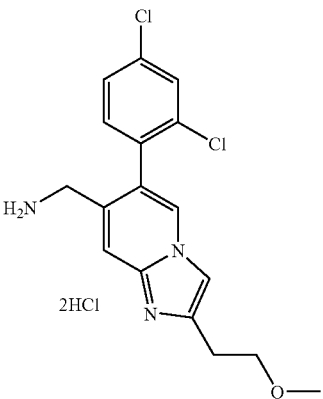
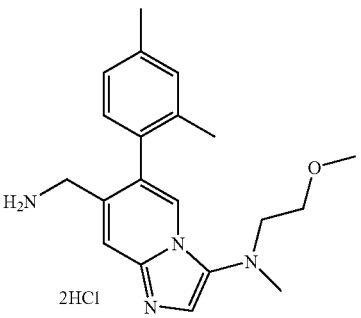
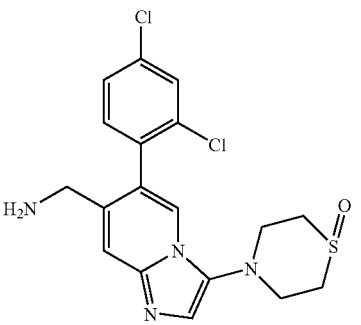
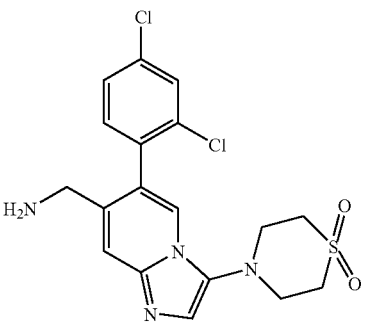

| 193 | 194 |
|---|---|
| -continued | -continued |
| 15 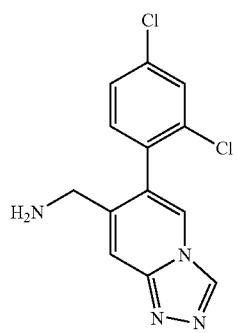 | 5 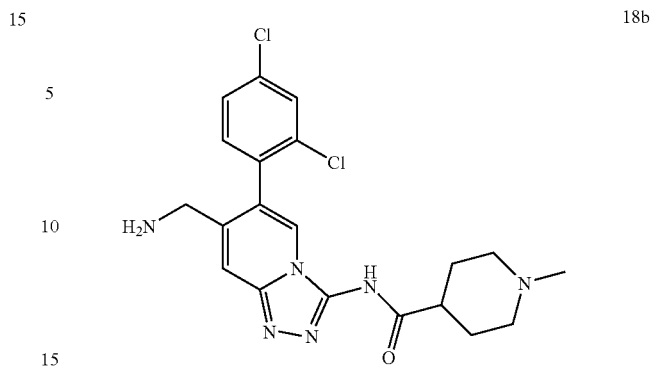 18b |
| 16 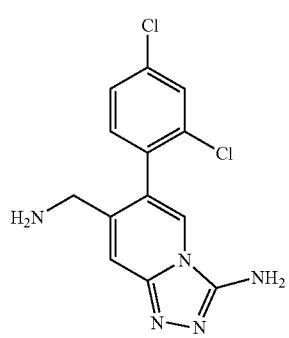 | 18c 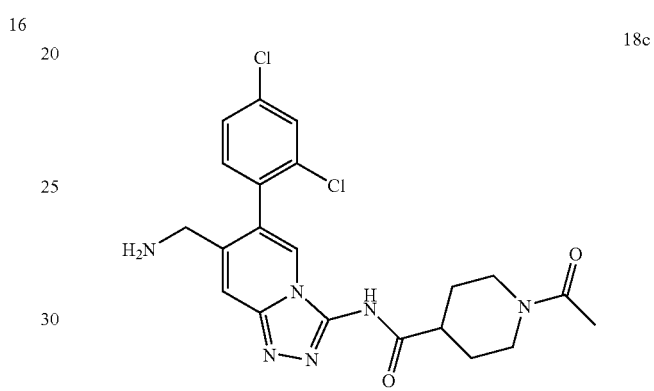 |
| 17 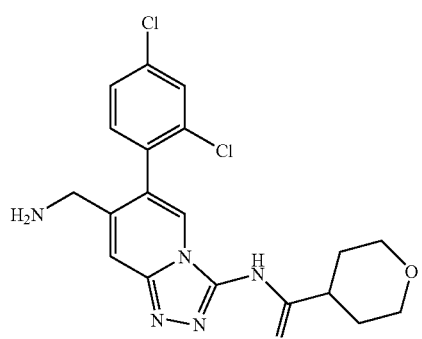 | 18d 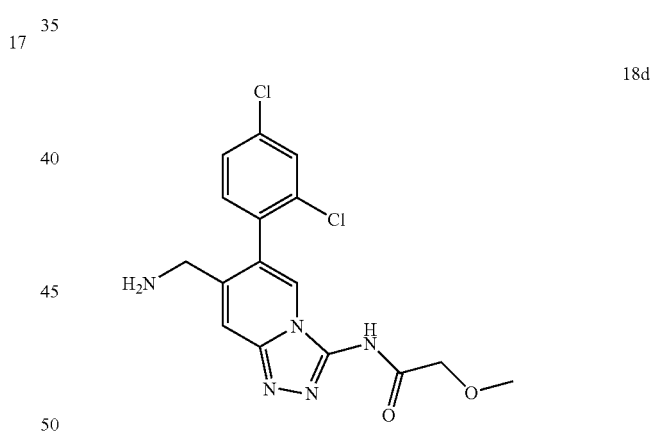 |
| 18a 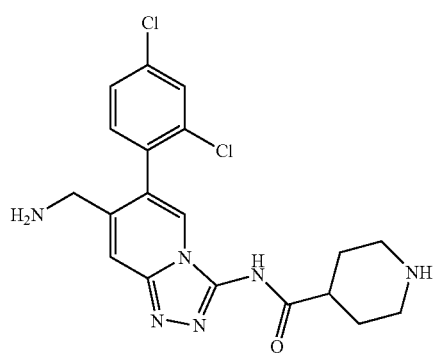 | 18e 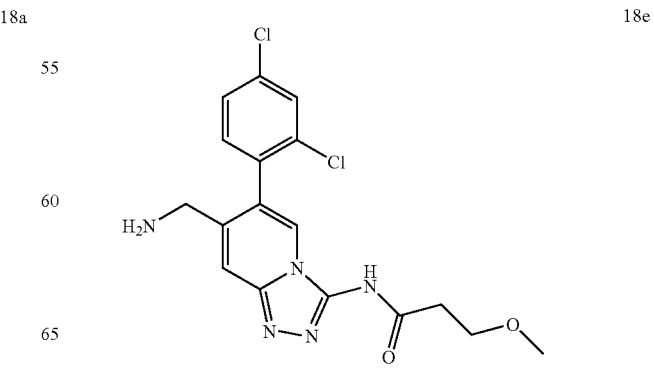 |

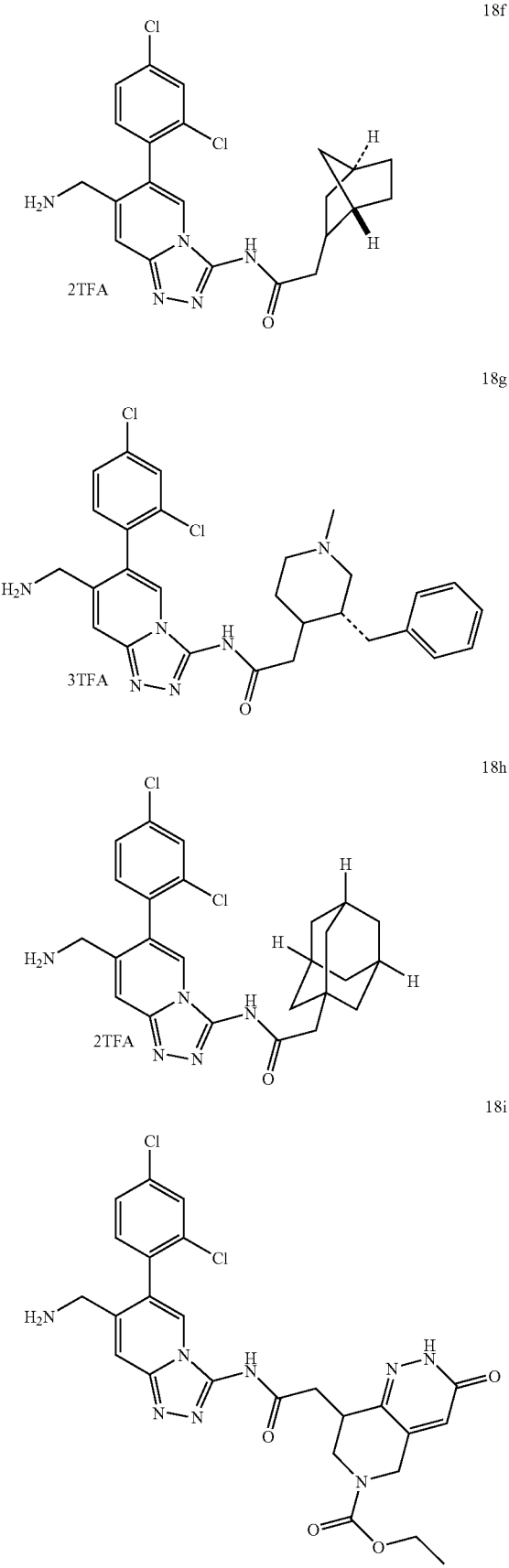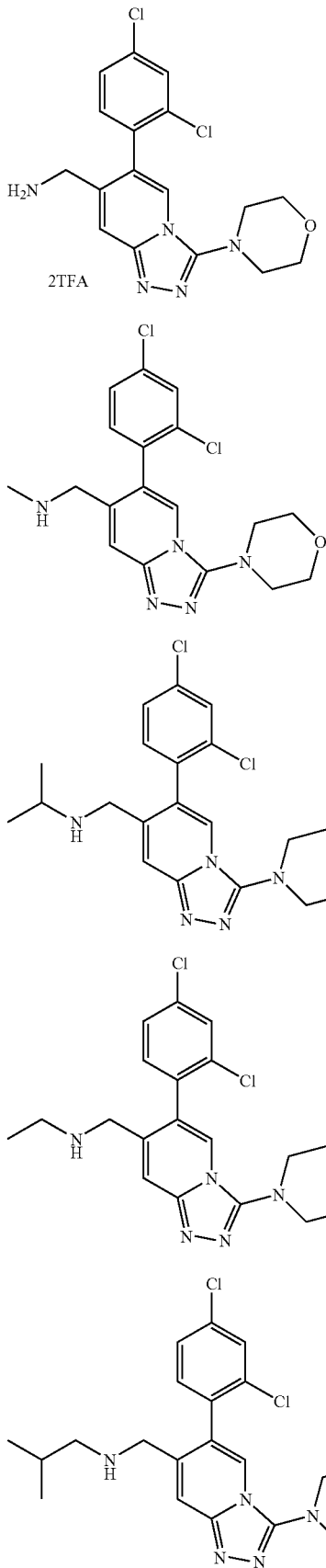

| 21d | 24b |
|---|---|
| 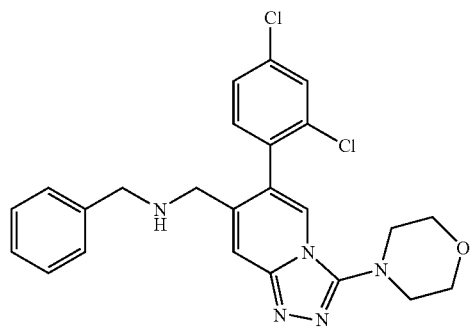 | 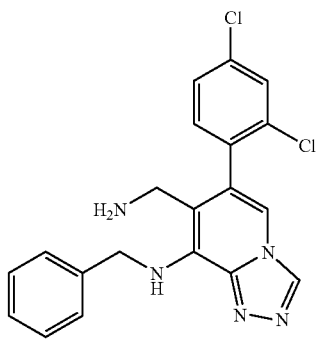 |
| 21e | 24c |
| 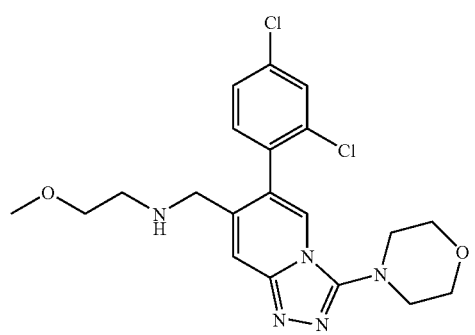 | 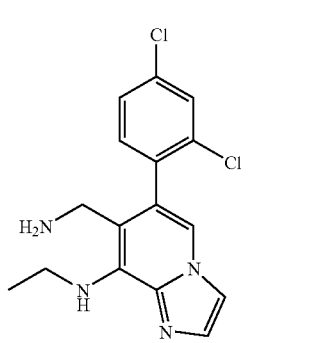 |
| 22 | 24d |
| 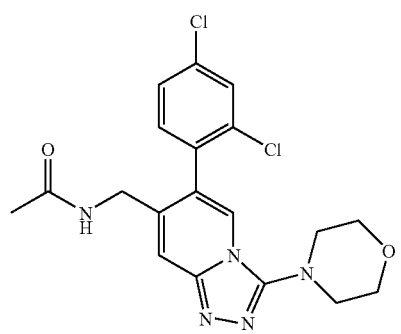 | 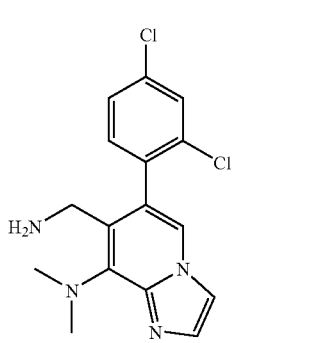 |
| 23 | 24e |
| 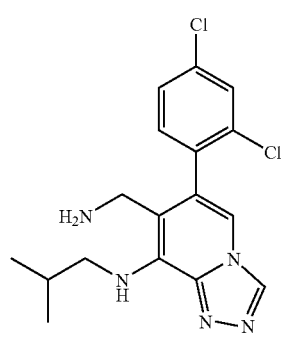 | 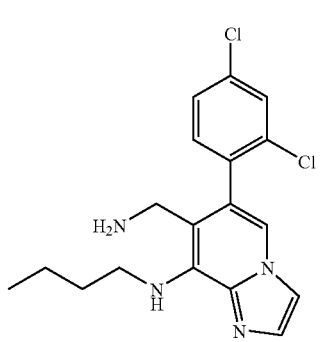 |
| 24a | 24f |
| 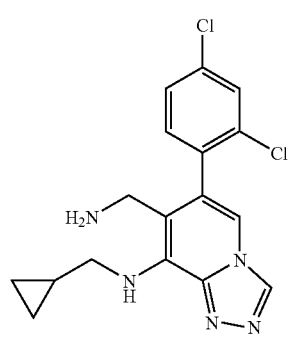 | 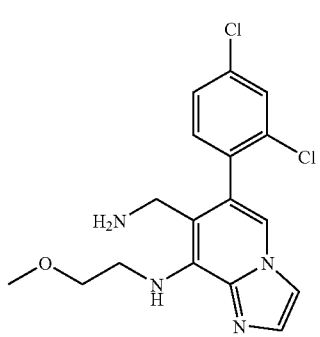 |

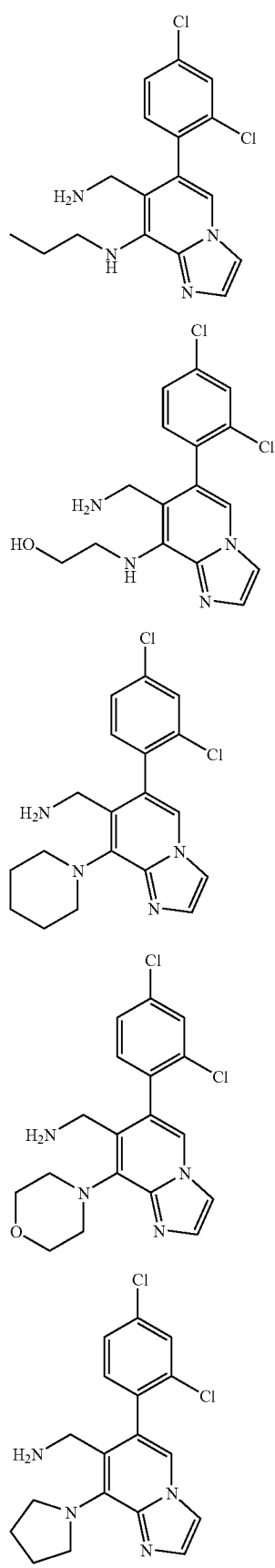
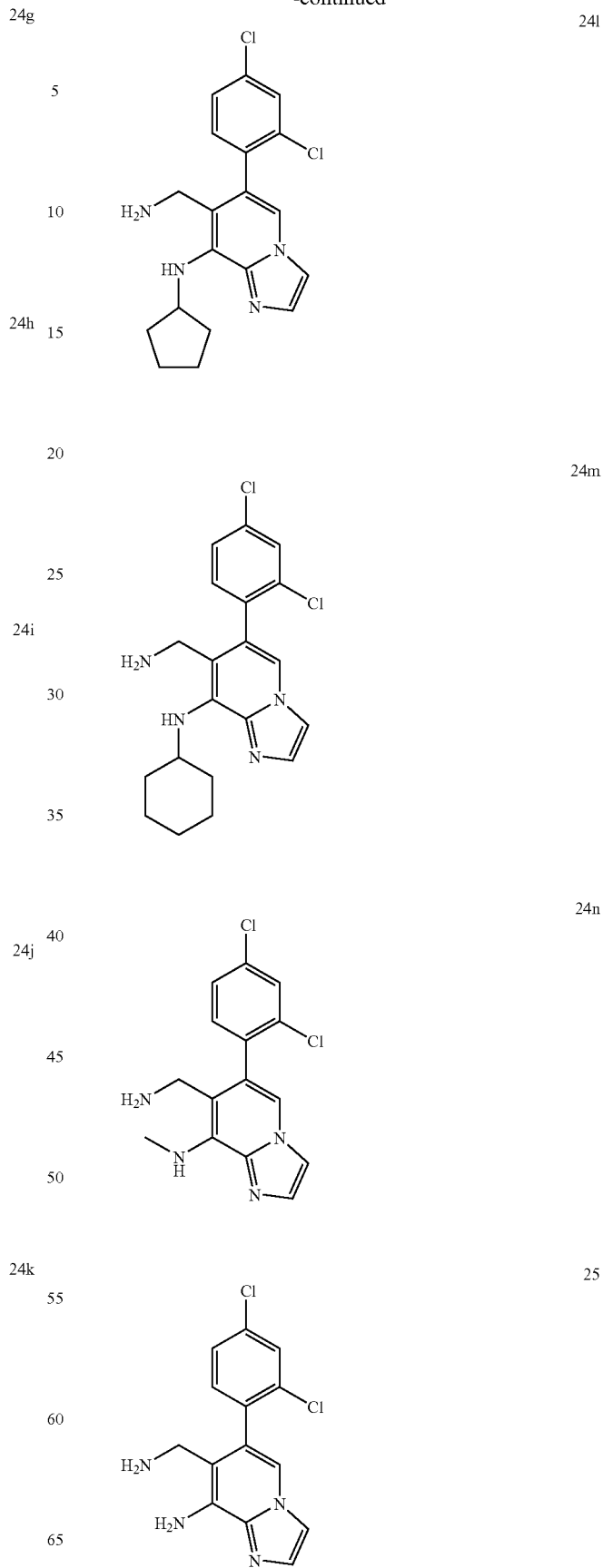

201
-continued
26
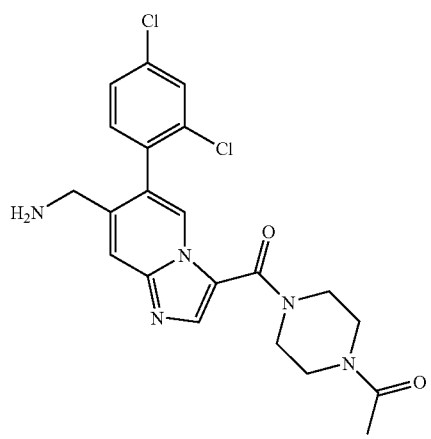
27a
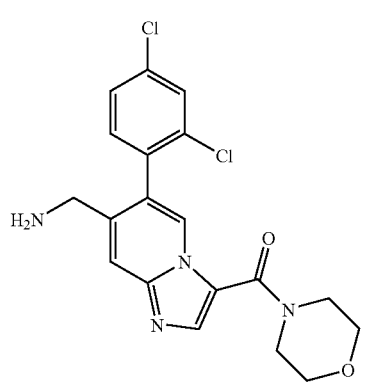
27b
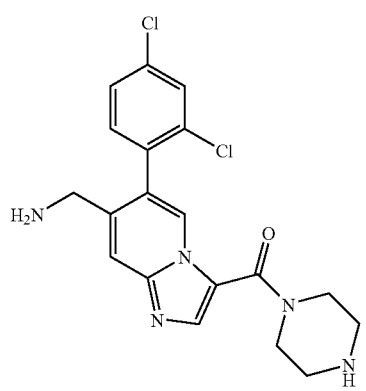
27c
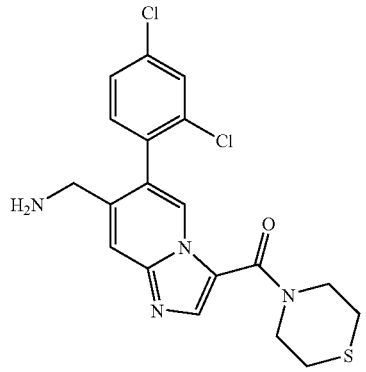
202
-continued
27d
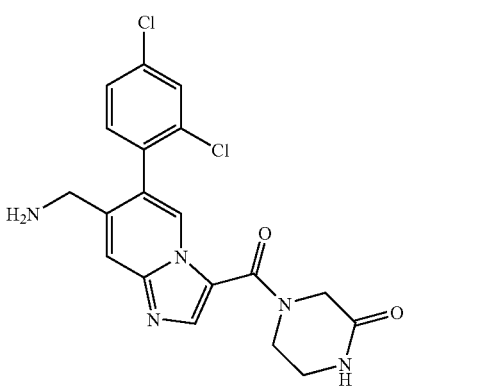
27e
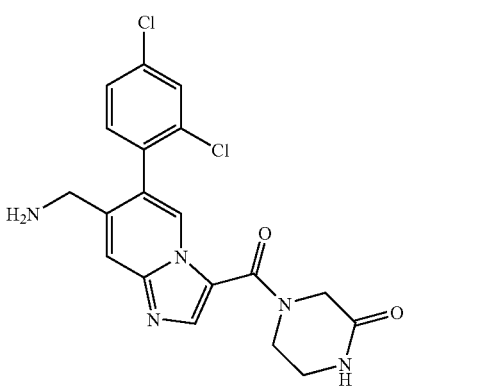
27f
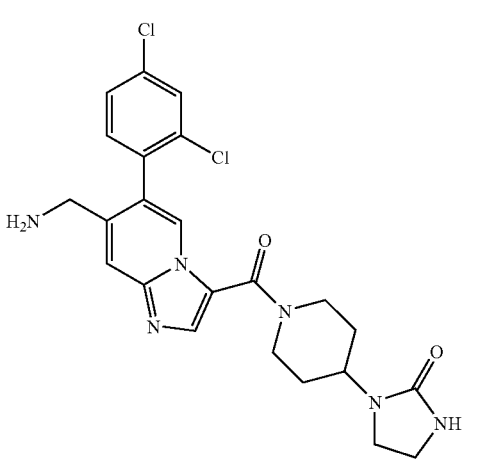

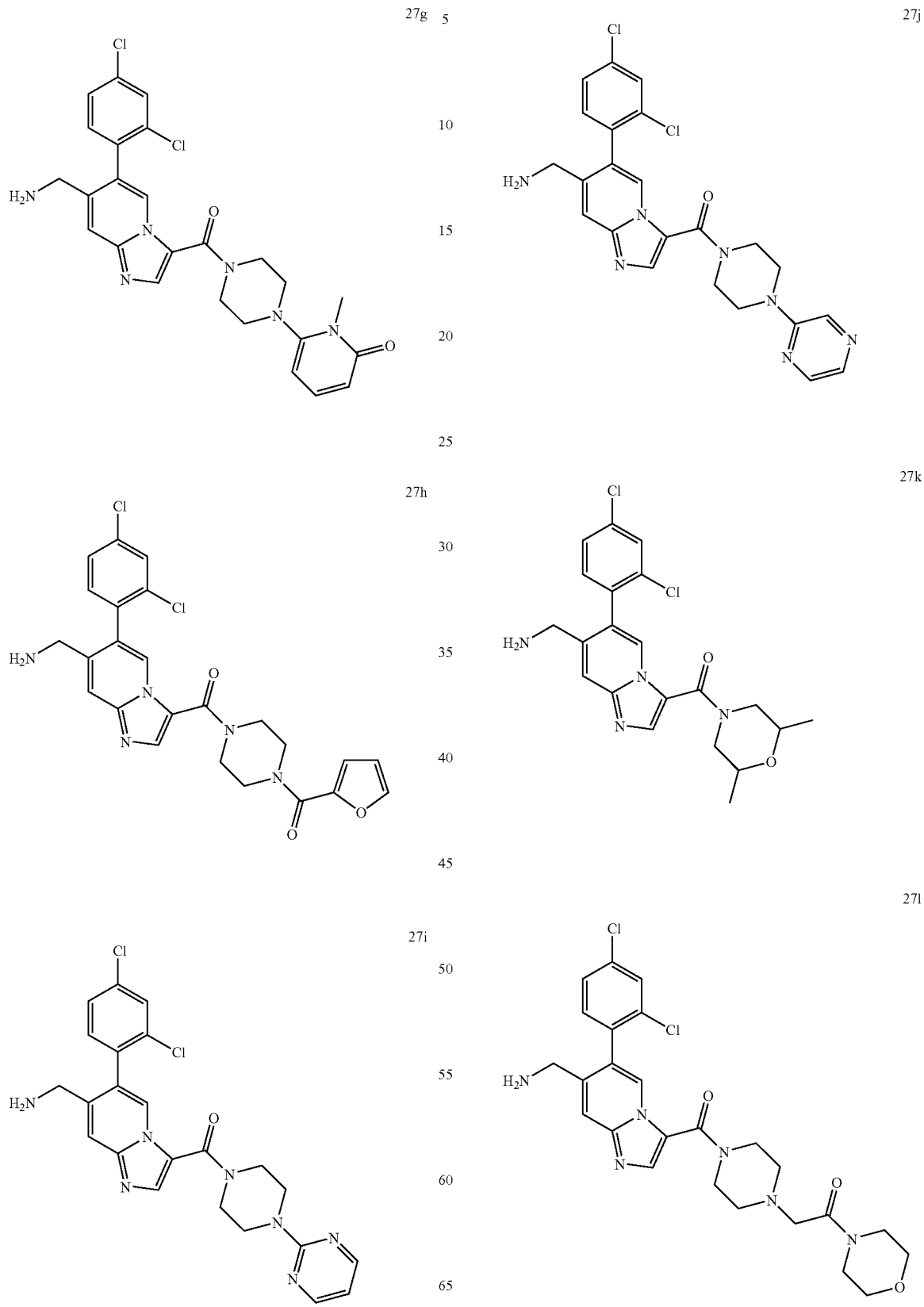

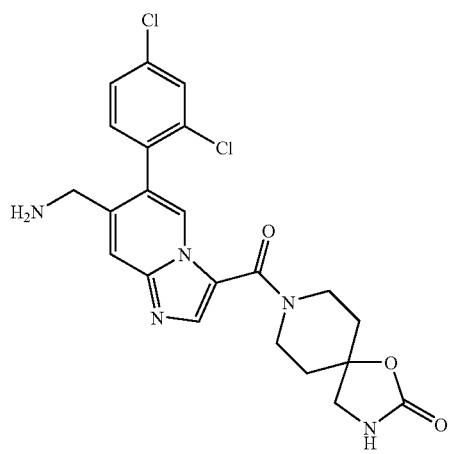
27m
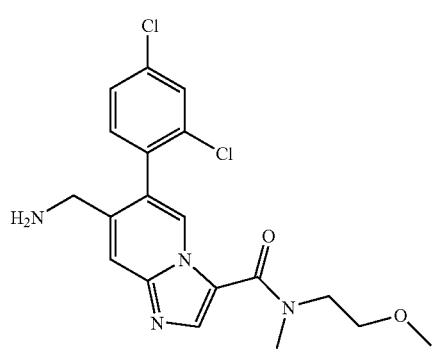
27n
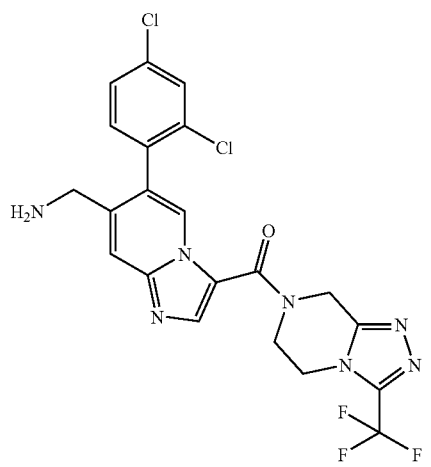
27o
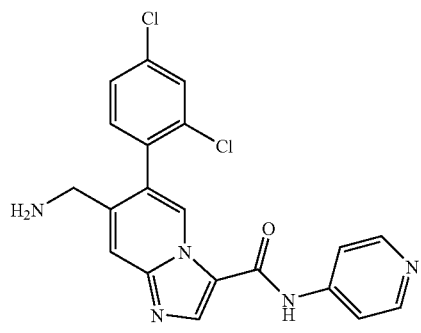
27p
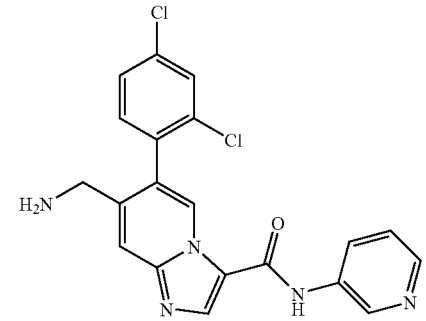
27q
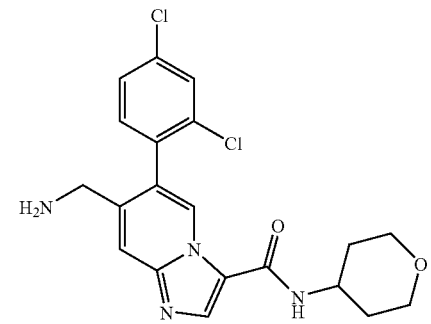
27r
27s
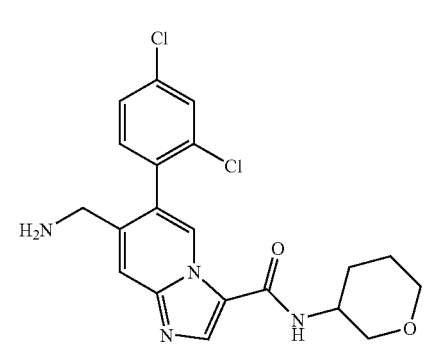
27t 207
-continued
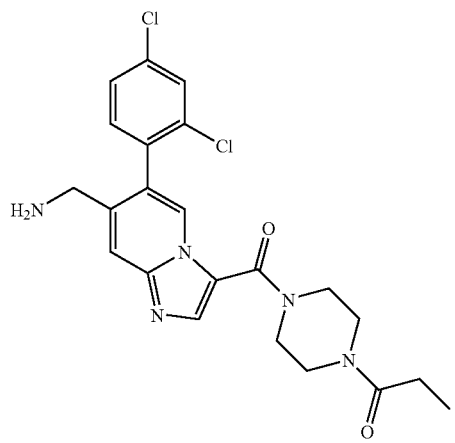
27u
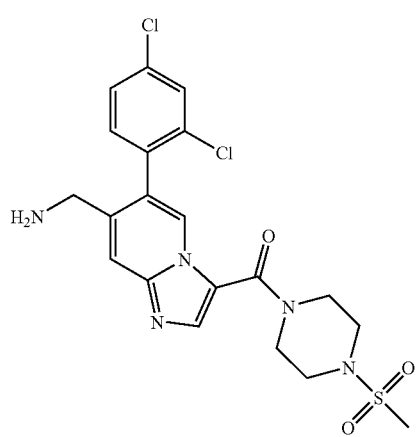
27w
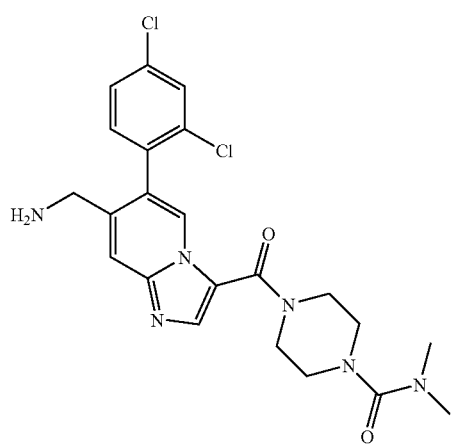
208
-continued
27b'
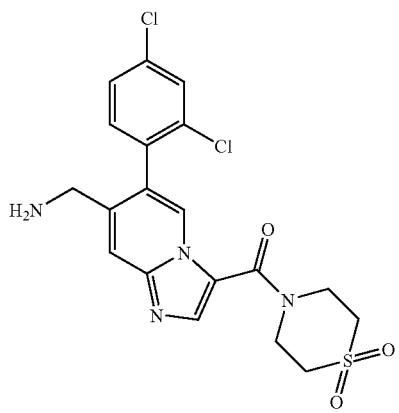
27c'
27v
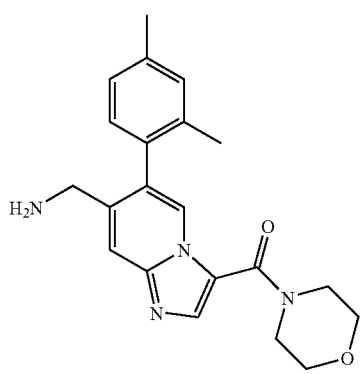
27d'
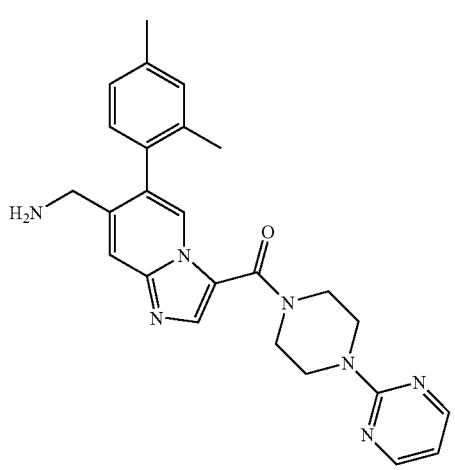
27e'

27b'
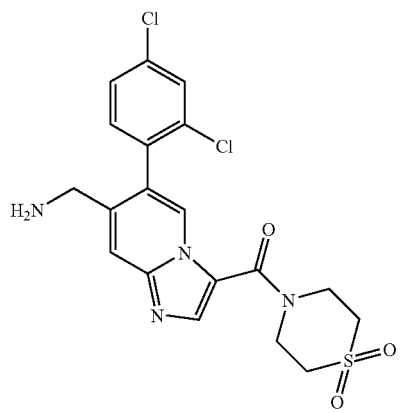
27c'
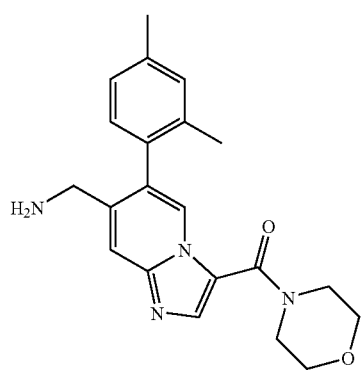
27d'
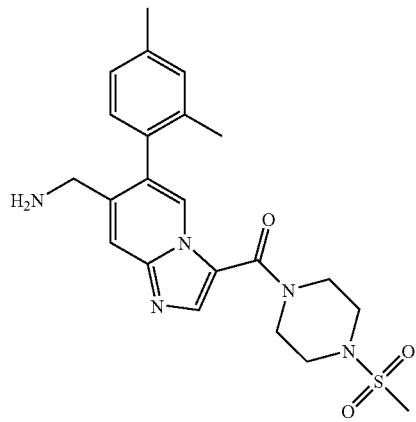
27e'
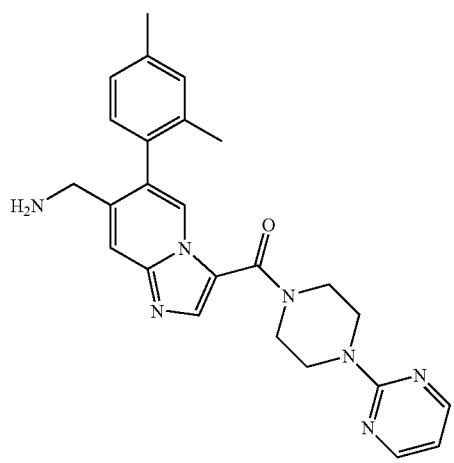
27f'
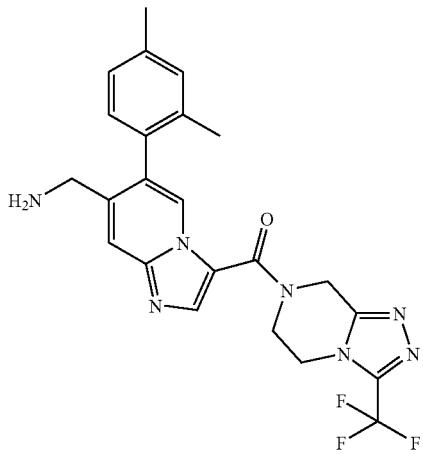
27g'
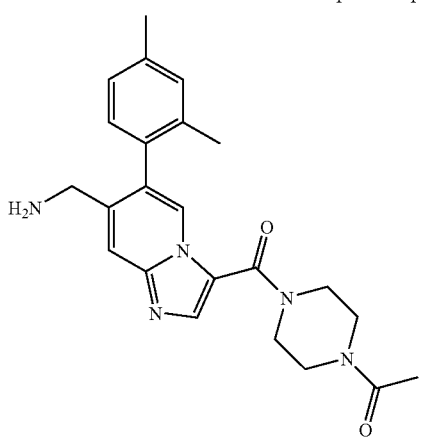
27h'
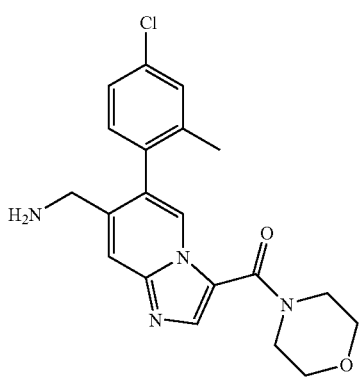
27i'
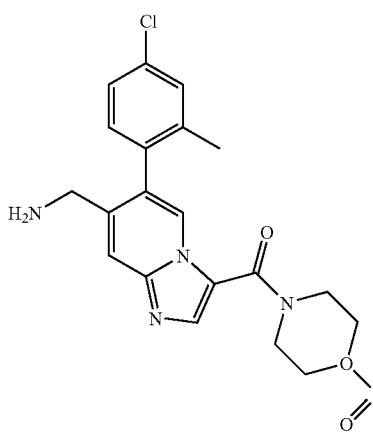

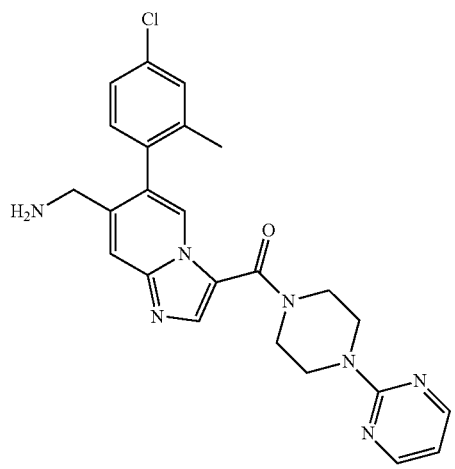
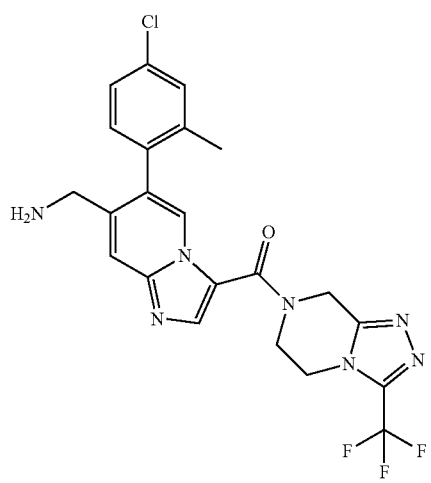
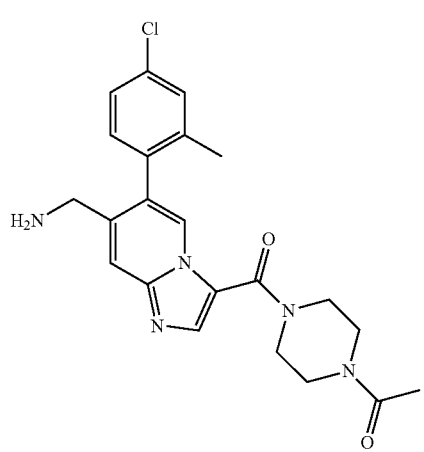
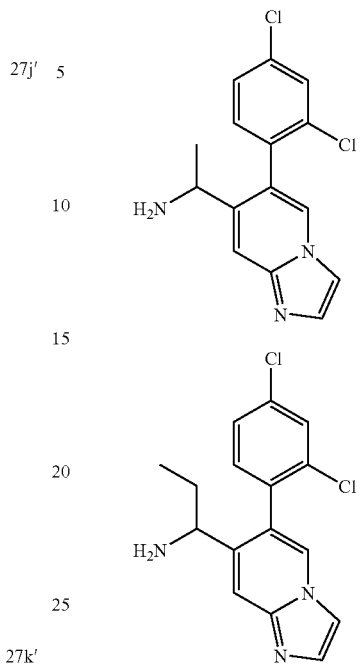
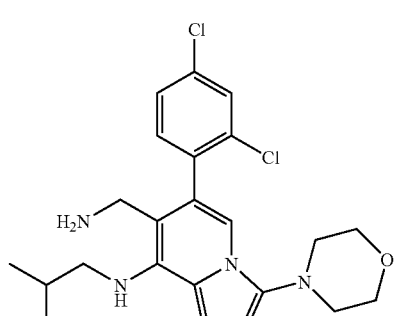
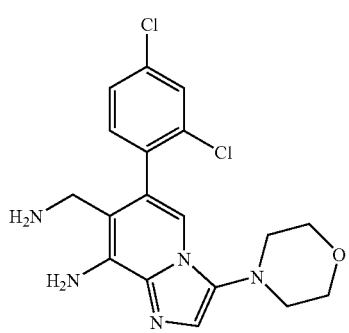

| | |
|---|---|
| 33a | 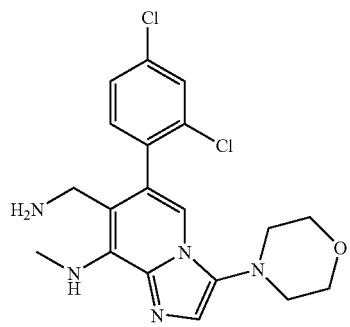 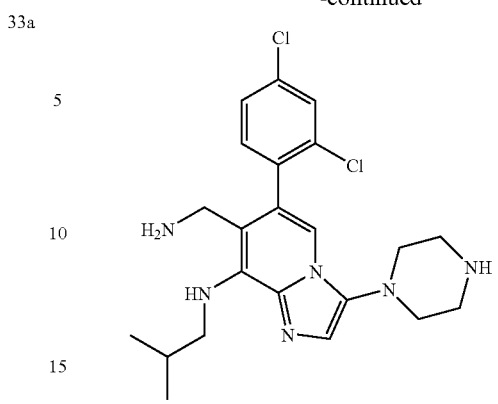 33e |
| 33b | 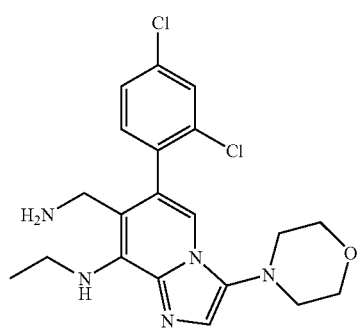 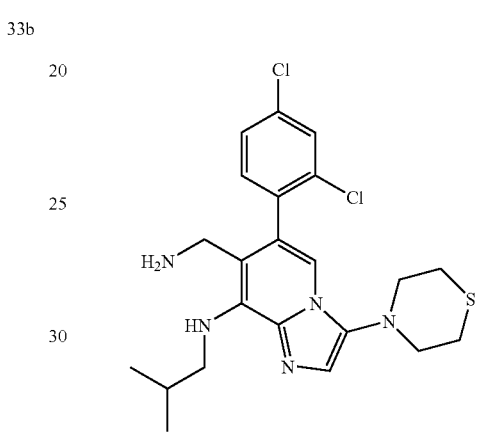 33f |
| 33c | 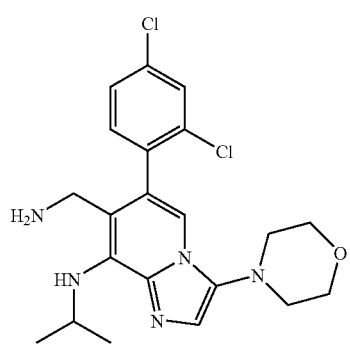 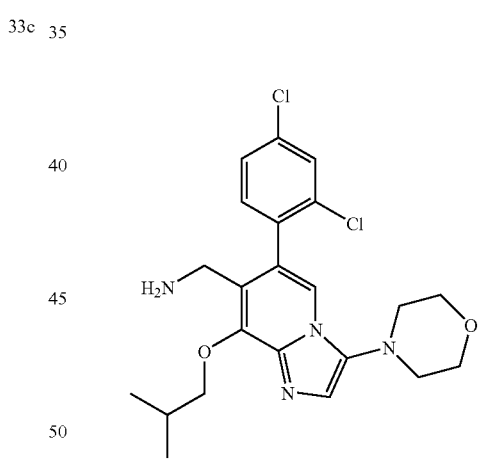 33g |
| 33d | 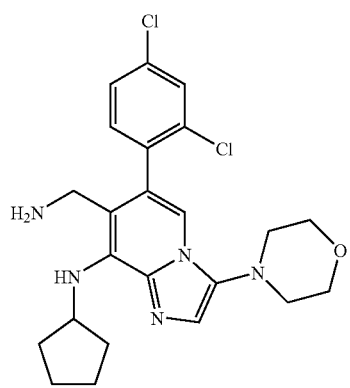 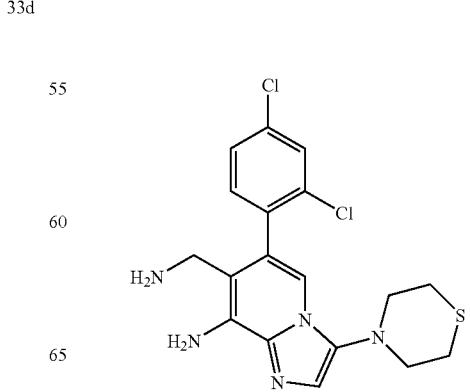 33h |

33i 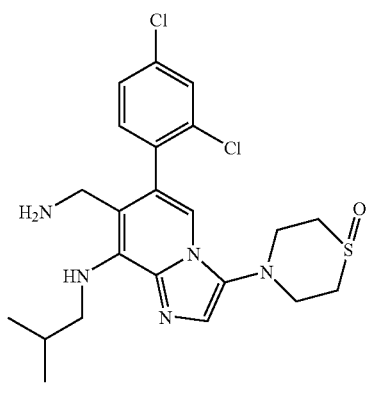
36 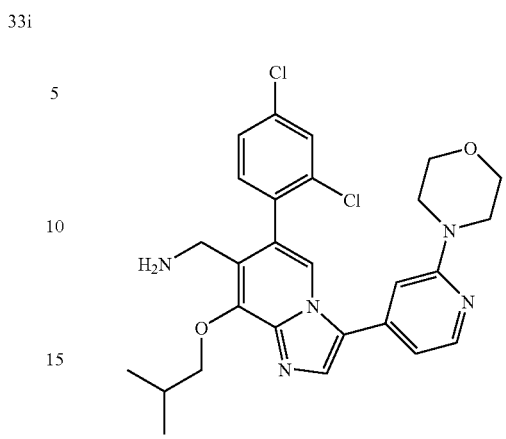
33j 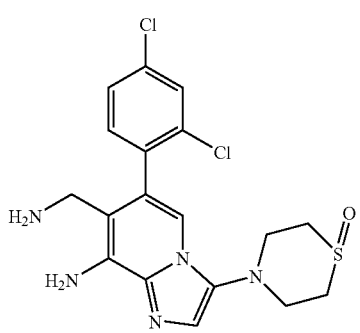
37 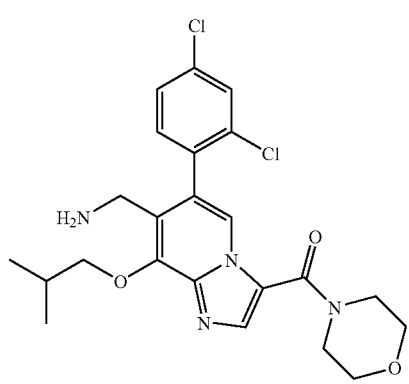
34 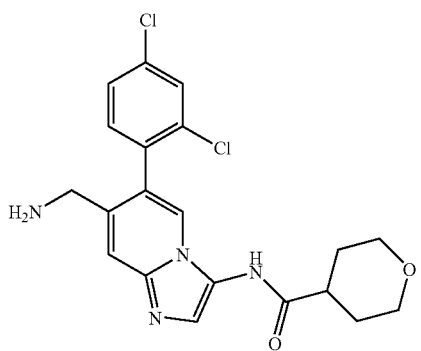
38 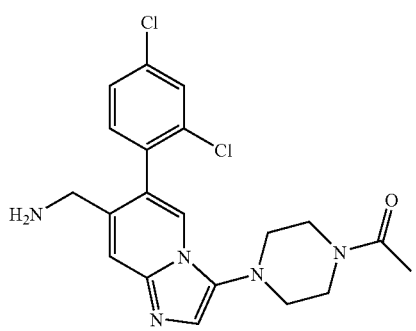
35 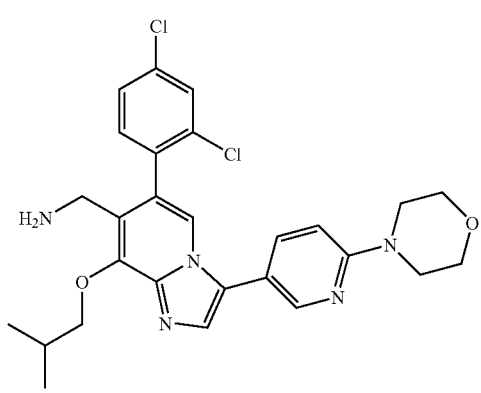
39 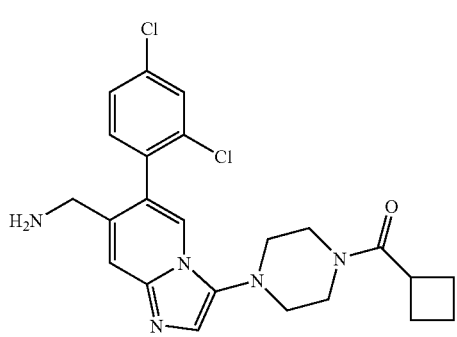

217
-continued
218
-continued
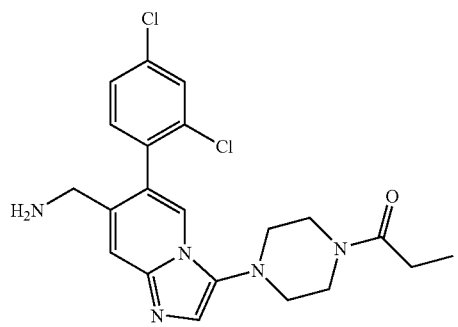
40a
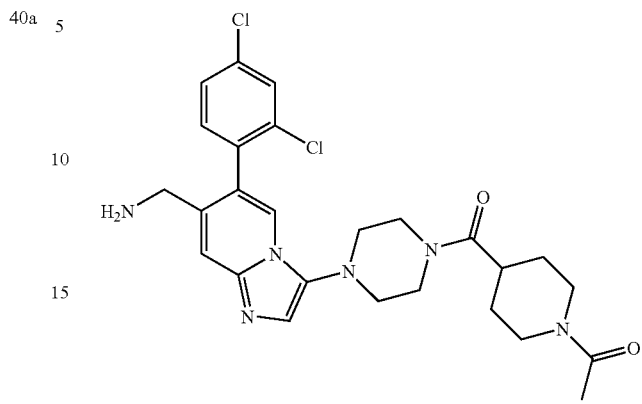
40e
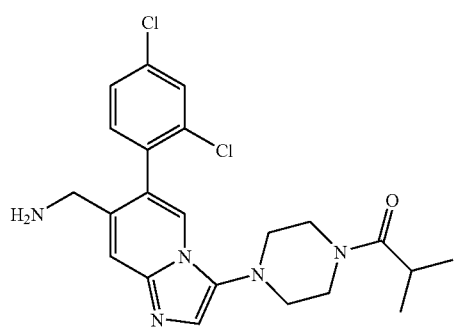
40b
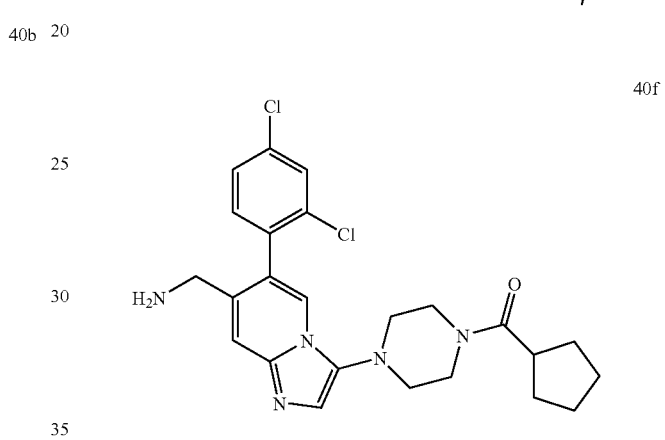
40f
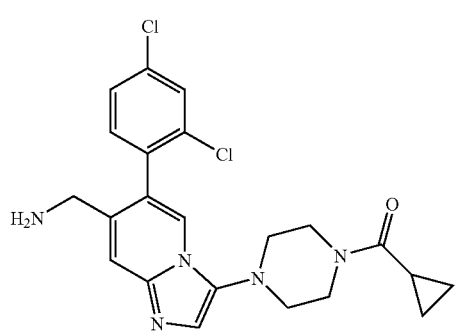
40c
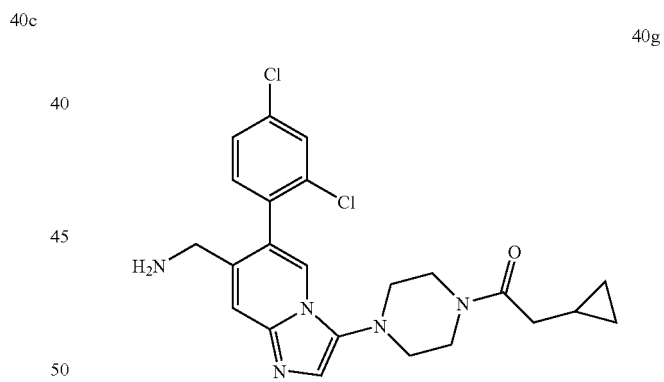
40g
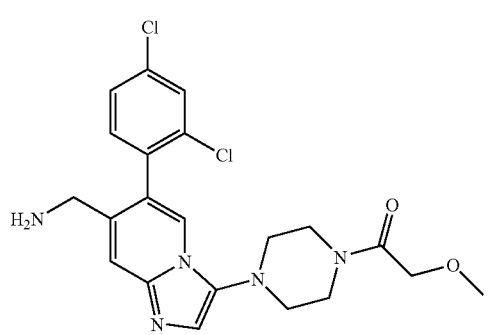
40d
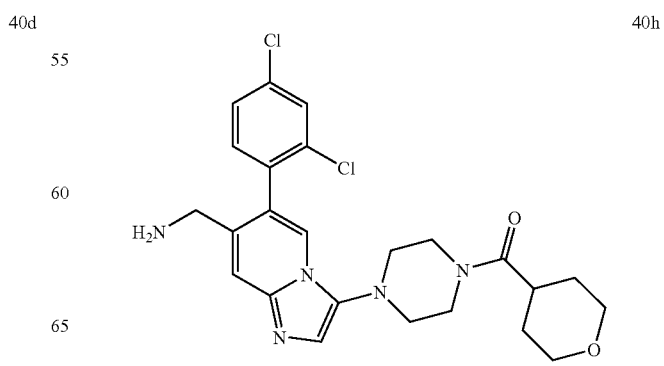
40h

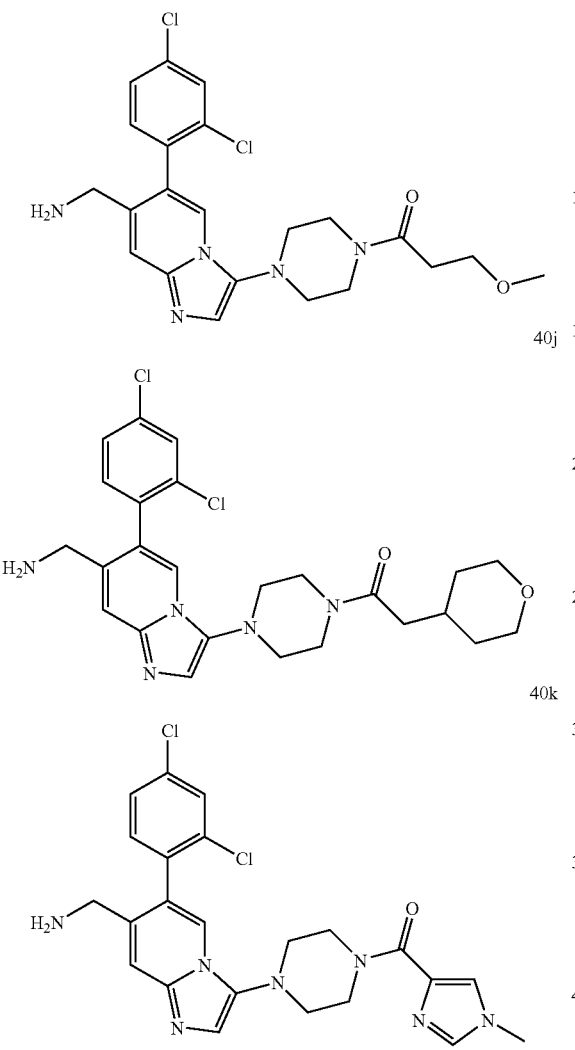

or, in each case, a pharmaceutically acceptable salt free form thereof.

16. A pharmaceutical formulation, comprising:
    a compound of claim 1, and
    a pharmaceutically acceptable excipient or carrier.

17. A formulation according to claim 16, which further comprises a therapeutic agent selected from antidiabetic agents, hypolipidemic agents, anti-obesity or appetite-regulating agents, anti-hypertensive agents, HDL-increasing agents, cholesterol absorption modulators, Apo-A1 analogues and mimetics, thrombin inhibitors, aldosterone inhibitors, inhibitors of platelet aggregation, estrogen, testosterone, selective estrogen receptor modulators, selective androgen receptor modulators, chemotherapeutic agents, and 5-$HT_3$ or 5-$HT_4$ receptor modulators; or pharmaceutically acceptable salts thereof.

* * * * *